US009205423B2

(12) United States Patent
Hansen et al.

(10) Patent No.: US 9,205,423 B2
(45) Date of Patent: *Dec. 8, 2015

(54) HIGH THROUGHPUT SCREENING OF CRYSTALLIZATION OF MATERIALS

(71) Applicants: California Institute of Technology, Pasadena, CA (US); The Regents of the University of California, Oakland, CA (US)

(72) Inventors: Carl L. Hansen, Pasadena, CA (US); Stephen R. Quake, Stanford, CA (US); James M. Berger, Kensington, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/776,646

(22) Filed: Feb. 25, 2013

(65) Prior Publication Data

US 2014/0041727 A1 Feb. 13, 2014

Related U.S. Application Data

(60) Continuation of application No. 11/668,263, filed on Jan. 29, 2007, now Pat. No. 8,382,896, which is a division of application No. 10/117,978, filed on Apr. 5, 2002, now Pat. No. 7,195,670, which is a (Continued)

(51) Int. Cl.
*C30B 7/14* (2006.01)
*B01L 3/06* (2006.01)

(Continued)

(52) U.S. Cl.
CPC .............. *B01L 3/06* (2013.01); *B01L 3/50273* (2013.01); *B01L 3/502707* (2013.01);

(Continued)

(58) Field of Classification Search
USPC ................................ 117/68, 69, 70, 201, 202
See application file for complete search history.

(56) References Cited

U.S. PATENT DOCUMENTS 2,620,938 A   12/1952 Jesnig
3,495,608 A   2/1970 O'Keefe (Continued)

FOREIGN PATENT DOCUMENTS

EP   0553539   4/1993
EP   592 094 A2   4/1994

(Continued)

OTHER PUBLICATIONS

Ahn et al., "Fluid Micropumps Based on Rotary Magnetic Actuators," Proceedings of 1995 IEEE Micro Electro Mechanical Systems Workshop (MEMS '95), held in Amsterdam, Netherlands on Jan. 29-Feb. 2, 1995, pp. 408-412 (1995).

(Continued)

*Primary Examiner* — Robert M Kunemund
(74) *Attorney, Agent, or Firm* — Kilpatrick Townsend & Stockton LLP

(57) ABSTRACT

High throughput screening of crystallization of a target material is accomplished by simultaneously introducing a solution of the target material into a plurality of chambers of a microfabricated fluidic device. The microfabricated fluidic device is then manipulated to vary the solution condition in the chambers, thereby simultaneously providing a large number of crystallization environments. Control over changed solution conditions may result from a variety of techniques, including but not limited to metering volumes of crystallizing agent into the chamber by volume exclusion, by entrapment of volumes of crystallizing agent determined by the dimensions of the microfabricated structure, or by cross-channel injection of sample and crystallizing agent into an array of junctions defined by intersecting orthogonal flow channels.

6 Claims, 66 Drawing Sheets

Related U.S. Application Data continuation-in-part of application No. 09/887,997, filed on Jun. 22, 2001, now Pat. No. 7,052,545, which is a continuation-in-part of application No. 09/826,583, filed on Apr. 6, 2001, now Pat. No. 6,899,137, which is a continuation-in-part of application No. 09/724,784, filed on Nov. 28, 2000, now Pat. No. 7,144,616, and a continuation-in-part of application No. 09/605,520, filed on Jun. 27, 2000, now Pat. No. 7,601,270.

(60) Provisional application No. 60/323,524, filed on Sep. 17, 2001.

(51) Int. Cl.
| | |
|---|---|
| *B01L 3/00* | (2006.01) |
| *B01L 9/00* | (2006.01) |
| *C12Q 1/68* | (2006.01) |
| *F04B 43/04* | (2006.01) |
| *F16K 99/00* | (2006.01) |
| *B01L 7/00* | (2006.01) |

(52) U.S. Cl.
CPC .... *B01L 3/502738* (2013.01); *B01L 3/502761* (2013.01); *B01L 9/527* (2013.01); *C12Q 1/6874* (2013.01); *F04B 43/043* (2013.01); *F16K 99/0001* (2013.01); *F16K 99/0015* (2013.01); *F16K 99/0026* (2013.01); *F16K 99/0059* (2013.01); *B01J 2219/00274* (2013.01); *B01L 7/54* (2013.01); *B01L 2200/025* (2013.01); *B01L 2200/027* (2013.01); *B01L 2200/0605* (2013.01); *B01L 2200/0642* (2013.01); *B01L 2200/10* (2013.01); *B01L 2300/0681* (2013.01); *B01L 2300/0816* (2013.01); *B01L 2300/0861* (2013.01); *B01L 2300/0887* (2013.01); *B01L 2300/123* (2013.01); *B01L 2300/14* (2013.01); *B01L 2300/18* (2013.01); *B01L 2300/1827* (2013.01); *B01L 2400/0481* (2013.01); *B01L 2400/0655* (2013.01); *B01L 2400/0688* (2013.01); *F16K 99/0034* (2013.01); *F16K 2099/008* (2013.01); *F16K 2099/0074* (2013.01); *F16K 2099/0078* (2013.01); *F16K 2099/0084* (2013.01); *F16K 2099/0094* (2013.01); *Y10T 117/1004* (2015.01); *Y10T 117/1008* (2015.01); *Y10T 137/0318* (2015.04); *Y10T 137/0396* (2015.04)

(56) References Cited

U.S. PATENT DOCUMENTS

| | | | |
|---|---|---|---|
| 3,570,515 | A | 3/1971 | Kinner |
| 3,747,628 | A | 7/1973 | Holster et al. |
| 4,046,159 | A | 9/1977 | Pegourie |
| 4,119,368 | A | 10/1978 | Yamazaki |
| 4,153,855 | A | 5/1979 | Feingold |
| 4,245,673 | A | 1/1981 | Bouteille et al. |
| 4,434,704 | A | 3/1984 | Surjaatmadja |
| 4,848,722 | A | 7/1989 | Webster |
| 4,898,582 | A | 2/1990 | Faste |
| 4,948,564 | A | 8/1990 | Root et al. |
| 4,992,312 | A | 2/1991 | Frisch |
| 5,085,562 | A | 2/1992 | van Lintel |
| 5,088,515 | A | 2/1992 | Kamen |
| 5,096,388 | A | 3/1992 | Weinberg |
| 5,126,115 | A | 6/1992 | Fujita et al. |
| 5,164,558 | A | 11/1992 | Huff et al. |
| 5,171,132 | A | 12/1992 | Miyazaki et al. |
| 5,224,843 | A | 7/1993 | van Lintel |
| 5,259,737 | A | 11/1993 | Kamisuki et al. |
| 5,265,327 | A | 11/1993 | Faris et al. |
| 5,290,240 | A | 3/1994 | Horres, Jr. |
| 5,336,062 | A | 8/1994 | Richter |
| 5,346,372 | A | 9/1994 | Naruse et al. |
| 5,375,979 | A | 12/1994 | Trah |
| 5,376,252 | A | 12/1994 | Ekstrom et al. |
| 5,400,741 | A | 3/1995 | DeTitta et al. |
| 5,423,287 | A | 6/1995 | Usami et al. |
| 5,529,465 | A | 6/1996 | Zengerle et al. |
| 5,593,130 | A | 1/1997 | Hansson et al. |
| 5,637,469 | A | 6/1997 | Wilding et al. |
| 5,642,015 | A | 6/1997 | Whitehead et al. |
| 5,659,171 | A | 8/1997 | Young et al. |
| 5,660,370 | A | 8/1997 | Webster |
| 5,681,024 | A | 10/1997 | Lisec et al. |
| 5,705,018 | A | 1/1998 | Hartley |
| 5,759,014 | A | 6/1998 | Van Lintel |
| 5,775,371 | A | 7/1998 | Pan et al. |
| 5,788,468 | A | 8/1998 | Dewa et al. |
| 5,836,750 | A | 11/1998 | Cabuz |
| 5,842,787 | A | 12/1998 | Kopf-Sill et al. |
| 5,856,174 | A | 1/1999 | Lipshutz et al. |
| 5,875,817 | A | 3/1999 | Carter |
| 5,876,187 | A | 3/1999 | Afromowitz et al. |
| 5,876,675 | A | 3/1999 | Kennedy |
| 5,885,470 | A | 3/1999 | Parce et al. |
| 5,932,100 | A | 8/1999 | Yager et al. |
| 5,932,799 | A | 8/1999 | Moles |
| 5,942,443 | A | 8/1999 | Parce et al. |
| 5,958,694 | A | 9/1999 | Nikiforov |
| 5,972,187 | A | 10/1999 | Parce et al. |
| 6,007,309 | A | 12/1999 | Hartley |
| 6,043,080 | A | 3/2000 | Lipshutz et al. |
| 6,046,056 | A | 4/2000 | Parce et al. |
| 6,123,769 | A | 9/2000 | Sanjoh |
| 6,155,282 | A | 12/2000 | Zachary et al. |
| 6,165,694 | A | 12/2000 | Liu |
| 6,168,948 | B1 | 1/2001 | Anderson et al. |
| 6,174,365 | B1 | 1/2001 | Sanjoh |
| 6,174,675 | B1 | 1/2001 | Chow et al. |
| 6,296,673 | B1 | 10/2001 | Santarsiero et al. |
| 6,306,659 | B1 | 10/2001 | Parce et al. |
| 6,345,502 | B1 | 2/2002 | Tai et al. |
| 6,395,232 | B1 | 5/2002 | McBride |
| 6,408,878 | B2 | 6/2002 | Unger et al. |
| 6,409,832 | B2 | 6/2002 | Weigl et al. |
| 6,448,090 | B1 | 9/2002 | McBride |
| 6,503,757 | B1 | 1/2003 | Chow |
| 6,582,969 | B1 | 6/2003 | Wagner et al. |
| 6,585,939 | B1 | 7/2003 | Dapprich |
| 6,664,104 | B2 | 12/2003 | Pourahmadi et al. |
| 6,719,840 | B2 | 4/2004 | David et al. |
| 6,767,706 | B2 | 7/2004 | Quake et al. |
| 6,793,753 | B2 | 9/2004 | Unger et al. |
| 6,797,056 | B2 | 9/2004 | David |
| 6,893,879 | B2 | 5/2005 | Petersen et al. |
| 6,899,137 | B2 | 5/2005 | Unger et al. |
| 6,929,030 | B2 | 8/2005 | Unger et al. |
| 6,939,452 | B2 | 9/2005 | Foret et al. |
| 6,977,145 | B2 | 12/2005 | Fouillet et al. |
| 7,052,545 | B2 | 5/2006 | Quake et al. |
| 7,144,616 | B1 | 12/2006 | Unger et al. |
| 7,195,670 | B2 | 3/2007 | Quake et al. |
| 7,601,270 | B1 | 10/2009 | Unger et al. |
| 8,382,896 | B2 * | 2/2013 | Hansen et al. .............. 117/68 |
| 2001/0027745 | A1 | 10/2001 | Weigl et al. |
| 2001/0033796 | A1 | 10/2001 | Unger et al. |
| 2001/0041357 | A1 | 11/2001 | Fouillet et al. |
| 2001/0054778 | A1 | 12/2001 | Unger et al. |
| 2002/0029814 | A1 | 3/2002 | Unger et al. |
| 2002/0037499 | A1 | 3/2002 | Quake et al. |
| 2002/0064885 | A1 | 5/2002 | Bedingham et al. |
| 2002/0144738 | A1 | 10/2002 | Unger et al. |
| 2002/0191048 | A1 | 12/2002 | Mutz et al. |
| 2002/0195050 | A1 | 12/2002 | David |
| 2003/0019833 | A1 | 1/2003 | Unger et al. |
| 2003/0027225 | A1 | 2/2003 | Wada et al. |
| 2003/0061687 | A1 | 4/2003 | Hansen et al. |
| 2003/0096310 | A1 | 5/2003 | Hansen et al. |

(56) References Cited

U.S. PATENT DOCUMENTS

| | | | |
|---|---|---|---|
| 2003/0143120 | A1 | 7/2003 | Ruediger et al. |
| 2003/0175947 | A1 | 9/2003 | Liu et al. |
| 2004/0115731 | A1 | 6/2004 | Hansen et al. |
| 2004/0141887 | A1 | 7/2004 | Mainquist et al. |
| 2004/0203055 | A1 | 10/2004 | Kennedy et al. |
| 2005/0019794 | A1 | 1/2005 | Nassef et al. |
| 2005/0062196 | A1 | 3/2005 | Hansen et al. |
| 2005/0112882 | A1 | 5/2005 | Unger et al. |
| 2005/0166980 | A1 | 8/2005 | Unger et al. |
| 2005/0201901 | A1 | 9/2005 | Grossman et al. |
| 2005/0205005 | A1 | 9/2005 | Hansen et al. |
| 2005/0214173 | A1 | 9/2005 | Facer et al. |
| 2005/0221373 | A1 | 10/2005 | Enzelberger et al. |
| 2005/0226742 | A1 | 10/2005 | Unger et al. |
| 2005/0229839 | A1 | 10/2005 | Quake et al. |
| 2005/0282175 | A1 | 12/2005 | Taylor et al. |
| 2006/0163070 | A1 | 7/2006 | Boronkay et al. |

FOREIGN PATENT DOCUMENTS

| | | |
|---|---|---|
| EP | 703 364 A1 | 3/1996 |
| EP | 706 004 A2 | 4/1996 |
| EP | 779 436 A2 | 6/1997 |
| EP | 829 360 A2 | 3/1998 |
| EP | 845 603 A1 | 6/1998 |
| EP | 999 055 A2 | 5/2000 |
| GB | 2 155 152 A | 9/1985 |
| GB | 2 308 460 A | 6/1997 |
| WO | 98/07069 A1 | 2/1998 |
| WO | 99/00655 A | 1/1999 |
| WO | 99/04361 A1 | 1/1999 |
| WO | 99/17093 A1 | 4/1999 |
| WO | 99/52633 A | 10/1999 |
| WO | 00/00678 A1 | 1/2000 |
| WO | 00/43748 A | 7/2000 |
| WO | 00/60345 A1 | 10/2000 |
| WO | 01/09595 A2 | 2/2001 |
| WO | 01/09595 A3 | 11/2001 |

OTHER PUBLICATIONS

Benard et al., "A Titanium-Nickel Shape-Memory Alloy Actuated Micropump," Proceedings of Transducers '97, 1997 International Conference on Solid-State Sensors and Actuators, held in Chicago, Il., Jun. 16-19, 1997, 1:361-364 (1997).
Brechtel et al., "Control of the electroosmotic flow by metal-salt-containing buffers," J Chromatography A, 716:97-105 (1995).
Bryzek et al., "Micromachines on the march," 8045 IEEE Spectrum, 31(5):20-31 (1994). XP 00045626.
Buchaillot et al., "Silicon Nitride Thin Films Young's Modulus Determination by an Optical Non-Destructive Method," Jpn. J. Appl. Phys., 36 Pt. 2(6B):L794-L797 (1997).
Chiu et al., "Patterned deposition of cells and proteins onto surfaces by using three-dimensional microfluidic systems", PNAS, 97(6):2408-2413 (2000).
Chou et al., "A microfabricated device for sizing and sorting DNA molecules," PNAS, 96:11-13 (1999).
Delamarche et al., "Patterned Delivery of Immunoglobulins to Surfaces Using Microfluidic Networks," Science, 276:779-781 (1997).
Duffy et al., "Rapid Prototyping of Microfluidic Systems in Poly(dimethylsiloxane)", Analytical Chemistry, 70(23):4974-4984 (1998).
Duffy et al., "Rapid prototyping of microfluidic switches in poly(dimethyl siloxane) and their actuation by electro-osmotic flow," J. Micromech. Microeng., 9:211-217 (1999).
Duffy et al., "Patterning Electroluminescence Materials with Feature Sizes as Small as 5 .mu.m Using Elastomeric Membranes as Masks for Dry Lift-Off," Adv. Mater., 11(7):546-552 (1999). XP-000849014.
Effenhauser et al., "Integrated Capillary Electrophoresis on Flexible Silicone Microdevices: Analysis of DNA Restriction Fragments and Detection of Single DNA Molecules on Microchips," Anal. Chem., 69(17):3451-3457 (1997).

Effenhauser et al., "Integrated chip-based capillary electrophoresis," Electrophoresis, 18:2203-2213 (1997).
Fahrenberg et al., "A microvalve system fabricated by thermoplastic molding," J. Micromech. Microeng., 5:169-171 (1995).
Fu et al., "A microfabricated fluorescence-activated cell sorter," Nature Biotechnology, 17:1109-1111 (1999).
Gass et al., "Integrated flow-regulated silicon micropump," Sensors and Actuators A, 43335-338 (1994).
Gerlach, T., "Pumping Gases by a Silicon Micro Pump with Dynamic Passive Valves," Proceedings of Transducers '97, 1997 International Conference on Solid-State Sensors and Actuators, held in Chicago, Il., Jun. 16-19, 1:357-360 (1997).
Goll et al., "Microvalves with bistable buckled polymer diaphragms," J. Micromech. Microeng., 6:77-79 (1996).
Graveson et al., "Microfluidics—a review", J. Micromech. Microeng. 3:168-182 (1993).
Harrison et al., "Micromachining a Miniaturized Capillary Electrophoresis-Based Chemical Analysis System on a Chip," Science, 261:895-897 (1993).
Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15-17, Optical Society of America, pp. 107-110 (1988).
Hosokawa et al., "Handling of Picoliter Liquid Samples in a Poly(dimethylsiloxane)-Based Microfluidic Device," Anal. Chem., 71(20):4781-4785 (1999).
Ikuta et al., "Three dimensional micro integrated fluid systems (MIFS) fabricated by stereo lithography," IEEE Kyushu Institute of Technology, pp. 1-6 (1994).
Jacobson et al., "High-speed separations on a microchip," Anal. Chem., 66(7):1114-1118 (1994).
Jacobson et al., "Microfluidic Devices for Electrokinetically Driven Parallel and Serial Mixing," Anal. Chem., 71(20):4455-4459 (1999).
Jerman, H., "Electrically-Activated, Normally-Closed Diaphragm Valves," Proceedings of Transducers '91, 1991 International Conference on Solid-State Sensors and Actuators, pp. 1045-1048 (1991).
Jung et al., "Chemical and Physical Interactions at Metal/Self-Assembled Organic Monolayer Interfaces," Critical Reviews in Solid State and Material Sciences, 19(1):2-10 (1994).
Kenis et al., "Microfabrication Inside Capillaries Using Multiphase Laminar Flow Patterning," Science, 285:83-85 (1999).
Kopp et al., "Chemical Amplification: Continuous-Flow PCR on a Chip", Science, 280:1046-1048 (1998).
Kuhn et al., "Silicon Charge Electrode Array for Ink Jet Printing", IEEE Transactions on Electron Devices, ED-25(10):1257-1260 (1978).
Lin et al., "Free-Space Micromachined Optical Switches for Optical Networking," IEEE J. Selected Topics in Quantum Electronics, 5(1):4-9 (1999).
Lotters et al., "The mechanical properties of the rubber elastic polymer polydimethylsiloxane for sensor applications," J. Micromech. Microeng., 7:145-147 (1997).
Lucy et al., "Characterization of the Cationic Surfactant Induced Reversal of Electroosmotic Flow in Capillary Electrophoresis," Anal. Chem., 68:300-305 (1996).
Maluf, N., An Introduction to Microelectromechanical Systems Engineering, Artech House Publishers, Boston London pp. 42-45 (2004).
Markx et al. "Applications of dielectrophoresis in biotechnology," Tibtech, 15:426-432 (1997).
Muller et al., "Surface-Micromachined Microoptical Elements and Systems," Proceedings of IEEE, 86(8):1705-1720 (1998).
Olsson et al., "Simulation Studies of Diffuser and Nozzle Elements for Valve-less Micropumps," Proceedings of Transducers '97, 1997 International Conference on Solid-State Sensors and Actuators, held in Chicago, Il., Jun. 16-19, 1997, 2:1039-1042 (1997).
Qin et al., "Elastomeric Light Valves**", Adv. Mater., 9(5):407-410. XP-000683891 (1997).
Qin et al., "Photolithography with transparent reflective photomasks," J. Vac.Sci. Technology, 16(1):98-103 (1998).
Rapp. R., "LIGA micropump for gases and liquids," Sensors and Actuators A, 40:57-61 (1994).

(56) References Cited

OTHER PUBLICATIONS

Roylance et al., "A Batch-Fabricated Silicon Accelerometer", IEEE Transactions on Electron Devices, ED-26(12):1911-1917 (1979).
Schasfoort et al., "Field-Effect Flow Control for Microfabricated Fluidic Networks," Science, 286:942-945 (1999).
Schueller et al., "Fabrication of glassy carbon microstructures by soft lithography," Sensors and Actuators, 72(2):125-139 (1999).
Shoji, S., "Fluids for Sensor Systems", Topics in Current Chemistry, 194:162-188 Springer Verlag Berlin Heidelberg (1998).
Shoji et al., "Smallest Dead Volume Microvalves for Integrated Chemical Analyzing Systems," Proceedings of Transducers '91, 1991 International Conference on Solid-State Sensors and Actuators, pp. 1052-1055 (1991).
Smits, J.G., "Piezoelectric Micropump with Three Valves Working Peristaltically", Sensors and Actuators, A21-A23:203-206 (1990).
Sohn et al., "Capacitance cytometry: Measuring biological cells one by one," PNAS, 97(20):10687-10690 (2000).
Tufte et al., "Silicon Diffused-Element Piezoresistive Diaphragms," J. Appl. Phys., 33(11):3322-3327 (1962).
Van der Pol et al., "Micro Liquid Handling Devices—A Review", Micro Systems Technologies, 90:799-805 (1990).
Vieider et al., "A Pneumatically Actuated Micro Valve with a Silicone Rubber Membrane for Integration with Fluid-Handling Systems," Proceedings of Transducers '95, the 8th International Conference on Solid-State Sensors and Actuators and Eurosensors IX, held in Stockholm, Sweden on Jun. 25-29, 1995, 2:284-286 (1995).
Washizu et al., "Molecular Dielectrophoresis of Biopolymers," IEEE Transactions on Industry Applications, 30(4):835-843 (1994).
Xia et al., "Complex Optical Surfaces Formed by Replica Molding Against Elastomeric Masters," Science, 273:347-349 (1996).
Xia et al., "Soft Lithography," Angew. Chem. Int. Ed. 37:551-575 (1998).
Xia et al., "Micromolding of Polymers in Capillaries: Applications in Microfabrication," Chemistry of Materials, 8(7):1558-1567 (1996).
Xia et al., "Micromolding in Capillaries: Applications in Material Science," J. American Chemical Society, 118:5722-5731 (1996).
Yang et al., "A Mems Thermopneumatic Silicone Membrane Valve", Proceedings of IEEE 10.sup.th Annual International Workshop on MicroElectro Mechanical Systems, Sensors and Actuators, A64(1):101-108 (1998).
Yang et al., "A MEMS Thermopneumatic silicone Membrane Valve," Proceedings of the IEEE 10th Annual Workshop of Micro Electro Mechanical Systems Workshop (MEMS '97), held Jan. 26-30, 1997 in Nagoya, Japan, pp. 114-118 (1997).
Yazdi et al., "Micromachined Inertial Sensors," Proceedings of IEEE, 86(8):1640-1659 (1998).
Young et al., "Contoured elastic-membrane microvalves for microfluidic network integration," J. Biomechanical Engineering, 121:2-6 (1999).
Zengerle et al., "A Micro Membrane Pump with Electrostatic Actuation," 1992 IEEE Conf. on Micro Electro Mechanical Systems, held Feb. 4-7, 1992 in Travemunde Germany, pp. 19-24.
Zengerle et al., "Performance Simulation of Microminiaturized Membrane Pumps," from 7th International Conference on Solid-State Sensors and Actuators held Jun. 7-10, 1993 in Yokohama Japan, pp. 106-109.
XP-002149046, Ullmann's Encyclopedia of Industrial Chemistry, Sixth Edition, 1999 Electronic Release, 6 pages.
Van de Pol et al., "A Thermo-Pneumatic Actuation Principle for a Microminature Pump and Other Micromechanical Devices," Sensors and Actuators, 17:139-143 (1989).
Quake et al., "From Micro- to Nanofabrication with Soft Materials," Science, 290:1536-1540 (2000).
Unger et al., "Monolithic Microfabricated Valves and Pumps by Multilayer Soft Lithography," Science, 288:113-116 (2000).
Luft et al., Microbatch Macromolecular Crystallization in Micropipettes, Journal of Crystal Growth, 196 (1999), pp. 450-455.
Sanjoh et al., Spatiotemporal Protein Crystal Growth Studies using Microfluidic Silicon Devices, Journal of Crystal Growth, 196 (1999), pp. 691-702.
Andersson et al., Consecutive Microcontact Printing—Ligands for Asymmetric Catalysis in Silicon Channel, Sensors and Actuators, B, 3997, pp. 1-7 (2001).
Chayen, The Role of Oil in Macromolecular Crystallization, Structure, vol. 5, No. 10, pp. 1269-1274 (1997).
Ducruix et al., Methods of Crystallization in Crystallization of Nucleic Acids and Proteins—A Practical Approach, IRL Press, Oxford. pp. 73-98 (1992).
McPherson, Crystallization of Macromolecules: General Principles, Methods Enzymol., pp. 114, 112 (1985).
McPherson et al., Crystallization of Proteins by Variations of pH of Temperature, Methods Enzymol., 114: pp. 125-127 (1985).
McPherson et al., Use of Polyethylene Glycol in the Crystallization of Macromolecules, Methods Enzymol., 114: pp. 120-125 (1985).
Phillips, Crystallization in Capillary Tubes, Methods Enzymol. 114: pp. 128-131 (1985).
Wu et al., MEMS Flow Sensors for Nano-Fluidic Applications, Sensors and Actuators A 89, pp. 152-158 (2001).
Carter et al., Protein Crystallization Using Incomplete Factorial Experiments, the Journal of Biological Chemistry, pp. 12219-12223, vol. 254, No. 23 (1979).
Carter et al., Statistical Design of Experiments for Protein Crystal Growth and the Use of a Precrystallization Assay, Journal of Crystal Growth 90, pp. 60-73 (1998).
López-Jaramillo, F. J. et al., "Crystallization and Cryocrystallography Inside X-ray Capillaries," Journal of Applied Crystallography, vol. 34, pp. 365-370 (2001).
Kamholz et al., Quantitative Analysis of Molecular Interaction in a Microfluidic Channel: The T-Sensor, Analytical Chemistry, vol. 71, No. 23, Dec. 1, pp. 5340-5347 (1999).
Lin et al., Convective-diffusive transport in protein crystal growth, Journal of Crystal Growth, 151, pp. 153-162 (1995).
Luft et al., Kinetic Aspects of Macromolecular Crystallization, Methods in Enzymology, pp. 110-130, vol. 276 (1997).
Miller et al., A Comparison between Protein Crystals Grown with Vapor Diffusion Methods in Microgravity and Protein Crystals using a Gel Liquid-liquid diffusion Ground-Based Method, Journal of Crystal Growth 132, pp. 306-309 (1992).
Nerad et al., Ground-Based Experiments on the Minimization of Convention During the Growth of Crystals From Solution, Journal of Crystal Growth, pp. 591-608, vol. 75 (1986).
Ruiz et al., Agarose as Crystallization Media for Proteins I: Transport Processes, Journal of Crystal Growth, pp. 165-172, vol. 232 (2001).
Ruiz et al., Investigations on Protein Crystal Growth by the Gel Acupuncture Method, Acta Crystallographica, pp. 484-490, Section D (1994).
Salemme, A Free Interface Diffusion Technique for the Crystallization of Proteins for X-Ray Crystallography, Archives of Biochemistry and Biophysics, pp. 533-539, vol. 151 (1972).
Thomas et al., Distribution coefficients of Protein Impurities in Ferritin and Lysozyme Crystals Self-Purification in Microgravity, Journal of Crystal Growth 211, pp. 149-156 (2000).
Ward et al., Automatic Preparation of Protein Crystals Using Laboratory Robotics and Automated Visual Inspection, Journal of Crystal Growth 90, pp. 325-339 (1988).
"Biochips," Nature Biotechnology, vol. 19, Supplement 2000, pp. IT43-IT44, (2000).
"Chapter 9: Microfluidic Devices," Micromachined Transducers Sourcebook, pp. 779-882, (1998).
"Electro Microfluidic Dual In-Line Package (EMDIP)," Sandia National Laboratories, 2 pages, SAND2001-3412P, Nov. 2001.
"Last Chance for Micromachines," The Economist Technology Quarterly, 8 pages, Dec. 7, 2000.
Abola, Enrique et al., "Automation of X-Ray Crystallography," Nature Structural Biology, Structural Genomics Supplement, pp. 973-977, Nov. 2000.
Andersen, Gregers Rom et al., "A Spreadsheet Approach to Automated Protein Crystallization," Journal of Applied Crystallography, vol. 29, pp. 236-240, 1996.
Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

(56) References Cited

OTHER PUBLICATIONS

Angell, James B. et al., "Silicon Micromechanical Devices," Scientific American, pp. cover, 44-55, Apr. 1983.
Armani, Deniz et al., "Re-Configurable Fluid Circuits by PDMS Elastomer Micromachining," IEEE Int. Conf. Micro Electro Mech. Syst. Tech. Digest, vol. 12, pp. 222-227, 1999.
Ballantyne, J. P. et al., "Selective Area Metallization by Electron-Beam Controlled Direct Metallic Deposition," J. Vac. Sci. Technol., vol. 10, No. 6, pp. 1094-1097, Nov. 1973.
Belgrader, Phillip et al., "Rapid Pathogen Detection Using a Microchip PCR Array Instrument," Clinical Chemistry, vol. 44, No. 10, pp. 2191-2194, 1998.
Berry, Michael B.,"Protein Crystallization: Theory and Practice," Excerpts from Doctoral Thesis, 36 pages, Sep. 17, 1995.
Black, Harvey, "Tiny Technology Promises Tremendous Profits," The Scientist, vol. 15, No. 21,4 pages, Oct. 29, 2001.
Bloomstein, T. M. et al., "Laser-Chemical Three-Dimensional Writing for Microelectromechanics and Application to Standard-Cell Microfluidics," J. Vac. Sci. Technol. B, vol. 10, No. 6, pp. 2671-2674, Nov. 1992.
Bousse, Luc et al., "Electrokinetically Controlled Microfluidic Analysis Systems," Annu. Rev. Biophys. Biomol. Struct., vol. 29, pp. 155-181, 2000.
Brush, Michael, "Automated Laboratories," The Scientist, vol. 13, No. 4, 10 pages, Feb. 15, 1999.
Burbaum, Jonathan J. et al., "New Technologies for High-Throughput Screening," Current Opinion in Chemical Biology, vol. 1, pp. 72-78, 1997.
Calkins, Kathryn,"Mycometrix: Rubber Chips," BioCentury, 2 pages, Oct. 16, 2000.
Chayen, Naomi E., "A Novel Technique to Control the Rate of Vapour Diffusion, Giving Larger Protein Crystals," Journal of Applied Crystallography, vol. 30, pp. 198-202, 1997.
Chayen, Naomi E. et al., "An Automated Systems for Micro-Batch Protein Crystallization and Screening," J. Appl. Cryst., vol. 23, pp. 297-302, 1990.
Chayen, Naomi E., "Comparative Studies of Protein Crystallization by Vapour-Diffusion and Microbatch Techniques," Acta Cryst., vol. D54, pp. 8-15, 1998.
Chayen, Naomi E. et al., "Microbatch Crystallization Under Oil—A New Technique Allowing Many Small-Volume Crystallization Trials," Journal of Crystal Growth, vol. 122, pp. 176-180, 1992.
Chayen, Naomi E. et al., "New Developments of the IMPAX Small-Volume Automated Crystallization System," Acta Cryst., vol. D50, pp. 456-458, 1994.
Chou, Hou-Pu et al., "A Microfabricated Rotary Pump," Biomedical Microdevices, vol. 3, No. 4, pp. 323-330, 2001.
Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head, South Carolina, 4 pages, 2000.
Chou, Hou-Pu et al., "Multiple Disease Diagnostics on a Single Chip," Biophysics Lab, Caltech, pp. 1-4, Mar. 1, 2000.
Cox, M. Jane et al., "Experiments With Automated Protein Crystallization," J. Appl. Cryst., vol. 20, pp. 366-373, 1987.
Eisele, Jean-Luc, "Preparation of Protein Crystallization Buffers With a Computer-Controlled Motorized Pipette—PIPEX," J. Appl. Cryst., vol. 26, pp. 92-96, 1993.
Eyal, Shulamit et al., "Velocity-Independent Microfluidic Flow Cytometry," Electrophoresis, vol. 23, pp. 2653-2657, 2002.
Fenna, R. E., "Crystallization of Human .alpha.-Lactalbumin," J. Mol. Biol., vol. 161, pp. 211-215, 1982.
Fettinger, J. C. et al., "Stacked Modules for Micro Flow Systems in Chemical Analysis: Concept and Studies Using an Enlarged Model," Sensors and Actuators B, vol. 17, pp. 19-25, 1993.
Fitzgerald, Deborah A., "Making Every Nanoliter Count," The Scientist, vol. 15, No. 21, 8 pages, Oct. 29, 2001.
Folch, A. et al., "Molding of Deep Polydimethylsiloxane Microstructures for Microfluidics and Biological Applications," Journal of Biomechanical Engineering, vol. 121, pp. 28-34, Feb. 1999.
Fox, Kristin M. et al., "Crystallization of Old Yellow Enzyme Illustrates an Effective Strategy for Increasing Protein Crystal Size," J. Mol. Biol., vol. 234, pp. 502-507, 1993.
Galambos, Paul et al., "Electrical and Fluidic Packaging of Surface Micromachined Electro-Microfluidic Devices," 8 pages, 2000.
Gao, Jun et al., "Integrated Microfluidic System Enabling Protein Digestion, Peptide Separation, and Protein Identification," Analytical Chemistry, vol. 73, No. 11, pp. 2648-2655, Jun. 1, 2001.
Greene, Chana, "Characterizing the Properties of PDMS," pp. 1-11, Summer 2000.
Guerin, L. J. et al., "Simple and Low Cost Fabrication of Embedded Micro-Channels by Using a New Thick Film Photoplastic," Transducers '97, 1997 International Conference on Solid-State Sensors and Actuators, Chicago, Illinois, pp. 1419-1422, Jun. 18-19, 1997.
Hicks, Jennifer, "Genetics and Drug Discovery Dominate Microarray Research," R&D Magazine, pp. 28-33, Feb. 1999.
Hofmann, Oliver et al., "Modular Approach to Fabrication of Three-Dimensional Microchannel Systems in PDMS—Application to Sheath Flow Microchips," Lab on a Chip, vol. 1, pp. 108-114, 2001.
Horn, Howard, "Lab Chips Sector: Microtechnologies Are Changing Healthcare and More," Life Sciences, pp. 19-21, Mar. 20, 2001.
Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.
Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.
Kagan, C. R., "Organic-Inorganic Hybrid Materials as Semiconducting Channels in Thin-Film Field-Effect Transistors," Science, vol. 286, pp. 945-947, Oct. 29, 1999.
Kapur, Ravi et al., "Fabrication and Selective Surface Modification of 3-Dimensionally Textured Biomedical Polymers From Etched Silicon Substrates," Journal of Biomedical Materials Research, vol. 33, pp. 205-216, 1996.
Khoo, Melvin et al., "A Novel Micromachined Magnetic Membrane Microfluid Pump," Engineering in Medicine and Biology Society, 2000, Proceedings of the 22$^{nd}$ Annual International Conference of the IEEE, pp. 1-4.
Kim, Enoch et al., "Polymer Microstructures Formed by Moulding in Capillaries," Nature, vol. 376, pp. 581-584, Aug. 17, 1995.
Kirk-Othmer, "Concise Encyclopedia of Chemical Technology," John Wiley & Sons, 5 pages, 1985.
Kuhn, Peter et al., "The Genesis of High-Throughput Structure-Based Drug Discovery Using Protein Crystallography," Current Opinion in Chemical Biology, vol. 6, pp. 704-710, 2002.
Kumar, Amit et al., "Features of Gold Having Micrometer to Centimeter Dimensions Can Be Formed Through a Combination of Stamping With an Elastomeric Stamp and an Alkanethiol 'Ink' Followed by Chemical Etching," Appl. Phys. Lett., vol. 63, No. 14, pp. 2002-2004, Oct. 4, 1993.
Kumar, Amit et al., "Patterning Self-Assembled Monolayers: Applications in Materials Science," Langmuir, vol. 10, pp. 1498-1511, 1994.
Kwong, Peter D. et al., "Probability Analysis of Variational Crystallization and Its Application to gp120, the Exterior Envelope Glycoprotein of Type 1 Human Immunodeficiency Virus (HIV-1)," Journal of Biological Chemistry, vol. 274, No. 7, pp. 4115-4123, Feb. 12, 1999.
Kwong, Peter D. et al., "Structure of an HIV gp 120 Envelope Glycoprotein in Complex With the CD4 Receptor and a Neutralizing Human Antibody," Nature, vol. 393, pp. 648-659, Jun. 18, 1998.
Lagally, Eric T. et al., "Fully Integrated PCR-Capillary Electrophoresis Microsystem for DNA Analysis," Lab on a Chip, vol. 1, pp. 102-107, 2001.
Lagally, Eric T. et al., "Monolithic Integrated Microfluidic DNA Amplification and Capillary Electrophoresis Analysis System," Sensore and Actuators B, vol. 63, pp. 138-146, 2000.

(56) References Cited

OTHER PUBLICATIONS

Lagally, E. T. et al., "Single-Molecule DNA Amplification and Analysis in an Integrated Microfluidic Device," Analytical Chemistry, vol. 73, No. 3, pp. 565-570, Feb. 1, 2001.
Lammerink, T. S. J. et al., "Modular Concept for Fluid Handling Systems," IEEE, pp. 389-394, 1996.
Li, Paul C. H. et at., "Transport, Manipulation, and Reaction of Biological Cells On-Chip Using Electrokinetic Effects," Analytical Chemistry, vol. 69, No. 8, pp. 1564-1568, Apr. 15, 1997.
Licklider, Larry et al., "A Micromachined Chip-Based Electrospray Source for Mass Spectrometry," Analytical Chemistry, vol. 72, No. 2, pp. 367-375, Jan. 15, 2000.
Liu, Jian et al., "A Nanoliter Rotary Device for Polymerase Chain Reaction," Electrophoresis, vol. 23, pp. 1531-1536, 2002.
Luft, Joseph R. et al., "A Method to Produce Microseed Stock for Use in the Crystallization of Biological Macromolecules," Acta Cryst., vol. D55, pp. 988-993, 1999.
Luft, Joseph R. et al., "Macromolecular Crystallization in a High Throughput Laboratory—The Search Phase," Journal of Crystal Growth, vol. 232, pp. 591-595, 2001.
Manz, A. et al., "Micromachining of Monocrystalline Silicon and Glass for Chemical Analysis Systems," Trends in Analytical Chemistry, vol. 10, No. 5, pp. 144-149, 1991.
Marshall, Sid, "Fundamental Changes Ahead for Lab Instrumentation," R&D Magazine, 5 pages, Feb. 1999.
Marsili, Ray, "Lab-On-A-Chip Poised to Revolutionize Sample Prep," R&D Magazine, 5 pages, Feb. 1999.
McDonald, J. Cooper et al., "Fabrication of Microfluidic Systems in Poly(dimethylsiloxane)," Electrophoresis, vol. 21, pp. 27-40, 2000.
Morris, Daniel W. et al., "Automation of Protein Crystallization Trials: Use of a Robot to Deliver Reagents to a Novel Multi-Chamber Vapor Diffusion Plate," BioTechniques, vol. 7, No. 5, pp. 522-527, 1989.
NG, Jessamine M. K. et al., "Components for Integrated Poly(Dimethylsiloxane) Microfluidic Systems," Electrophoresis, vol. 23, pp. 3461-3473, 2002.
Nollert, Peter et al., "Crystallization of Membrane Proteins in Cubo" Methods in Enzymology, vol. 343, pp. 183-199, 2002.
Oldfield, T. J. et al., "A Flexible Approach to Automated Protein Crystallization," J. Appl. Cryst., vol. 24, pp. 255-260, 1991.
Oleschuk, Richard D. et al., "Analytical Microdevices for Mass Spectrometry," Trends in Analytical Chemistry, vol. 19, No. 6., pp. 379-388, 2000.
Reshetnyak, I. I., "Characteristics of the Influence of Ultrasound on the Crystallization Kinetics in Small-Volume Solutions," Sov. Phys. Acoust., vol. 21, No. 1, pp. 61-63, Jul. 1975.
Rubin, Byron et al., "Minimal Intervention Robotic Protein Crystallization," Journal of Crystal Growth, vol. 110, pp. 156-163, 1991.
Rummel, Gabriele et al., "Lipidic Cubic Phases: New Matrices for the Three-Dimensional Crystallization of Membrane Proteins," Journal of Structural Biology, vol. 121, pp. 82-91, 1998.
Sadaoui, Nouredine et al., "TAOS: An Automatic System for Protein Crystallization," Journal of Applied Crystallography, vol. 27, pp. 622-626, 1994.
Santarsiero, B. D. et al., "An Approach to Rapid Protein Crystallization Using Nanodroplets," Journal of Applied Crystallography, vol. 35, pp. 278-281, 2002.
Snook, Christopher F. et al., "Use of a Crystallization Robot to Set Up Sitting-Drop Vapor-Diffusion Crystallization and in situ Crystallization Screens," Journal of Applied Crystallography, vol. 33, pp. 344-349, 2000.
Soriano, Thierry M. B. et al., "ASTEC: An Automated System for Sitting-Drop Protein Crystallization," Journal of Applied Crystallography, vol. 26, pp. 558-562, 1993.
Stevens, Raymond C., "High-Throughput Protein Crystallization," Current Opinion in Structural Biology, vol. 10, pp. 558-563, 2000.
Thompson, L. F. et al., "Introduction to Microlithography," 185th Meeting of the American Chemical Society, Seattle, WA, pp. 2 cover pages, 1-13, Mar. 20-25, 1983.
Thorsen, Todd et al., "Dynamic Pattern Formation in a Vesicle-Generating Microfluidic Devices," Physical Review Letters, vol. 86, No. 18, pp. 4163-4166, Apr. 30, 2001.
Todd, Paul et al., "Application of Osmotic Dewatering to the Controlled Crystallization of Biological Macromolecules and Organic Compounds," Journal of Crystal Growth, vol. 110, pp. 283-292, 1991.
Van Den Berg, A. et al., "Micro Total Analysis Systems," Proceedings of the .mu.TAS '94 Workshop, University of Twente, The Netherlands, 17 pages, Nov. 21-22, 1994.
Van Der Woerd, Mark et al., "Lab-On-A-Chip Based Protein Crystallization," National Aeronautics and Space Administration and Caliper, pp. 1-27, Oct. 25, 2001.
Verpoorte, Elisabeth M. J. et al., "Three-Dimensional Micro Flow Manifolds for Miniaturized Chemical Analysis Systems," J. Micromech. Microeng., vol. 7 pp. 246-256, 1994.
Vogelstein, Bert et al., "Digital PCT," Proc. Natl. Acad. Sci. USA, vol. 96, pp. 9236-9241, Aug. 1999.
Webster's II Dictionary, p. 421, 1984.
Weselak, Mark et al., "Robotics for Automated Crystal Formation and Analysis," Methods in Enzymology, pp. 1-13, 2002.
Whelen, A. Christian et al., "The Role of Nucleic Acid Amplification and Detection in the Clinical Microbiology Laboratory," Annu. Rev. Microbiol., vol. 50, pp. 349-373, 1996.
Whitesides, George M. et al., "Flexible Methods for Microfluidics," Physics Today, pp. 42-48, Jun. 2001.
Whitesides, George M. et al., "Soft Lithography in Biology and Biochemistry," Annu. Rev. Biomed. Eng., vol. 3, pp. 335-373, 2001.
Wiencek, J. M., "New Strategies for Protein Crystal Growth," Annu. Rev. Biomed. Eng., vol. 1, pp. 505-534, 1999.
Wilbur, James L. et al., "Lithographic Molding: A Convenient Route to Structures With Sub-Micrometer Dimensions," Adv. Mater., vol. 7, No. 7, pp. 649-652. 1995.
Xia, Younan et al., "Reduction in the Size of Features of Patterned SAMs Generated by Microcontact Printing With Mechanical Compression of the Stamp," Adv. Mater., vol. 7, No. 5, pp. 471-473, 1995.
Xu, Bing et al., "Making Negative Poisson's Ratio Microstructures by Soft Lithography," Adv. Mater., vol. 11, No. 14, pp. 1186-1189, 1999.
Yang, Xing et al., "A Low Power MEMS Silicone/Parytene Valve," Solid-State Sensor and Actuator Workshop, Hilton Head Island, South Carolina, 4 pages, Jun. 7-11, 1998.
Zampighi, G. et al., "Structural Organization of (Na+ + K+)-ATPase in Purified Membranes," Journal of Cell Biology, vol. 98, pp. 1851-1864, May 1984.
Zhao, Zhan, et al., "An Integrated Biochip Design and Fabrication," Proceedings of SPIE, vol. 4936, pp. 321-326, 2002.
"The Liver Chip," Technology Review, pp. 64-67, Mar. 2003.
Affholter, Joseph et al., "Engineering a Revolution," Chemistry in Britain, pp. 48-51, Apr. 1999.
Arnold, Frances H., "Design by Directed Evolution," Accounts of Chemical Research, vol. 31, No. 3, pp. 125-131, 1998.
Ashkin, A. et al., "Optical Trapping and Manipulation of Single Cells Using Infrared Laser Beams," Nature, vol. 330, No. 24, pp. 769-771, Dec. 31, 1987.
Ashkin, A. et al., "Optical Trapping and Manipulation of Viruses and Bacteria," Science, vol. 235, pp. 1517-1520, Mar. 20, 1987.
Buican, Tudor N. et al., "Automated Single-Cell Manipulation and Sorting by Light Trapping," Applied Optics, vol. 26, No. 24, pp. 5311-5316, Dec. 15, 1987.
Chang, Jun Keun et al., "Functional Integration of Serial Dilution and Capillary Electrophoresis on a PDMS Microchip," Biotechnology and Bioprocess Engineering, vol. 8, No. 4, pp. 233-239, 2003.
Chayen, Naomi E., "Protein Crystallization for Genomics: Throughput Versus Output," Journal of Structural and Functional Genomics, vol. 4, pp. 115-120, 2003.
Chen, Chihchen et al., "Gray-Scale Photolithography Using Microfluidic Photomasks," PNAS, vol. 100, No. 4, pp. 1499-1504, Feb. 18, 2003.
D'Arcy, Allan et al., "The Advantages of Using a Modified Microbatch Method for Rapid Screening of Protein Crystallization Conditions," Acta Crystallographica, vol. D59, pp. 1-3, 2003.

(56) References Cited

OTHER PUBLICATIONS

Darlington, J., Proc. Nat. Acad. Sci. USA, vol. 69, No. 5, pp. 1239-1243, May 1972.

De Lucas et al., Journal of Structural Biology, vol. 142, Issue 1, Apr. 2003, pp. 188-206.

Garno, Jayne C. et al., "Production of Periodic Arrays of Protein Nanostructures Using Particle Lithography," Langmuir, vol. 18, No. 21, pp. 8186-8192, 2002.

Grover, William H. et al., "Monolithic Membrane Valves and Diaphragm Pumps for Practical Large-Scale Integration Into Glass Microfluidic Devices," Sensors and Actuators B, vol. 89, pp. 315-323, 2003.

Hanes, Jozef, et al., "In Vitro Selection and Evolution of Functional Proteins by Using Ribosome Display," Proc. Natl. Acad. Sci. USA, vol. 94, pp. 4937-4942, May 1997.

Hansen, Carl et al., "Crystallography in Drug Discovery," Feb. 20, 2004, Chapter 11, pp. 238-245.

Hansen, Carl. L. et al., "A Robust and Scalable Microfluidic Metering Method That Allows Protein Crystal Growth by Free Interface Diffusion," PNAS, vol. 99, No. 26, pp. 16531-16536, Dec. 24, 2002.

Hansen, Carl. L. et al., "Systematic Investigation of Protein-Phase Behavior With a Microfluidic Formulator," PNAS Early Edition, 6 pages, 2004.

Hoffmuller, Ulrich et al., "In Vitro Evolution and Selection of Proteins: Ribosome Display for Larger Libraries," Angew. Chem. Int. Ed., vol. 37, No. 23, pp. 3241-3243, 1998.

Hong, Jong Wook et al., "A Nanoliter-Scale Nucleic Acid Processor With Parallel Architecture," Nature Biotechnology, vol. 22, No. 4, pp. 1-5, Apr. 2004.

Hosokawa, Kazuo et al., "A Microfluidic Device for Mixing of Capillary-Driven Liquids," IEEJ Trans. SM, vol. 123, No. 1, pp. 23-24, 2003.

Juárez-Martínez, G. et al., "High-Throughput Screens for Postgenomics: Studies of Protein Crystallization Using Microsystems Technology," Analytical Chemistry, vol. 74, No. 14, pp. 3505-3510, Jul. 15, 2002.

Kamentsky, Louis A. et al., "Spectrophotometer: New Instrument for Ultrarapid Cell Analysis," Science, vol. 150, pp. 630-631, Oct. 29, 1965.

McDonald, J. Cooper et al., "Poly(dimethylsiloxane) as a Material for Fabricating Microfluidic Devices," Accounts of Chemical Research, vol. 35, No. 7, pp. 491-499, 2002.

Phillips, W.C. and Rayment, I. "A systematic method for aligning double focusing mirrors." Methods in Enzymology, 1985, vol. 114 (Wyckoff, Hirs and Timasheff, eds.), 316-329, Academic Press.

Roberts, Richard W. et al., "RNA-Peptide Fusions for the In Vitro Selection of Peptides and Proteins," Proc. Natl. Acad. Sci. USA, vol. 94, pp. 12297-12302, Nov. 1997.

Sasserath, J. et al., "Rapid Prototyping and Development of Microfluidic and BioMEMS Devices," IVD Technology, 12 pages, Jun. 2002.

Sklar, Larry A. et al., Sample Handling for Kinetics and Molecular Assembly in Flow Cytometry, SPIE, vol. 3256, pp. 144-153, 1998.

Stevens, Raymond C., "The Cost and Value of Three-Dimensional Protein Structure," Drug Discovery World, pp. 35-48, Summer 2003.

Tawfik, Dan S. et al., "Man-Made Cell-Like Compartments for Molecular Evolution," Nature Biotechnology, vol. 16, pp. 652-656, Jul. 1998.

Thorsen, Todd et al., "Microfluidic Large-Scale Integration," Science, vol. 298, No. 5593, pp. 580-584, Oct. 18, 2002.

Tsutsumi et al., Applied Energy vol. 67, Issues 1-2, Sep. 2000, pp. 195-219.

Van Der Woerd, Mark et al., "The Promise of Macromolecular Crystallization in Microfluidic Chips," Journal of Structural Biology, vol. 142, pp. 180-187, 2003.

Velev, Orlin D., "On-Chip Manipulation of Free Droplets," Nature, vol. 426, pp. 515-516, Dec. 4, 2003.

Weber, Patricia C. et al., "Applications of Calorimetric Methods to Drug Discovery and the Study of Protein Interactions," Current Opinion in Structural Biology, vol. 13, pp. 115-121, 2003.

Wu, Hongkai et al., "Fabrication of Complex Three-Dimensional Microchannel Systems in PDMS," J. Am. Chem. Soc., vol. 125, No. 2, pp. 554-559, 2003.

Yeh, Joanne I., "A Manual Nanoscale Method for Protein Crystallization," Acta Crystallographica, vol. D59, pp. 1408-1413, 2003.

Zheng, Bo et al., "A Droplet-Based, Composite PDMS/Glass Capillary Microfluidic System for Evaluating Protein Crystallization Conditions by Microbatch and Vapor-Diffusion Methods With On-Chip X-Ray Diffraction," Angew. Chem., pp. 1-4, 2004.

\* cited by examiner

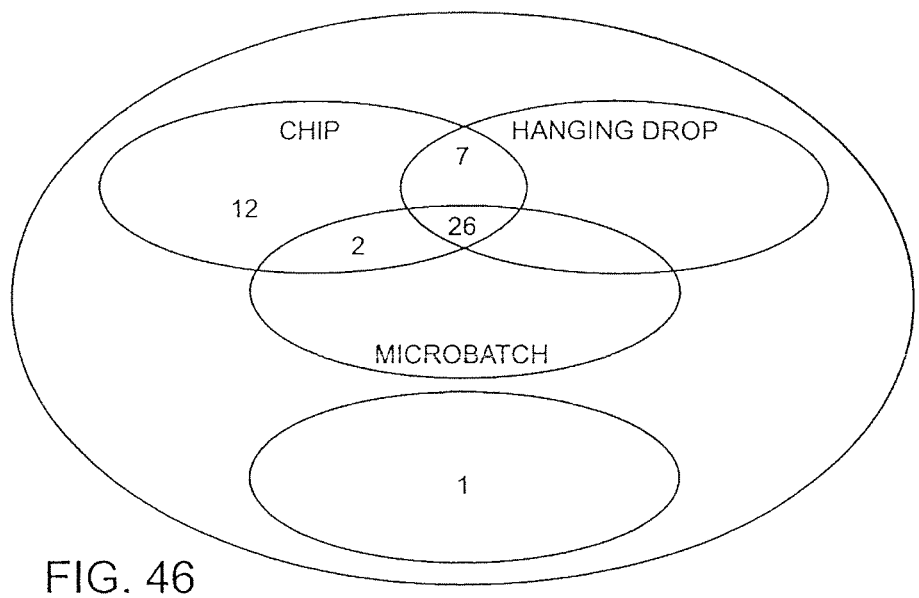
FIG. 46
FIG. 47A  FIG. 47B
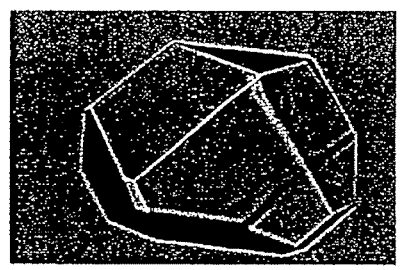 

FIG. 58A  FIG. 58B
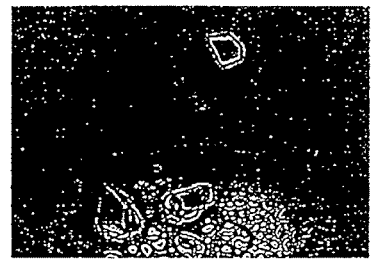
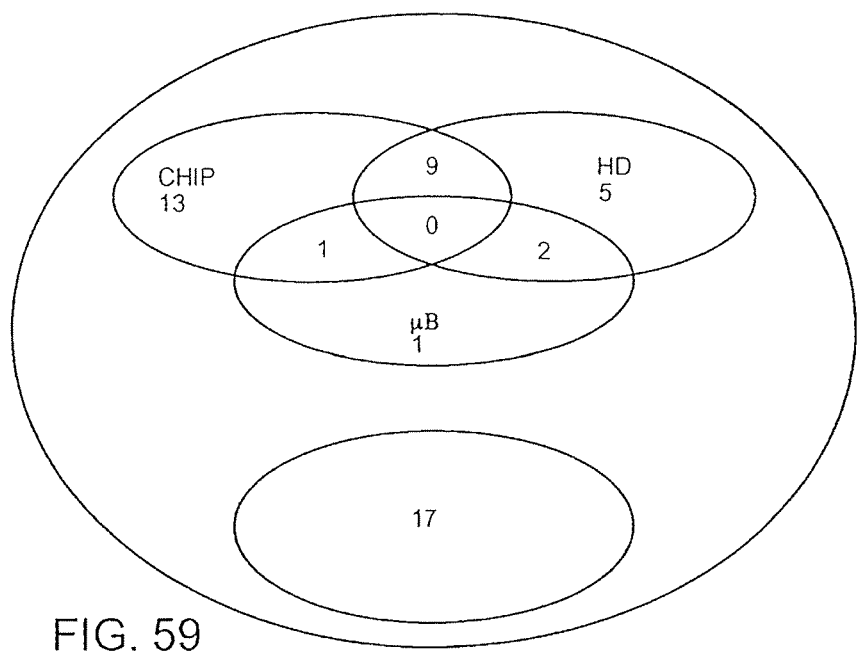
FIG. 59
FIG. 60A  FIG. 60B
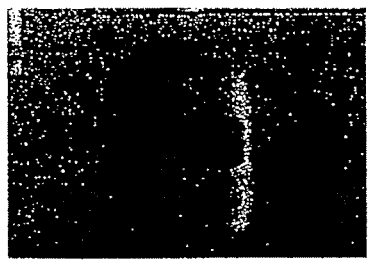
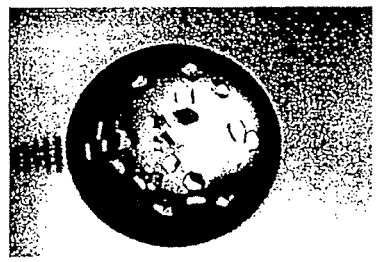

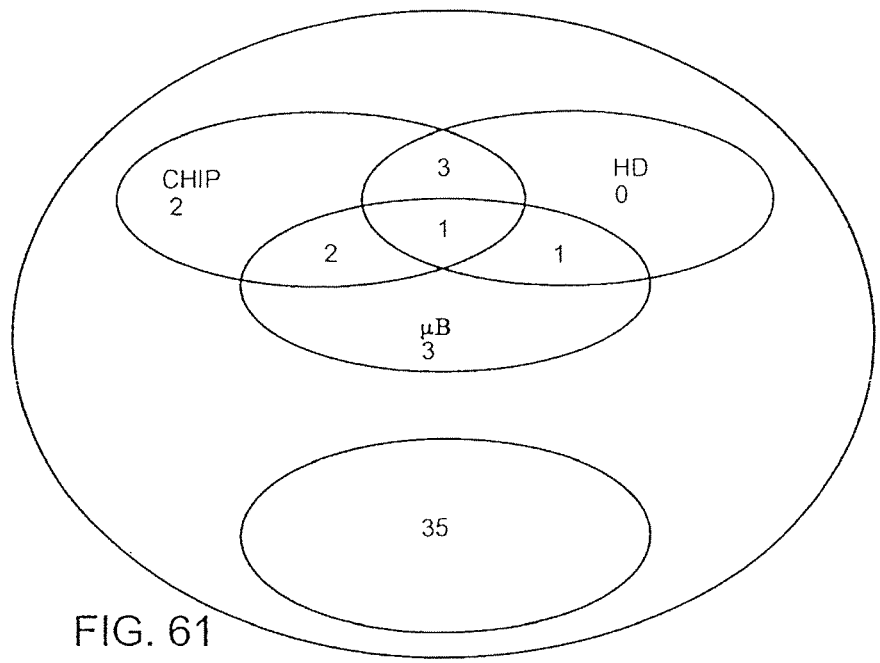
FIG. 61
FIG. 62A
FIG. 62B
FIG. 63A
FIG. 63B
50% Xylanase
1 M Na/K PO4; pH = 6.4
25% Xylanase
1 M Na/K PO4; pH = 6.4

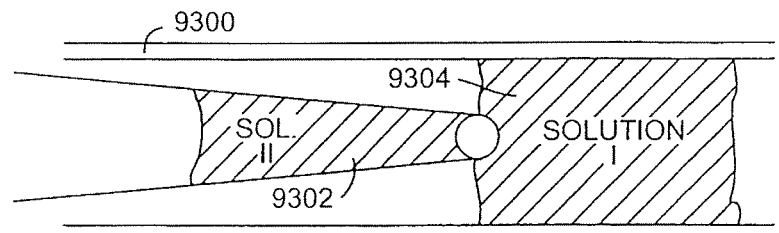
FIG. 72A
(Prior Art)
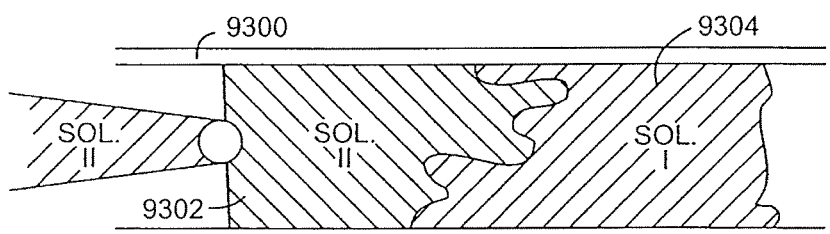
FIG. 72B
(Prior Art)
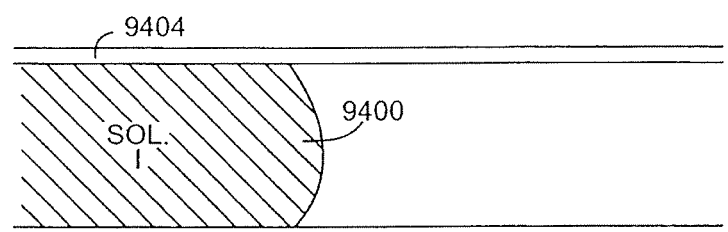
FIG. 73A
(Prior Art)
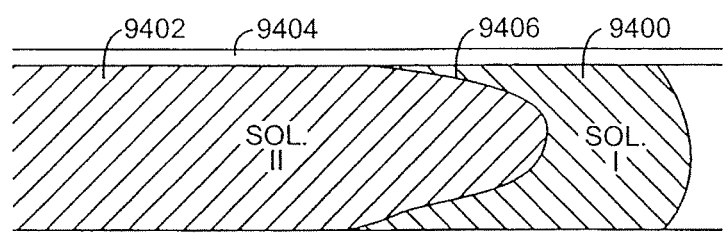
FIG. 73.B
(Prior Art)

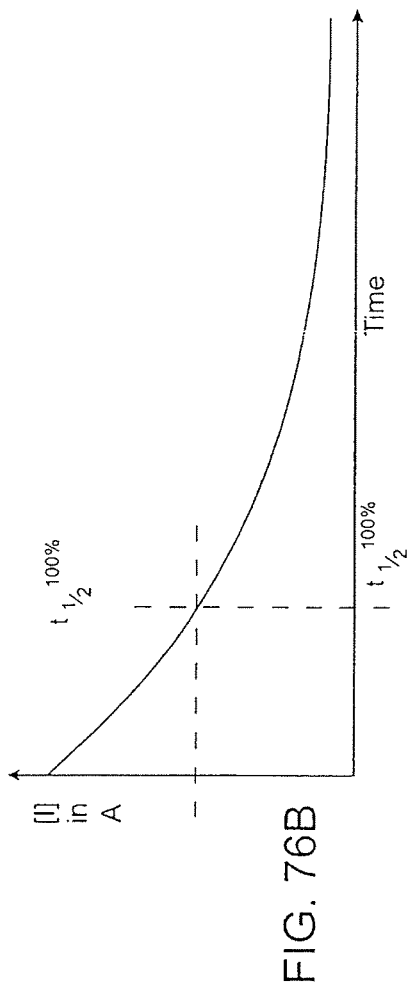
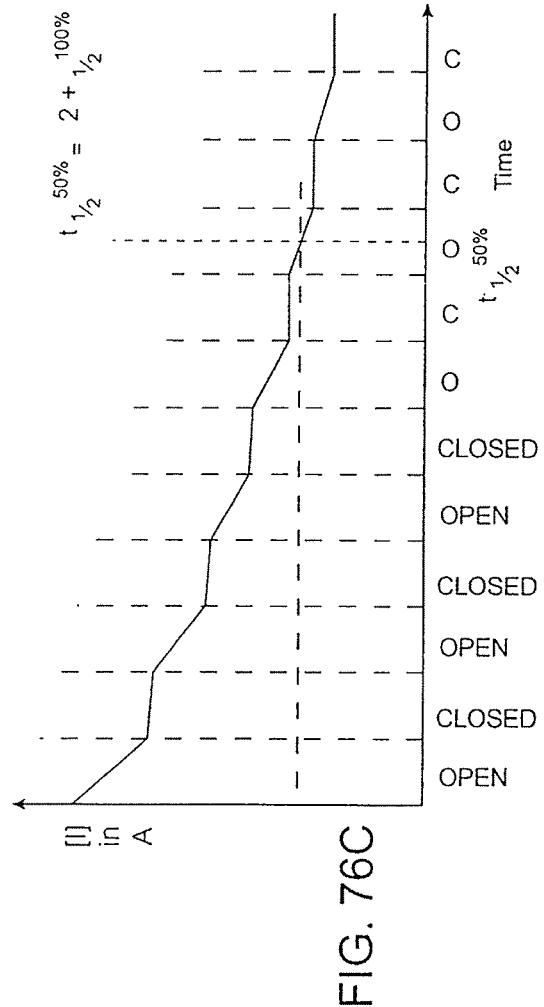
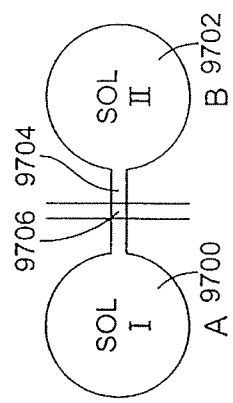
FIG. 76B
FIG. 76C
FIG. 76A

Fig. 77B the 2 and 4 should be regular case not subscript in the equation to the right side

HIGH THROUGHPUT SCREENING OF CRYSTALLIZATION OF MATERIALS

CROSS-REFERENCE TO RELATED APPLICATIONS

This application is a continuation of U.S. patent application Ser. No. 11/668,263, filed Jan. 29, 2007, (now U.S. Pat. No. 8,382,896), which is a divisional of U.S. patent application Ser. No. 10/117,978 filed Apr. 5, 2002, (now U.S. Pat. No. 7,195,670), which claims the benefit of U.S. Provisional Patent Application No. 60/323,524, filed Sep. 17, 2001, and which is a continuation-in-part of U.S. patent application Ser. No. 09/887,997 filed Jun. 22, 2001, (now U.S. Pat. No. 7,052,545), which is a continuation-in-part of U.S. patent application Ser. No. 09/826,583 filed Apr. 6, 2001, (now U.S. Pat. No. 6,899,137), which is a continuation-in-part of U.S. patent application Ser. No. 09/724,784 filed Nov. 28, 2000, (now U.S. Pat. No. 7,144,616) and U.S. patent application Ser. No. 09/605,520 filed Jun. 27, 2000, the entireties of which are incorporated by reference herein.

STATEMENT AS TO RIGHTS TO INVENTIONS MADE UNDER FEDERALLY SPONSORED RESEARCH AND DEVELOPMENT

This invention was made with government support under Grant No. HG01642-02 awarded by the National Institutes of Health. The government has certain rights in the invention.

BACKGROUND OF THE INVENTION

Crystallization is an important technique to the biological and chemical arts. Specifically, a high-quality crystal of a target compound can be analyzed by x-ray diffraction techniques to produce an accurate three-dimensional structure of the target. This three-dimensional structure information can then be utilized to predict functionality and behavior of the target.

In theory, the crystallization process is simple. A target compound in pure form is dissolved in solvent. The chemical environment of the dissolved target material is then altered such that the target is less soluble and reverts to the solid phase in crystalline form. This change in chemical environment typically accomplished by introducing a crystallizing agent that makes the target material is less soluble, although changes in temperature and pressure can also influence solubility of the target material.

In practice however, forming a high quality crystal is generally difficult and sometimes impossible, requiring much trial and error and patience on the part of the researcher. Specifically, the highly complex structure of even simple biological compounds means that they are not amenable to forming a highly ordered crystalline structure. Therefore, a researcher must be patient and methodical, experimenting with a large number of conditions for crystallization, altering parameters such as sample concentration, solvent type, countersolvent type, temperature, and duration in order to obtain a high quality crystal, if in fact a crystal can be obtained at all.

Accordingly, there is a need in the art for methods and structures for performing high throughput screening of crystallization of target materials.

SUMMARY OF THE INVENTION

The present invention sets forth method and structures for performing high throughput screening of crystallization of target materials. Methods and structures for purifying small samples by recrystallization are also provided.

High throughput screening of crystallization of a target material is accomplished by simultaneously introducing a solution of the target material at a known concentration into a plurality of chambers of a microfabricated fluidic device. The microfabricated fluidic device is then manipulated to vary the solvent concentration in each of the chambers, thereby simultaneously providing a large number of crystallization environments. Control over changed solvent conditions may result from a variety of techniques, including but not limited to metering of a crystallizing agent through exclusion of volume from the chamber, entrapment of precisely controlled volumes of crystallizing agent as determined by the dimensions of the microfluidic device, or cross-channel injection into an array of junctions defined by intersecting orthogonal flow channels.

An embodiment of a method of metering a volume of a crystallizing agent to promote crystallization in accordance with the present invention comprises providing a chamber having a volume in an elastomeric block separated from a control recess by an elastomeric membrane, and supplying a pressure to the control recess such that the membrane is deflected into the chamber and the volume is reduced by a calibrated amount, thereby excluding from the chamber a calibrated volume of a crystallization sample. This method may further comprise providing a second fluid to an opening of the chamber, and ceasing application of the pressure such that the membrane relaxes back to an original position and the calibrated volume of a crystallizing agent is drawn into the chamber. This method may also further comprise the parallelization of multiple chambers with varying calibrated volumes.

An embodiment of a system for crystallizing a target material in accordance with the present invention comprises an elastomeric block including a microfabricated chamber configured to contain a volume of a solution of the target material, and a microfabricated flow channel in fluid communication with the chamber, the flow channel introducing a volume of a crystallizing agent into the chamber. The crystallization system may further comprise an isolation structure configured to selectively isolate the chamber from the flow channel as the flow channel receives a volume of a crystallizing agent, and then to place the chamber into contact with the flow channel to alter a solution condition within the chamber. Alternatively, the crystallization system may further comprise a control channel overlying the chamber and separated from the chamber by a membrane, the membrane deflectable into the chamber to exclude a calibrated volume of sample solution from the chamber, such that relaxation of the membrane draws the calibrated volume of the crystallizing agent into the chamber. Further alternatively, the crystallization system may comprise a plurality of first parallel flow channels in fluid communication with a target material, and a plurality of second parallel flow channels orthogonal to and intersecting the first flow channels to create a plurality of junctions, the second flow channels in fluid communication with a crystallizing agent such that an array of solution environments can be created at the junctions.

Another embodiment of a system for crystallizing a target material in accordance with the present invention comprises an elastomeric block including a microfabricated chamber configured to contain a volume of a solution of the target material, and a crystallizing agent reservoir in fluid communication with the microfabricated chamber through a dialysis membrane, the dialysis membrane configured to prevent flow of the target material into the crystallizing agent reservoir.

The crystallizing agent reservoir may be formed in a second elastomeric block, the dialysis membrane may be present within the elastomeric block, and the dialysis membrane may comprise a polymer introduced between the chamber and the reservoir and then subjected to cross-linking.

An embodiment of a method for crystallizing a target material in accordance with the present invention comprises charging a chamber of a microfabricated elastomeric block with a volume of solution of the target material; and introducing a volume of a crystallizing agent into the chamber to change a solvent environment of the chamber. The volume of crystallizing agent may be introduced into the chamber by deforming an elastomer membrane overlying the chamber to exclude the volume of the sample from the chamber, followed by relaxing the membrane to cause the volume of a surrounding crystallizing agent to flow into the chamber. Alternatively, the volume of crystallizing agent may be introduced into the chamber by entrapping a volume of crystallizing agent proximate to the chamber, and then opening an elastomer valve positioned between the chamber and the crystallizing agent to allow diffusion of crystallizing agent into the chamber. Further alternatively, the volume of crystallizing agent may be introduced into the chamber by diffusion across a dialysis membrane.

Still further alternatively, the chamber may be defined by a junction between a first flow channel orthogonal to a second flow channel, and wherein the sample is flowed through the first flow channel and the crystallizing agent flowed through the second flow channel. An array of such chambers may be defined by a junction between a first set of parallel flow channels orthogonal to a second set of parallel flow channels, with samples flowed through the first flow channels and crystallizing agent flowed through the second flow channels to create an array of solution conditions.

An embodiment of a method for crystallizing a target material comprises introducing a crystallizing agent to a target material solution in the presence of a surface having a morphology calculated to serve as a template for formation of a crystal of the target material. In certain embodiments, this morphology may take the form of a regular morphology of a mineral surface, or features of a semiconductor substrate patterned by lithography.

An embodiment of a method for crystallizing a target material by vapor diffusion in accordance with the present invention comprises providing a target material solution within a microfabricated chamber, and providing a recrystallizing agent in fluid communication with the microfabricated chamber. An air pocket is provided between the chamber and the recrystallization agent, such that the crystallizing agent diffuses in the vapor phase across the air pocket into the target material solution. In certain embodiments, the air pocket may be secured in place through formation of a hydrophobic material utilizing microcontact printing techniques.

These and other embodiments of the present invention, as well as its advantages and features, are described in more detail in conjunction with the text below and attached figures.

BRIEF DESCRIPTION OF THE DRAWINGS

FIG. 46 shows a Venn diagram summarizing the results of one set of experiments for crystallization of glucose isomerase.

FIG. 47A shows a photograph of a salt crystal. FIG. 47B shows photograph of a crumbled protein crystal.

FIG. 58A shows a photograph of bovine pancreas trypsin crystals produced by microbatch. FIG. 58B shows bovine pancreas trypsin crystals formed on a chip in accordance with one embodiment of the present invention.

FIG. 59 is a Venn diagram summarizing experiments for crystallization of lysozyme.

FIG. 60A shows a photograph of a lysozyme crystal formed on a chip in accordance with one embodiment of the present invention. FIG. 60B shows a photograph of a lysozyme crystal formed utilizing a conventional microbatch method.

FIG. 61 is a Venn diagram summarizing experiments for crystallization of Xylanase.

FIG. 62A shows a photograph of a Xylanase crystal formed utilizing a conventional microbatch technique. FIG. 62B shows a photograph of a Xylanase crystal formed on a chip in accordance with an embodiment of the present invention.

FIGS. 63A-B show photographs of Xylanase crystals formed utilizing a chip in accordance with one embodiment of the present invention.

FIGS. 72A-B show simplified cross-sectional views of the attempted formation of a microscopic free interface in a capillary tube.

FIGS. 73A-B show mixing of solutions in a capillary tube as a result of the parabolic velocity distribution of pressure driven Poiseuille flow.

FIG. 76A shows a simplified plan view of two microfluidic chamber whose communication through a flow channel is controlled by a valve.

FIG. 76B plots concentration of the first solution in the first chamber versus time flowing actuation of the interface valve. FIG. 76C plots concentration of the first solution in the first chamber versus time following actuation of the interface valve at 50% the duty cycle of FIG. 76B.

DETAILED DESCRIPTION OF THE PRESENT INVENTION

I. Microfabrication Overview

The following discussion relates to formation of microfabricated fluidic devices utilizing elastomer materials, as described generally in U.S. patent application Ser. No. 09/826,585 filed Apr. 6, 2001, Ser. No. 09/724,784 filed Nov. 28, 2000, and Ser. No. 09/605,520, filed Jun. 27, 2000. These patent applications are hereby incorporated by reference.

1. Methods of Fabricating

Exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 1 to 7B illustrate sequential steps of a first preferred method of fabricating the present microstructure, (which may be used as a pump or valve). FIGS. 8 to 18 illustrate sequential steps of a second preferred method of fabricating the present microstructure, (which also may be used as a pump or valve).

As will be explained, the preferred method of FIGS. 1 to 7B involves using pre-cured elastomer layers which are assembled and bonded. In an alternative method, each layer of elastomer may be cured "in place". In the following description "channel" refers to a recess in the elastomeric structure which can contain a flow of fluid or gas.

Figure 1:
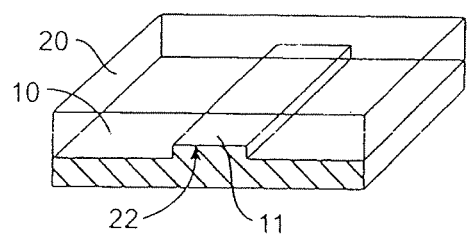
FIG. 1 is an illustration of a first elastomeric layer formed on top of a micromachined mold.

Referring to FIG. 1, a first micro-machined mold 10 is provided. Micro-machined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 21 corresponding in dimension to protrusion 11), as shown.

Figure 2:
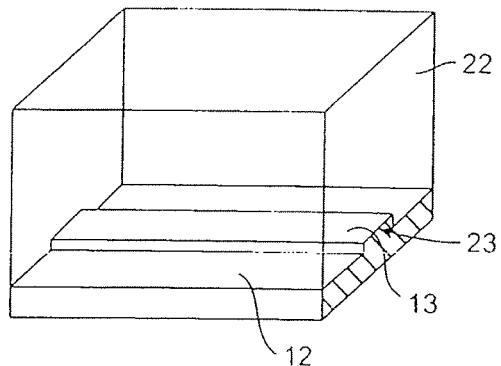
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 3:
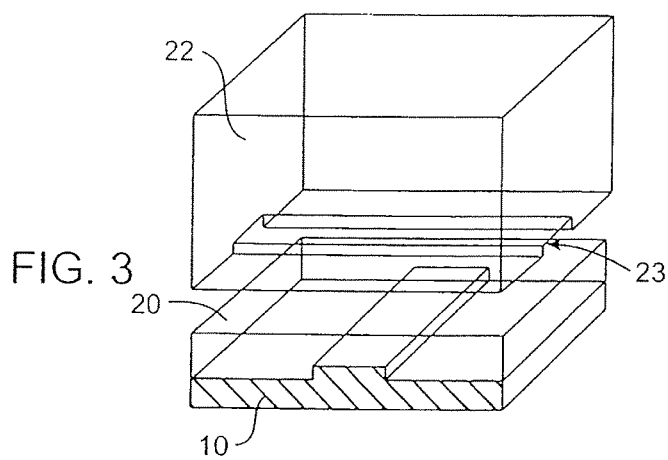
FIG. 3 is an illustration of the elastomeric layer of FIG. 2 removed from the micromachined mold and positioned over the top of the elastomeric layer of FIG. 1.
Figure 4:
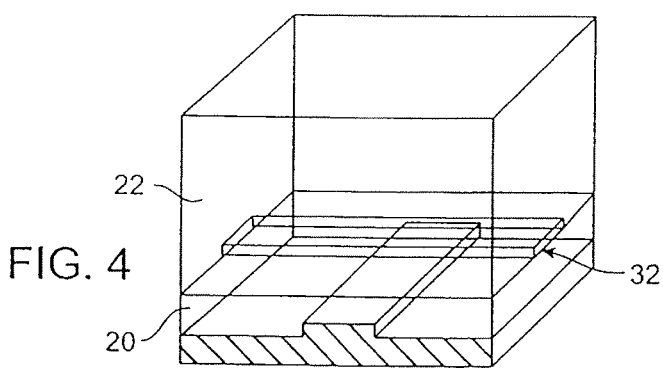
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 will form a flow channel 32.

Figure 5:
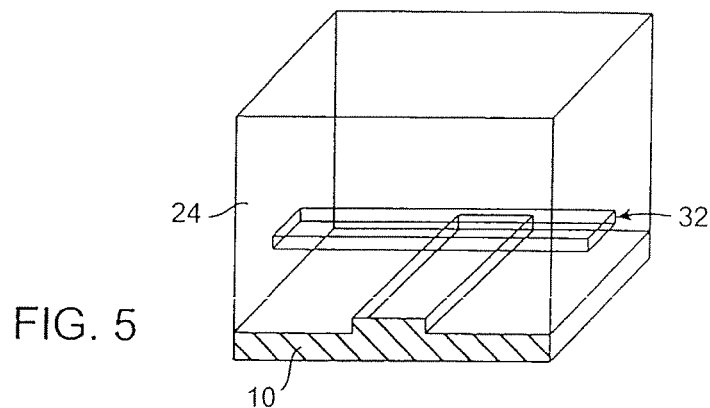
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
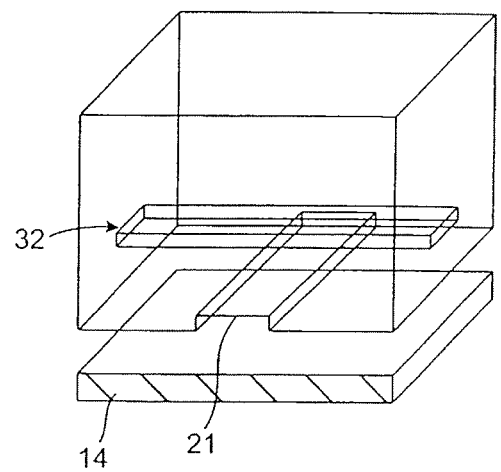
FIG. 6 is an illustration corresponding to FIG. 5, but showing the first micromachined mold removed and a planar substrate positioned in its place.
Figure 7A:
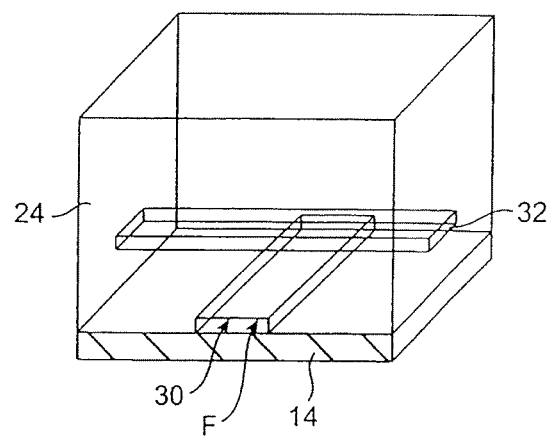
FIG. 7A is an illustration corresponding to FIG. 6, but showing the elastomeric structure sealed onto the planar substrate.
Figure 7B:
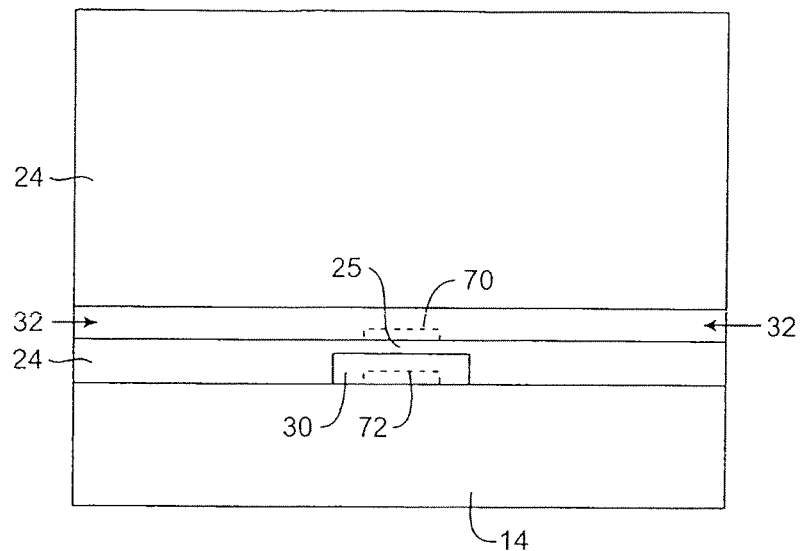
FIG. 7B is a front sectional view corresponding to FIG. 7A, showing an open flow channel.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 7A and 7B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 7C-7G.

Figure 7H:
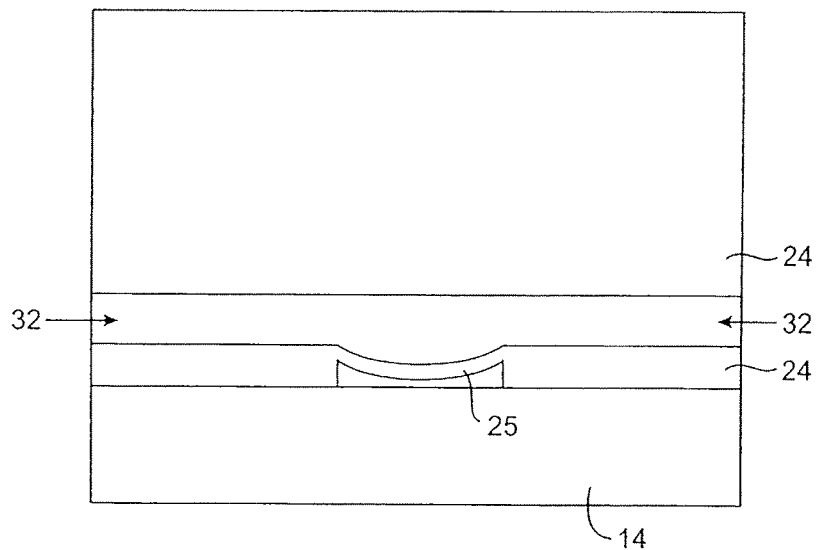
FIG. 7H is a front sectional view showing the valve of FIG. 7B in an actuated state.
Figure 7C:
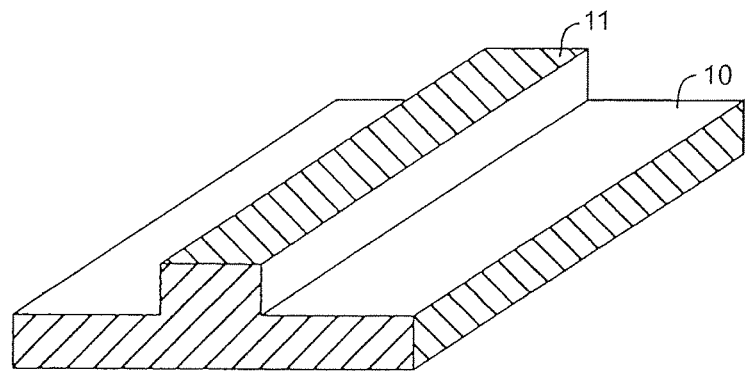
FIGS. 7C-7G are illustrations showing steps of a method for forming an elastomeric structure having a membrane formed from a separate elastomeric layer.
Figure 7D:
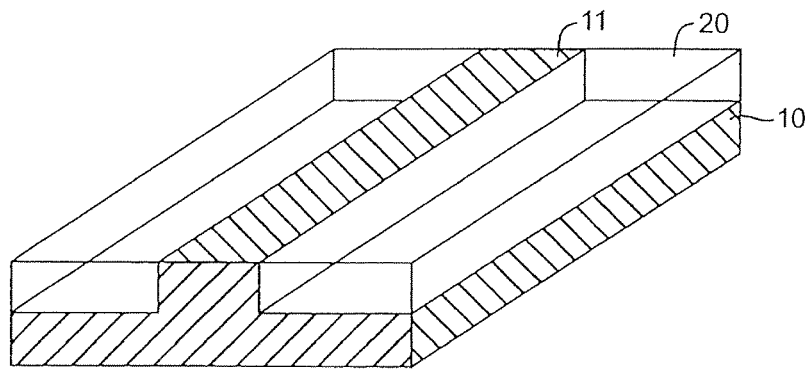

Referring to FIG. 7C, a first micro-machined mold 10 is provided. Micro-machined mold 10 has a raised line or protrusion 11 extending therealong. In FIG. 7D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 7E:
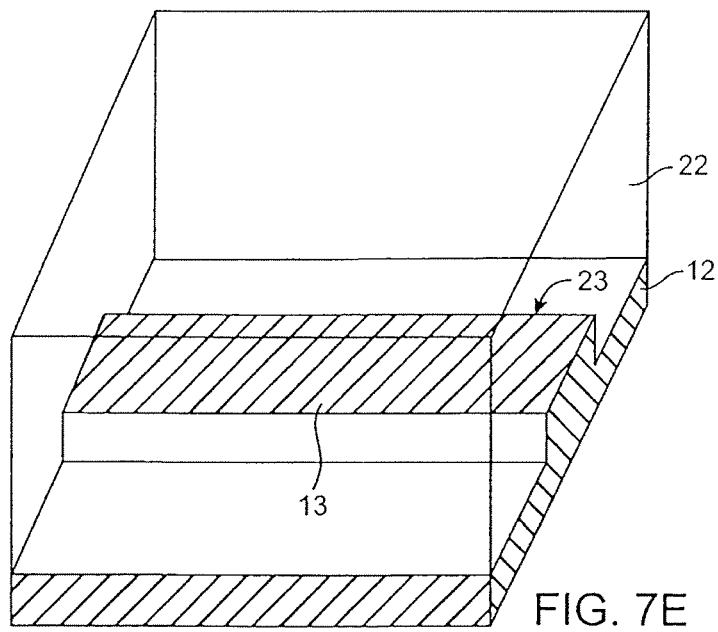

In FIG. 7E, second micro-machined mold 12 having a raised protrusion 13 extending therealong is also provided. Second elastomeric layer 22 is cast on top of second mold 12 as shown, such that recess 23 is formed in its bottom surface corresponding to the dimensions of protrusion 13.

Figure 7F:
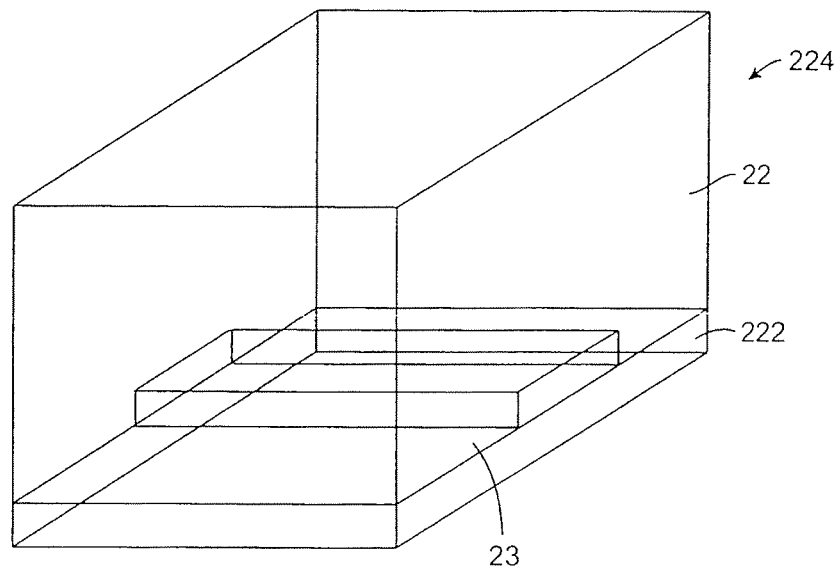

In FIG. 7F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 7G:
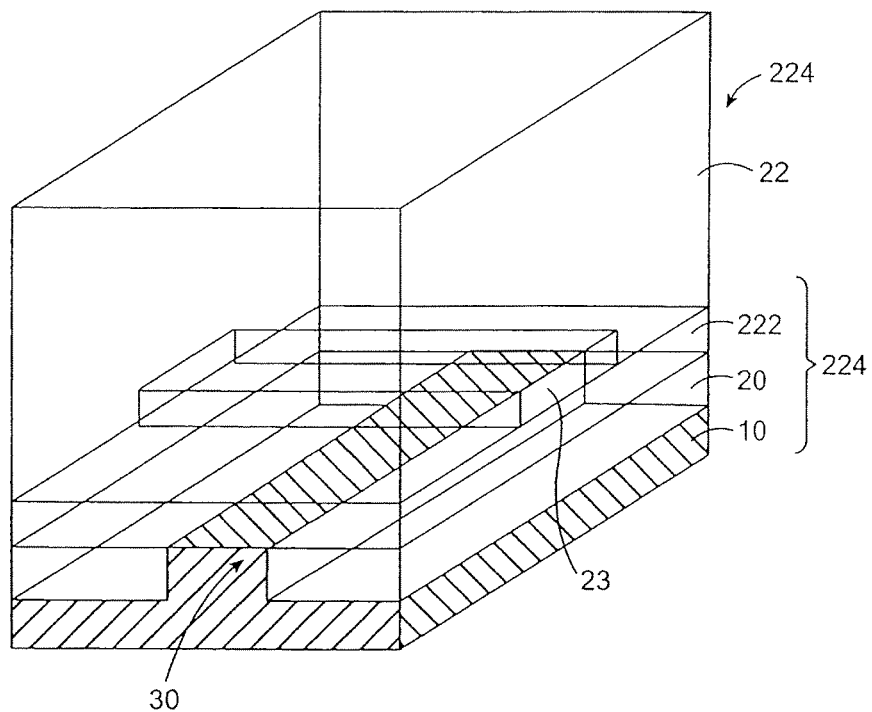

In FIG. 7G, elastomeric block 224 is placed on top of first micro-machined mold 10 and first elastomeric layer 20. Elastomeric block and first elastomeric layer 20 are then bonded together to form an integrated (i.e.: monolithic) elastomeric structure 24 having a membrane composed of a separate elastomeric layer 222.

When elastomeric structure 24 has been sealed at its bottom surface to a planar substrate in the manner described above in connection with FIG. 7A, the recess formerly occupied by raised line 11 will form flow channel 30.

The variant fabrication method illustrated above in conjunction with FIGS. 7C-7G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

An alternative method fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, gold metal may be etched selective to RTV 615 elastomer utilizing the appropriate chemical mixture.

2. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 μm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 μm, 1 μm, 2 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels 30, 32, 60, and 62 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, and 250 μm.

The flow channels are not limited to these specific dimension ranges and examples given above, and may vary in width in order to affect the magnitude of force required to deflect the membrane as discussed at length below in conjunction with FIG. 27. For example, extremely narrow flow channels having a width on the order of 0.01 μm may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

The Elastomeric layers may be cast thick for mechanical stability. In an exemplary embodiment, elastomeric layer 22 of FIG. 1 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 μm, 0.02 μm, 0.03 μm, 0.05 μm, 0.1 μm, 0.2 μm, 0.3 μm, 0.5 μm, 1 μm, 2 μm, 3 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, 250 μm, 300 μm, 400 μm, 500 μm, 750 μm, and 1000 μm.

3. Soft Lithographic Bonding

Preferably, elastomeric layers are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogenous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly(dimethylsiloxane)", *Analytical Chemistry* (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 1 to 7B, first elastomeric layer 20 may be created by spin-coating an RTV mixture on microfabricated mold 12 at 2000 rpm's for 30 seconds yielding a thickness of approximately 40 microns. Second elastomeric layer 22 may be created by spin-coating an RTV mixture on microfabricated mold 11. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

4. Suitable Elastomeric Materials

Allcock et al, Contemporary *Polymer Chemistry*, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, the elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, Polybutadiene, Polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene:

Pure Polyisobutylene has no double bonds, but is crosslinked to use as an elastomer by including a small amount (~1%) of isoprene in the polymerization. The isoprene monomers give pendant double bonds on the Polyisobutylene backbone, which may then be vulcanized as above.

Poly(Styrene-Butadiene-Styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes:

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

5. Operation of Device

FIGS. 7B and 7H together show the closing of a first flow channel by pressurizing a second flow channel, with FIG. 7B (a front sectional view cutting through flow channel 32 in corresponding FIG. 7A), showing an open first flow channel 30; with FIG. 7H showing first flow channel 30 closed by pressurization of the second flow channel 32.

Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7H, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired. (For illustration purposes only, channel 30 in FIG. 7G is shown in a "mostly closed" position, rather than a "fully closed" position).

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 μm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 nL, 1 fL to 10 nL, 100 fL to 1 nL, and 1 pL to 100 pL.

The extremely small volumes capable of being delivered by pumps and valves in accordance with the present invention represent a substantial advantage. Specifically, the smallest known volumes of fluid capable of being manually metered is around 0.1 μl. The smallest known volumes capable of being metered by automated systems is about ten-times larger (1 μl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$$w=(BPb^4)/(Eh^3), \text{ where:} \tag{1}$$

w=deflection of plate;
B=shape coefficient (dependent upon length vs. width and support of edges of plate);
P=applied pressure;
b=plate width
E=Young's modulus; and
h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticity's, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 8A:
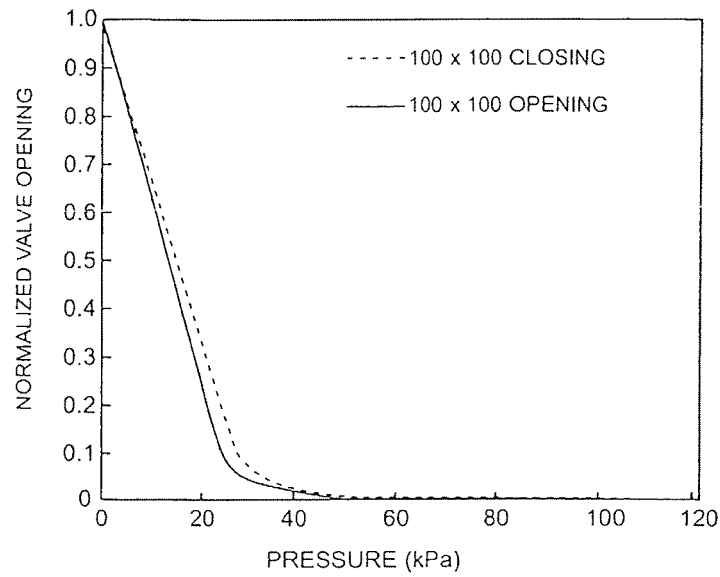
FIGS. 8A and 8B illustrates valve opening vs. applied pressure for various flow channels.
Figure 8B:
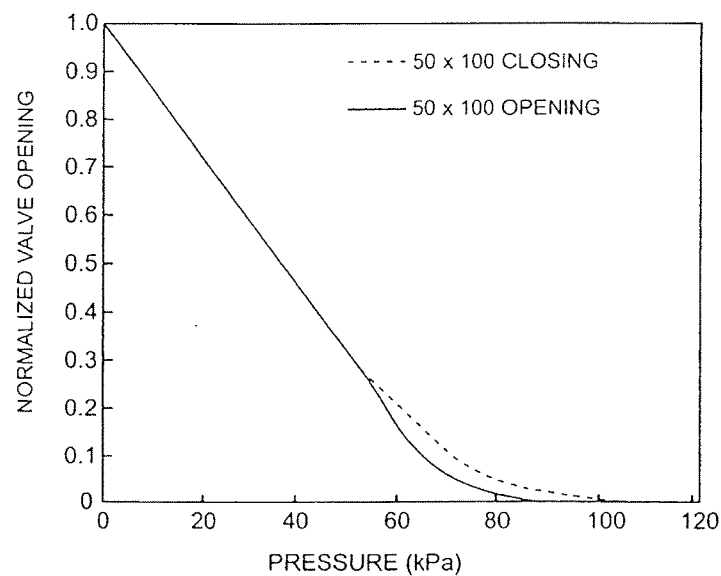
Figure 21A:
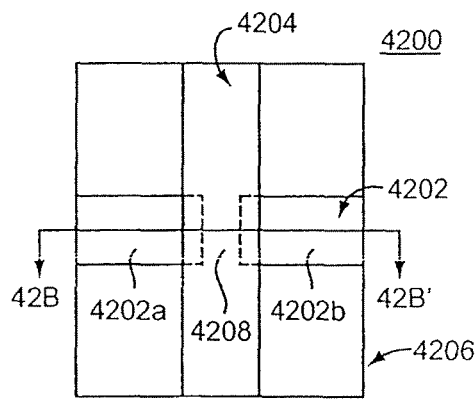
FIGS. 21A-21J show views of one embodiment of a normally-closed valve structure in accordance with the present invention.

FIGS. 8A and 8B illustrate valve opening vs. applied pressure for a 100 μm wide first flow channel 30 and a 50 μm wide second flow channel 32. The membrane of this device was formed by a layer of General Electric Silicones RTV 615 having a thickness of approximately 30 μm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a noncompressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebro-spinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa-25 MPa; 100 Pa-10 Mpa, 1 kPa-1 MPa, 1 kPa-300 kPa, 5 kPa-200 kPa, and 15 kPa-100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and non-linearly actuable valves are contemplated in the present invention, and the pressure ranges over which a valve is linearly actuable will vary with the specific embodiment.

Figure 9:
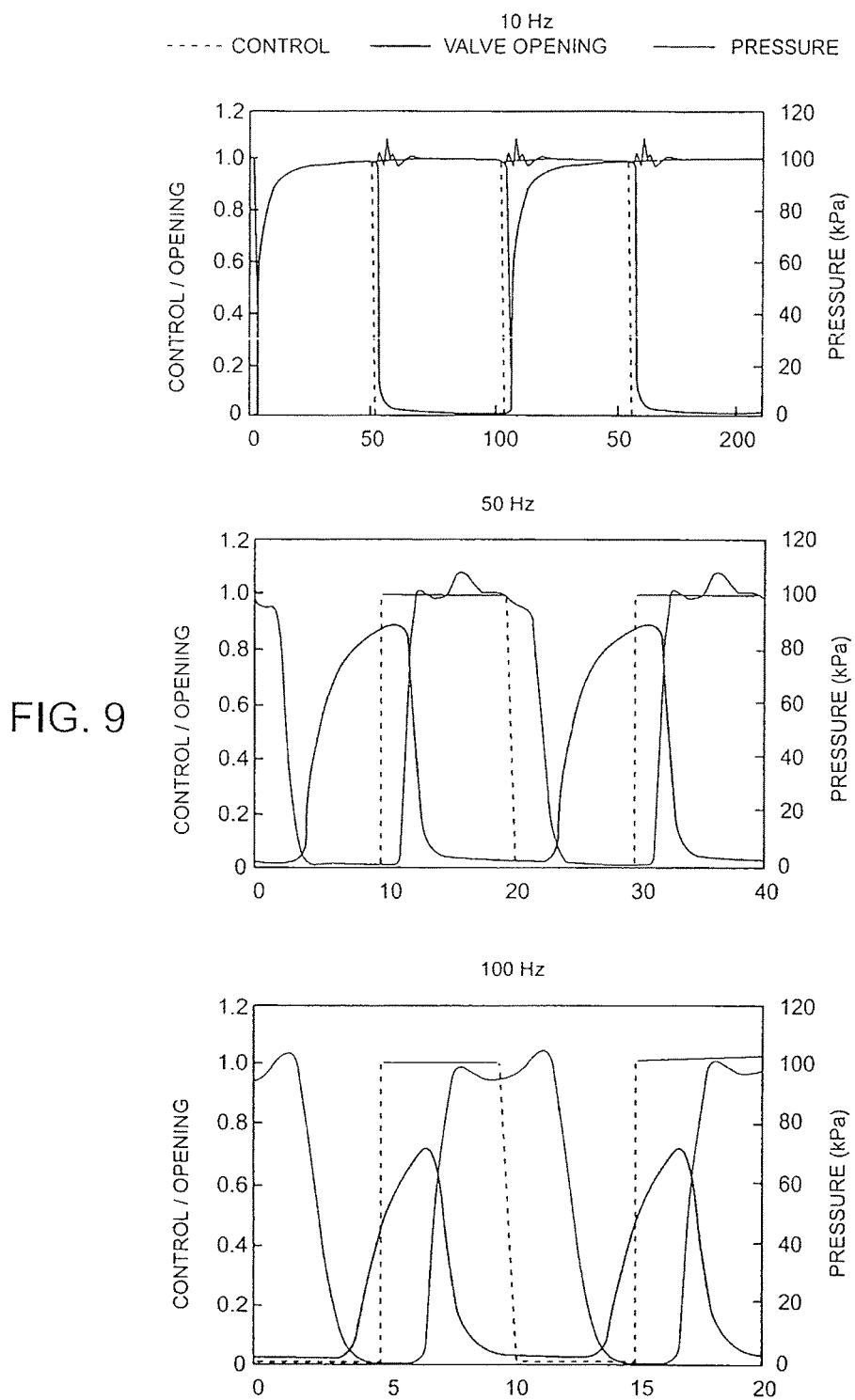
FIG. 9 illustrates time response of a 100 µm×100 µm×10 µm RTV microvalve.

FIG. 9 illustrates time response (i.e.: closure of valve as a function of time in response to a change in applied pressure) of a 100 µm×100 µm×10 µm RTV microvalve with 10-cm-long air tubing connected from the chip to a pneumatic valve as described above.

Two periods of digital control signal, actual air pressure at the end of the tubing and valve opening are shown in FIG. 9. The pressure applied on the control line is 100 kPa, which is substantially higher than the ~40 kPa required to close the valve. Thus, when closing, the valve is pushed closed with a pressure 60 kPa greater than required. When opening, however, the valve is driven back to its rest position only by its own spring force 40 kPa). Thus, $\tau_{close}$ is expected to be smaller than $\tau_{open}$. There is also a lag between the control signal and control pressure response, due to the limitations of the miniature valve used to control the pressure. Calling such lags t and the 1/e time constants $\tau$, the values are: $t_{open}$=3.63 ms, $\tau_{open}$=1.88 ms, $t_{close}$=2.15 ms, $\tau_{close}$=0.51 ms. If 3τ each are allowed for opening and closing, the valve runs comfortably at 75 Hz when filled with aqueous solution.

If one used another actuation method which did not suffer from opening and closing lag, this valve would run at ~375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 7C-7H.)

When experimentally measuring the valve properties as illustrated in FIG. 9 the valve opening was measured by fluorescence. In these experiments, the flow channel was filled with a solution of fluorescein isothiocyanate (FITC) in buffer (pH≥8) and the fluorescence of a square area occupying the center ~⅓rd of the channel is monitored on an epifluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

6. Flow Channel Cross Sections

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Figure 10:
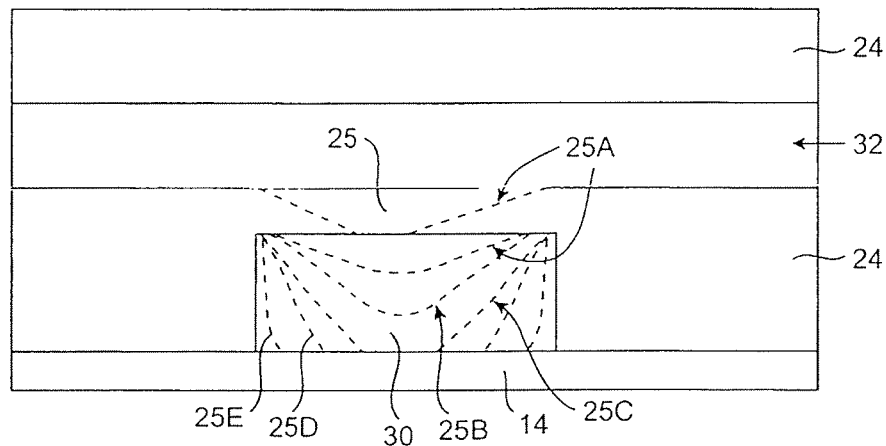
FIG. 10 is a front sectional view of the valve of FIG. 7B showing actuation of the membrane.

Referring to FIG. 10, a cross sectional view (similar to that of FIG. 7B) through flow channels 30 and 32 is shown. As can be seen, flow channel 30 is rectangular in cross sectional shape. In an alternate preferred aspect of the invention, as shown in FIG. 10, the cross-section of a flow channel 30 instead has an upper curved surface.

Referring first to FIG. 10, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

Figure 11:
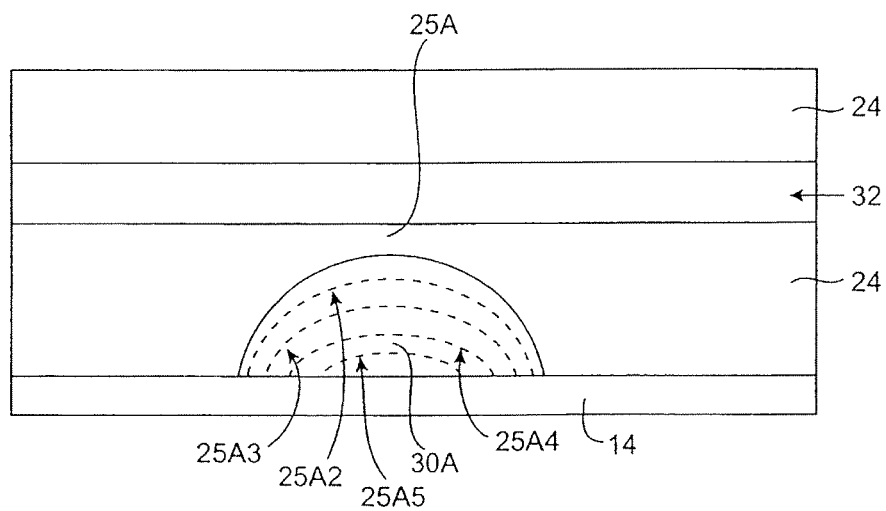
FIG. 11 is a front sectional view of an alternative embodiment of a valve having a flow channel with a curved upper surface.

In the alternate preferred embodiment of FIG. 11, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 10.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel.

In an alternate aspect, (not illustrated), the bottom of flow channel 30 is rounded such that its curved surface mates with the curved upper wall 25A as seen in FIG. 20 described above.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

7. Alternate Valve Actuation Techniques

In addition to pressure based actuation systems described above, optional electrostatic and magnetic actuation systems are also contemplated, as follows.

Electrostatic actuation can be accomplished by forming oppositely charged electrodes (which will tend to attract one another when a voltage differential is applied to them) directly into the monolithic elastomeric structure. For example, referring to FIG. 7B, an optional first electrode 70 (shown in phantom) can be positioned on (or in) membrane 25 and an optional second electrode 72 (also shown in phantom) can be positioned on (or in) planar substrate 14. When electrodes 70 and 72 are charged with opposite polarities, an attractive force between the two electrodes will cause membrane 25 to deflect downwardly, thereby closing the "valve" (i.e.: closing flow channel 30).

For the membrane electrode to be sufficiently conductive to support electrostatic actuation, but not so mechanically stiff so as to impede the valve's motion, a sufficiently flexible electrode must be provided in or over membrane 25. Such an electrode may be provided by a thin metallization layer, doping the polymer with conductive material, or making the surface layer out of a conductive material.

In an exemplary aspect, the electrode present at the deflecting membrane can be provided by a thin metallization layer which can be provided, for example, by sputtering a thin layer of metal such as 20 nm of gold. In addition to the formation of a metallized membrane by sputtering, other metallization approaches such as chemical epitaxy, evaporation, electroplating, and electroless plating are also available. Physical transfer of a metal layer to the surface of the elastomer is also available, for example by evaporating a metal onto a flat substrate to which it adheres poorly, and then placing the elastomer onto the metal and peeling the metal off of the substrate.

A conductive electrode 70 may also be formed by depositing carbon black (i.e. Cabot Vulcan XC72R) on the elastomer surface, either by wiping on the dry powder or by exposing the elastomer to a suspension of carbon black in a solvent which causes swelling of the elastomer, (such as a chlorinated solvent in the case of PDMS). Alternatively, the electrode 70 may be formed by constructing the entire layer 20 out of elastomer doped with conductive material (i.e. carbon black or finely divided metal particles). Yet further alternatively, the electrode may be formed by electrostatic deposition, or by a chemical reaction that produces carbon. In experiments conducted by the present inventors, conductivity was shown to increase with carbon black concentration from $5.6 \times 10^{-16}$ to about $5 \times 10^{-3}$ $(\Omega\text{-cm})^{-1}$. The lower electrode 72, which is not required to move, may be either a compliant electrode as described above, or a conventional electrode such as evaporated gold, a metal plate, or a doped semiconductor electrode.

Magnetic actuation of the flow channels can be achieved by fabricating the membrane separating the flow channels with a magnetically polarizable material such as iron, or a permanently magnetized material such as polarized NdFeB. In experiments conducted by the present inventors, magnetic silicone was created by the addition of iron powder (about 1 um particle size), up to 20% iron by weight.

Where the membrane is fabricated with a magnetically polarizable material, the membrane can be actuated by attraction in response to an applied magnetic field Where the membrane is fabricated with a material capable of maintaining permanent magnetization, the material can first be magnetized by exposure to a sufficiently high magnetic field, and then actuated either by attraction or repulsion in response to the polarity of an applied inhomogenous magnetic field.

The magnetic field causing actuation of the membrane can be generated in a variety of ways. In one embodiment, the magnetic field is generated by an extremely small inductive coil formed in or proximate to the elastomer membrane. The actuation effect of such a magnetic coil would be localized, allowing actuation of individual pump and/or valve structures. Alternatively, the magnetic field could be generated by a larger, more powerful source, in which case actuation would be global and would actuate multiple pump and/or valve structures at one time.

It is also possible to actuate the device by causing a fluid flow in the control channel based upon the application of thermal energy, either by thermal expansion or by production of gas from liquid. For example, in one alternative embodiment in accordance with the present invention, a pocket of fluid (e.g. in a fluid-filled control channel) is positioned over the flow channel. Fluid in the pocket can be in communication with a temperature variation system, for example a heater. Thermal expansion of the fluid, or conversion of material from the liquid to the gas phase, could result in an increase in pressure, closing the adjacent flow channel. Subsequent cooling of the fluid would relieve pressure and permit the flow channel to open.

8. Networked Systems

Figure 12A:
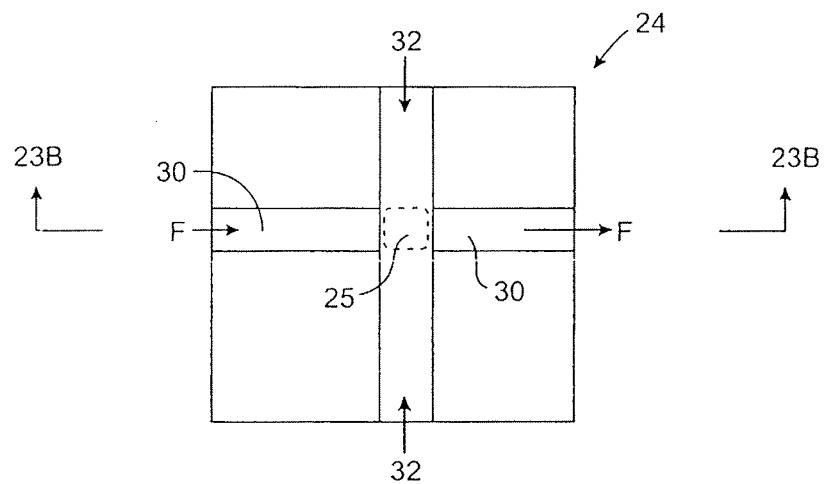
FIG. 12A is a top schematic view of an on/off valve.
Figure 13A:
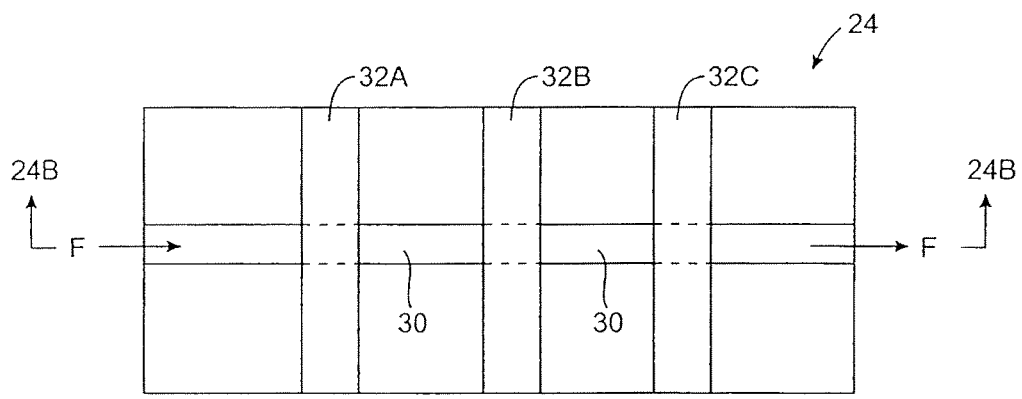
FIG. 13A is a top schematic view of a peristaltic pumping system.
Figure 12B:
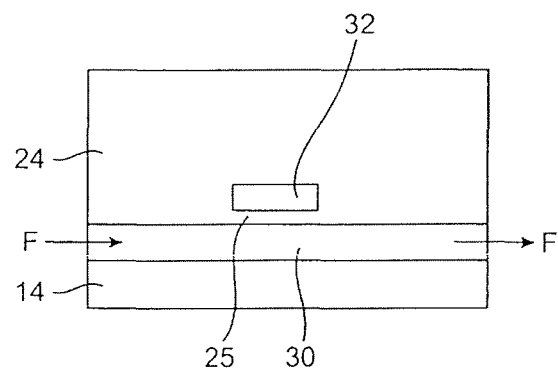
FIG. 12B is a sectional elevation view along line 23B-23B in FIG. 12A.
Figure 13B:
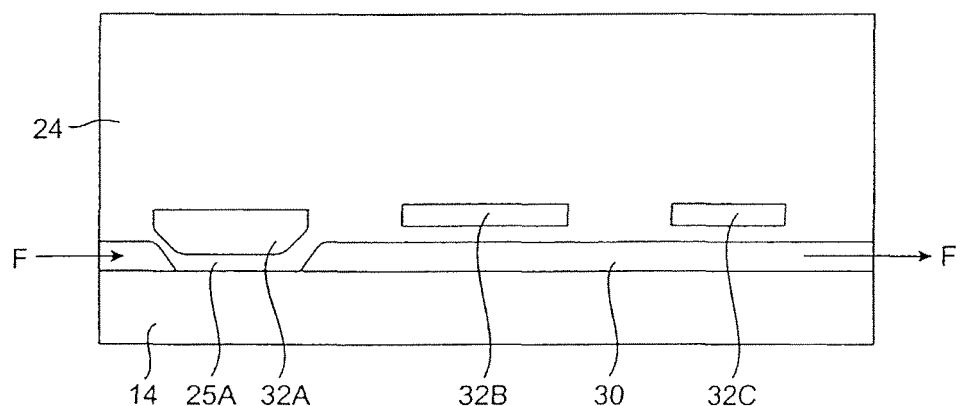
FIG. 13B is a sectional elevation view along line 24B-24B in FIG. 13A.
Figure 14:
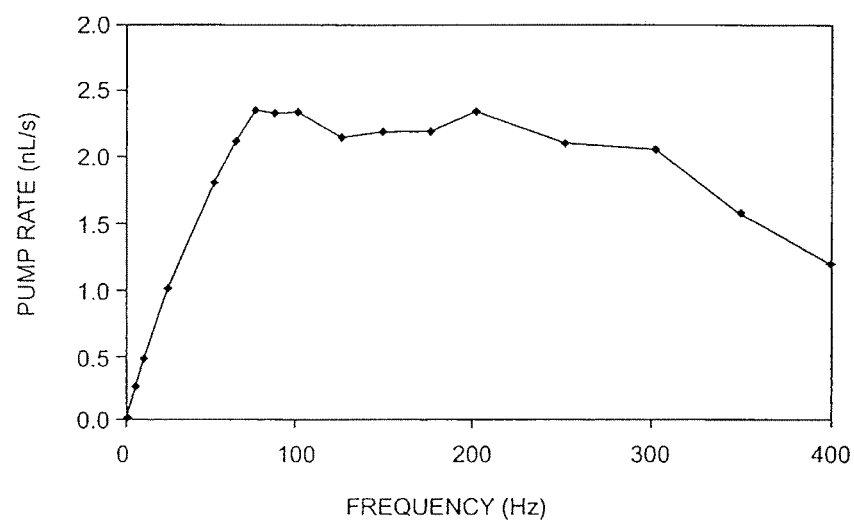
FIG. 14 is a graph showing experimentally achieved pumping rates vs. frequency for an embodiment of the peristaltic pumping system of FIG. 13.

FIGS. 12A and 12B show a views of a single on/off valve, identical to the systems set forth above, (for example in FIG. 7A). FIGS. 13A and 13B shows a peristaltic pumping system comprised of a plurality of the single addressable on/off valves as seen in FIG. 12, but networked together. FIG. 14 is a graph showing experimentally achieved pumping rates vs. frequency for the peristaltic pumping system of FIG. 13.

Figure 15A:
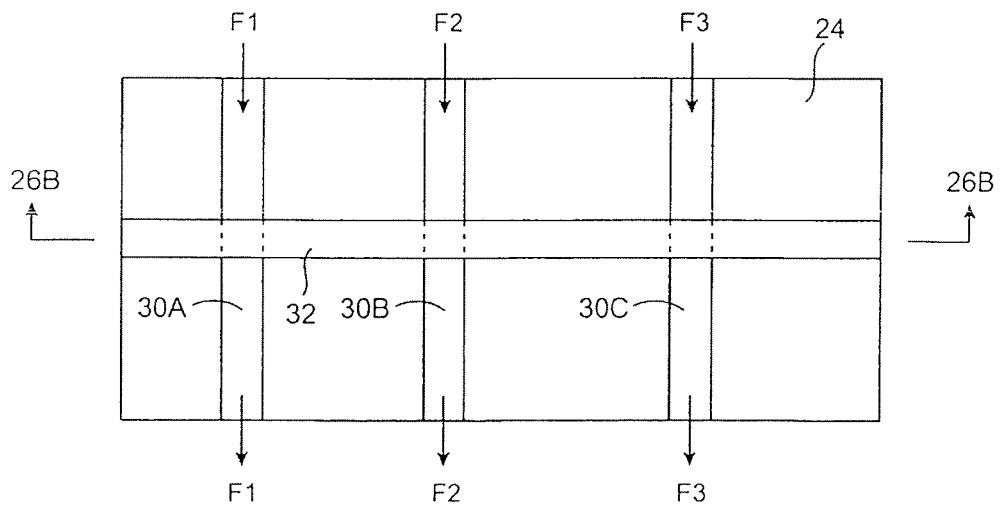
FIG. 15A is a top schematic view of one control line actuating multiple flow lines simultaneously.
Figure 15B:
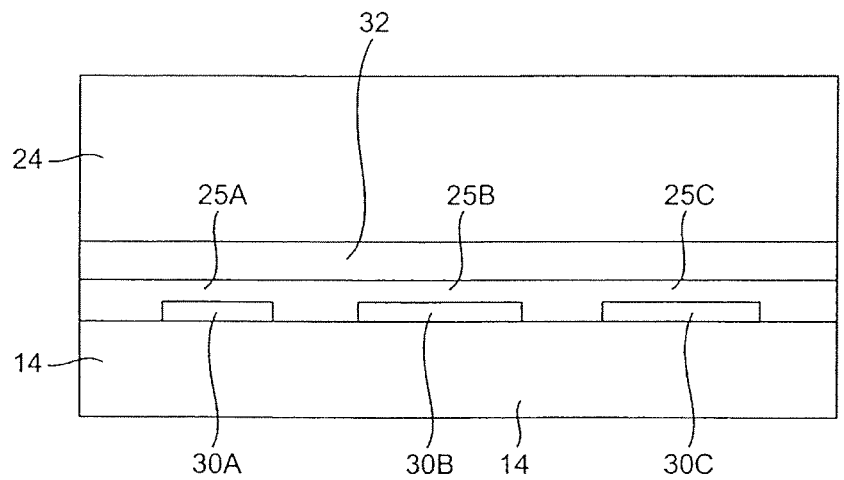
FIG. 15B is a sectional elevation view along line 26B-26B in FIG. 15A.
Figure 16:
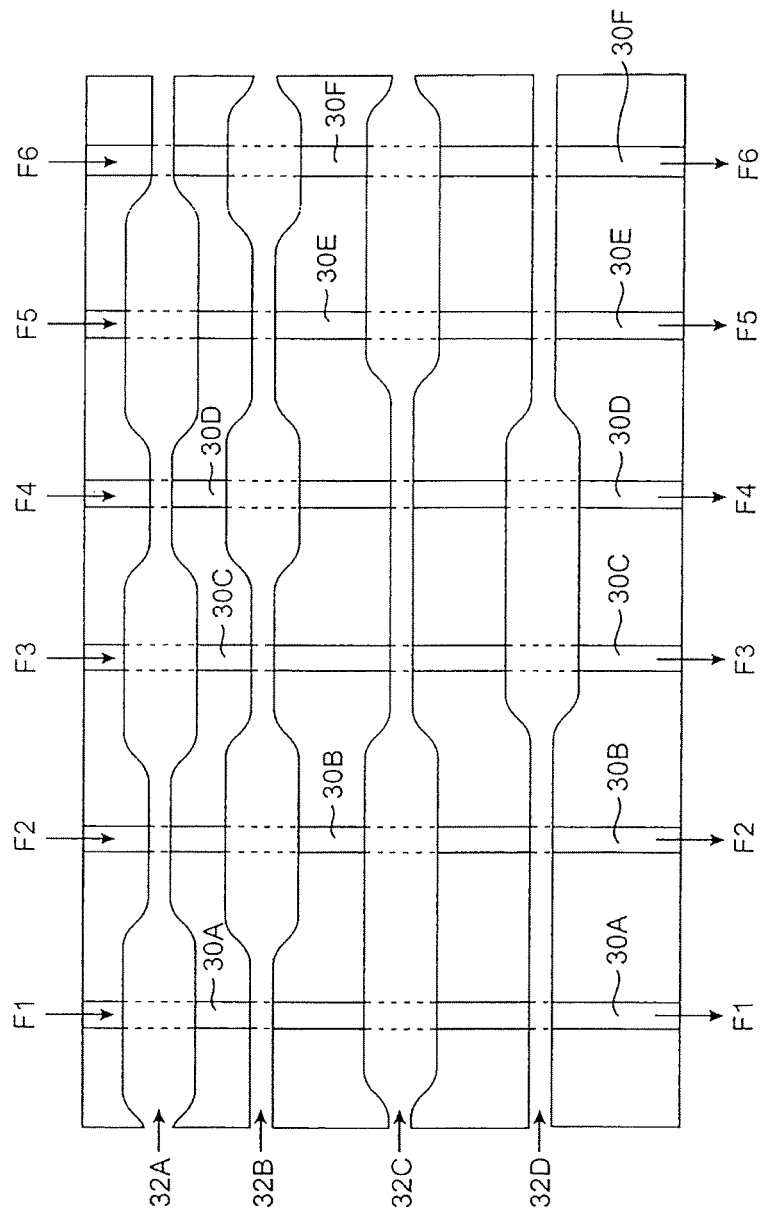
FIG. 16 is a schematic illustration of a multiplexed system adapted to permit flow through various channels.

FIGS. 15A and 15B show a schematic view of a plurality of flow channels which are controllable by a single control line. This system is also comprised of a plurality of the single addressable on/off valves of FIG. 12, multiplexed together, but in a different arrangement than that of FIG. 12. FIG. 16 is a schematic illustration of a multiplexing system adapted to permit fluid flow through selected channels, comprised of a plurality of the single on/off valves of FIG. 12, joined or networked together.

Referring first to FIGS. 12A and 12B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 12 to 15, a plurality of such addressable valves are joined or networked together in various arrangements to produce pumps, capable of peristaltic pumping, and other fluidic logic applications.

Referring to FIGS. 13A and 13B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×100×10 µm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of *E. Coli* pumped through a channel and tested for viability showed a 94% survival rate.

FIG. 14 is a graph showing experimentally achieved pumping rates vs. frequency for the peristaltic pumping system of FIG. 13.

FIGS. 15A and 15B illustrates another way of assembling a plurality of the addressable valves of FIG. 12. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 16 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 15A and 15B) depends strongly upon the membrane dimensions. Accordingly, by varying the widths of flow channel control line 32 in FIGS. 15A and 15B, it is possible to have a control line pass over multiple flow channels, yet only actuate (i.e.: seal) desired flow channels. FIG. 16 illustrates a schematic of such a system, as follows.

A plurality of parallel flow channels 30A, 30B, 30C, 30D, 30E and 30F are positioned under a plurality of parallel control lines 32A, 32B, 32C, 32D, 32E and 32F. Control channels 32A, 32B, 32C, 32D, 32E and 32F are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, 32D, 32E and 32F have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only $2(\log_2 n)$ control lines.

9. Selectively Addressable Reaction Chambers Along Flow Lines

In a further embodiment of the invention, illustrated in FIGS. 17A, 17B, 17C and 17D, a system for selectively directing fluid flow into one more of a plurality of reaction chambers disposed along a flow line is provided.

Figure 17A:
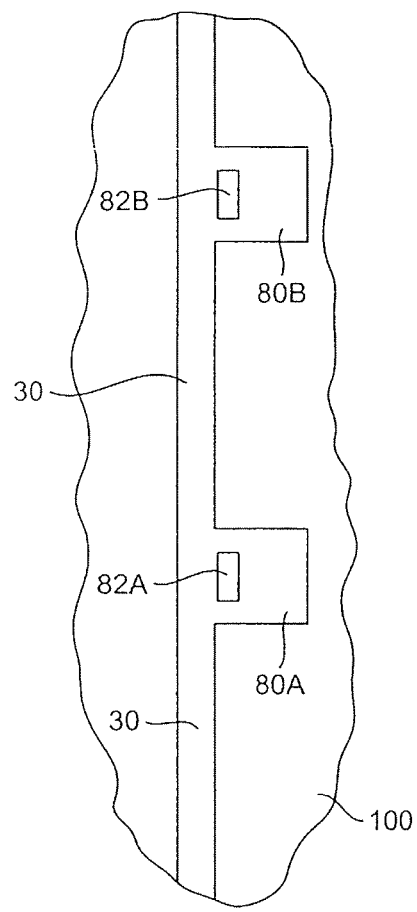
FIG. 17A is a plan view of a flow layer of an addressable reaction chamber structure.

FIG. 17A shows a top view of a flow channel 30 having a plurality of reaction chambers 80A and 80B disposed therealong. Preferably flow channel 30 and reaction chambers 80A and 80B are formed together as recesses into the bottom surface of a first layer 100 of elastomer.

Figure 17B:
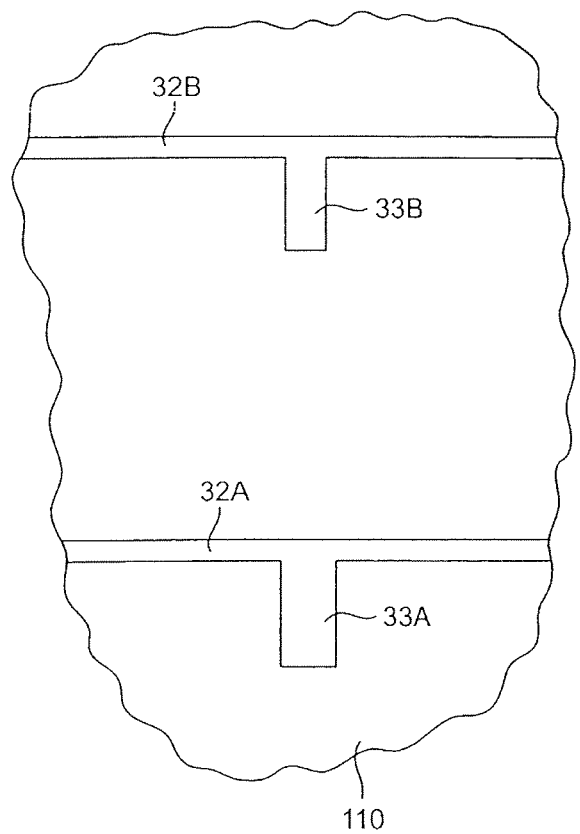
FIG. 17B is a bottom plan view of a control channel layer of an addressable reaction chamber structure.

FIG. 17B shows a bottom plan view of another elastomeric layer 110 with two control lines 32A and 32B each being generally narrow, but having wide extending portions 33A and 33B formed as recesses therein.

Figure 17C:
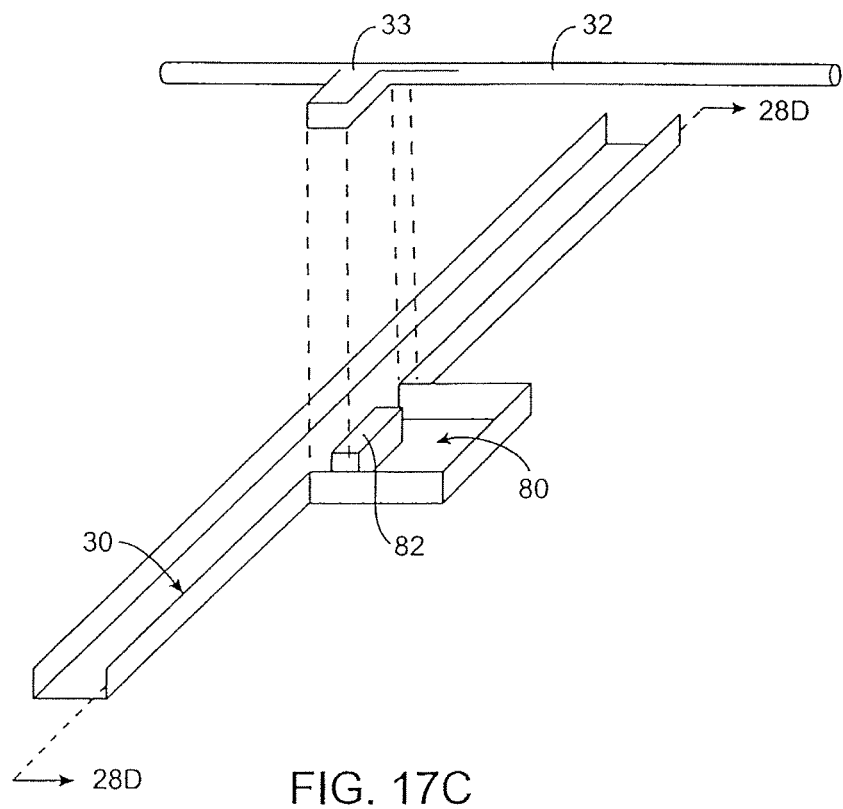
FIG. 17C is an exploded perspective view of the addressable reaction chamber structure formed by bonding the control channel layer of FIG. 17B to the top of the flow layer of FIG. 17A.
Figure 17D:
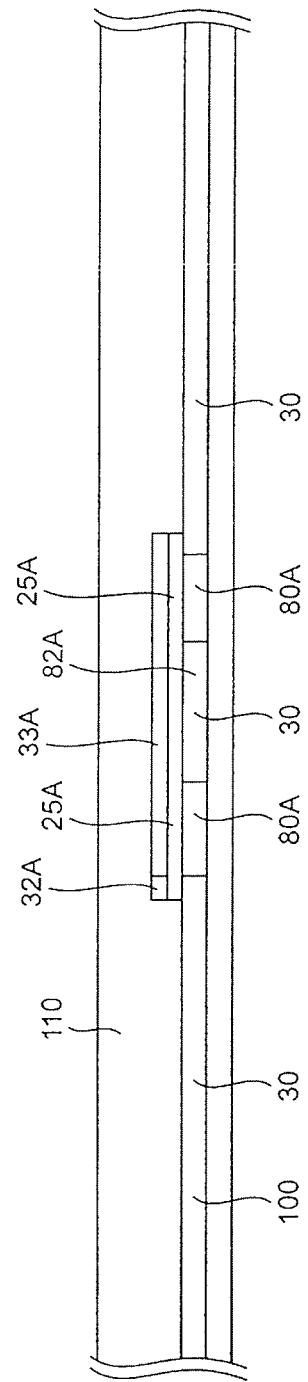
FIG. 17D is a sectional elevation view corresponding to FIG. 17C, taken along line 28D-28D in FIG. 17C.
Figure 18:
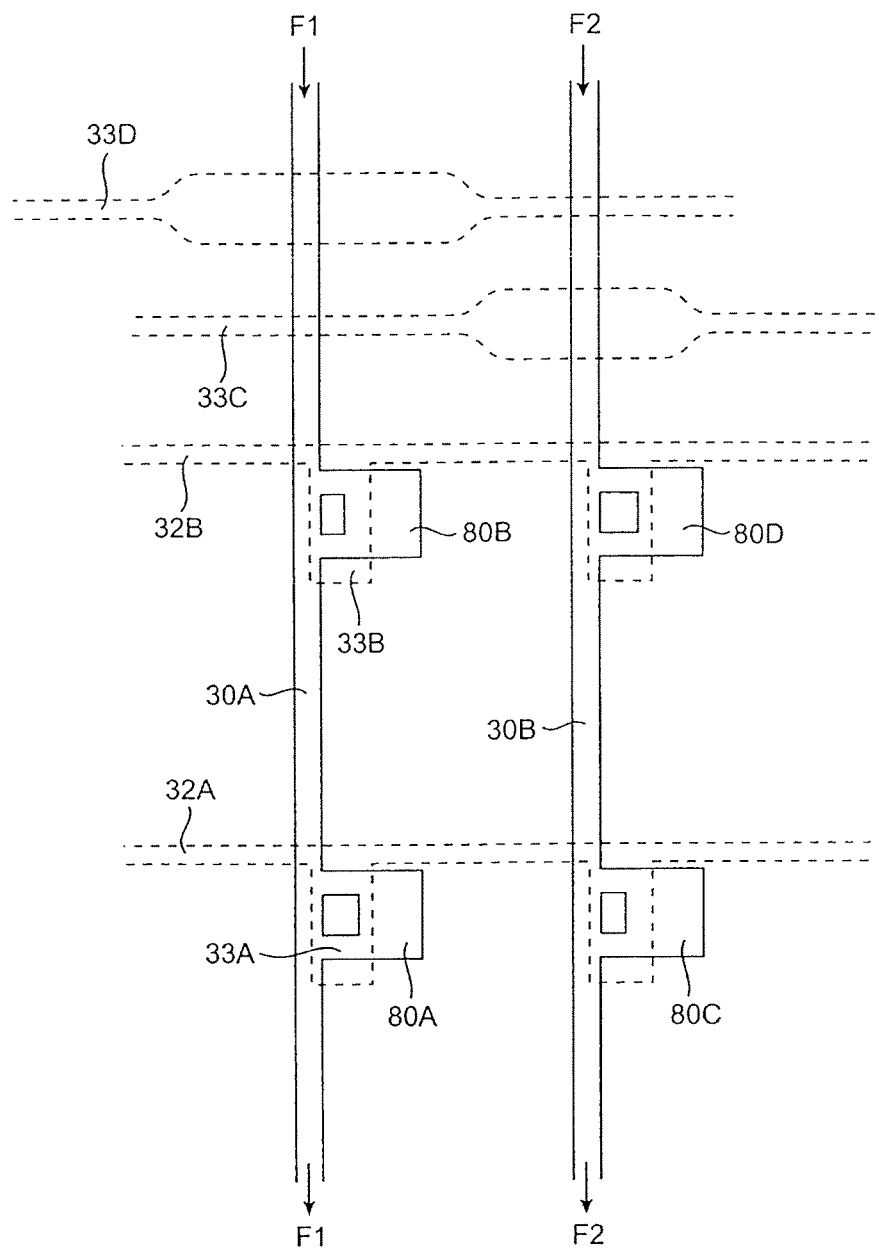
FIG. 18 is a schematic of a system adapted to selectively direct fluid flow into any of an array of reaction wells.

As seen in the exploded view of FIG. 17C, and assembled view of FIG. 17D, elastomeric layer 110 is placed over elastomeric layer 100. Layers 100 and 110 are then bonded together, and the integrated system operates to selectively direct fluid flow F (through flow channel 30) into either or both of reaction chambers 80A and 80B, as follows. Pressurization of control line 32A will cause the membrane 25 (i.e.: the thin portion of elastomer layer 100 located below extending portion 33A and over regions 82A of reaction chamber 80A) to become depressed, thereby shutting off fluid flow passage in regions 82A, effectively sealing reaction chamber 80 from flow channel 30. As can also be seen, extending portion 33A is wider than the remainder of control line 32A. As such, pressurization of control line 32A will not result in control line 32A sealing flow channel 30.

As can be appreciated, either or both of control lines 32A and 32B can be actuated at once. When both control lines 32A and 32B are pressurized together, sample flow in flow channel 30 will enter neither of reaction chambers 80A or 80B.

The concept of selectably controlling fluid introduction into various addressable reaction chambers disposed along a flow line (FIGS. 17A-D) can be combined with concept of selectably controlling fluid flow through one or more of a plurality of parallel flow lines (FIG. 16) to yield a system in which a fluid sample or samples can be can be sent to any particular reaction chamber in an array of reaction chambers. An example of such a system is provided in FIG. 18, in which parallel control channels 32A, 32B and 32C with extending portions 34 (all shown in phantom) selectively direct fluid flows F1 and F2 into any of the array of reaction wells 80A, 80B, 80C or 80D as explained above; while pressurization of control lines 32C and 32D selectively shuts off flows F2 and F1, respectively.

Figure 19:
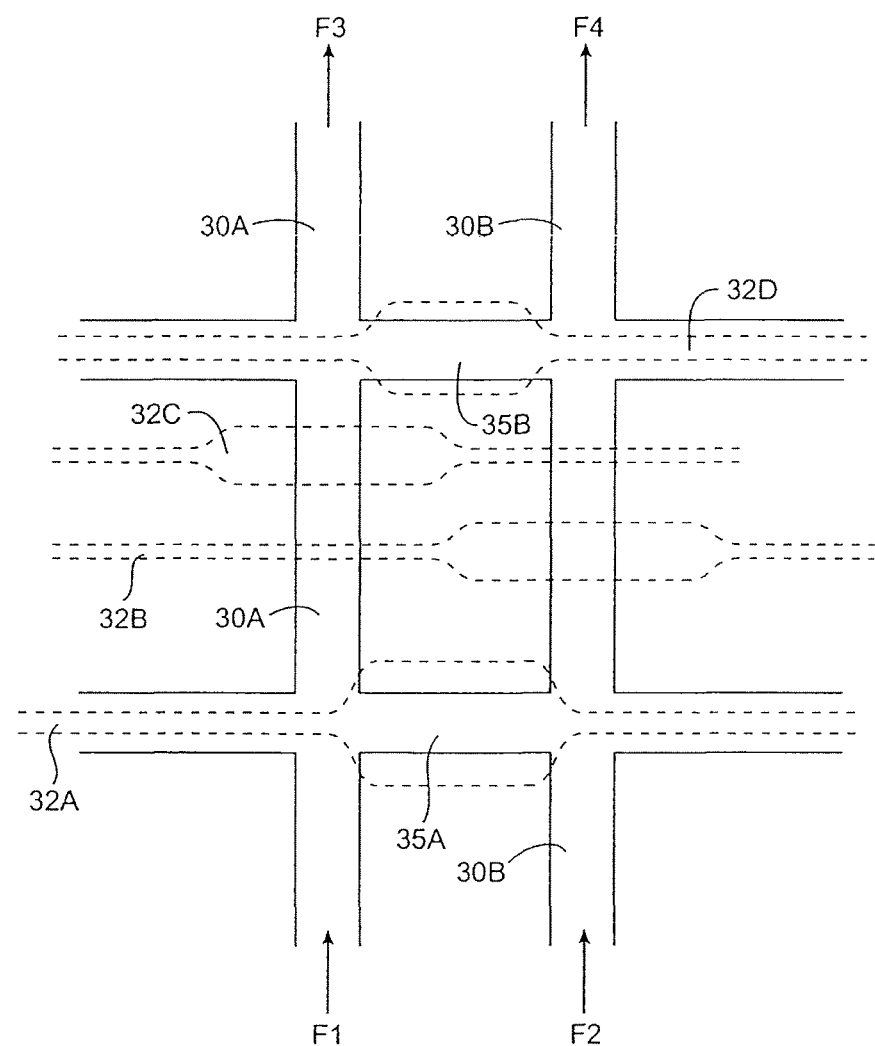
FIG. 19 is a schematic of a system adapted for selectable lateral flow between parallel flow channels.

In yet another novel embodiment, fluid passage between parallel flow channels is possible. Referring to FIG. 19, either or both of control lines 32A or 32D can be depressurized such that fluid flow through lateral passageways 35 (between parallel flow channels 30A and 30B) is permitted. In this aspect of the invention, pressurization of control lines 32C and 32D would shut flow channel 30A between 35A and 35B, and would also shut lateral passageways 35B. As such, flow entering as flow F1 would sequentially travel through 30A, 35A and leave 30B as flow F4.

10. Switchable Flow Arrays

Figure 20A:
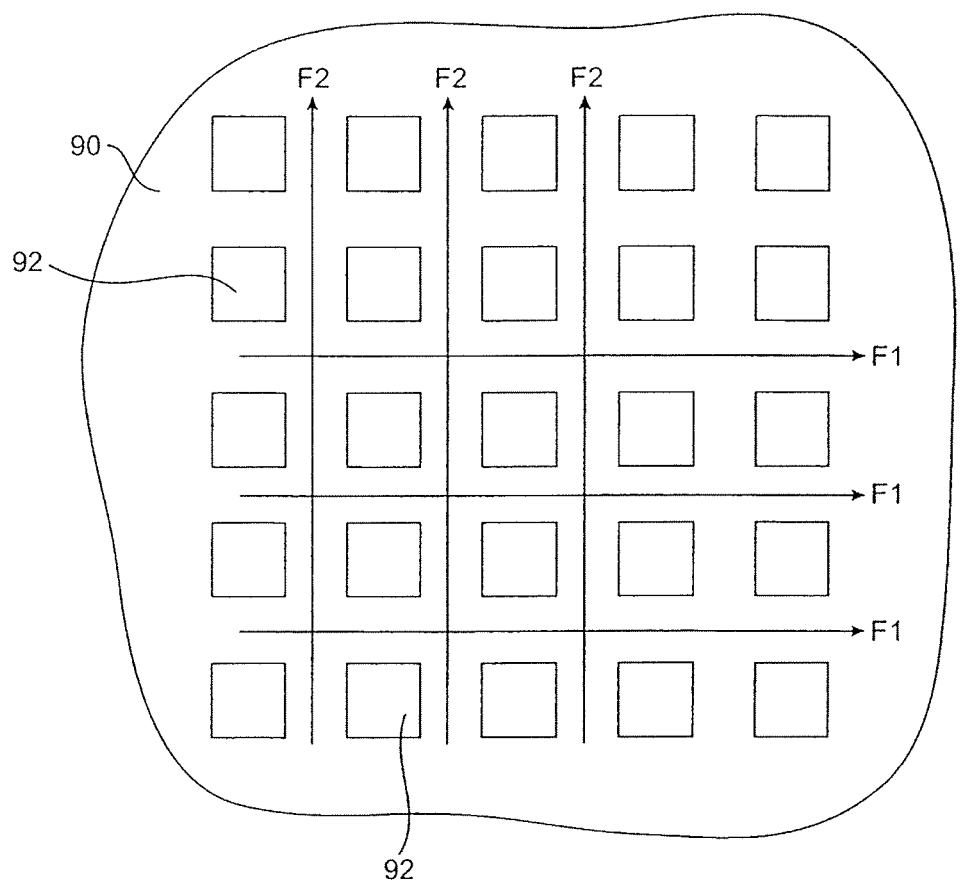
FIG. 20A is a bottom plan view of first layer (i.e.: the flow channel layer) of elastomer of a switchable flow array.
Figure 20B:
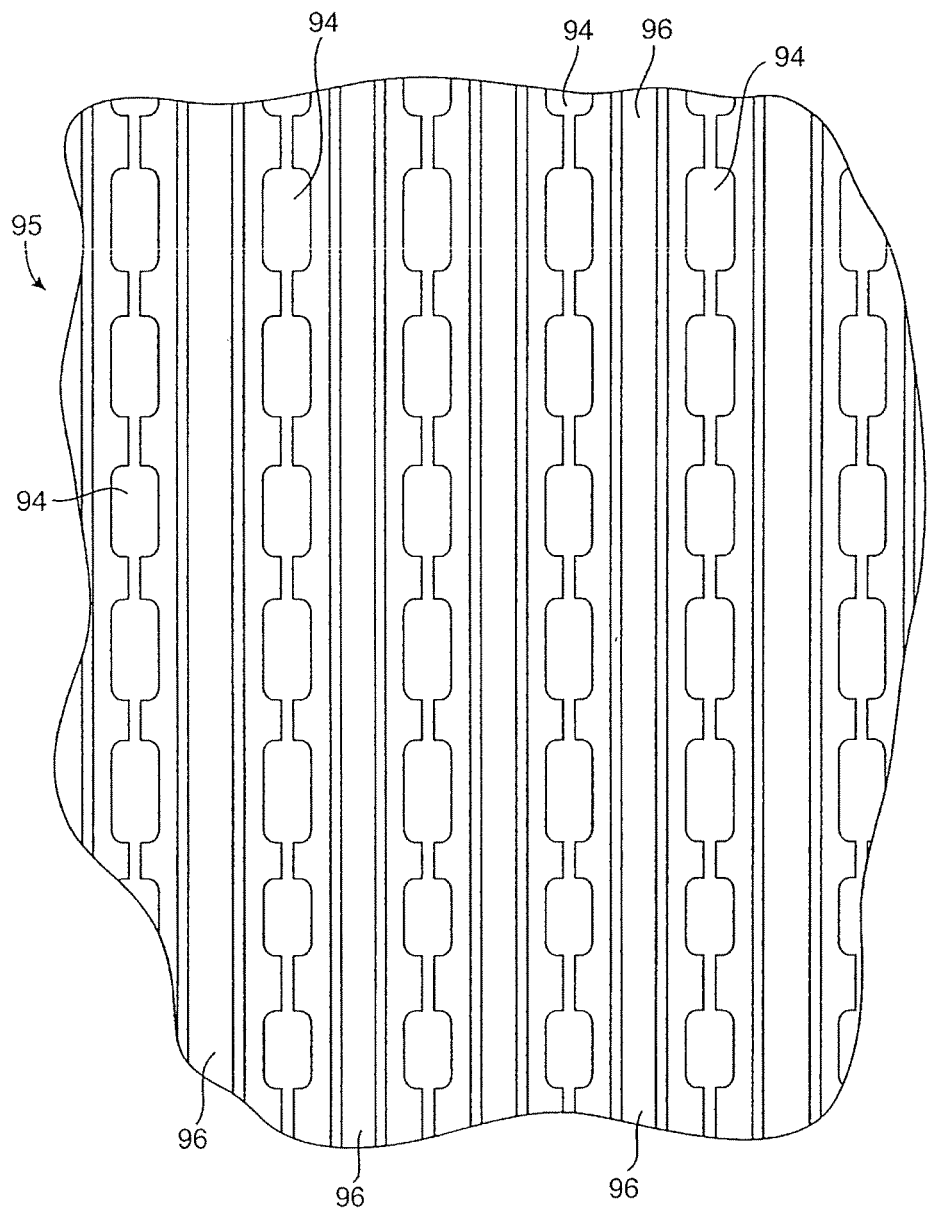
FIG. 20B is a bottom plan view of a control channel layer of a switchable flow array.

In yet another novel embodiment, fluid passage can be selectively directed to flow in either of two perpendicular directions. An example of such a "switchable flow array" system is provided in FIGS. 20A to 20D. FIG. 20A shows a bottom view of a first layer of elastomer 90, (or any other suitable substrate), having a bottom surface with a pattern of recesses forming a flow channel grid defined by an array of solid posts 92, each having flow channels passing therearound.

In preferred aspects, an additional layer of elastomer is bound to the top surface of layer 90 such that fluid flow can be selectively directed to move either in direction F1, or perpendicular direction F2. FIG. 20 is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Figure 20C:
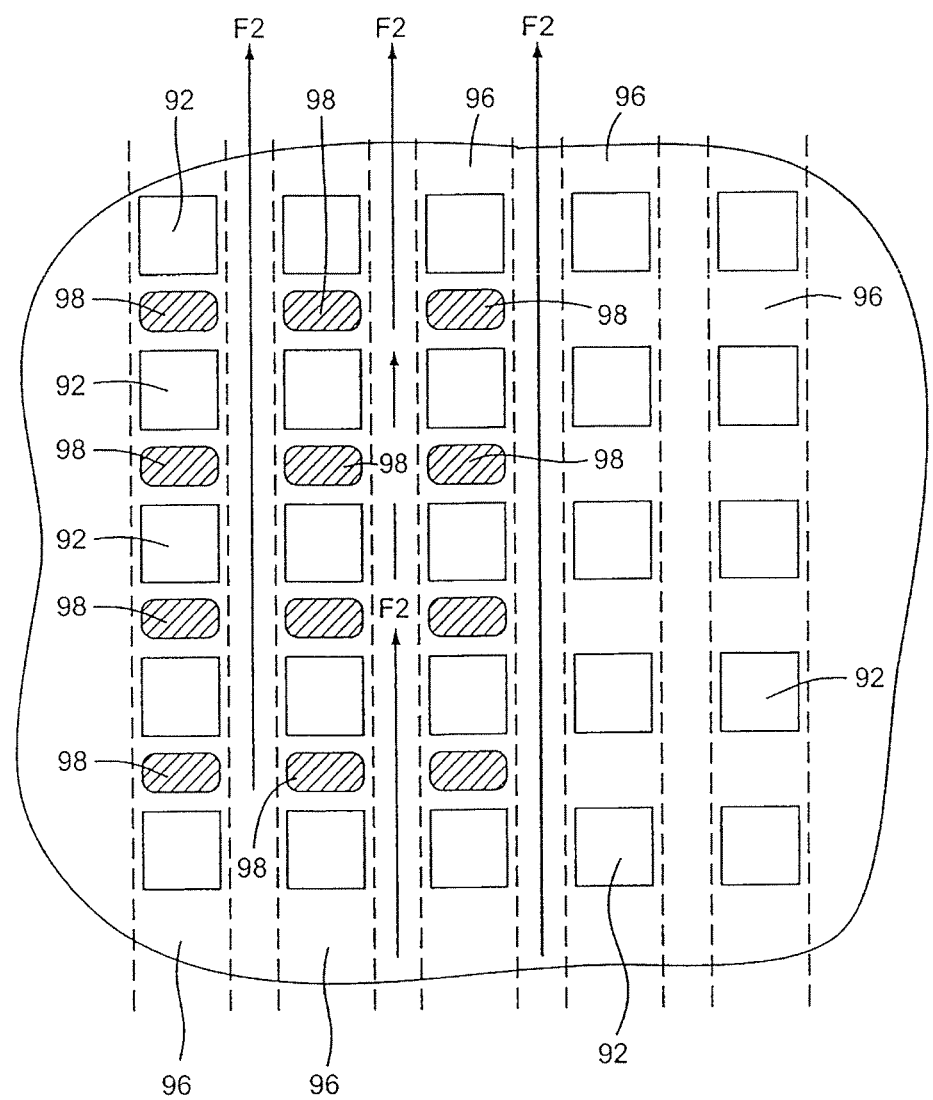
FIG. 20C shows the alignment of the first layer of elastomer of FIG. 20A with one set of control channels in the second layer of elastomer of FIG. 20B.
Figure 20D:
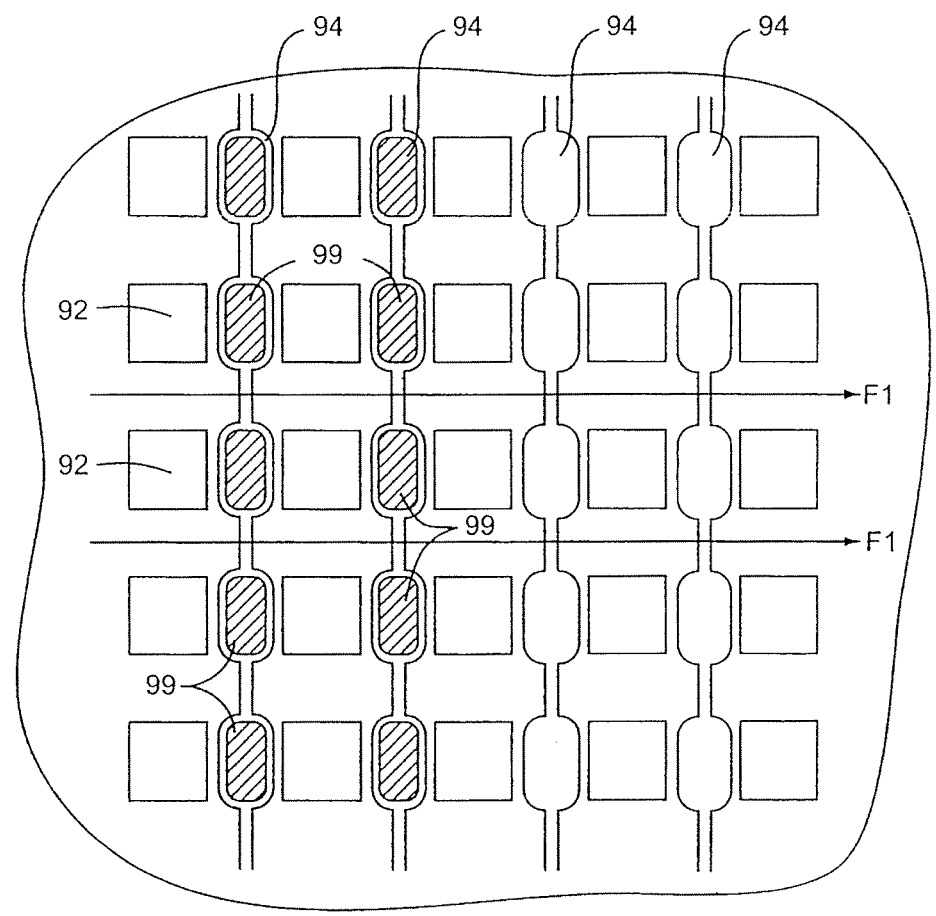
FIG. 20D also shows the alignment of the first layer of elastomer of FIG. 20A with the other set of control channels in the second layer of elastomer of FIG. 20B.

Elastomeric layer 95 is positioned over top of elastomeric layer 90 such that "vertical" control lines 96 are positioned over posts 92 as shown in FIG. 20C and "horizontal" control lines 94 are positioned with their wide portions between posts 92, as shown in FIG. 20D.

As can be seen in FIG. 20C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 20D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIG. 20 allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

11. Normally-Closed Valve Structure

FIGS. 7B and 7H above depict a valve structure in which the elastomeric membrane is moveable from a first relaxed position to a second actuated position in which the flow channel is blocked. However, the present invention is not limited to this particular valve configuration.

FIGS. 21A-21J show a variety of views of a normally-closed valve structure in which the elastomeric membrane is moveable from a first relaxed position blocking a flow channel, to a second actuated position in which the flow channel is open, utilizing a negative control pressure.

FIG. 21A shows a plan view, and FIG. 21B shows a cross sectional view along line 42B-42B', of normally-closed valve 4200 in an unactuated state. Flow channel 4202 and control channel 4204 are formed in elastomeric block 4206 overlying substrate 4205. Flow channel 4202 includes a first portion 4202a and a second portion 4202b separated by separating portion 4208. Control channel 4204 overlies separating portion 4208. As shown in FIG. 42B, in its relaxed, unactuated position, separating portion 4008 remains positioned between flow channel portions 4202a and 4202b, interrupting flow channel 4202.

Figure 21D:
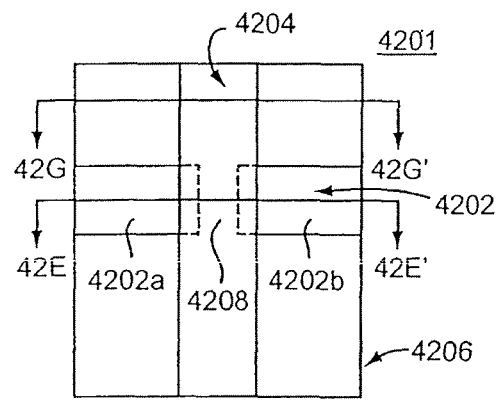
Figure 21B:
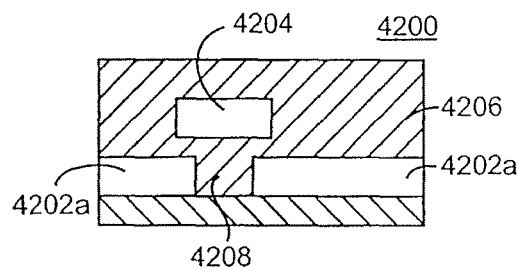
Figure 21E:
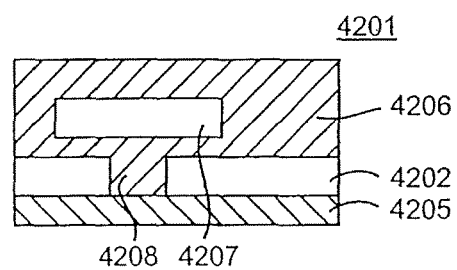
Figure 21C:
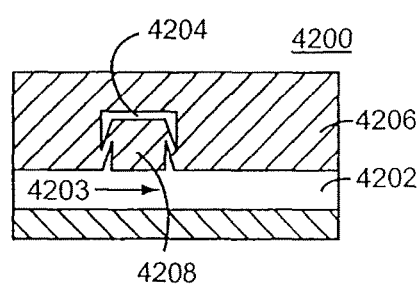
Figure 21F:
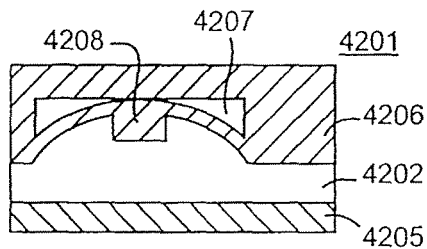

FIG. 21C shows a cross-sectional view of valve 4200 wherein separating portion 4208 is in an actuated position. When the pressure within control channel 4204 is reduced to below the pressure in the flow channel (for example by vacuum pump), separating portion 4208 experiences an actuating force drawing it into control channel 4204. As a result of this actuation force membrane 4208 projects into control channel 4204, thereby removing the obstacle to a flow of material through flow channel 4202 and creating a passageway 4203. Upon elevation of pressure within control channel 4204, separating portion 4208 will assume its natural position, relaxing back into and obstructing flow channel 4202.

The behavior of the membrane in response to an actuation force may be changed by varying the width of the overlying control channel. Accordingly, FIGS. 21D-42H show plan and cross-sectional views of an alternative embodiment of a normally-closed valve 4201 in which control channel 4207 is substantially wider than separating portion 4208. As shown in cross-sectional views FIG. 21E-F along line 42E-42E' of FIG.

21D, because a larger area of elastomeric material is required to be moved during actuation, the actuation force necessary to be applied is reduced.

Figure 21I:
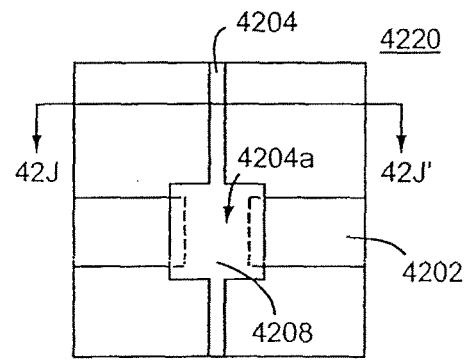
Figure 21G:
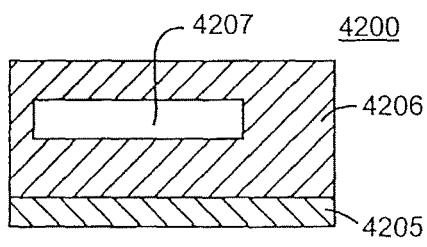

FIGS. 21G and H show a cross-sectional views along line 40G-40G' of FIG. 21D. In comparison with the unactuated valve configuration shown in FIG. 21G, FIG. 21H shows that reduced pressure within wider control channel 4207 may under certain circumstances have the unwanted effect of pulling underlying elastomer 4206 away from substrate 4205, thereby creating undesirable void 4212.

Figure 21J:
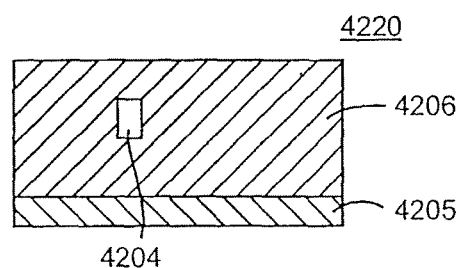
Figure 21H:
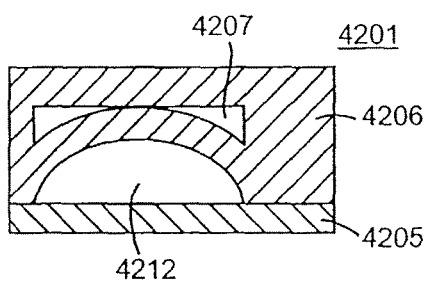

Accordingly, FIG. 21I shows a plan view, and FIG. 21J shows a cross-sectional view along line 21I-21F of FIG. 21I, of valve structure 4220 which avoids this problem by featuring control line 4204 with a minimum width except in segment 4204a overlapping separating portion 4208. As shown in FIG. 21J, even under actuated conditions the narrower cross-section of control channel 4204 reduces the attractive force on the underlying elastomer material 4206, thereby preventing this elastomer material from being drawn away from substrate 4205 and creating an undesirable void.

While a normally-closed valve structure actuated in response to pressure is shown in FIGS. 21A-21J, a normally-closed valve in accordance with the present invention is not limited to this configuration. For example, the separating portion obstructing the flow channel could alternatively be manipulated by electric or magnetic fields, as described extensively above.

12. Side-Actuated Valve

Figure 22A:
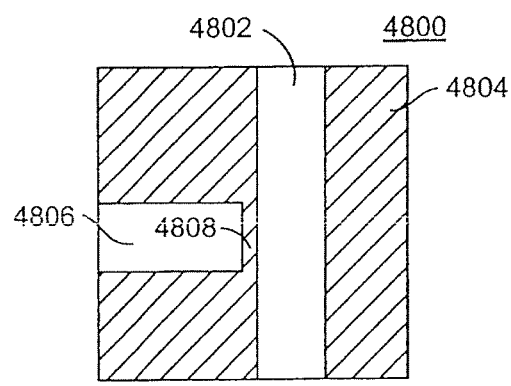
FIGS. 22A and 22B show plan views illustrating operation of one embodiment of a side-actuated valve structure in accordance with the present invention.
Figure 22B:
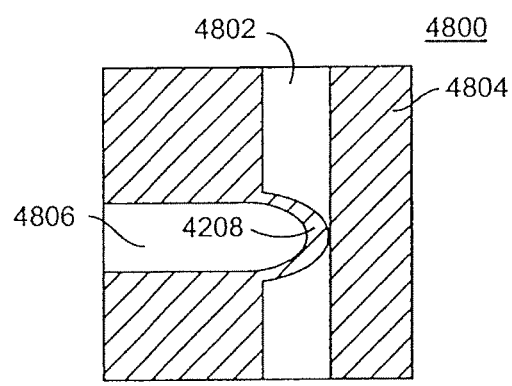

While the above description has focused upon microfabricated elastomeric valve structures in which a control channel is positioned above and separated by an intervening elastomeric membrane from an underlying flow channel, the present invention is not limited to this configuration. FIGS. 22A and 22B show plan views of one embodiment of a side-actuated valve structure in accordance with one embodiment of the present invention.

FIG. 22A shows side-actuated valve structure 4800 in an unactuated position. Flow channel 4802 is formed in elastomeric layer 4804. Control channel 4806 abutting flow channel 4802 is also formed in elastomeric layer 4804. Control channel 4806 is separated from flow channel 4802 by elastomeric membrane portion 4808. A second elastomeric layer (not shown) is bonded over bottom elastomeric layer 4804 to enclose flow channel 4802 and control channel 4806.

FIG. 22B shows side-actuated valve structure 4800 in an actuated position. In response to a build up of pressure within control channel 4806, membrane 4808 deforms into flow channel 4802, blocking flow channel 4802. Upon release of pressure within control channel 4806, membrane 4808 would relax back into control channel 4806 and open flow channel 4802.

While a side-actuated valve structure actuated in response to pressure is shown in FIGS. 22A and 22B, a side-actuated valve in accordance with the present invention is not limited to this configuration. For example, the elastomeric membrane portion located between the abutting flow and control channels could alternatively be manipulated by electric or magnetic fields, as described extensively above.

13. Composite Structures

Figure 23:
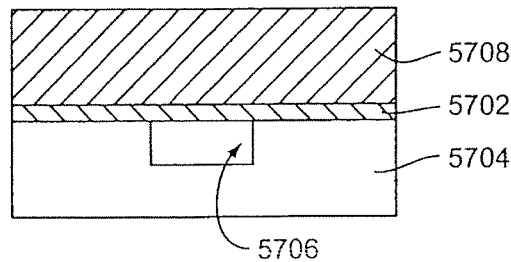
FIG. 23 shows a cross-sectional view of one embodiment of a composite structure in accordance with the present invention.

Microfabricated elastomeric structures of the present invention may be combined with non-elastomeric materials to create composite structures. FIG. 23 shows a cross-sectional view of one embodiment of a composite structure in accordance with the present invention. FIG. 23 shows composite valve structure 5700 including first, thin elastomer layer 5702 overlying semiconductor-type substrate 5704 having channel 5706 formed therein. Second, thicker elastomer layer 5708 overlies first elastomer layer 5702. Actuation of first elastomer layer 5702 to drive it into channel 5706, will cause composite structure 5700 to operate as a valve.

Figure 24:
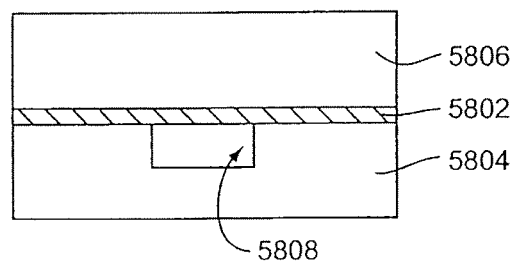
FIG. 24 shows a cross-sectional view of another embodiment of a composite structure in accordance with the present invention.

FIG. 24 shows a cross-sectional view of a variation on this theme, wherein thin elastomer layer 5802 is sandwiched between two hard, semiconductor substrates 5804 and 5806, with lower substrate 5804 featuring channel 5808. Again, actuation of thin elastomer layer 5802 to drive it into channel 5808 will cause composite structure 5810 to operate as a valve.

The structures shown in FIG. 23 or 24 may be fabricated utilizing either the multilayer soft lithography or encapsulation techniques described above. In the multilayer soft lithography method, the elastomer layer(s) would be formed and then placed over the semiconductor substrate bearing the channel. In the encapsulation method, the channel would be first formed in the semiconductor substrate, and then the channel would be filled with a sacrificial material such as photoresist. The elastomer would then be formed in place over the substrate, with removal of the sacrificial material producing the channel overlaid by the elastomer membrane. As is discussed in detail below in connection with bonding of elastomer to other types of materials, the encapsulation approach may result in a stronger seal between the elastomer membrane component and the underlying nonelastomer substrate component.

Figure 25:
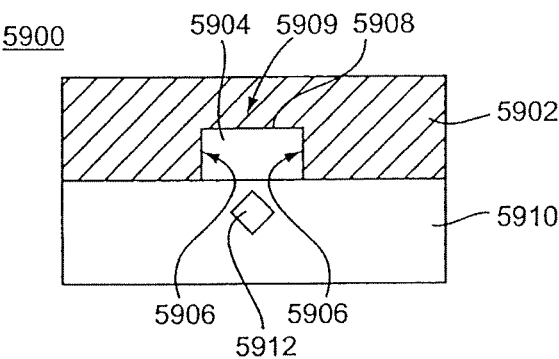
FIG. 25 shows a cross-sectional view of another embodiment of a composite structure in accordance with the present invention.

As shown in FIGS. 23 and 24, a composite structure in accordance with embodiments of the present invention may include a hard substrate that bears a passive feature such as a channels. However, the present invention is not limited to this approach, and the underlying hard substrate may bear active features that interact with an elastomer component bearing a recess. This is shown in FIG. 25, wherein composite structure 5900 includes elastomer component 5902 containing recess 5904 having walls 5906 and ceiling 5908. Ceiling 5908 forms flexible membrane portion 5909. Elastomer component 5902 is sealed against substantially planar nonelastomeric component 5910 that includes active device 5912. Active device 5912 may interact with material present in recess 5904 and/or flexible membrane portion 5909.

Many Types of active structures may be present in the nonelastomer substrate. Active structures that could be present in an underlying hard substrate include, but are not limited to, resistors, capacitors, photodiodes, transistors, chemical field effect transistors (chem FET's), amperometric/coulometric electrochemical sensors, fiber optics, fiber optic interconnects, light emitting diodes, laser diodes, vertical cavity surface emitting lasers (VCSEL's), micromirrors, accelerometers, pressure sensors, flow sensors, CMOS imaging arrays, CCD cameras, electronic logic, microprocessors, thermistors, Peltier coolers, waveguides, resistive heaters, chemical sensors, strain gauges, inductors, actuators (including electrostatic, magnetic, electromagnetic, bimetallic, piezoelectric, shape-memory-alloy based, and others), coils, magnets, electromagnets, magnetic sensors (such as those used in hard drives, superconducting quantum interference devices (SQUIDS) and other types), radio frequency sources and receivers, microwave frequency sources and receivers, sources and receivers for other regions of the electromagnetic spectrum, radioactive particle counters, and electrometers.

As is well known in the art, a vast variety of technologies can be utilized to fabricate active features in semiconductor and other types of hard substrates, including but not limited printed circuit board (PCB) technology, CMOS, surface micromachining, bulk micromachining, printable polymer electronics, and TFT and other amorphous/polycrystalline techniques as are employed to fabricate laptop and flat screen displays.

A variety of approaches can be employed to seal the elastomeric structure against the nonelastomeric substrate, ranging from the creation of a Van der Waals bond between the elastomeric and nonelastomeric components, to creation of covalent or ionic bonds between the elastomeric and nonelastomeric components of the composite structure. Example approaches to sealing the components together are discussed below, approximately in order of increasing strength.

A first approach is to rely upon the simple hermetic seal resulting from Van der Waals bonds formed when a substantially planar elastomer layer is placed into contact with a substantially planar layer of a harder, non-elastomer material. In one embodiment, bonding of RTV elastomer to a glass substrate created a composite structure capable of withstanding up to about 3-4 psi of pressure. This may be sufficient for many potential applications.

A second approach is to utilize a liquid layer to assist in bonding. One example of this involves bonding elastomer to a hard glass substrate, wherein a weakly acidic solution (5 µl HCl in $H_2O$, pH 2) was applied to a glass substrate. The elastomer component was then placed into contact with the glass substrate, and the composite structure baked at 37° C. to remove the water. This resulted in a bond between elastomer and non-elastomer able to withstand a pressure of about 20 psi. In this case, the acid may neutralize silanol groups present on the glass surface, permitting the elastomer and non-elastomer to enter into good Van der Waals contact with each other.

Exposure to ethanol can also cause device components to adhere together. In one embodiment, an RTV elastomer material and a glass substrate were washed with ethanol and then dried under Nitrogen. The RTV elastomer was then placed into contact with the glass and the combination baked for 3 hours at 80° C. Optionally, the RTV may also be exposed to a vacuum to remove any air bubbles trapped between the slide and the RTV. The strength of the adhesion between elastomer and glass using this method has withstood pressures in excess of 35 psi. The adhesion created using this method is not permanent, and the elastomer may be peeled off of the glass, washed, and resealed against the glass. This ethanol washing approach can also be employed used to cause successive layers of elastomer to bond together with sufficient strength to resist a pressure of 30 psi. In alternative embodiments, chemicals such as other alcohols or diols could be used to promote adhesion between layers.

An embodiment of a method of promoting adhesion between layers of a microfabricated structure in accordance with the present invention comprises exposing a surface of a first component layer to a chemical, exposing a surface of a second component layer to the chemical, and placing the surface of the first component layer into contact with the surface of the second elastomer layer.

A third approach is to create a covalent chemical bond between the elastomer component and functional groups introduced onto the surface of a nonelastomer component. Examples of derivitization of a nonelastomer substrate surface to produce such functional groups include exposing a glass substrate to agents such as vinyl silane or aminopropyltriethoxy silane (APTES), which may be useful to allow bonding of the glass to silicone elastomer and polyurethane elastomer materials, respectively.

A fourth approach is to create a covalent chemical bond between the elastomer component and a functional group native to the surface of the nonelastomer component. For example, RTV elastomer can be created with an excess of vinyl groups on its surface. These vinyl groups can be caused to react with corresponding functional groups present on the exterior of a hard substrate material, for example the Si—H bonds prevalent on the surface of a single crystal silicon substrate after removal of native oxide by etching. In this example, the strength of the bond created between the elastomer component and the nonelastomer component has been observed to exceed the materials strength of the elastomer components.

14. Cell Pen/Cell Cage

In yet a further application of the present invention, an elastomeric structure can be utilized to manipulate organisms or other biological material. FIGS. 26A-26D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 26A:
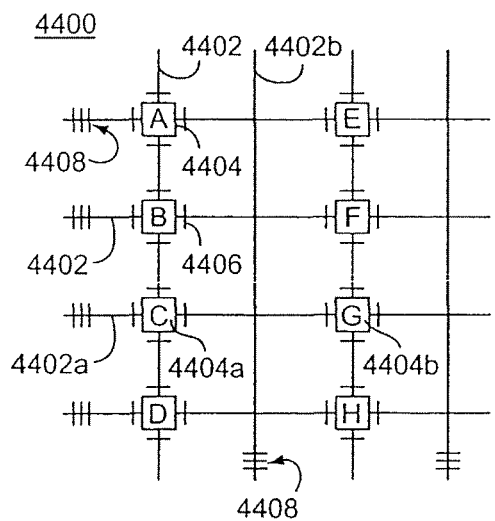
FIGS. 26A-26D show plan views illustrating operation of one embodiment of a cell pen structure in accordance with the present invention.
Figure 26C:
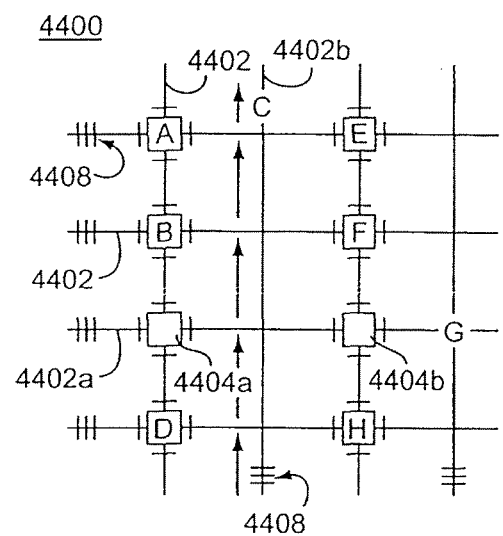
Figure 26B:
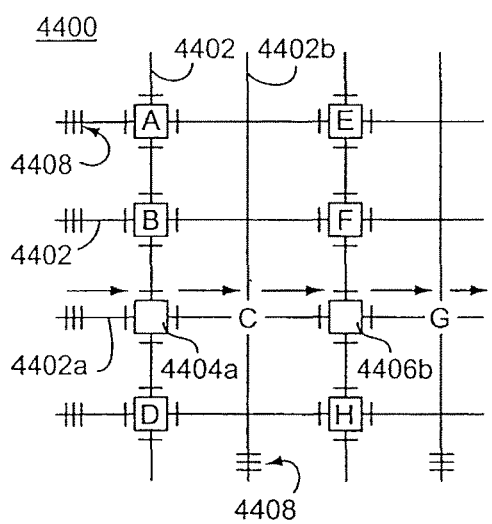
Figure 26D:
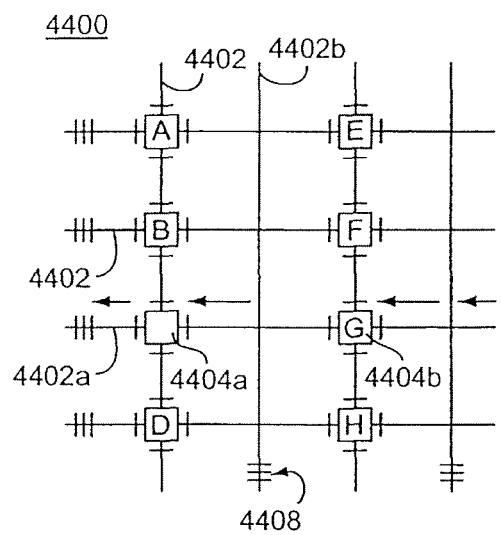

Cell pen array 4400 of FIG. 26A has been loaded with cells A-H that have been previously sorted. FIGS. 26B-26C show the accessing and removal of individually stored cell C by 1) opening valves 4406 on either side of adjacent pens 4404*a* and 4404*b*, 2) pumping horizontal flow channel 4402*a* to displace cells C and G, and then 3) pumping vertical flow channel 4402*b* to remove cell C. FIG. 26D shows that second cell G is moved back into its prior position in cell pen array 4400 by reversing the direction of liquid flow through horizontal flow channel 4402*a*.

Figure 27A:
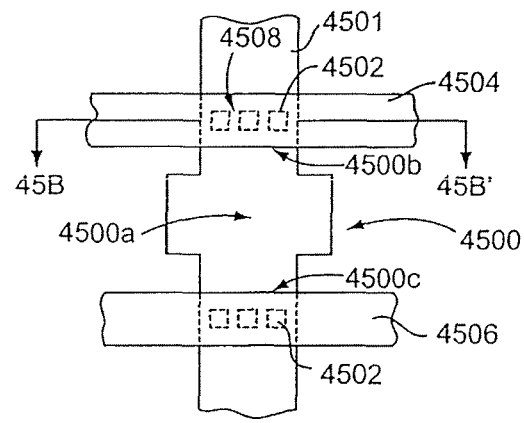
FIGS. 27A-27B show plan and cross-sectional views illustrating operation of one embodiment of a cell cage structure in accordance with the present invention.
Figure 27B:
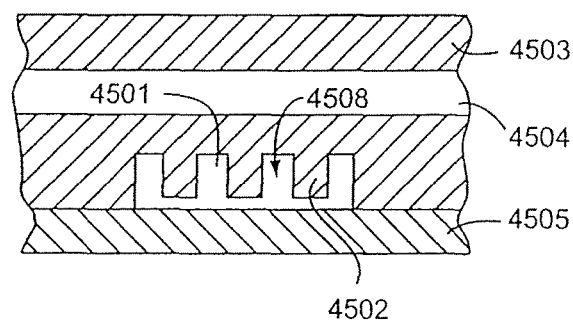

The cell pen array 4404 described above is capable of storing materials within a selected, addressable position for ready access. However, living organisms such as cells may require a continuous intake of foods and expulsion of wastes in order to remain viable. Accordingly, FIGS. 27A and 27B show plan and cross-sectional views (along line 45B-45B') respectively, of one embodiment of a cell cage structure in accordance with the present invention.

Cell cage 4500 is formed as an enlarged portion 4500*a* of a flow channel 4501 in an elastomeric block 4503 in contact with substrate 4505. Cell cage 4500 is similar to an individual cell pen as described above in FIGS. 26A-26D, except that ends 4500*b* and 4500*c* of cell cage 4500 do not completely enclose interior region 4500*a*. Rather, ends 4500*a* and 4500*b* of cage 4500 are formed by a plurality of retractable pillars 4502. Pillars 4502 may be part of a membrane structure of a normally-closed valve structure as described extensively above in connection with FIGS. 21A-21J.

Specifically, control channel 4504 overlies pillars 4502. When the pressure in control channel 4504 is reduced, elastomeric pillars 4502 are drawn upward into control channel 4504, thereby opening end 4500*b* of cell cage 4500 and permitting a cell to enter. Upon elevation of pressure in control channel 4504, pillars 4502 relax downward against substrate 4505 and prevent a cell from exiting cage 4500.

Elastomeric pillars 4502 are of a sufficient size and number to prevent movement of a cell out of cage 4500, but also include gaps 4508 which allow the flow of nutrients into cage interior 4500*a* in order to sustain cell(s) stored therein. Pillars 4502 on opposite end 4500*c* are similarly configured beneath second control channel 4506 to permit opening of the cage and removal of the cell as desired.

The cross-flow channel architecture illustrated shown in FIGS. 26A-26D can be used to perform functions other than the cell pen just described. For example, the cross-flow channel architecture can be utilized in mixing applications.

Figure 28A:
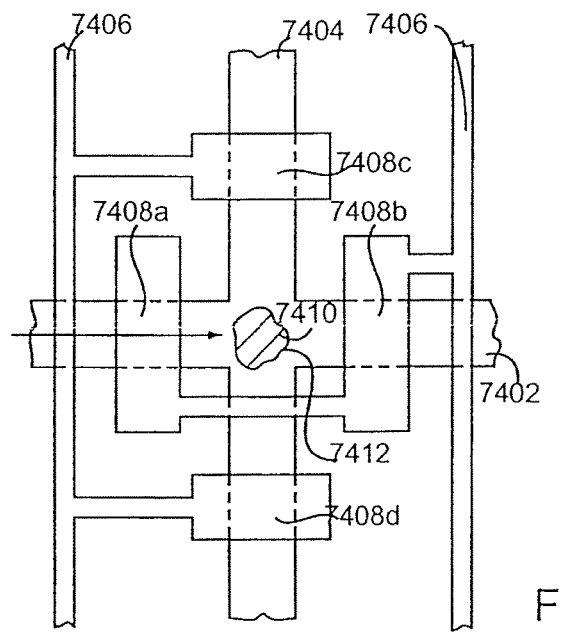
FIGS. 28A-28B show plan views of operation of a wiring structure utilizing cross-channel injection in accordance with the embodiment of the present invention.
Figure 28B:
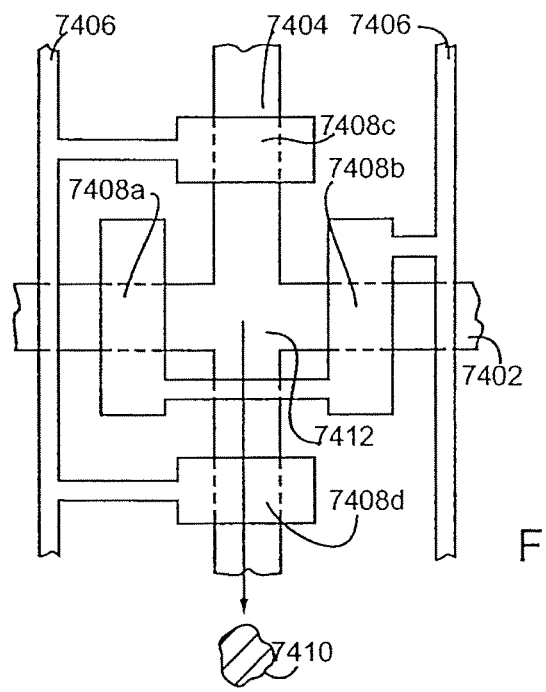

This is shown in FIGS. 28A-B, which illustrate a plan view of mixing steps performed by a microfabricated structure in accordance another embodiment of the present invention. Specifically, portion 7400 of a microfabricated mixing structure comprises first flow channel 7402 orthogonal to and intersecting with second flow channel 7404. Control channels 7406 overlie flow channels 7402 and 7404 and form valve pairs 7408a-b and 7408c-d that surround each intersection 7412.

As shown in FIG. 28A, valve pair 7408a-b is initially opened while valve pair 7408c-d is closed, and fluid sample 7410 is flowed to intersection 7412 through flow channel 7402. Valve pair 7408c-d is then actuated, trapping fluid sample 7410 at intersection 7412.

Figure 44:
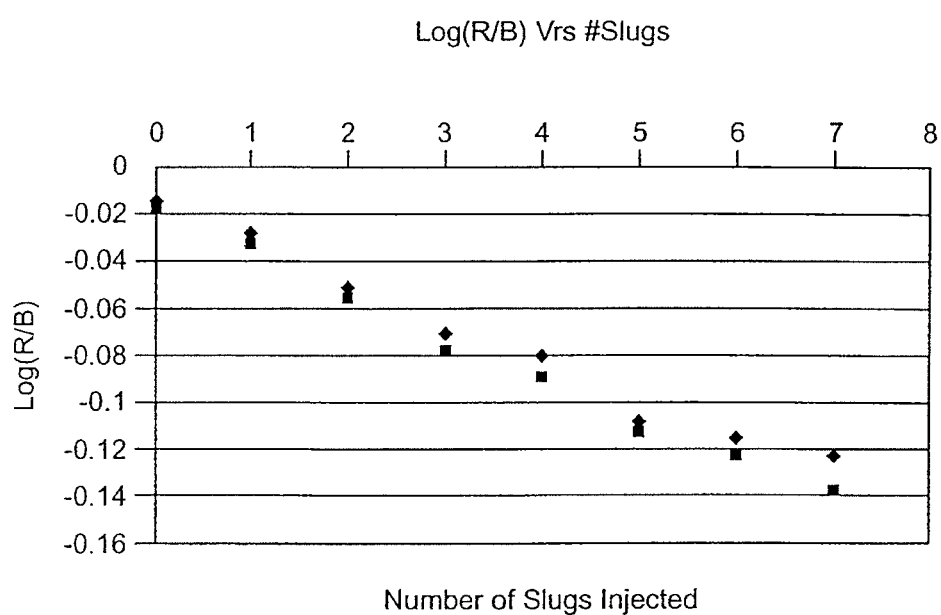
FIG. 44 plots Log(R/B) vs. number of slugs injected for one embodiment of a cross-flow injection system in accordance with the present invention.
Figure 82:
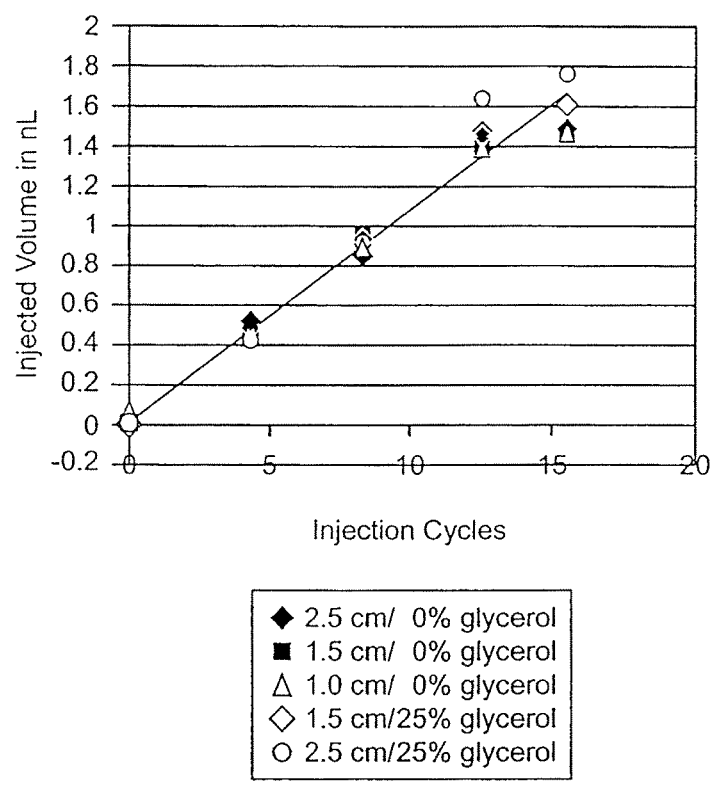
FIG. 82 plots injected volume versus number of injection cycles for cross-channel flow injection over a variety of flow conditions.

Next, as shown in FIG. 28B, valve pairs 7408a-b and 7408c-d are opened, such that fluid sample 7410 is injected from intersection 7412 into flow channel 7404 bearing a cross-flow of fluid. The process shown in FIGS. 28A-B can be repeated to accurately dispense any number of fluid samples down cross-flow channel 7404. FIG. 44 plots Log(R/B) vs. number of slugs injected for one embodiment of a cross-flow injection system in accordance with the present invention. The reproducibility and relative independence of metering by cross-flow injection from process parameters such as flow resistance is further evidenced by FIG. 82, which plots injected volume versus number of injection cycles for cross-channel flow injection under a variety of flow conditions. FIG. 82 shows that volumes metered by cross-flow injection techniques increase on a linear basis over a succession of injection cycles. This linear relationship between volume and number of injection cycles is relatively independent of flow resistance parameters such as elevated fluid viscosity (imparted by adding 25% glycerol) and the length of the flow channel (1.0-2.5 cm).

While the embodiment shown and described above in connection with FIGS. 28A-28B utilizes linked valve pairs on opposite sides of the flow channel intersections, this is not required by the present invention. Other configurations, including linking of adjacent valves of an intersection, or independent actuation of each valve surrounding an intersection, are possible to provide the desired flow characteristics. With the independent valve actuation approach however, it should be recognized that separate control structures would be utilized for each valve, complicating device layout.

15. Metering by Volume Exclusion

Many high throughput screening and diagnostic applications call for accurate combination and of different reagents in a reaction chamber. Given that it is frequently necessary to prime the channels of a microfluidic device in order to ensure fluid flow, it may be difficult to ensure mixed solutions do not become diluted or contaminated by the contents of the reaction chamber prior to sample introduction.

Volume exclusion is one technique enabling precise metering of the introduction of fluids into a reaction chamber. In this approach, a reaction chamber may be completely or partially emptied prior to sample injection. This method reduces contamination from residual contents of the chamber contents, and may be used to accurately meter the introduction of solutions in a reaction chamber.

Figure 29A:
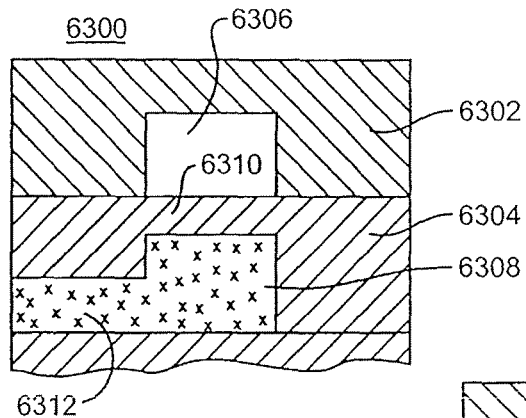
FIGS. 29A-29D illustrate cross-sectional views of metering by volume exclusion in accordance with an embodiment of the present invention.

Specifically, FIGS. 29A-29D show cross-sectional views of a reaction chamber in which volume exclusion is employed to meter reactants. FIG. 29A shows a cross-sectional view of portion 6300 of a microfluidic device comprising first elastomer layer 6302 overlying second elastomer layer 6304. First elastomer layer 6302 includes control chamber 6306 in fluid communication with a control channel (not shown). Control chamber 6306 overlies and is separated from dead-end reaction chamber 6308 of second elastomer layer 6304 by membrane 6310. Second elastomer layer 6304 further comprises flow channel 6312 leading to dead-end reaction chamber 6308.

Figure 29B:
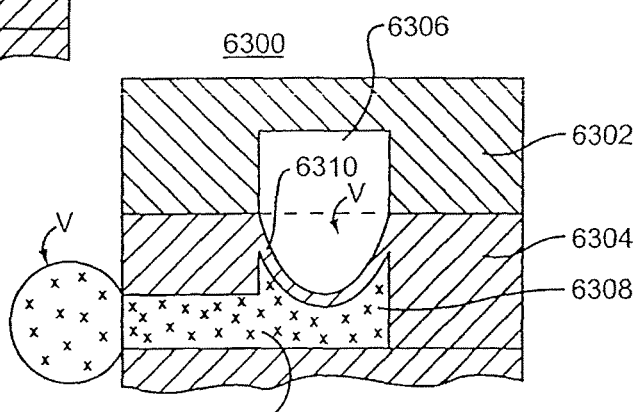

FIG. 29B shows the result of a pressure increase within control chamber 6306. Specifically, increased control chamber pressure causes membrane 6310 to flex downward into reaction chamber 6308, reducing by volume V the effective volume of reaction chamber 6308. This in turn excludes an equivalent volume V of reactant from reaction chamber 6308, such that volume V of first reactant X is output from flow channel 6312. The exact correlation between a pressure increase in control chamber 6306 and the volume of material output from flow channel 6312 can be precisely calibrated.

Figure 29C:
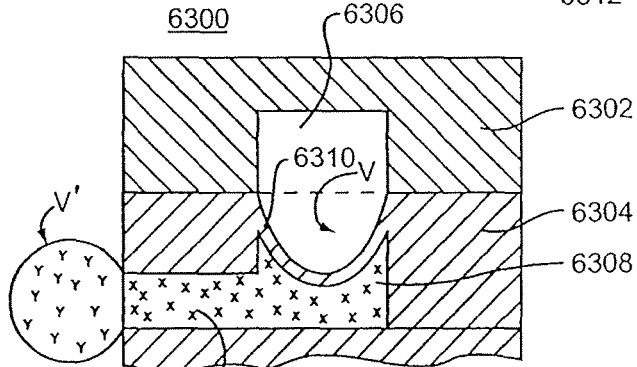

As shown in FIG. 29C, while elevated pressure is maintained within control chamber 6306, volume V' of second reactant Y is placed into contact with flow channel 6312 and reaction chamber 6308.

Figure 29D:
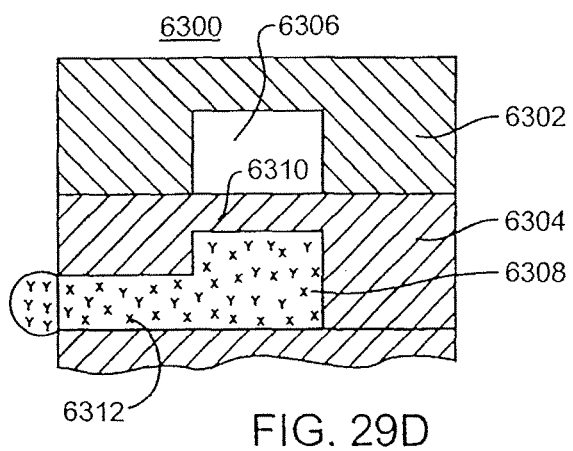

In the next step shown in FIG. 29D, pressure within control chamber 6306 is reduced to original levels. As a result, membrane 6310 relaxes and the effective volume of reaction chamber 6308 increases. Volume V of second reactant Y is sucked into the device. By varying the relative size of the reaction and control chambers, it is possible to accurately mix solutions at a specified relative concentration. It is worth noting that the amount of the second reactant Y that is sucked into the device is solely dependent upon the excluded volume V, and is independent of volume V' of Y made available at the opening of the flow channel.

While FIGS. 29A-29D show a simple embodiment of the present invention involving a single reaction chamber, in more complex embodiments parallel structures of hundreds or thousands of reaction chambers could be actuated by a pressure increase in a single control line.

Moreover, while the above description illustrates two reactants being combined at a relative concentration that fixed by the size of the control and reaction chambers, a volume exclusion technique could be employed to combine several reagents at variable concentrations in a single reaction chamber. One possible approach is to use several, separately addressable control chambers above each reaction chamber. An example of this architecture would be to have ten separate control lines instead of a single control chamber, allowing ten equivalent volumes to be pushed out or sucked in.

Another possible approach would utilize a single control chamber overlying the entire reaction chamber, with the effective volume of the reaction chamber modulated by varying the control chamber pressure. In this manner, analog control over the effective volume of the reaction chamber is possible. Analog volume control would in turn permit the combination of many solutions reactants at arbitrary relative concentrations.

An embodiment of a method of metering a volume of fluid in accordance with the present invention comprises providing a chamber having a volume in an elastomeric block separated from a control recess by an elastomeric membrane, and supplying a pressure to the control recess such that the membrane is deflected into the chamber and the volume is reduced by a calibrated amount, thereby excluding from the chamber the calibrated volume of fluid.

II. Crystallization Structures and Methods

High throughput screening of crystallization of a target material, or purification of small samples of target material by recrystallization, is accomplished by simultaneously introducing a solution of the target material at known concentrations into a plurality of chambers of a microfabricated fluidic device. The microfabricated fluidic device is then manipulated to vary solution conditions in the chambers, thereby simultaneously providing a large number of crystallization environments. Control over changed solvent conditions may result from a variety of techniques, including but not limited to metering of volumes of a crystallizing agent into the chamber by volume exclusion, by entrapment of liquid volumes determined by the dimensions of the microfabricated structure, or by cross-channel injection into a matrix of junctions defined by intersecting orthogonal flow channels.

Crystals resulting from crystallization in accordance with embodiments of the present invention can be utilized for x-ray crystallography to determine three-dimensional molecular structure. Alternatively, where high throughput screening in accordance with embodiments of the present invention does not produce crystals of sufficient size for direct x-ray crystallography, the crystals can be utilized as seed crystals for further crystallization experiments. Promising screening results can also be utilized as a basis for further screening focusing on a narrower spectrum of crystallization conditions, in a manner analogous to the use of standardized sparse matrix techniques.

Systems and methods in accordance with embodiments of the present invention are particularly suited to crystallizing larger biological macromolecules or aggregates thereof, such as proteins, nucleic acids, viruses, and protein/ligand complexes. However, crystallization in accordance with the present invention is not limited to any particular type of target material.

As employed in the following discussion, the term "crystallizing agent" describes a substance that is introduced to a solution of target material to lessen solubility of the target material and thereby induce crystal formation. Crystallizing agents typically include countersolvents in which the target exhibits reduced solubility, but may also describe materials affecting solution pH or materials such as polyethylene glycol that effectively reduce the volume of solvent available to the target material. The term "countersolvent" is used interchangeably with "crystallizing agent".

1. Crystallization by Volume Exclusion

Figure 30:
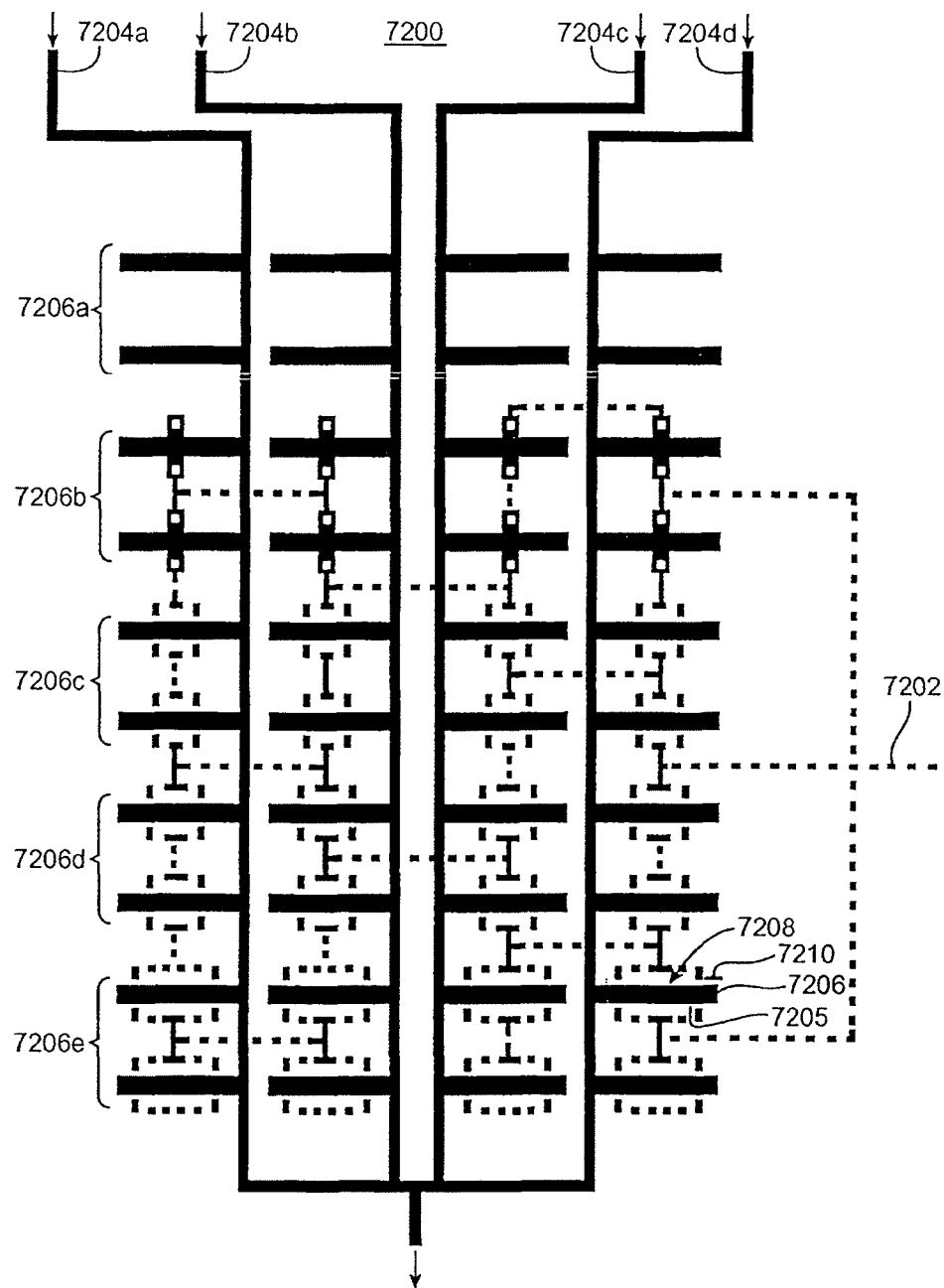
FIG. 30 is a plan view of one embodiment of a recrystallization system in accordance with one embodiment of the present invention utilizing volume exclusion.

FIG. 30 shows a plan view of one embodiment of a crystallization system that allows mass crystallization attempts employing the volume exclusion technique described in conjunction with prior FIGS. 29A-D.

Crystallization system 7200 comprises control channel 7202 and flow channels 7204a, 7204b, 7204c, and 7204d. Each of flow channels 7204a, 7204b, 7204c, and 7204d feature dead-end chambers 7206 that serve as the site for crystallization. Control channel 7202 features a network of control chambers 7205 of varying widths that overlie and are separated from chambers 7206 by membranes 7208 having the same widths as control chambers 7205. Although not shown to clarify the drawing, a second control featuring a second network of membranes may be utilized to create stop valves for selectively opening and closing the openings to dead-end chambers 7206. A full discussion of the function and role of such stop valves is provided below in conjunction with FIG. 31.

Operation of crystallization system 7200 is as follows. Initially, an aqueous solution containing the target protein is flushed through each of flow channels 7204a, 7204b, 7204c, and 7204d, filling each dead-end chamber 7206. Next, a high pressure is applied to control channel 7202 to deflect membranes 7208 into the underlying chambers 7206, excluding a given volume from chamber 7206 and flushing this excluded volume of the original protein solution out of chamber 7206.

Next, while pressure is maintained in control channel 7202, a different countersolvent is flowed into each flow channel 7204a, 7204b, 7204c, and 7204d. Pressure is then released in control line 7202, and membranes 7208 relax back into their original position, permitting the formerly excluded volume of countersolvent to enter chambers 7206 and mix with the original protein solution. Because of the differing widths of control chambers 7205 and underlying membranes 7208, a variety of volumes of the countersolvent enters into chambers 7206 during this process.

For example, chambers 7206a in the first two rows of system 7200 do not receive any countersolvent because no volume is excluded by an overlying membrane. Chambers 7106b in the second two rows of system 7200 receive a volume of countersolvent that is 1:5 with the original protein solution. Chambers 7206c in the third two rows of system 7200 receive a volume of countersolvent that is 1:3 with the original protein solution. Chambers 7206d in the fourth two rows of system 7200 receive a volume of countersolvent that is 1:2 with the original protein solution, and chambers 7206e in the fifth two rows of system 7200 receive a volume of countersolvent that is 4:5 with the original protein solution.

Once the countersolvent has been introduced into the chambers 7206, they may be resealed against the environment by again applying a high pressure to control line 7202 to deflect the membranes into the chambers. Resealing may be necessary given that crystallization can require on the order of days or weeks to occur. Where visual inspection of a chamber reveals the presence of a high quality crystal, the crystal may be physically removed from the chamber of the disposable elastomer system.

2. Crystallization by Volume Entrapment

Figure 31:
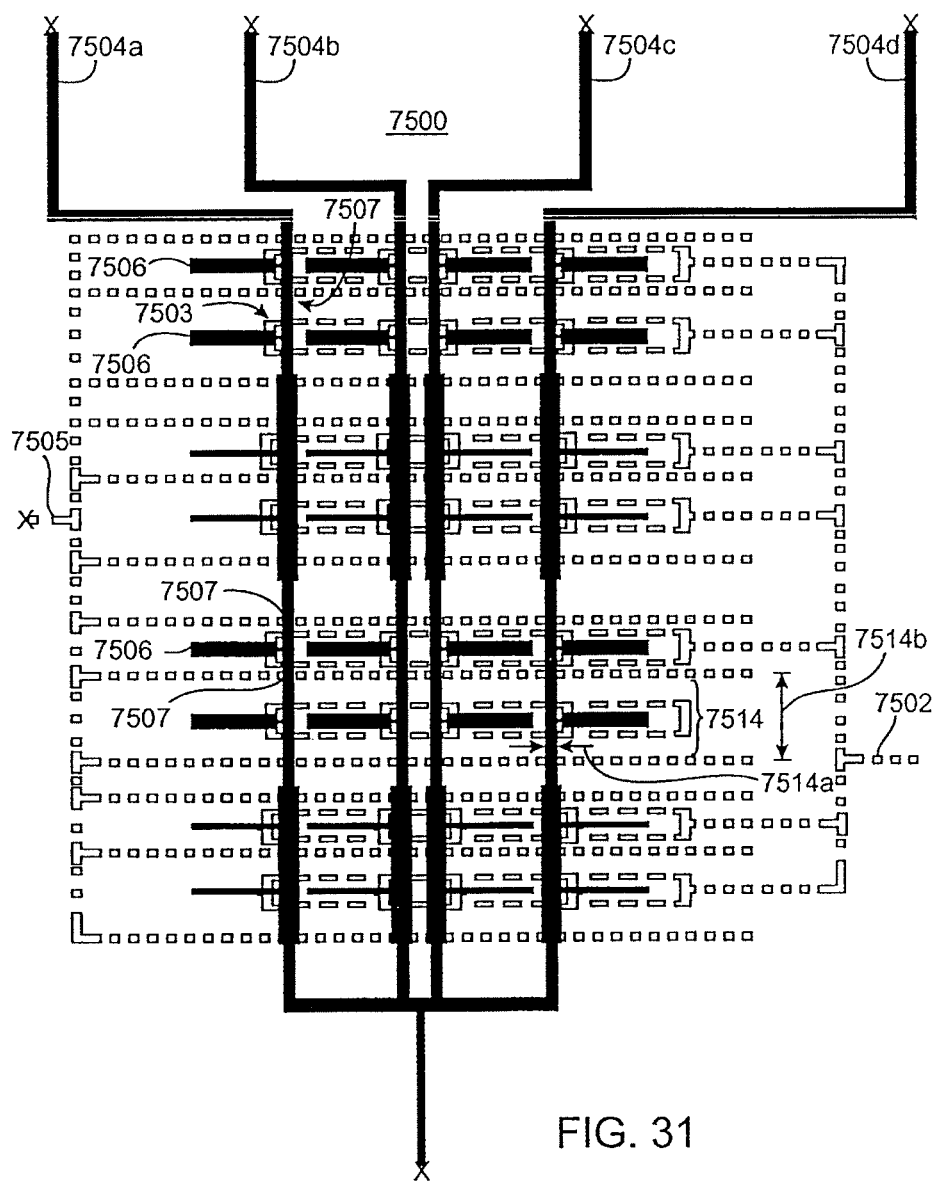
FIG. 31 is a plan view of one embodiment of a recrystallization system in accordance with the present invention utilizing volume entrapment.

While the above description has described a crystallization system that relies upon volume exclusion to meter varying amounts of countersolvent, the invention is not limited to this particular embodiment. Accordingly, FIG. 31 shows a plan view of an alternative crystallization system wherein metering of different volumes of countersolvent is determined by photolithography during formation of the flow channels.

Crystallization system 7500 comprises flow channels 7504a, 7504b, 7504c, and 7504d. Each of flow channels 7504a, 7504b, 7504c, and 7504d feature dead-end chambers 7506 that serve as the site for recrystallization.

System 7500 further comprises two sets of control channels. First set 7502 of control channels overlie the opening of chambers 7506 and define stop valves 7503 that, when actuated, block access to chambers 7506. Second control channels 7505 overlie flow channels 7504a-d and define segment valves 7507 that, when actuated, block flow between different segments 7514 of a flow channel 7404.

Operation of crystallization system 7500 is as follows. Initially, an aqueous solution containing the target protein is flushed through each of flow channels 7504a, 7504b, 7504c, and 7504d, filling dead-end chambers 7506. Next, a high pressure is applied to control channel 7502 to actuate stop valves 7503, thereby preventing fluid from entering or exiting chambers 7506.

While maintaining stop valves 7503 closed, each flow channel 7504a-d is then filled with a different countersolvent. Next, second control line 7505 is pressurized, isolating flow channels 7504a-d into segments 7514 and trapping differing volumes of countersolvent. Specifically, as shown in FIG. 31 segments 7514 are of unequal volumes. During formation of protein crystallization structure 7500 by soft lithography, photolithographic techniques are employed to define flow channels 7504*a-d* having segments 7514 of different widths 7514*a* and lengths 7514*b*.

Thus, when pressure is released from first control line 7502 and stop valves 7503 open, a different volume of countersolvent from the various segments 7514 may diffuse into chambers 7506. In this manner, precise dimensions defined by photolithography can be employed to determine the volume of countersolvent trapped in the flow channel segments and then introduced to the protein solution. This volume of countersolvent in turn establishes the environment for crystallization of the protein.

While the crystallization system described in connection with FIG. 31 utilizes the dimensions of the flow channels to dictate the volumes of countersolvents introduced into the crystallization chamber, the present invention is not limited to this approach.

Figure 32:
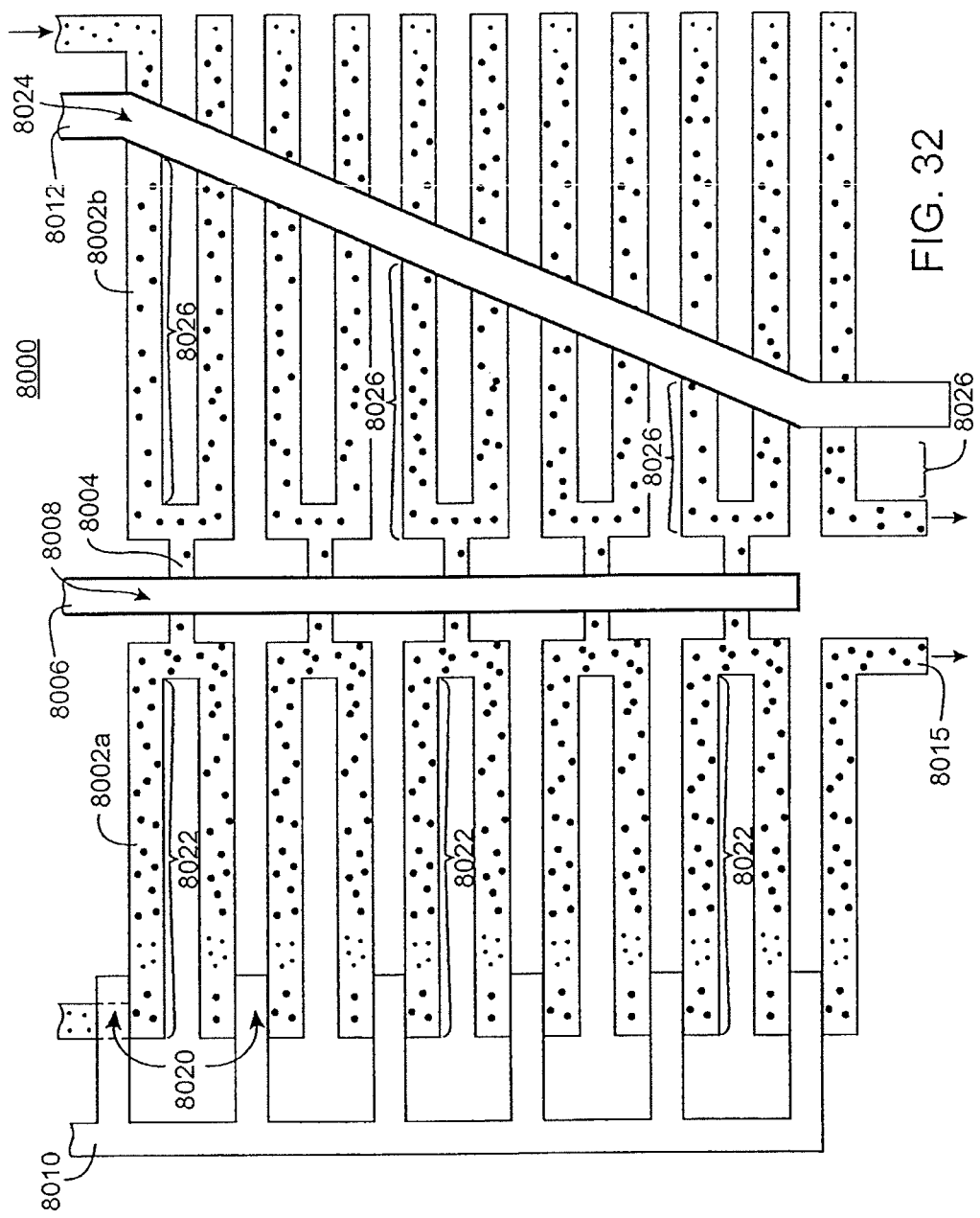
FIG. 32 is a plan view of an alternative embodiment of a recrystallization system in accordance with the present invention utilizing volume entrapment.

FIG. 32 shows a microfabricated crystallization system wherein the volumes of countersolvent metered to the recrystallization chambers is dictated by the angle of orientation of a control channel relative to underlying flow channels. Specifically, microfabricated crystallization system 8000 includes adjacent serpentine flow channels 8002*a* and 8002*b* connected through a series of bridging channels 8004. First control line 8006 overlies bridging channels 8004 and thereby forms valves 8008 isolating serpentine channels 8002*a* and 8002*b* from each other. Second control line 8010 includes projections over portions of first serpentine channel 8002*a* defining valves 8020.

Initially, first control line 8006 is closed while second and third control lines 8010 and 8012 remain open. First serpentine channel 8002*a* is filled with target material solution through inlet 8014. While first serpentine channel 8002*a* of FIG. 31 is depicted as having an outlet 8015, channel 8002*a* may also be dead-ended. Second serpentine channel 8002*b* is filled with a countersolvent to be mixed with the target material solution. As with first serpentine channel 8002*a*, second serpentine channel 8002*b* may also terminate at an outlet or a dead end.

Next, second control channel 8010 is activated to close valves 8020, thereby isolating equal volumes of target solution trapped in region 8022. Third control channel 8012 is also activated to close valves 8024, thereby isolating countersolvent trapped in region 8026*b*. However, because third control channel 8012 runs obliquely across second serpentine channel 8002*b*, the volumes of countersolvent entrapped between valves 8008 and 8024 is unequal and becomes progressively smaller.

Next, first control channel 8006 is activated and valves 8008 opened. The volumes of countersolvent entrapped in region 8026 are now free to diffuse into the volume of sample entrapped in region 8022, with the respective ratios of mixing determined by the relative angular orientation of third control channel 8012.

The crystallization system of FIG. 32 permits one type of countersolvent to be introduced to the sample through a single serpentine channel. However, in order to facilitate high throughput crystallization conditions, a series of crystallization systems as shown in FIG. 32 sharing a common sample source could be fabricated on a substrate, with different countersolvent provided to each system.

Moreover, other variations of crystallization system embodiment utilizing metering of countersolvent volume by entrapment are also possible. For example, in one alternative embodiment the relative volumes of a sample could be determined by the angle of orientation of the second control channel overlying the samples. Moreover, the shape of the flow channels on either side of the bridging channels could be modified to provide additional volume between successive valves. Other lithographically determined dimensions such as flow channel depth and width could also be controlled to affect the relative volumes of countersolvent and sample.

Figure 43:
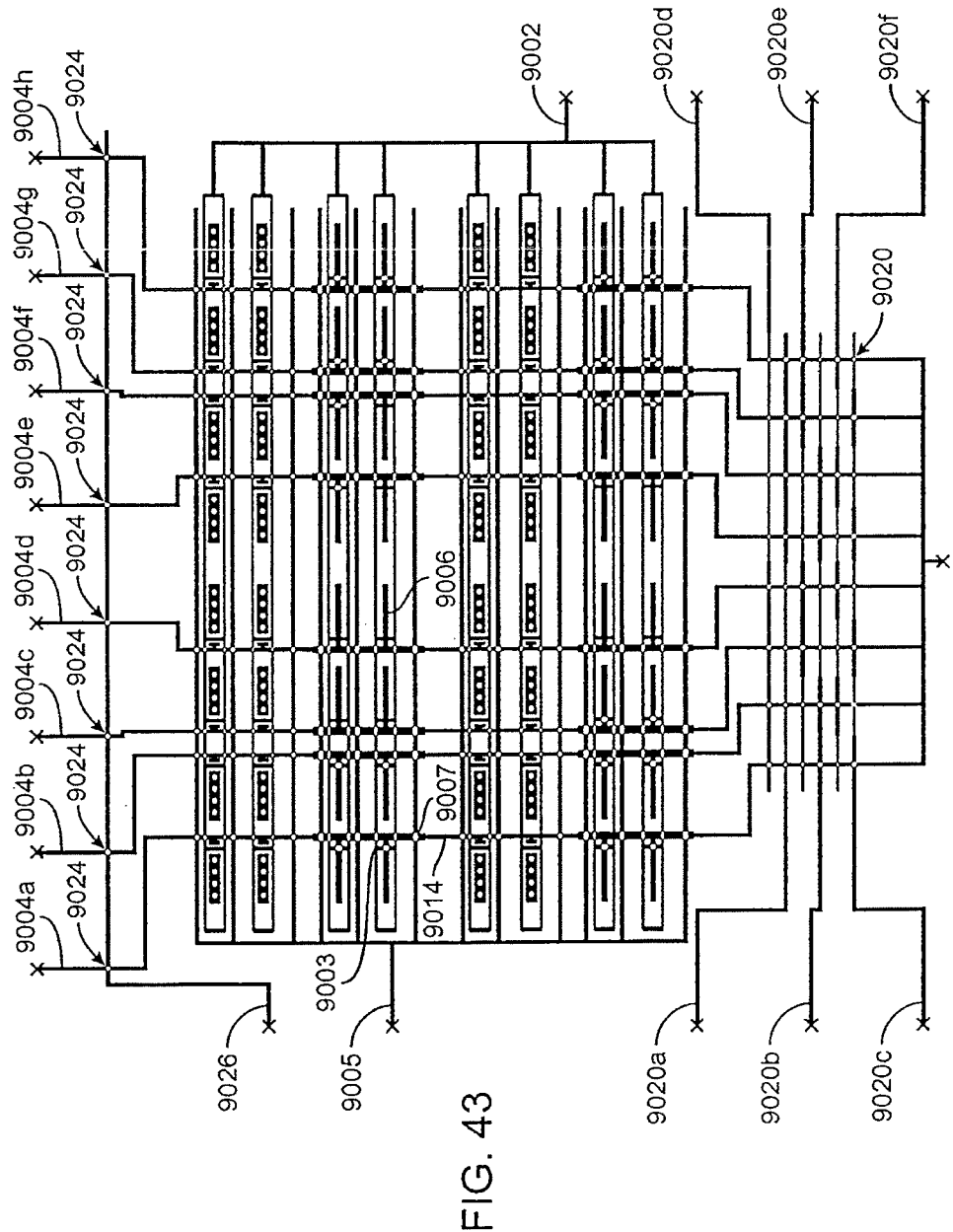
FIG. 43 is a plan view of an alternative embodiment of a recrystallization system in accordance with the present invention utilizing volume entrapment.

FIG. 43 is a plan view of an alternative embodiment of a recrystallization system in accordance with the present invention utilizing volume entrapment. The system of FIG. 43 is similar to that shown in FIG. 31, except that it includes a larger number of flow channels, along with several features that enhance control over the flow of materials down those channels.

Crystallization system 9000 comprises flow channels 9004*a*, 9004*b*, 9004*c*, 9004*d*, 9004*e*, 9004*f*, 9004*g*, and 9004*h*. Each of flow channels 9004*a-h* feature dead-end chambers 9006 that serve as the site for recrystallization. The protein crystallization structure illustrated in this embodiment of the present invention may utilize less than 1 µL of sample while creating 64 1 nL recrystallization environments.

The flow of materials down each flow channel 9004*a-h* is controlled by several valve and pump structures. An initial set of gate valves 9024 is formed by the overlap of gate control channel 9026 over the upstream portions of respective flow channels 9004*a-h*.

A first set 9002 of control channels overlie the opening of chambers 9006 and define stop valves 9003 that, when actuated, block access to chambers 9006. Second control channels 9005 overlie flow channels 9004*a-h* and define segment valves 9007 that, when actuated, block flow between different segments 9014 of a flow channel 9004.

The operation of system 9000 is similar to that described above for the system of FIG. 31, with charging of chambers and segments with a sample volume, followed by introduction of volumes of countersolvent. However, Rather than utilizing a simultaneous flow of samples or countersolvents through all of the flow channels 8604, system 9000 includes multiplexer structure 9020 on the output side of the flow channel. Specifically, peristaltic pumping control channels 9020*a-f* of varying widths overlie the downstream ends of each of flow channels 9004*a-h*. By select manipulation of the pressure within pumping control channels 9020*a-f*, sample or countersolvents may be independently flowed down each of flow channels 9004*a-h*.

The enhanced precision in control over the flow of materials down the flow channels of the system offers a number of benefits. One benefit is reduced risk of cross-contamination. Because the flow channels are independently controlled and are in contact with one another only downstream of multiplexer structure 9020, incidental pressure differences arising between flow channels will not result in unwanted backflow of material between flow channels.

3. Crystallization by Cross-Channel Injection

The cross-flow channel architecture illustrated in prior FIGS. 26A-26D can be used to perform high throughput crystallization of a target material. This approach is shown in FIG. 33, which illustrates an alternative embodiment of a crystallization structure in accordance with the present invention.

Figure 33:
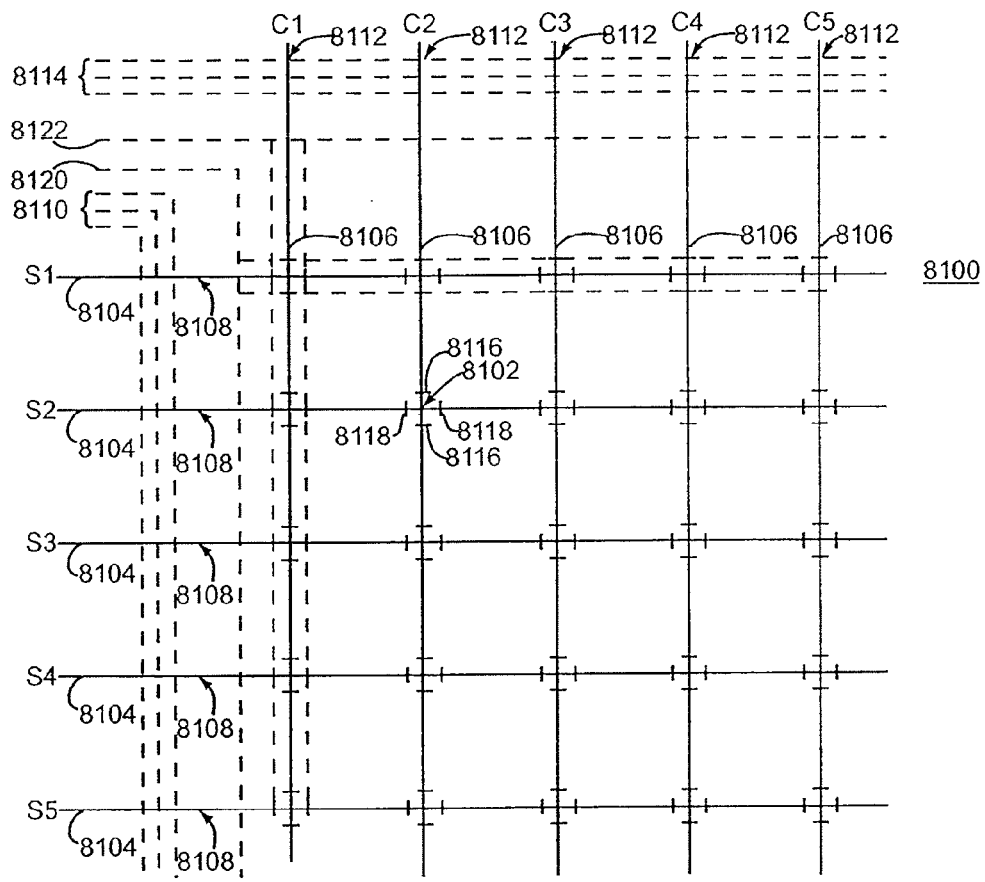
FIG. 33 is a plan view of a protein crystallization system in allowance with one embodiment in accordance with the present invention utilizing cross-channel injection.

The microfabricated cross-channel high throughput crystallization structure of FIG. 33 comprises a five-by-five array 8100 of cross-injection junctions 8102 formed by the intersection of parallel horizontal flow channels 8104 and parallel vertical flow channels 8106. Array 8100 enables the mixing and storage of each sample S1-S5 with each countersolvent C1-C5, for a total of 5×5=25 simultaneous crystallization conditions. Movement of the fluid along horizontal flow channels 8104 is controlled in parallel by peristaltic pumps 8108 formed by overlying control channels 8110. Movement of fluid along vertical flow channels 8106 is controlled in parallel by peristatic pump 8112 formed by overlying control channels 8114. As shown in prior FIG. 28A-B, column valves 8116 and row valves 8118 surround each junction 8102 formed by the intersection of horizontal and vertical flow lines 8104 and 8106.

Column valves 8116 blocking flow in the vertical direction are controlled by a single control line 8120. Row valves 8110 blocking flow in the horizontal direction are controlled a single control line 8122. For purposes of illustration, only the first portion of control lines 8120 and 8122 are shown in FIG. 33, it is to be understood that every row and column valve is controlled by these control lines.

During crystallization, horizontal flow channels 8104 introduce samples of five different concentrations of target material to junctions 8102, while vertical flow channels 8106 introduce to junctions 8102 five different concentrations and/or compositions of countersolvent. Through the metering technique described below in connection with FIGS. 34A-34C, all 5×5=25 possible combinations of sample and countersolvent are stored at the 5×5=25 junctions 8102 of array 8100.

Figure 34A:
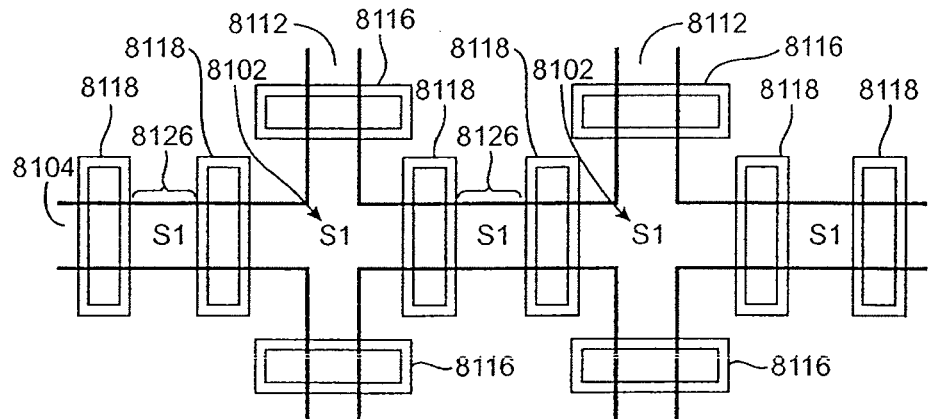
FIGS. 34A-34C are enlarged views of a portion of the recrystallization system of FIG. 32 showing its operation.
Figure 34B:
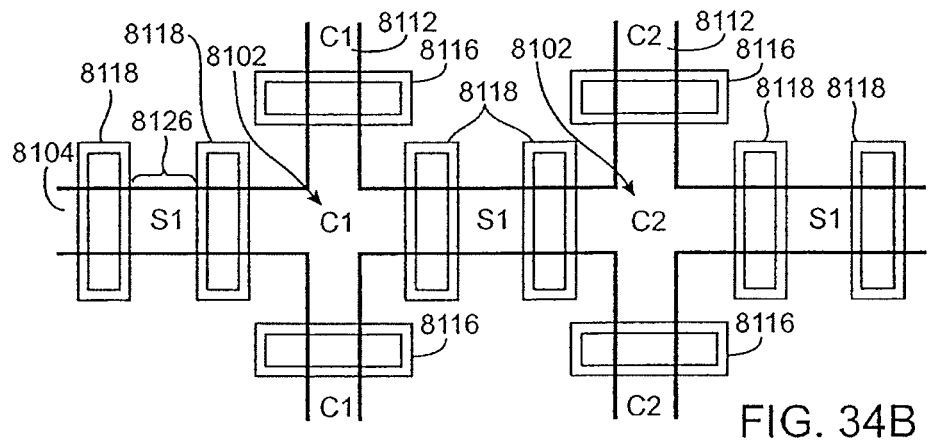
Figure 34C:
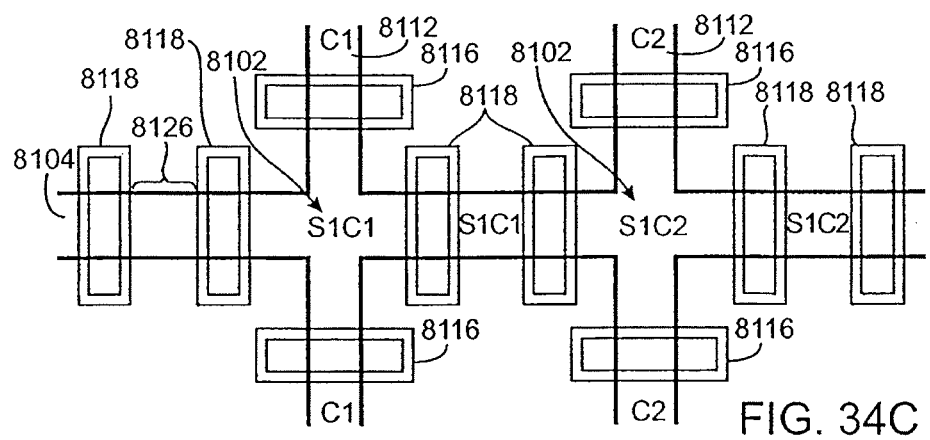

FIGS. 34A-34C show enlarged plan views of adjacent junctions of array 8100 of FIG. 32. For purposes of illustration, the control lines are omitted in FIGS. 34A-34C. Also, the lateral distance between junctions is considerably shortened, and in actuality the junctions would be separated by a considerable distance to prevent cross-contamination.

In a first step shown in FIG. 34A, column valves 8116 are closed and a sample of target material at a given concentration is flowed down first each of horizontal flow channels 8104. In the array portion shown enlarged in FIG. 34A, inter-row valve regions 8126 are thereby charged with sample material S1.

Next, as shown in FIG. 34B, row valves 8118 are closed, and column valves 8116 are opened. Countersolvents of different concentrations and/or compositions are flowed down each of vertical flow channels 8106. In the array portion enlarged in FIG. 34B, junctions 8102 are thereby charged with countersolvents C1 and C2.

As shown in FIG. 34C, column valves 8116 are closed and row valves 8118 are opened. Pumping of the peripheral peristaltic pumps of the array causes the sample in inter-valve regions 8126 to mingle with countersolvent of junctions 8102 as both are flowed into junctions 8102 and inter-valve regions 8126. Row valves 8118 are then closed as column valves 8116 are maintained closed to prevent cross-contamination between crystallization sites. In the array portion enlarged in FIG. 34C, crystallization may then take place in solvent environments S1C1 and S1C2.

In an alternative embodiment of the present invention, separate control lines could be used to control actuation of alternate row valves. In such an embodiment, once the inter-row valve regions and the junctions have been charged with sample and countersolvent as described above in FIGS. 34A and 34B, in the third step the alternate row valves are opened such that sample in inter-row valve regions mixes by diffusion with countersolvent in junctions. This alternative embodiment does not require pumping, and the closed state of the other set of alternate row valves prevents cross-contamination.

In yet another alternative embodiment of a structure for performing high-throughput crystallization screening in accordance with the present invention, a single control line may be utilized to control alternate row valves to define a plurality of crystallization screening chambers. This embodiment is shown in FIGS. 81A-81B.

Figure 81A:
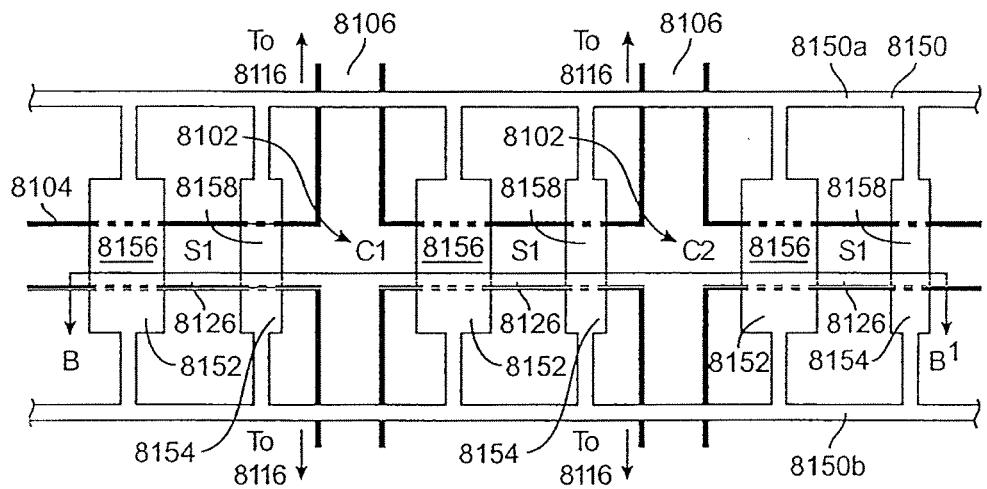
FIG. 81A shows an enlarged view of a portion of one flow channel in accordance with an alternative embodiment of the present invention.
Figure 81B:
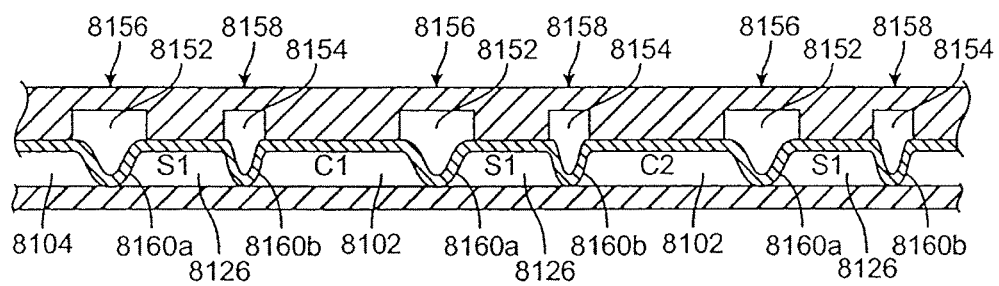
FIG. 81B shows cross-sectional view along line B-B' of the enlarged flow channel portion of FIG. 81A prior to deactuation of alternative row valves to allow diffusion between crystallizing agent and target material in adjacent chambers.
Figure 81C:
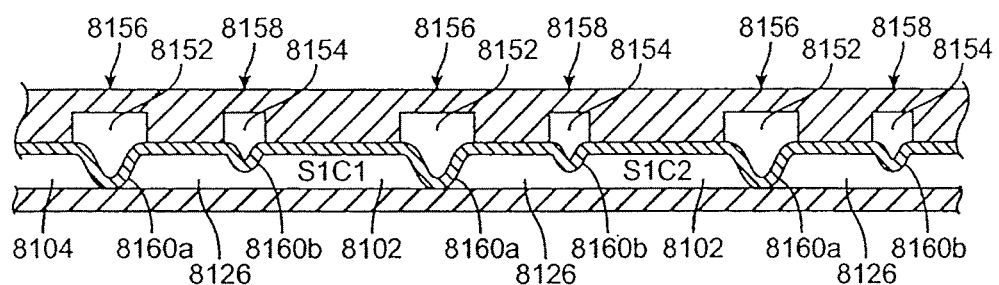
FIG. 81C shows cross-sectional view along line B-B' of the enlarged flow channel portion of FIG. 81A after deactuation of alternative row valves to allow diffusion between crystallizing agent and target material in adjacent chambers.

FIG. 81A shows an enlarged view of a portion of one flow channel in accordance with an alternative embodiment of the present invention. FIG. 81B shows cross-sectional view along line B-B' of the enlarged flow channel portion of FIG. 81A prior to deactuation of alternative row valves to allow diffusion between crystallizing agent and target material in adjacent chambers. FIG. 81C shows cross-sectional view along line B-B' of the enlarged flow channel portion of FIG. 81A after deactuation of alternative row valves to allow diffusion between crystallizing agent and target material in adjacent chambers.

Control line 8150 comprises parallel branches 8150a and 8150b positioned on either side of flow channel 8104. Branches 8150a-b are connected by alternating wide cross-over portions 8152 and narrow cross-over portions 8154, thereby defining large valves 8156 and small valves 8158, respectively. Because of the differing width of cross-over portions 8152 and 8154, elastomer membranes 8160a and 8160b of valves 8156 and 8158 are deactuated and actuated, respectively, when different pressures are applied to control line 8150.

Specifically, application of a highest pressure to control line 8150 will cause the deflection of both elastomer membranes 8160a and 8160b into the underlying flow channel 8104, closing both large valves 8156 and small valves 8158. Application of a lowest pressure to control line 8150 will cause both elastomer membranes 8160a and 8160b to relax out of the underlying flow channel 8104, opening both large valves 8156 and small valves 8158.

Due to their increased area, wide membranes 8160a are easier to actuate than narrow membranes 8160b. Accordingly, application of an intermediate pressure to control line 8150 will result in only wide membranes 8160a of large valve structures 8156 remaining actuated, with narrow membranes 8160b of small valve structures 8158 being deactuated to open the valve. This differential response to an applied pressure can allow the use of only one control line to define a plurality of crystallization screening chambers, and then to allow alternative valves along a horizontal flow channel to relax, permitting diffusion of target material and crystallizing agent.

During operation of the microfluidic structure shown in FIGS. 81A-C, as described above in connection with FIGS. 34A-B, in FIGS. 81A-B, flow channel junctions 8102 are filled with crystallizing agent and inter-valve regions 8126 are filled with target sample by applying high and low pressures to the control line 8150.

As shown in FIG. 81C, when an intermediate pressure is applied to control line 8150, narrow membranes 8160a of small valve structures 8158 to relax out of flow channel 8104, while wide membranes 8160a of large valve structures 8156 remain within flow channel 8104 to prevent cross-contamination between adjacent crystallization sites.

4. Crystallization Utilizing Diffusion/Dialysis

One conventional approach to crystallization has been to effect a gradual change in target solution conditions by introducing a crystallizing agent through slow diffusion, or slow diffusion in conjunction with dialysis. For example, in the crystallization of proteins, imposing a dialysis membrane between sample and crystallizing agent results in diffusion of crystallizing agent into the protein solution without reduction in concentration of the protein sample.

Crystallization methods and structures in accordance with embodiments of the present invention utilizing slow diffusion and/or dialysis may employ a variety of techniques. Several possible approaches are described below.

Figure 35:
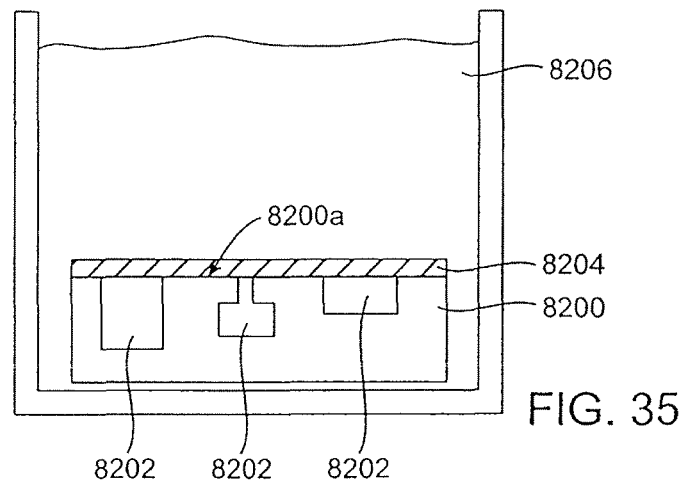
FIG. 35 is a cross-sectional view of one embodiment of a recrystallization system in accordance with the present invention utilizing a dialysis membrane.

In a first embodiment shown in FIG. 35, microfabricated elastomeric structure 8200 features chambers 8202 of varying volumes that may be initially charged with samples through pump/valve network. Chambers 8202 are also in fluid communication with face 8200a of structure 8200. Dialysis membrane 8204 is fixed to face 8200a, and then the entire microfabricated structure 8200 is immersed in bulk countersolvent reservoir 8200 as shown. Over time, countersolvent from reservoir 8206 diffuses across membrane 8204 and into chambers 8202 and solvent from the sample diffuses across membrane 8204 into reservoir 8206. Protein of the sample is prevented from diffusing by membrane 8204. When the desired solution conditions are achieved, a crystal may form in chamber 8202.

The advantage of this approach to crystallization is simplicity, in that once charged with sample, the microfabricated elastomeric structure is simply dunked in the countersolvent. This approach also enables direct monitoring of solution conditions, as the pH, temperature, and other aspects of the bulk countersolvent reservoir can be monitored for changes using conventional detection methods. Moreover, in alternative embodiments of the present invention, a continuous supply of dissolved target material may be flowed past the dialysis membrane to ensure an adequate supply for growth of large crystals.

Embodiments in accordance with the present invention may also be implemented in conjunction with double dialysis, wherein rate of change in condition of the target solution is slowed by imposing a second dialysis membrane and an intermediate solution between the crystallizing agent and the first dialysis membrane. In such an approach, the intermediate solution serves to buffer changes in the target solution arising from diffusion of crystallizing agent. In the technique just described, double dialysis could be accomplished by immersing the microfluidic structure and the associated dialysis membrane in an intermediate solution in fluid communication with a crystallizing agent reservoir through a second dialysis membrane.

Figure 36:
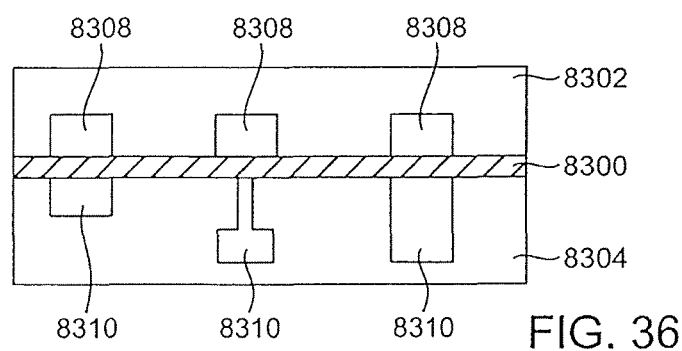
FIG. 36 is a cross-sectional view of another embodiment of a recrystallization system in accordance with the present invention utilizing a dialysis membrane.

A second embodiment of the present invention employing dialysis techniques is illustrated in FIG. 36. This approach utilizes dialysis membrane 8300 sandwiched between opposing microfabricated elastomeric structures 8302 and 8304. Upon assembly of this structure and proper alignment of respective chambers/channels 8306 of opposing structures 8302 and 8304, countersolvent from reservoirs 8308 of structure 8302 will diffuse across membrane 8300 into the corresponding recrystallization chamber 8310 of structure 8304. Solvent from crystallization chamber 8310 will correspondingly diffuse across membrane 8300 into reservoir 8308 of first structure 8302. However, protein in crystallization chamber 8310 will be prevented by membrane 8300 from similarly diffusing, and will thus be retained in chamber 8310 as the solution environment is changed.

Double dialysis employing a structure similar to that of FIG. 36 could be accomplished by fabricating an intermediate chamber between the crystallization chamber and the first dialysis membrane, and then filling this intermediate chamber with a buffer solution. A second dialysis membrane could be introduced into the microfabricated structure between the intermediate and crystallization chambers in the form of a plug of a cross-linked polymer, as described below in FIG. 37.

The embodiments just described in FIGS. 35 and 36 utilize large scale bonding of a dialysis membrane to an entire face of a microfabricated structure. However, other embodiments may utilize the insertion or placement of a dialysis membrane within local regions of a microfabricated structure. This is shown in FIG. 36, wherein a dialysis membrane is created within the microfabricated structure in the form of a polyacrylamide gel.

Figure 37:
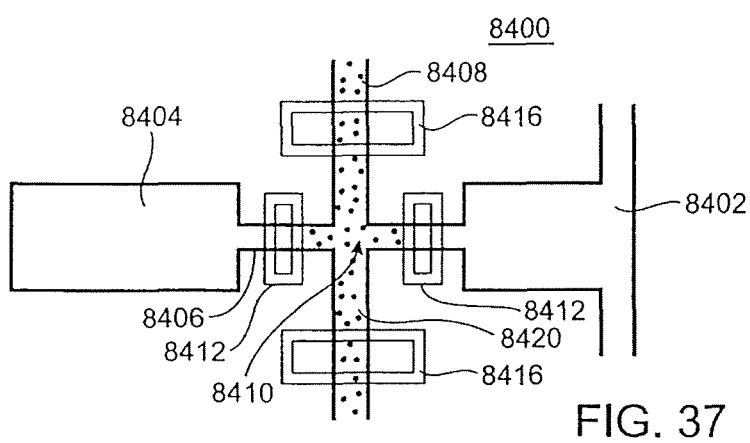
FIG. 37 is a plan view of still another embodiment of a recrystallization system in accordance with the present invention utilizing a dialysis membrane.

Specifically, recrystallization structure 8400 of FIG. 37 includes first chamber 8402 in fluid communication with dead-ended chamber 8404 through horizontal flow channel 8406. The intersection of horizontal flow channel 8406 and vertical flow channel 8408 creates junction 8410. First valve set 8412 is defined by the overlap of first control channel 8414 and portions 8416a of horizontal flow channel 8406 on opposite sides of junction 8410. Second valve set 8416 is defined by the overlap of second control channel 8418 and portions 8408a of vertical flow channel 8408 on opposite sides of junction 8410.

Operation of this embodiment is as follows. Second valve set 8416 is closed while first valve set 8412 is opened. Dead-ended chamber 8404 is charged with a sample through horizontal flow channel 8406.

Next, second valve set 8416 is opened and first valve set 8412 is closed. Vertical flow channel 8408 is charged with a cross-linkable polymer 8420 such as a polyacrylamide gel. Cross-linking of the polymer within vertical flow channel is then induced, for example by irradiation of the flow channel or by mixing slow acting cross-linking chemicals with the polymer prior or during charging of the vertical flow channel with gel. Once the desired amount of cross-linking of the polymer has occurred, it will serve as a selective barrier to diffusion (i.e. as a dialysis membrane).

Finally, second valve set 8416 is closed and first valve set 8412 is again opened, and first chamber 8402 is charged with countersolvent. This countersolvent diffuses across cross-linked polymer membrane 8420 to alter the solution conditions in dead-ended chamber 8404.

Double dialysis to further mediate change in target material solution conditions over time, could be effected by introducing a microfabricated chamber and second polyacrylamide plug intermediate to the crystallization chamber and the chamber containing the crystallizing agent.

In any of the embodiments of double dialysis described above, the second dialysis membrane could be eliminated, and diffusion of crystallizing agent across the intermediate solution relied upon to slow changes in condition of the target material solution. Diffusion rates of the crystallizing agent across the intermediate solution could be controlled by the physical dimensions (i.e. length, cross-section) of the intervening structure, such as a microfabricated chamber/channel or a capillary or larger diameter tube connecting reservoirs in which microfabricated structure has been immersed.

Figure 38A:
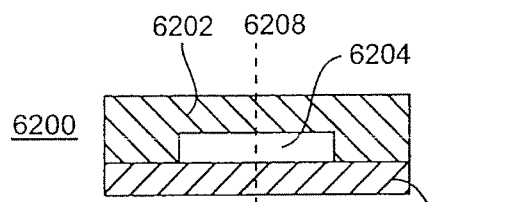
FIGS. 38A-C show cross-sectional views of a process for forming elastomer structures by bonding along a vertical line.
Figure 38B:
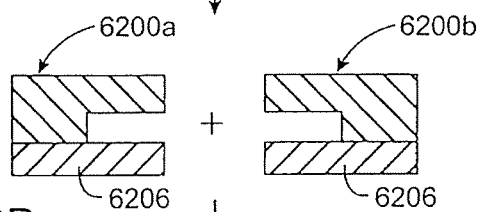
Figure 38C:
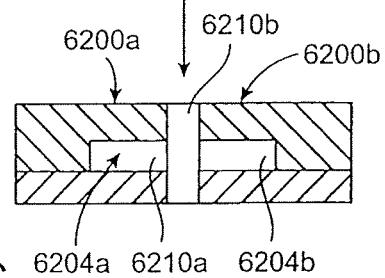

In other embodiments, a microfabricated elastomer structure may be sliced vertically, often preferably along a channel cross section. In accordance with embodiments of the present invention, a non-elastomer component may be inserted into the elastomer structure that has been opened by such a cut, with the elastomer structure then resealed. One example of such an approach is shown in FIGS. 38A-38C, which illustrates cross-sectional views of a process for forming a flow channel having a membrane positioned therein. Specifically, FIG. 38A shows a cross-section of a portion of device 6200 including elastomer membrane 6202 overlying flow channel 6204, and elastomer substrate 6206.

FIG. 38B shows the results of cutting device 6200 along vertical line 6208 extending along the length of flow channel 6204, such that halves 6200a and 6200b are formed. FIG. 38C shows insertion of permeable membrane element 6210 between halves 6200a and 6200b, followed by attachment of halves 6200a and 6200b to permeable membrane 6210. As a result of this configuration, the flow channel of the device actually comprises channel portions 6204a and 6204b separated by permeable membrane 6210.

The structure of FIG. 38C could be utilized in a variety of applications. For example, the membrane could be used to perform dialysis, altering the salt concentration of samples in the flow channel. This would result in a change of the solution environment of a crystallized target material.

Figure 40:
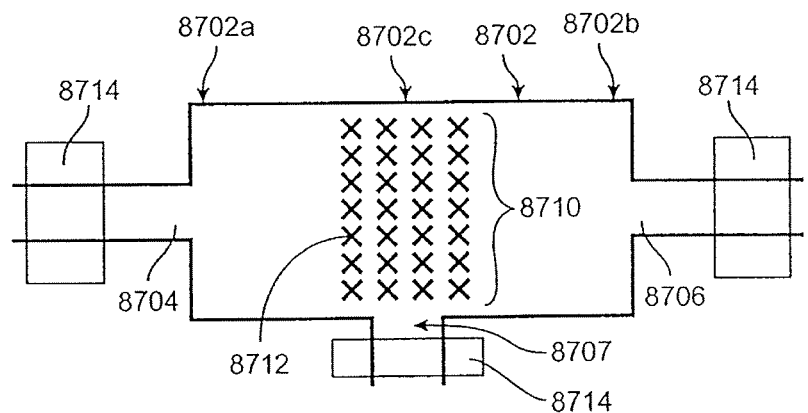
FIG. 40 shows a plan view of another embodiment of a structure in accordance with the present invention for performing crystallization by vapor phase diffusion.
Figure 41:
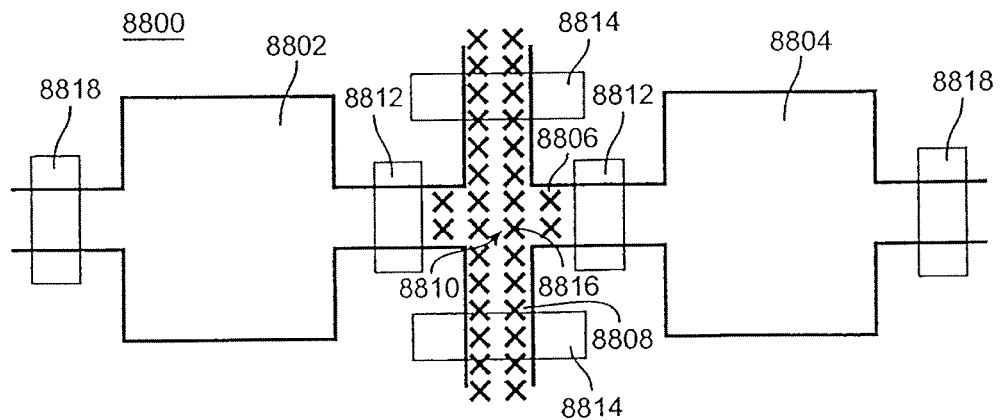
FIG. 41 shows a plan view of still another embodiment of a structure in accordance with the present invention for performing crystallization by vapor phase diffusion.

While embodiments of the present invention discussed so far utilize diffusion of crystallizing agent in the liquid phase, vapor diffusion is another technique that has been employed to induce crystal formation. Accordingly, FIGS. 39-41 show a plan view of several embodiments of vapor diffusion structures in accordance with embodiments of the present invention.

Figure 39:
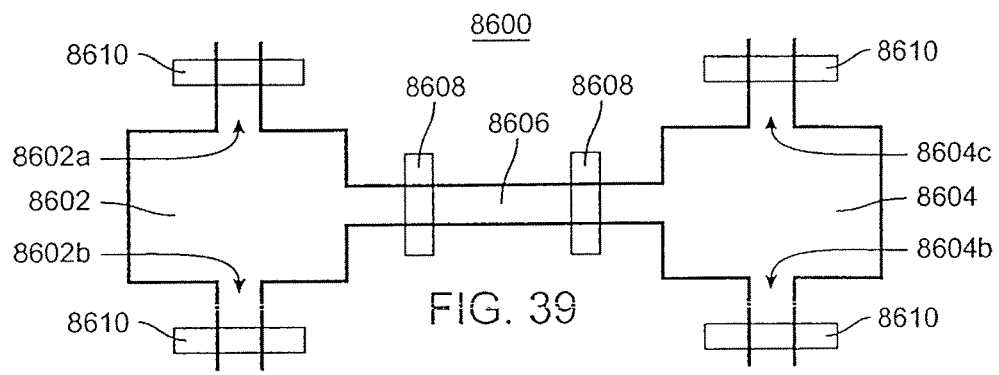
FIG. 39 shows a plan view of an embodiment of a structure in accordance with the present invention for performing crystallization by vapor phase diffusion.

FIG. 39 shows a simple embodiment of a vapor diffusion structure 8600, wherein first microfabricated chamber 8602 having inlet 8602a and outlet 8602b and second microfabricated chamber 8604 having inlet 8604a and outlet 8604b are connected by cross flow channel 8606. Initially, the entire structure 8600 is filled with air. Cross-valves 8608 are then actuated to trap air within cross-flow channel 8606. Target solution is then introduced to first chamber 8602 through inlet 8602a, with displaced air escaping through outlet 8602b. Crystallizing agent is introduced to second chamber 8604 through inlet 8604a, with displaced air escaping through outlet 8604b.

Cross-valves 8608 are then opened, such that air remains trapped within cross-flow channel 8606 between sample and crystallizing agent. Vapor diffusion of solvent and crystallizing agent may then slowly take place across the air pocket of cross-flow channel 8606 to change the solution conditions and thereby induce crystal formation in first chamber 8602. Structure 8600 may be sealed against the outside environment by valves 8610 during this process.

While the above embodiment is functional, the air pocket trapped between the liquid-filled chambers may move or deform in response to environmental conditions, permitting unwanted direct fluid contact between target material solution and crystallizing agent. It is therefore desirable to anchor the air pocket at specific locations within the microfabricated structure.

Accordingly, FIG. 40 shows an alternative embodiment of a structure for performing crystallization by vapor diffusion. Specifically, structure 8700 comprises chamber 8702 having first inlet 8704 at a first end 8702a, second inlet 8706 at a second end 8702b, and vent 8707 at middle portion 8702c. Middle portion 8702c of chamber 8702 includes hydrophobic region 8708 which may be formed by microcontact printing. Microcontact printing techniques are described in detail by Andersson et al., "Consecutive Microcontact Printing—Ligands for Asymmetric Catalysis in Silicon Channels", *Sensors and Actuators B,* 3997 pp. 1-7 (2001), hereby incorporated by reference for all purposes.

Specifically, during fabrication of structure 8700, the underlying substrate may be stamped with pattern 8710 of octadecyltrichlorosilane (OTS). Subsequent alignment of microfabricated elastomeric chamber 8702 over pattern 8710 would form central hydrophobic region 8712.

Initially, structure 8700 would be filled with air. Aqueous target solution would then carefully be introduced through first inlet 8706, with air displaced from chamber 8702 through vent 8707. Because of the presence of hydrophobic chamber region 8712, filling of chamber 8702 with target solution would halt as the solution encountered region 8712. Similarly, hydrophilic crystallizing agent would carefully be introduced through second inlet 8708 to chamber 8702, stopping at hydrophobic region 8712. Air displaced by filling of chamber 8702 with crystallizing agent would exit chamber 8702 through vent 8707. Thus secured in place by the underlying patterned hydrophobic region 8712, the air pocket in central region 8712 would permit slow vapor diffusion of crystallizing agent into target sample to induce crystal formation on the right side of chamber 8702. Surrounding valves 8714 could be actuated to isolate the structure during this process.

While useful, the embodiment of a vapor diffusion structure just described in conjunction with FIG. 40 requires alignment of the microfabricated elastomeric channel to a patterned hydrophobic region on an underlying substrate. This alignment process may be difficult given the small feature sizes of structures in accordance with embodiments of the present invention. Moreover, during the fabrication process the hydrophobic material would likely be formed only on underlying substrate, and not on the channel walls.

Accordingly, FIG. 41 shows still another embodiment of a structure for performing crystallization of target materials by vapor diffusion, which does not require an alignment step. Specifically, recrystallization structure 8800 includes first chamber 8802 connected to second chamber 8804 by cross-flow channel 8806. Second flow channel 8808 intersects with cross-flow channel 8806, forming junction 8810. Flow across junction 8810 along cross-flow channel 8806 is controlled by first valve pair 8812. Flow across junction 8810 along second flow channel 8808 is controlled by second valve pair 8814.

Initially, first chamber 8802 is charged with target material solution and second chamber 8804 is charged with crystallizing agent. Next, first valve pair 8812 is closed and second valve pair 8814 is opened, and hydrophobic material such as OTS is flowed down second flow channel 8808 through junction 8810. As a result of this flow of material, hydrophobic residue 8816 remains on the substrate and possibly on the flow channel walls in junction 8810.

Next, air is introduced into second flow channel 8808, and second valve pair 8814 is closed. First valve pair 8812 is then opened to permit vapor diffusion of crystallizing agent in chamber 8804 across air-filled junction 8810 into target material solution in chamber 8802. During this vapor diffusion process, the air pocket is fixed in junction 8810 by closed valve pair 8814 and the presence of hydrophobic residue 8816. Valves 8818 could be closed to completely seal structure 8800 against the outside environment.

While the above embodiment has focused upon microcontact printing of hydrophobic moieties to fix in place air pockets during vapor diffusion, the present invention is not limited to this approach. Hydrophobic regions selectively introduced into portions of a microfabricated crystallization structure in accordance with the present invention could alternatively be utilized to fix in place barriers or impediments to diffusion in the form of hydrophobic oils.

Hydrophobic oil materials may also be utilized to coat the exterior surface of microfabricated elastomer structures in accordance with embodiments of the present invention. Such a coating may be impermeable to outdiffusion of vapor from the elastomer, thereby preventing dehydration of the structure during the potentially long crystallization durations. Alternatively, the coating oil may be somewhat permeable to water or other gases, thereby allowing for slow, controlled outdiffusion of water or gases to create within the structure conditions favorable to crystallization.

5. Control Over Other Factors Influencing Crystallization

While the above crystallization structures describe altering the environment of the target material through introduction of volumes of an appropriate crystallization agent, many other factors are relevant to crystallization. Such additional factors include, but are not limited to, temperature, pressure, concentration of target material in solution, equilibration dynamics, and the presence of seed materials.

In specific embodiments of the present invention, control over temperature during crystallization may be accomplished utilizing a composite elastomer/silicon structure previously described. Specifically, a Peltier temperature control structure may be fabricated in an underlying silicon substrate, with the elastomer aligned to the silicon such that a crystallization chamber is proximate to the Peltier device. Application of voltage of an appropriate polarity and magnitude to the Peltier device may control the temperature of solvent and countersolvent within the chamber.

Alternatively, as described by Wu et al. in "MEMS Flow Sensors for Nano-fluidic Applications", *Sensors and Actuators A* 89 152-158 (2001), crystallization chambers could be heated and cooled through the selective application of current to a micromachined resistor structure resulting in ohmic heating. Moreover, the temperature of crystallization could be detected by monitoring the resistance of the heater over time. The Wu et al. paper is hereby incorporated by reference for all purposes.

It may also be useful to establish a temperature gradient across a microfabricated elastomeric crystallization structure in accordance with the present invention. Such a temperature gradient would subject target materials to a broad spectrum of temperatures during crystallization, allowing for extremely precise determination of optimum temperatures for crystallization.

With regard to controlling pressure during crystallization, embodiments of the present invention employing metering of countersolvent by volume exclusion are particularly advantageous. Specifically, once the chamber has been charged with appropriate volumes of solvent and countersolvent, a chamber inlet valve may be maintained shut while the membrane overlying the chamber is actuated, thereby causing pressure to increase in the chamber. Structures in accordance with the present invention employing techniques other than volume exclusion could exert pressure control by including flow channels and associated membranes adjacent to the crystallization chamber and specifically relegated to controlling pressure within the channel.

Another factor influencing crystallization is the amount of target material available in the solution. As a crystal forms, it acts as a sink to target material available in solution, to the point where the amount of target material remaining in solution may be inadequate to sustain continued crystal growth. Therefore, in order to grow sufficiently large crystals it may be necessary to provide additional target material during the crystallization process.

Accordingly, the cell pen structure previously described in connection with FIGS. 27A-27B may be advantageously employed in crystallization structures in accordance with embodiments of the present invention to confine growing crystals within a chamber. This obviates the danger of washing growing crystals down a flow channel that is providing additional target material, causing the growing crystals to be lost in the waste.

Moreover, the cell cage structure of FIGS. 27A-27B may also be useful during the process of crystal identification. Specifically, salts are often present in the sample or countersolvent, and these salts may form crystals during crystallization attempts. One popular method of distinguishing the growth of salt crystals from the target crystals of interest is through exposure to a staining dye such as IZIT™, manufactured by Hampton Research of Laguna Niguel, Calif. This IZIT™ dye stains protein crystals blue, but does not stain salt crystals.

However, in the process of flowing the IZIT™ dye to the crystallization chamber holding the crystals, the crystals may be dislodged, swept away, and lost. Therefore, the cell pen structure can further be employed in crystallization structures and methods in accordance with the present invention to secure crystals in place during the staining process.

Figure 42:
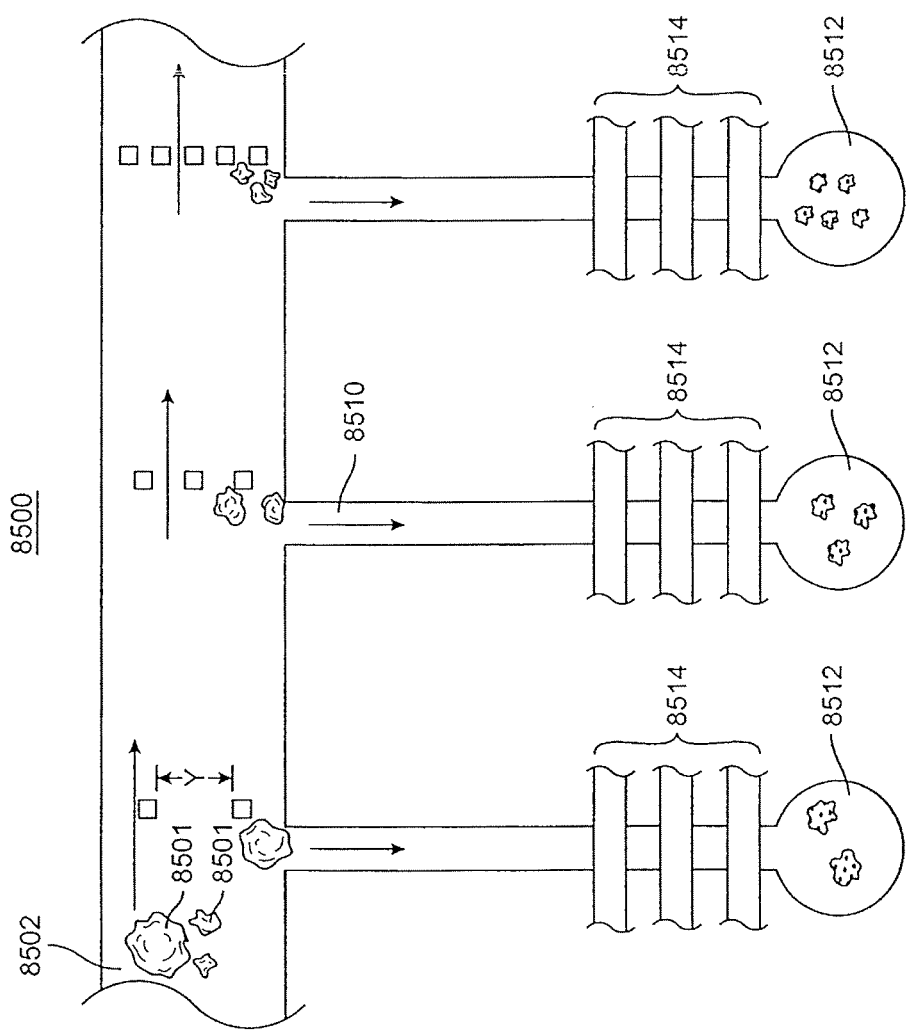
FIG. 42 shows a plan view of an embodiment of a structure in accordance with the present invention for sorting crystals of various sizes.

FIG. 42 shows an embodiment of a sorting device for crystals based upon the cell cage concept. Specifically, crystals 8501 of varying sizes may be formed in flow channel 8502 upstream of sorting device 8500. Sorting device 8500 comprises successive rows 8504 of pillars 8506 spaced at different distances. Inlets 8508 of branch channels 8510 are positioned in front of rows 8504. As crystals 8501 flow down channel 8502, they encounter rows 8504 of pillars 8506. The largest crystals are unable to pass between gap Y between pillars 8506 of first row 8504a, and accumulate in front of row 8504a. Smaller sized crystals are gathered in front of successive rows having successively smaller spacings between pillars. Once sorted in the manner described above, the crystals of various sizes can be collected in chambers 8512 by pumping fluid through branch channels 8510 utilizing peristaltic pumps 8514 as previously described. Larger crystals collected by the sorting structure may be subjected to x-ray crystallographic analysis. Smaller crystals collected by the sorting structure may be utilized as seed crystals in further crystallization attempts.

Another factor influencing crystal growth is seeding. Introduction of a seed crystal to the target solution can greatly enhance crystal formation by providing a template to which molecules in solution can align. Where no seed crystal is available, embodiments of microfluidic crystallization methods and systems in accordance with the present invention may utilize other structures to perform a similar function.

For example, as discussed above, flow channels and chambers of structures in accordance with the present invention are typically defined by placing an elastomeric layer containing microfabricated features into contact with an underlying substrate such as glass. This substrate need not be planar, but rather may include projections or recesses of a size and/or shape calculated to induce crystal formation. In accordance with one embodiment of the present invention, the underlying substrate could be a mineral matrix exhibiting a regular desired morphology. Alternatively, the underlying substrate could be patterned (i.e. by conventional semiconductor lithography techniques) to exhibit a desired morphology or a spectrum of morphologies calculated to induce crystal formation. The optimal form of such a substrate surface morphology could be determined by prior knowledge of the target crystals.

Embodiments of crystallization structures and methods in accordance with the present invention offer a number of advantages over conventional approaches. One advantage is that the extremely small volumes (nanoliter/sub-nanoliter) of sample and crystallizing agent permit a wide variety of recrystallization conditions to be employed utilizing a relatively small amount of sample.

Another advantage of crystallization structures and methods in accordance with embodiments of the present invention is that the small size of the crystallization chambers allows crystallization attempts under hundreds or even thousands of different sets of conditions to be performed simultaneously. The small volumes of sample and crystallizing agent employed in recrystallization also result in a minimum waste of valuable purified target material.

A further advantage of crystallization in accordance with embodiments of the present invention is relative simplicity of operation. Specifically, control over flow utilizing parallel actuation requires the presence of only a few control lines, with the introduction of sample and crystallizing agent automatically performed by operation of the microfabricated device permits very rapid preparation times for a large number of samples.

Still another advantage of crystallization systems in accordance with embodiments of the present invention is the ability to control solution equilibration rates. Crystal growth is often very slow, and no crystals will be formed if the solution rapidly passes through an optimal concentration on the way to equilibrium. It may therefore be advantageous to control the rate of equilibration and thereby promote crystal growth at intermediate concentrations. In conventional approaches to crystallization, slow-paced equilibrium is achieved using such techniques as vapor diffusion, slow dialysis, and very small physical interfaces.

However, crystallization in accordance with embodiments of the present invention allows for unprecedented control over the rate of solution equilibrium. In systems metering crystallizing agent by volume exclusion, the overlying membrane can be repeatedly deformed, with each deformation giving rise to the introduction of additional crystallizing agent. In systems that meter crystallizing agent by volume entrapment, the valves separating sample from crystallizing agent may be opened for a short time to allow for partial diffusive mixing, and then closed to allow chamber equilibration at an intermediate concentration. The process is repeated until the final concentration is reached. Either the volume exclusion or entrapment approaches enables a whole range of intermediate concentrations to be screened in one experiment utilizing a single reaction chamber.

The manipulation of solution equilibrium over time also exploits differential rates of diffusion of macromolecules such as proteins versus much smaller crystallizing agents such as salts. As large protein molecules diffuse much more slowly than the salts, rapidly opening and closing interface valves allows the concentration of crystallizing agent to be significantly changed, while at the same time very little sample is lost by diffusion into the larger volume of crystallizing agent. Moreover, as described above, many crystallization structures described readily allow for introduction of different crystallizing agents at different times to the same reaction chamber. This allows for crystallization protocols prescribing changed solvent conditions over time.

6. Experimental Results

In order to compare results of crystallization utilizing the current protein crystallization chip with results from two current popular macroscopic methods of protein crystallization (hanging drop vapor diffusion and microbatch) a number of experiments were performed. The results are discussed below.

Model proteins were chosen based on their availability, and difficulty to crystallize. The difficulty of protein crystallization was defined as the number of conditions claimed by vendor Hampton Research (Laguna Nigel, Calif.) to crystallize the protein using vapor diffusion or microbatch techniques. Difficulty levels of easy, medium, and difficult are assigned to proteins for which greater than 10 of 48, between 5 and 10, and less than 5 conditions will produce crystallization. Both easy and difficult proteins were chosen.

Difficult to crystallize proteins were chosen to apply a stringent test to the chip, to show whether the chip can crystallize proteins requiring a very specific crystallization condition, or even detect crystallization conditions not detectable using standard crystallization techniques. Easy proteins were chosen to better understand the differences in behavior between the chip and conventional techniques, and to discover which conditions are incompatible with the chip. The model proteins employed in this study were glucose isomerase (medium) proteinase K (easy), beef liver catalase (difficult), bovine pancreas trypsin (medium), lysozyme (easy), and xylanase (medium), and the B subunit of topoisomerase VI (medium, not previously crystallized).

Embodiments of the invention present a viable alternative to conventional crystallization methods. Microfluidic devices offer parsimonious use of protein, simpler and more rapid experimental set up, and reduced storage space requirements as compared with conventional methods. As discussed below, in nearly all protein models, the chip produced more hits then conventional methods. It has further been shown that large high quality crystals may be grown in chip, and that it is possible to harvest these crystals directly from the chip.

Several routes from the chip to an x-ray beam for collecting are proposed, including harvesting of crystals directly from the chip. Correspondence of about 50-80% between the chip and conventional methods has been determined, a level of correspondence approximately the same as between conventional methods. An analysis of the chip equilibration suggests that macro free-interface diffusion might better emulate the chip. This analysis further shows that the chip samples a larger region in phase space, and hence is more likely to encounter favorable crystallization conditions.

While permeability of the PDMS material of the chip is a significant factor in crystallization, nearly all conditions in the Hampton screen produced crystal hits over the course of target screening. The use of a permeable material in the development of a macroscopic method corresponding to chip conditions may be beneficial, as has been shown to be the case in micro-batch.

a. Reagents and Proteins

Crystal Screen Kit 1, Izit dye, greased Linbro plates, and siliconized coverslips were purchased from Hampton Research. Costar 96 well round bottom plates were purchased from VWR (West Chester, Pa.). HEPES was purchased from Fluka (St. Louis, Mo.). Calcium chloride, PMSF, benzamidine hydrochloride, and mineral oil were obtained from Sigma Aldrich (St. Louis, Mo.).

Glucose isomerase was obtained from Hampton Research and dialyzed into distilled, deionized water at 4° C. overnight. The protein concentration was approximately 30 mg/mL. Protein was aliquotted into 1 mL samples, snap frozen in liquid nitrogen and stored at −20° C.

Proteinase K was obtained from Worthington Biochemicals (Lakewood, N.J.), dialyzed for 5 to 6 hours at 4 C into 1 mM calcium chloride, 25 mM HEPES buffer, pH 7.0, filtered through a 0.22 m syringe filter, aliquotted into 100 L samples, and stored frozen at −20° C. Proteinase K was approximately 20 mg/mL and the inhibitor PMSF was added prior to use in some experiments at a final concentration of 1 mM.

Beef liver catalase was purchased from Sigma-Aldrich, dialyzed overnight at 4° C. into 25 mM HEPES, pH 7.0, aliquotted into 1 mL samples, snap frozen in liquid nitrogen, and stored at −20° C. Beef liver catalase was approximately 30 mg/mL and centrifuged at 12,000 rpm for 5 minutes prior to use, changing the solution from a dark brown to a slightly tinted solution.

Lysozyme was purchased from Sigma-Aldrich, and dissolved in 0.2 Molar Sodium Acetate (pH 4.7) to a final concentration of 50 mg/mL. This solution was then centrifuged in an eppendorf centrifuge (16 000 g) for 10 minutes at 4° C.

Xylanase was purchased from Hampton Research. Prior to crystallization experiments, the stock solution containing 36 mg/mL protein, 43% Glycerol, and 0.18 Molar Ma/K Phosphate, was diluted by half with deionized water.

Bovine pancreas trypsin was dialyzed for 5-6 hours at 4° C. into 10 mM calcium chloride, 25 mM HEPES buffer, pH 7.0, filtered through a 0.22 μm syringe filter, aliquotted into 100 μL samples, and stored frozen at −20° C. Bovine pancreas trypsin was approximately 60 mg/mL and contained 10 mg/mL of the inhibitor benzamidine hydrochloride. One additional protein, with an unpublished structure, was also evaluated in chip. The B subunit of topoisomerase VI is a 50 KDa, ATP-binding, force-generating subunit of an archaeal type IIB topoisomerase complex. This protein was prepared at a concentration of 12 mg/mL in a 100 mMol solution of NaCl, buffered at pH 7.0 with 20 mM TRIS.

Negative controls of buffer without protein were set up on chip to help determine the difference between salt crystals and protein crystals. On chip no protein controls comprised one chip containing 20 mM calcium chloride, in 25 mM HEPES, buffered at pH 7.0, and one chip containing 20 mM calcium chloride, in 1 mM HEPES, buffered at pH 7.0. Individual no protein controls for Xylanase, Lysozyme, Glucose Isomerase, and the B subunit of topoisomerase VI were conducted using the specific buffers described above. Controls were also set up in microbatch with 1 mM calcium chloride, 25 mM HEPES, pH 7.0, and distilled deionized water.

c. Crystallization Utilizing Hanging Drop

Conventional hanging drop techniques involve hermetically sealing the target molecule(s)/crystallization-agent mixture (referred to as the 'drop') over a well of some type of fluid with a higher osmotic potential than the drop (typically a higher concentration of crystallizing-agent mix) to induce the slow dehydration of the drop with a concomitant increase in concentration of both the target molecule and the crystallization reagents in the drop. As this concentration process occurs, the target is slowly driven out of the liquid phase and into a solid phase, hopefully in a crystalline form.

Hanging drop experiments were performed in greased Linbro 24 well plates. 500 μL of Hampton Crystal Screens 1-48 were placed in the bottom of the well. 1 μL of protein and 1 μL of the crystal screen were combined in the center of a siliconized glass coverslip. The coverslip was sealed over the well containing 0.5 mL of screen solution, and the plates were kept at ambient temperatures over a period of two weeks. Plates were monitored for crystal growth daily over a period of one to two weeks. For duplicates, both drops were placed on a single coverslip over the same reagent well.

d. Crystallization Utilizing Microbatch

Microbatch another conventional crystallization approach. Microbatch is similar to the hanging drop technique described above, but involves placing the 'drop' under some type of impermeable or semi-permeable vapor barrier such as oil. Over time, in a manner similar to the vapor diffusion occurring in hanging drop, crystallization reagents promote aggregation of the target, again, preferably in a crystalline state.

Microbatch experiments were performed in 96 well plates. 100 μl of mineral oil was pipetted into each well. 1 μL of Hampton Crystal Screens 1-48 was added to each well followed by 1 μL of protein and the plate was centrifuged at 1000 rpm for 5 minutes to mix the two drops below the oil layer. The plates were kept at ambient temperatures up to two weeks and monitored daily for crystal growth.

e. On-Chip Crystallization

Figure 45A:
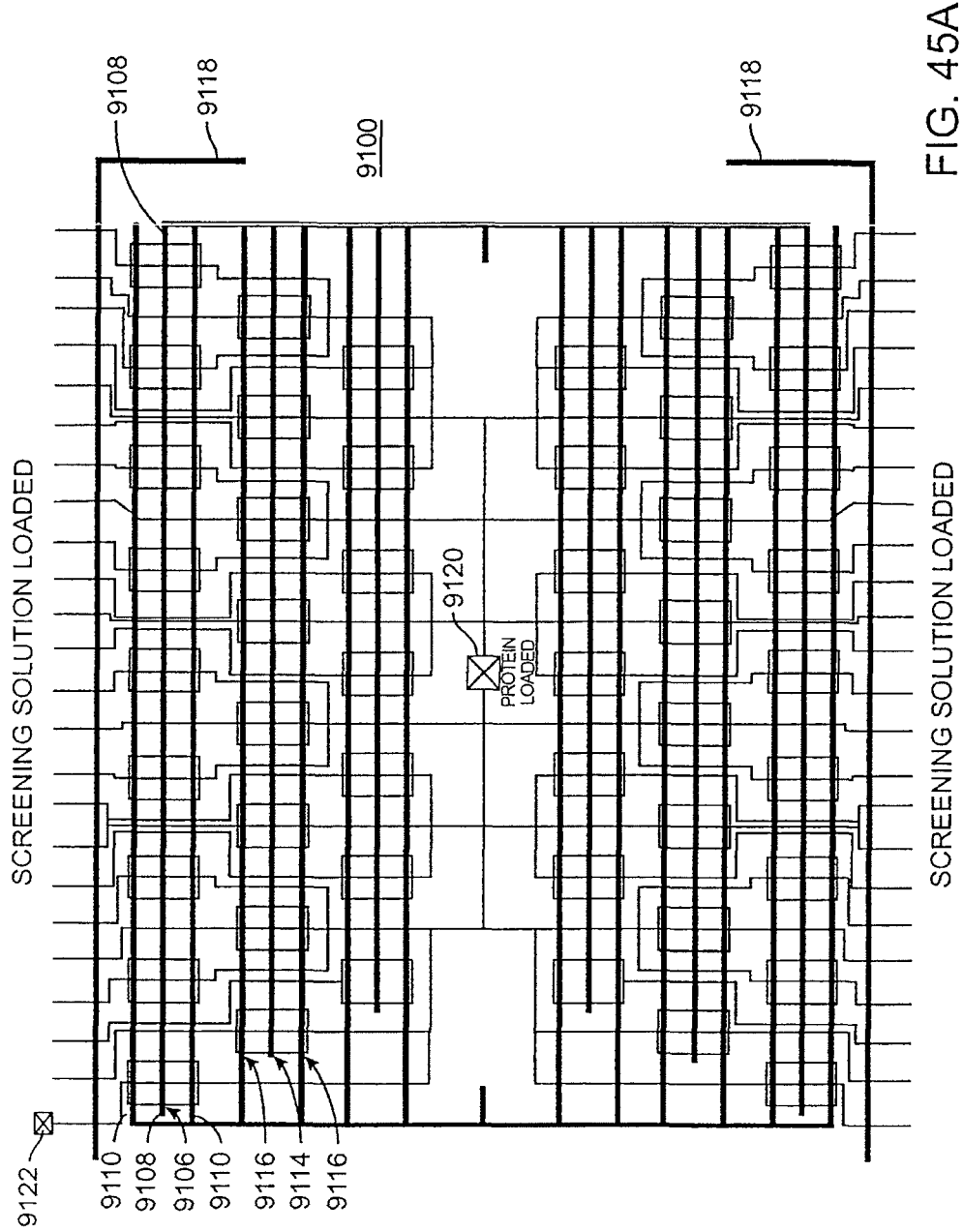
FIG. 45A shows a simplified plan view of the alternative embodiment of the chip utilized to obtain experimental results.
Figure 45B:
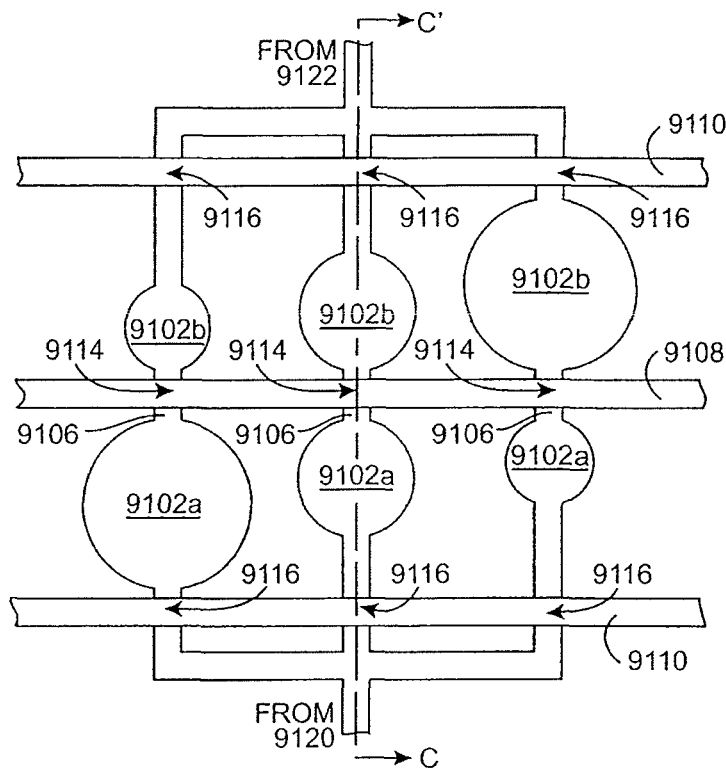
FIG. 45B shows as simplified enlarged plan view of a set of three compound wells of the chip shown in FIG. 45A.
Figure 45C:
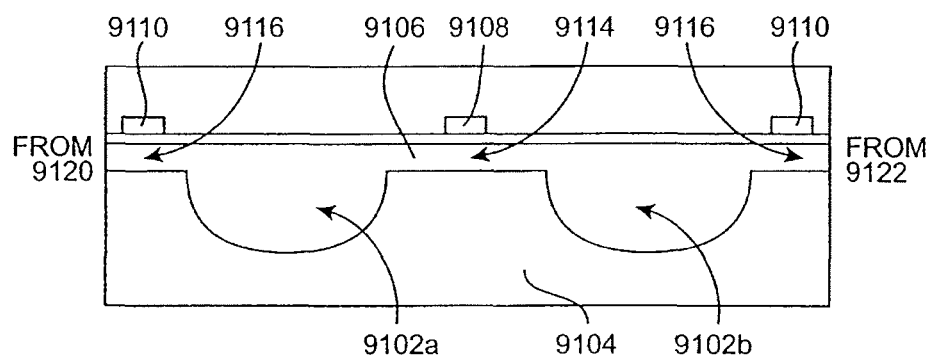
FIG. 45C shows a simplified cross-sectional view of the compound wells of FIGS. 45A-B.

The particular design for the crystallization chip utilized in the experiments is shown in FIGS. 45A-C. FIG. 45A shows a simplified plan view of the alternative embodiment of the chip. FIG. 45B shows a simplified enlarged plan view of a set of three compound wells. FIG. 45C shows a simplified cross-sectional view of the wells of FIG. 45B along line C-C'. This chip design employed metering of target solution and crystallizing agent utilizing the volume entrapment technique.

Specifically, each chip 9100 contains three compound wells 9102 for each of the 48 different screen conditions, for a total of 144 assays per chip. A compound well 9102 consists of two adjacent wells 9102a and 9102b etched in a glass substrate 9104, and in fluidic contact via a microchannel 9106. In each of the compound wells 9102, the protein solution is combined with the screen solution at a ratio that is defined by the relative size of the adjacent wells 9102a-b. In the particular embodiment shown in FIGS. 45A-C, the three ratios were (protein:solution) 4:1, 1:1, and 1:4. The total volume of each assay, including screen solution, is approximately 25 nL. However, the present invention is not limited to any particular volume or range of volumes. Alternative embodiments in accordance with the present invention may utilize total assay volumes of less than 10 nL, less than 5 nL, less than 2.5 nL, less than 1.0 nL, and less than 0.5 nL.

The chip control layer 9106 includes an interface control line 9108, a containment control line 9110 and two safety control lines 9112. Control lines 9108, 9110, and 9112 are filled with water rather than air in order to maintain a humid environment within the chip and to prevent dehydration of the flow channels and chambers in which crystallization is to be performed.

The interface valves 9114 bisect the compound wells 9102, separating the protein from the screen until completion of loading. Containment valves 9116 block the ports of each compound well 9102, isolating each condition for the duration of the experiment. The two safety valves 9118 are actuated during protein loading, and prevent spillage of protein solution in the event of a failed interface valve.

Fabrication of the microfluidic devices utilized in the experiments were prepared by standard multilayer soft lithography techniques and sealed to an etched glass slide by baking at 80° C. for 5 hours or greater. The glass substrate is masked with a 16 um layer of 5740 photoresist, and is patterned using standard photolithography. The glass substrate is then etched in a solution of 1:1:1 (BOE:$H_2O$:2N HCl) for 60 minutes, creating micro-wells with a maximum depth of approximately 80 μm.

The chip fabrication protocol just described is only one example of a possible embodiment of the present invention. In accordance with alternative embodiments, the crystallization chambers and flow channels could be defined between a planar substrate and a pattern of recesses formed entirely in the lower surface of the elastomer portion. Still further alternatively, the crystallization chambers and flow channels could be defined between a planar, featureless lower surface of the elastomer portion and a pattern of recesses formed entirely in the substrate.

Crystallization on chip is set up as follows. All control lines in chip control layer 9106 are loaded with water at a pressure of 15-17 psi. Once the control lines are filled and valves 9114 and 9116 are completely actuated, the containment valve 9116 is released, and protein is loaded through the center via 9120 using about 5-7 psi. The protein solution completely fills the protein side of each compound well 9102. Failed valves, if present, are then identified, and vacuum grease is placed over the corresponding screen via to prevent subsequent pressurization, and possible contamination of the remaining conditions. 2.5 to 4 µL of a sparse matrix screen (typically Hampton Crystal Screen I, 1-48) are then pipetted into the screen vias 9122. The safety valves 9118 are released, and a specially designed chip holder (described below) is used to create a pressurized (5-7 psi) seal over all 48 screen vias 9122. The screen solutions are dead end loaded, filling the screen side of each compound well. Protein and crystal screen reagents are kept separate with the interface valve until all wells are loaded, at which point the containment valve is closed and the interface valve opened to allow diffusion between liquid volumes present in the two halves of the compound wells 9102 f. Chip Performance

Chip performance varied between experiments. Initially, the chips exhibited an interface valve failure rate of approximately 30%. However, later experiments typically had between about 3-10 failures out of 48 conditions. A total of nine chips had a 100% success rate.

The average protein solution volume used per chip, as measured by tracking the protein meniscus, was approximately 3 uL.

For these experiments, the average time spent setting up an experiment, including filling control lines, was approximately 35 min, with the fastest experiment taking only 20 minutes to set up. This set up time could potentially be reduced even further through the use of robotic pipetting of solutions to the chip, or through the use of pressures to load and prime delivered solutions, as discussed below in conjunction with FIG. 80.

g. General Crystal Growth Observation and Data Analysis

Hanging drop, microbatch, and chip experiments were observed for hits for up to 2 weeks. Unless otherwise specified, hits are defined as single crystals, needle crystals, plate crystals, rod crystals, spherulites, or precipitate. Phase separation or oil droplets are not counted as hits. In some cases, crystals were confirmed to be protein crystals by dying with Izit dye, which does not stain salt crystals. Izit dye was diluted 1/20 in the corresponding crystal screen and 1 µL was added to the crystal drop. Protein crystals were also confirmed by probing the crystal with a crystal probe.

Comparisons on crystal growth patterns between techniques were based on similarities in conditions producing hits. For duplicate and triplicate tests, comparisons were made such that two techniques were considered to have similar growth patterns if one or both of the duplicates produced a hit in both techniques (e.g. chip and microbatch are considered to have similar crystal growth patterns if chip 1 or chip 2 produced a hit and microbatch 1 or microbatch 2 produced a hit).

h. Glucose Isomerase Crystallization

Glucose isomerase crystallization was set up in one hanging drop experiment, two microbatch experiments, and on six separate chips. Hanging drop experiments were monitored daily for one week, and then every other day for a second week, microbatch plates were observed for two weeks, and chips were monitored for up to 9 days. The results were consistent between chips when other factors (valve failure, failure to load with protein or crystal screen) were taken into consideration.

Results of these experiments are summarized in the Venn diagram shown in FIG. 46. One crystal screen (reagent #33) failed to produce crystals or precipitate in any of the experiments. 33 of the 48 screens produced hits in the hanging drop experiments; 28 of 48 produced hits in the microbatch method, and 47 of 48 produced hits on chip. There was significant agreement between the microbatch and hanging drop experiments: 81% of the microbatch results agreed with hanging drop results, where 13 conditions produced no hits in either of the techniques, and 26 conditions produced crystal or precipitate in both techniques.

There was less agreement between the chip and microbatch results (60% agreement) or between the chip and hanging drop methods (71%). Twelve conditions that were observed to produce hits in the chip, which did not in the other methods. Table 1 shows the results of glucose isomerase crystallization in the three techniques.

TABLE 1

Glucose Isomerase Crystallization Results

| Reagent number | precipitant classification | salt condition | acid/base | chip day 9 | micro-batch day 14 | hanging drop day 14 |
|---|---|---|---|---|---|---|
| 1 | organic | low | acid | C1 | C1 | C1 |
| 2 | salt | high | no buffer | C1 | | |
| 3 | salt | high | no buffer | C1 | | |
| 4 | salt | high | base | C1 | | C1 |
| 5 | organic | high | weak base | C1 | | C1 |
| 6 | polymer | high | base | C1 | C1 | C1 |
| 7 | salt | high | weak acid | A1 | | |
| 8 | organic | high | weak acid | C1 | | C1 |
| 9 | polymer | high | acid | A1 | A1 | C1 |
| 10 | polymer | high | acid | C1 | A1 | C1 |
| 11 | salt | high | acid | C1 | | A1 |
| 12 | organic | high | weak base | C1 | A1 | A1 |
| 13 | polymer | high | base | C1 | | |
| 14 | polymer | high | weak base | A1 | A1 | A1 |
| 15 | polymer | high | weak acid | A1 | A1 | A1 |
| 16 | salt | high | weak base | C1 | | |
| 17 | polymer | high | base | C1 | A1 | C1 |
| 18 | polymer | high | weak acid | B1 | B1 | C1 |
| 19 | organic | high | base | A1 | | |
| 20 | polymer | high | acid | A1 | C1 | C1 |
| 21 | organic | high | weak acid | C1 | A1 | A1 |
| 22 | polymer | high | base | A1 | A1 | A1 |
| 23 | polymer | high | weak base | B1 | A1 | A1 |
| 24 | organic | high | acid | A1 | B1 | C1 |
| 25 | salt | high | weak acid | B1 | | |
| 26 | organic | high | acid | B1 | | |
| 27 | organic | high | weak base | A1 | | |
| 28 | polymer | high | weak acid | C1 | C1 | C1 |
| 29 | salt | high | weak base | B1 | | |
| 30 | polymer | high | no buffer | C1 | C1 | C1 |
| 31 | polymer | high | no buffer | C1 | A1 | C1 |
| 32 | salt | high | no buffer | C1 | A1 | C1 |
| 33 | salt | high | no buffer | | | |
| 34 | salt | high | acid | C1 | | |
| 35 | salt | high | weak base | C1 | A1 | C1 |
| 36 | polymer | none | base | C1 | C1 | |
| 37 | polymer | none | acid | B1 | | C1 |
| 38 | salt | high | weak base | A1 | | C1 |
| 39 | polymer | none | weak base | C1 | | C1 |
| 40 | organic | none | acid | B1 | A1 | A1 |
| 41 | organic | none | weak base | B1 | | |
| 42 | polymer | low | no buffer | C1 | C1 | C1 |
| 43 | polymer | none | no buffer | C1 | C1 | |
| 44 | salt | high | no buffer | C1 | A1 | A1 |
| 45 | polymer | high | weak acid | C1 | C1 | C1 |
| 46 | polymer | high | weak acid | B1 | B1 | C1 |
| 47 | salt | high | acid | C1 | C1 | C1 |
| 48 | salt | high | base | C1 | C1 | C1 |
| X49 | polymer | high | no buffer | X | X | X |

TABLE 1-continued

Glucose Isomerase Crystallization Results

| Reagent number | precipitant classification | salt condition | acid/base | chip day 9 | micro-batch day 14 | hanging drop day 14 |
|---|---|---|---|---|---|---|
| X50 | polymer | high | no buffer | X 47 | X 28 | X 33 |

Figure 48A:
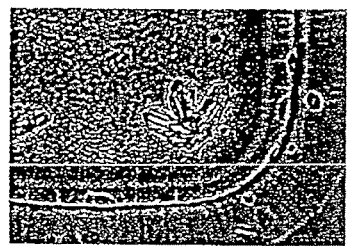
FIGS. 48A-B show photographs of large, high quality glucose isomerase crystals formed a chip.
Figure 48B:

Key:
A1 = Crystals;
B1 = Needle; Plate; or Rod Microcrystals;
C1 = Precipitate;
X = N/A or Failed Valve Where crystal growth was observed in microbatch and hanging drop methods, the crystals were confirmed to be proteins by poking the crystal with a crystal probe. As shown in FIGS. 47A-B crystals that crumble under pressure (FIG. 47B) should be protein. Crystals that do not crumble or shatter (FIG. 47A) are salt crystals. As shown in FIG. 48A-B large high quality crystals were produced utilizing the chip.

Figure 49:
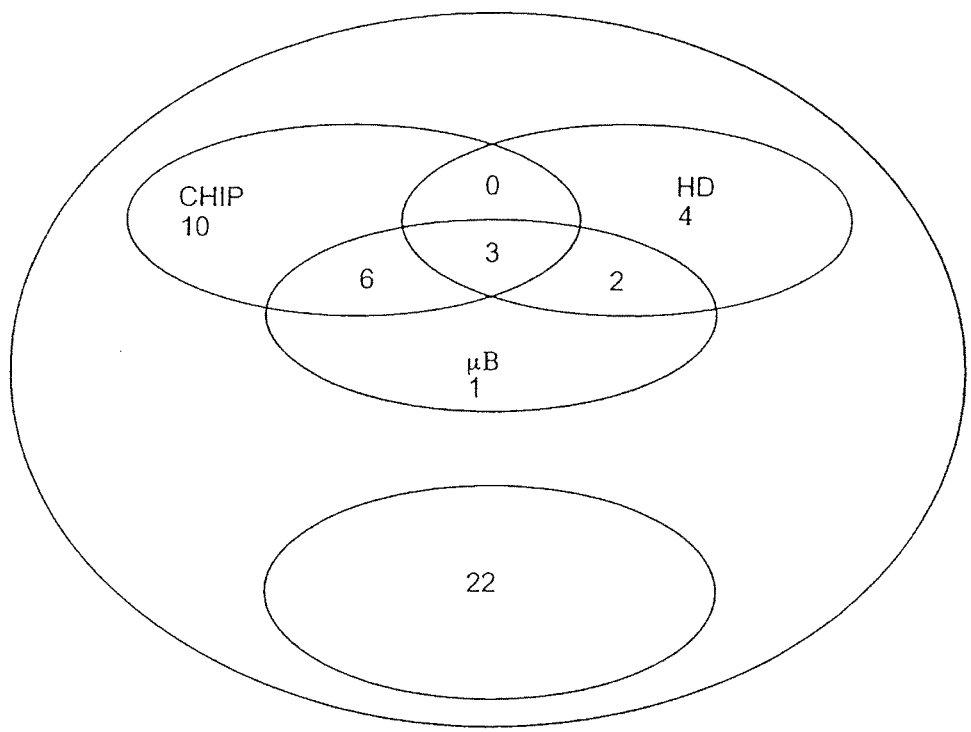
FIG. 49 shows a Venn diagram summarizing a second set of experiments for crystallization of glucose isomerase.

Glucose Isomerase crystallization on chip vs. microbatch was also evaluated in a separate set of experiments. The Glucose Isomerase was dialyzed against deionized water to a final concentration of 31 mg/mL. Hits in these experiments were defined as crystals, microcrystals, needles, plates, rods, or spherulites, while precipitation was not counted as a hit. The microbatch experiment was run for 2 weeks, while the chip experiment was run for 3 days. At the end of three days, the chip became dehydrated due to insufficient water in the containment control tube. The results of these experiments are summarized in the Venn Diagram shown in FIG. 49.

The identity of the crystals, and the reproducibility of the results, was investigated in the following experiment. The hits from the initial screen, Hampton conditions 3, 4, 6, 9, 10, 14, 15 (in triplicate), 17, 18, 20, 22, 28, 30, 32, 38, 39, 42, 43, and 46 (in duplicate), were set up again on a single chip. On the same chip, 2 protein vs. water controls, and a complete set of water vs. screen controls were set up. All of the 22 conditions again gave hits. Both protein vs. water, and all 24 water vs. screen controls were clear (except for some phase separation). The duplicate condition 46 wells showed similar crystals in the mpms (medium protein:medium solution) and spls (small protein:large solution) wells, with morphology depending on the protein to solution ratio. The lpss (large protein:small solution) well was clear in both cases. The triplicate condition 15 showed crystals in all mpms and spls conditions, and was clear in the lpss condition. The morphology of all the spls conditions was identical, while one of the mpms conditions showed a different morphology.

Figure 50:
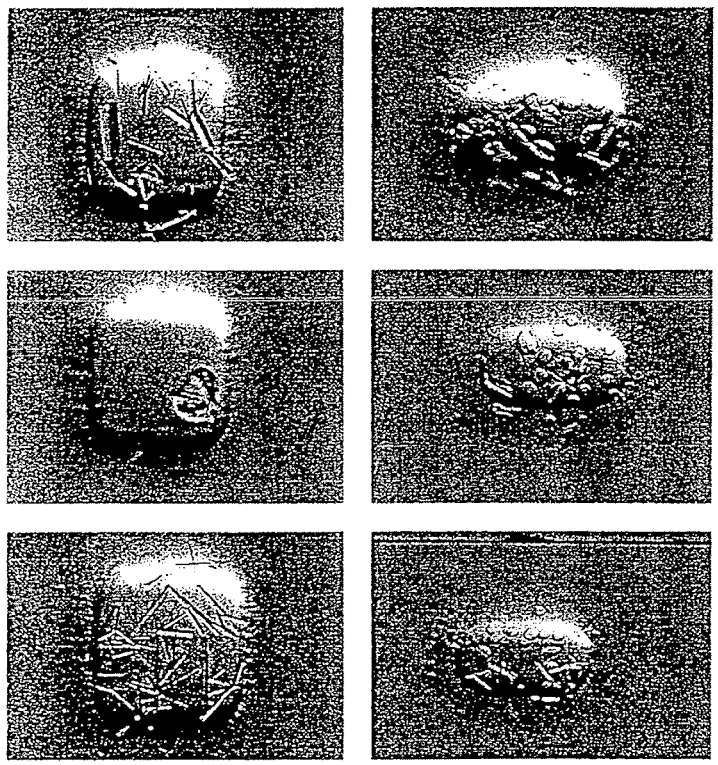
FIG. 50 shows photographs of a number of glucose isomerase crystals formed utilizing the Hampton condition IS.
Figure 51:
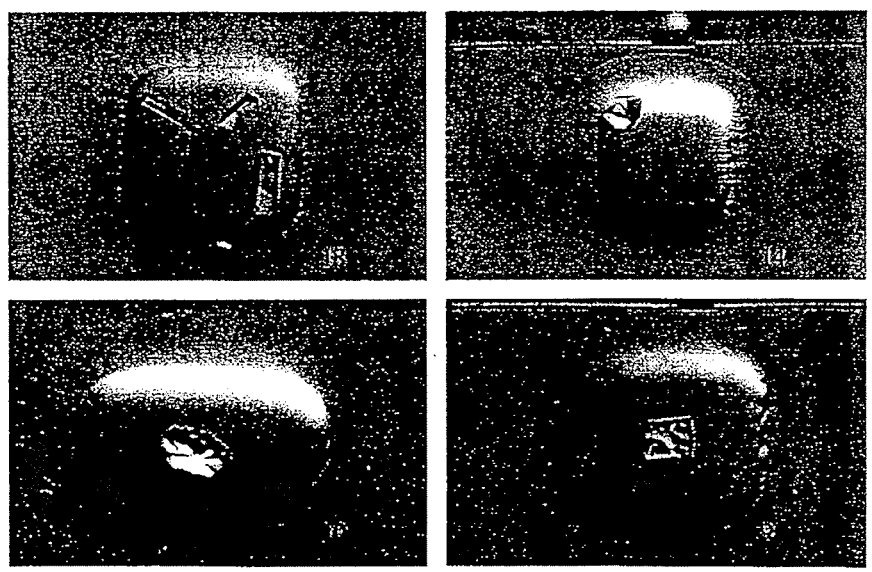
FIG. 51 shows additional photographs of glucose isomerase crystals.

A comparison of the three condition 15 results is shown in FIG. 50. Many of the crystals were large, and of x-ray diffraction quality, showing largest dimensions greater than 150 um, and smallest dimension of approximately 30 um. The first crystals appeared after 4 hrs of incubation, and approximately 80% of crystals had appeared after 1 day. A gallery of these pictures is shown in FIG. 51. All crystals are shown after a single day of incubation.

i. Proteinase K

Proteinase K was crystallized in two microbatch, two hanging drop, and three microfluidic chip experiments. The two microbatch experiments and the two hanging drop experiments were monitored for seven days. Three chip experiments were monitored, one for five days, another for six days, and a third for seven days. Due to the difficulty of crystallizing proteinase K, two conditions, proteinase K with the inhibitor PMSF and proteinase K without the inhibitor PMSF, were employed.

Figure 52:
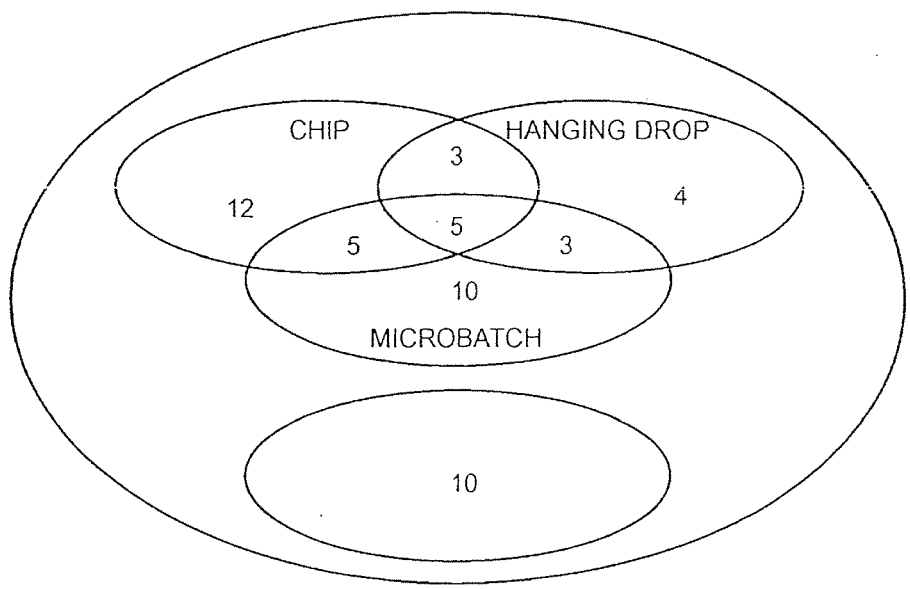
FIG. 52 is a Venn diagram summarizing experiments for crystallization of proteinase K.

FIG. 52 is a Venn diagram summarizing the crystallization results on the last day of observation. The results show that protein crystallization of proteinase K is relatively inconsistent from technique to technique. Out of 48 conditions, only 15 conditions, or 31%, gave similar results across all three techniques. There were 5 conditions that produced hits in all three techniques and 10 conditions in which no crystals or precipitate was found. Eight conditions produced hits in the chip only, 10 conditions produced hits in microbatch only, and 4 conditions produced hits in hanging drop only. Only 18 out of 38 hits or no hits (28 total hits in chip and hanging drop and 10 no hits in either method) were common to the chip and hanging drop (47%). Twenty out of 44 hits or no hits were common to the chip and microbatch (45%). Eighteen out of 40 hits or no hits were in common to the hanging drop and microbatch (45%). Table 2 shows the actual results of proteinase K crystallization in the three techniques.

TABLE 2

Proteinase K Crystallization Results.

| Reagent number | precipitant classification | salt condition | acid/base | microbatch 1 w/o PMSF day 7 | microbatch 2 w/ PMSF day 7 | Hanging drop 1 w/PMSF day 10 | hanging drop 2 w/PMSF day 10 | chip 1 w/PMSF day 7 | chip 2 w/PMSF day 6 | chip 3 w/o PMSF day 5 |
|---|---|---|---|---|---|---|---|---|---|---|
| 1 | organic | low | acid | | | | | A1 | | X |
| A2 | salt | high | no buffer | | | A1 | | | | X |
| A3 | salt | high | no buffer | | | | | X | | X |
| A4 | salt | high | base | | | C1 | C1 | | | X |
| 5 | organic | high | weak base | | | | | | X | X |
| A6 | polymer | high | base | A1 | | | | | | X |
| A7 | salt | high | weak acid | | | | | C1 | | |
| 8 | organic | high | weak acid | | | | | C1 | | X |
| A9 | polymer | high | acid | | | | | C1 | C1 | C1 |
| A10 | polymer | high | acid | | | A1 | A1 | | | |
| A11 | salt | high | acid | | | A1 | | | | |
| 12 | organic | high | weak base | | | A1 | | | B1 | |
| 13 | polymer | high | base | | | | | | | X |
| 14 | polymer | high | weak base | | | | | | | X |
| A15 | polymer | high | weak acid | | | | | C1 | B1 | X |
| A16 | salt | high | weak base | | | C1 | C1 | | | X |
| A17 | polymer | high | base | B1 | A1 | | | X | C1 | X |
| A18 | polymer | high | weak acid | | | A1 | | | | C1 |
| 19 | organic | high | base | | A1 | | | | | |

TABLE 2-continued

Proteinase K Crystallization Results.

| Reagent number | precipitant classification | salt condition | acid/base | microbatch 1 w/o PMSF day 7 | microbatch 2 w/ PMSF day 7 | Hanging drop 1 w/PMSF day 10 | hanging drop 2 w/PMSF day 10 | chip 1 w/PMSF day 7 | chip 2 w/PMSF day 6 | chip 3 w/o PMSF day 5 |
|---|---|---|---|---|---|---|---|---|---|---|
| A20 | polymer | high | acid | | | A1 | | | C1 | B1 |
| 21 | organic | high | weak acid | | | | | | | |
| A22 | polymer | high | base | | A1 | | | | | |
| 23 | polymer | high | weak base | | | | | | | |
| 24 | organic | high | acid | | | | | | X | |
| A25 | salt | high | weak acid | | A1 | | | | | |
| 26 | organic | high | acid | | | | | | | C1 |
| 27 | organic | high | weak base | | | | | | | |
| A28 | polymer | high | weak acid | | A1 | | | | | |
| A29 | salt | high | weak base | | A1 | | | | | |
| A30 | polymer | high | no buffer | B1 | A1 | C1 | C1 | C1 | C1 | B1 |
| A31 | polymer | high | no buffer | A1 | | | C1 | C1 | C1 | B1 |
| A32 | salt | high | no buffer | | | C1 | C1 | | | B1 |
| A33 | salt | high | no buffer | | | C1 | C1 | | | |
| A34 | salt | high | acid | A1 | | | | | C1 | |
| A35 | salt | high | weak base | A1 | | C1 | C1 | X | | |
| A36 | polymer | none | base | | A1 | | | X | | |
| 37 | polymer | none | acid | | | | | | | |
| A38 | salt | high | weak base | C1 | C1 | C1 | C1 | X | | |
| A39 | polymer | none | weak base | | A1 | | | | | B1 |
| A40 | organic | none | acid | | A1 | C1 | C1 | C1 | C1 | C1 |
| A41 | organic | none | weak base | | A1 | | | | | |
| A42 | polymer | low | no buffer | A1 | | A1 | | | C1 | C1 |
| 43 | polymer | none | no buffer | A1 | | | | C1 | | |
| A44 | salt | high | no buffer | | | | | | | |
| A45 | polymer | high | weak acid | | | | | X | C1 | C1 |
| A46 | polymer | high | weak acid | | | | | | C1 | |
| A47 | salt | high | acid | B1 | | C1 | C1 | C1 | | B1 |
| A48 | salt | high | base | A1 | | C1 | C1 | X | | |
| 49 | polymer | high | no buffer | X | X | X | X | X | X | X |
| 50 | polymer | high | no buffer | X | X | X | X | X | X | X |
| | | | | 11 | 13 | 16 | 12 | 10 | 12 | 12 |

Key:
A1 = Crystal;
B1 = Needle; Plate; or Rod;
C1 = Precipitate;
X = N/A or Failed Valve These results indicate that crystallization is a stochastic event, depending on technique, nucleation, and other variables. Hits were seen in some techniques, but not others. Hits were also seen in one duplicate, but not the other. Where duplicates in hanging drop were set up in the same well on the same coverslip, hits were even seen in one drop, but not a neighboring drop, not an atypical result for crystallization of certain proteins. Also, although there are many overlaps on hits between techniques, the types of hits vary. Many hits produced by microbatch are single crystals, some hits produced by hanging drop are crystals and most are precipitate, and hits produced in the chip tend to be either needles or precipitate.

Figure 53A:
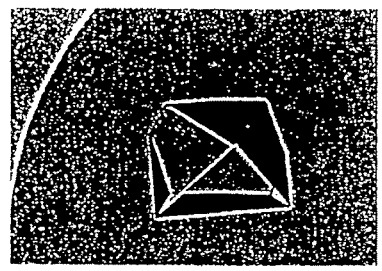
FIG. 53A shows a proteinase K crystal formed by conventional microbatch.
Figure 53B:
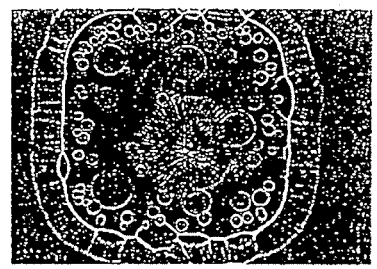
FIG. 53B shows proteinase K crystals observed on the chip.

FIG. 53A shows proteinase K crystal observed in microbatch. FIG. 53A shows needles observed on chip. Reagent 30 is a good example of the variations on the types of hits. In microbatch, a crystal formed in one duplicate and needles were produced in the other, precipitate was found in hanging drop, and one chip resulted in precipitate, while the other resulted in needle crystals.

The chip was able to produce hits in conditions that contained acidic buffers (pH 5.6 or pH 4.6), basic buffers (pH 8.5), and even isopropyl alcohol. Furthermore, of the 17 conditions that produced hits in hanging drop or microbatch, but not in the chip, the reagents ranged from organic or polymer precipitant to salt precipitant, from high salt to no salt, and from acidic buffers to basic buffers. These results indicate that the chip can withstand acids, bases, and organic materials used in the Hampton crystallization screens.

The PDMS elastomer material utilized in certain embodiments of the present invention is generally compatible with most solvents used in protein crystallization. A nonexclusive list of solvents that are not compatible with PDMS includes concentrated acids such as hydrofluoric acid, nitric acid, sulfuric acid, and Aqua Regia, as well as benzaldehyde, benzene, carbon tetrachloride, chlorobenzene, chloroform, cyclohexane, ether, diethyl ether, isopopyl ether, methyl ketone, ethel ketone, methylene chloride, petroleum ether, tetrahydrofuran, toluene, trichloroethylene, acetates, and xylene. Where such materials are to be utilized in conjunction with PDMS-based microfluidic devices in accordance with embodiments of the present invention, a surface coating or modification of the PDMS may be required. Alternatively, PDMS may be replaced by a different elastomer material having appropriate solvent compatibility. A large number of possible alternative elastomer materials have been discussed previously.

j. Beef Liver Catalase Crystallization

Figure 54:
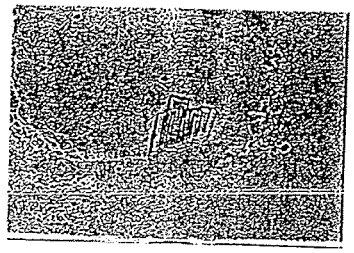
FIG. 54 shows photographs of additional proteinase K crystals.

Beef liver catalase was crystallized in two chips, two hanging drops, and one microbatch experiment. Crystal screens 1-48, excluding 6, were tested in duplicate in hanging drop and carried out for 7 days. Crystal screens 25-36 were tested in duplicate in the chip for 3 days and crystal screens 1-48 were set up in another chip and monitored for 7 days. Crystal screens 1-48 in microbatch were observed for 7 days. As shown in FIG. 54, in some cases crystals grew in wells experiencing significant dehydration. Table 3 shows results of the crystallization for beef liver catalase.

TABLE 3

Beef Liver Catalase Crystallization Results

| Reagent number | precipitant classification | salt condition | acid/base | chip 1 top day 3 | chip 1 bottom day 3 | chip 2 day 7 | hanging drop 1 day 7 | hanging drop 2 day 7 | microbatch day 7 |
|---|---|---|---|---|---|---|---|---|---|
| 1 | organic | low | acid | X | X | C1 | C1 | C1 | |
| 2 | salt | high | no buffer | X | X | A1 | | | |
| 3 | salt | high | no buffer | X | X | C1 | C1 | C1 | C1 |
| 4 | salt | high | base | X | X | C1 | C1 | C1 | |
| 5 | organic | high | weak base | X | X | A1 | C1 | C1 | |
| 6 | polymer | high | base | X | X | B1 | X | X | C1 |
| 7 | salt | high | weak acid | X | X | A1 | | | |
| 8 | organic | high | weak acid | X | X | C1 | C1 | C1 | |
| 9 | polymer | high | acid | X | X | B1 | C1 | C1 | B1 |
| 10 | polymer | high | acid | X | X | B1 | C1 | C1 | C1 |
| 11 | salt | high | acid | X | X | | C1 | C1 | C1 |
| 12 | organic | high | weak base | X | X | | C1 | C1 | |
| 13 | polymer | high | base | X | X | A1 | | | |
| 14 | polymer | high | weak base | X | X | C1 | | | |
| 15 | polymer | high | weak acid | X | X | B1 | C1 | C1 | B1 |
| 16 | salt | high | weak base | X | X | C1 | C1 | C1 | C1 |
| 17 | polymer | high | base | X | X | B1 | C1 | C1 | C1 |
| 18 | polymer | high | weak | X | X | B1 | C1 | C1 | B1 |
| 19 | organic | high | base | X | X | A1 | C1 | C1 | |
| 20 | polymer | high | acid | X | X | B1 | C1 | C1 | C1 |
| 21 | organic | high | weak acid | X | X | A1 | | | |
| 22 | polymer | high | base | X | X | B1 | C1 | C1 | C1 |
| 23 | polymer | high | weak base | X | X | | | | |
| 24 | organic | high | acid | X | X | C1 | C1 | C1 | C1 |
| 25* | salt | high | weak acid | C1 | A1 | C1 | | | |
| 26 | organic | high | acid | A1 | A1 | A1 | C1 | C1 | |
| 27 | organic | high | weak base | A1 | A1 | | C1 | C1 | |
| 28 | polymer | high | weak acid | B1 | C1 | B1 | C1 | C1 | B1 |
| 29 | salt | high | weak base | C1 | C1 | C1 | B1 | C1 | |
| 30 | polymer | high | no buffer | B1 | C1 | B1 | C1 | C1 | C1 |
| 31 | polymer | high | no buffer | B1 | B1 | B1 | C1 | C1 | B1 |
| 32 | salt | high | no buffer | A1 | | C1 | C1 | C1 | B1 |
| 33 | salt | high | no buffer | C1 | C1 | C1 | C1 | C1 | C1 |
| 34 | salt | high | acid | C1 | C1 | C1 | C1 | C1 | C1 |
| 35 | salt | high | weak base | C1 | C1 | C1 | | | |
| 36* | polymer | none | base | B1 | B1 | B1 | C1 | B1 | |
| 37 | polymer | none | acid | X | X | B1 | C1 | C1 | C1 |
| 38 | salt | high | weak base | X | X | C1 | C1 | A1 | C1 |
| 39 | polymer | none | weak base | X | X | C1 | C1 | C1 | B1 |
| 40 | organic | none | acid | X | X | B1 | C1 | C1 | B1 |
| 41 | organic | none | weak base | X | X | B1 | C1 | C1 | B1 |
| 42 | polymer | low | no buffer | X | X | C1 | C1 | C1 | C1 |
| 43 | polymer | none | no buffer | X | X | B1 | C1 | C1 | |
| 44 | salt | high | no buffer | X | X | | | | |
| 45 | polymer | high | weak acid | X | X | C1 | | | C1 |
| 46 | polymer | high | weak acid | X | X | B1 | C1 | C1 | B1 |
| 47 | salt | high | acid | X | X | C1 | C1 | C1 | C1 |
| 48 | salt | high | base | X | X | C1 | | | C1 |
| X49 | polymer | high | no buffer | X | X | X | X | X | X |
| X50 | polymer | high | no buffer | X | X | X | X | X | X |

TABLE 3-continued

Beef Liver Catalase Crystallization Results

| Reagent number | precipitant classification | salt condition | acid/base | chip 1 top day 3 | chip 1 bottom day 3 | chip 2 day 7 | hanging drop 1 day 7 | hanging drop 2 day 7 | microbatch day 7 |
|---|---|---|---|---|---|---|---|---|---|
| | | | sum 25-36 | 12 | 11 | 11 | 10 | 10 | 6 |
| | | | sum 1-48 | 12 | 11 | 43 | 36 | 36 | 28 |

Figure 55:
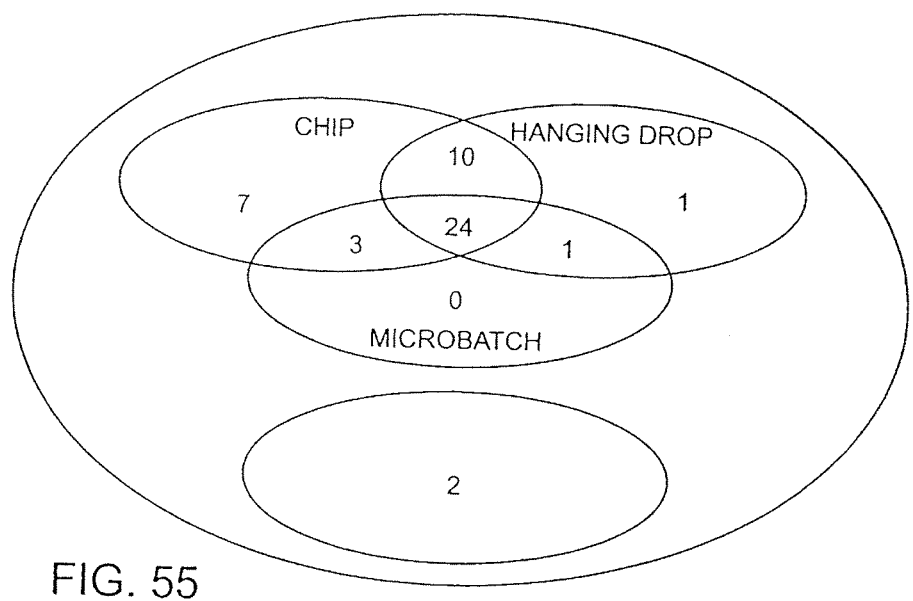
FIG. 55 is a Venn diagram summarizing experiments for crystallization of the beef liver catalase protein.

Key:
A1 = Crystal;
B1 = Needle;
Plate; or Rod;
C1 = Precipitate;
X = N/A or Failed Valve;
* = Dehydration Beef liver catalase shows more promising conditions in the chip than in conventional hanging drop techniques. As shown in the Venn diagram of FIG. 55 conditions produced hits in the chip versus 36 in hanging drop and 28 in microbatch. Only 2 conditions resulted in no hits in any of the three techniques. This was contrary to expectations that beef liver catalase is a difficult protein to crystallize, as Hampton research reported crystals in only 2 out of 48 screens.

Initially it was hypothesized that the chip might mimic the microbatch condition over hanging drop. However, the chip produced results more similar to hanging drop than microbatch. Thirty-six out of 48 hits or no hits were common to the chip and hanging drop (75%). Twenty-nine out of 47 (62%), and 27 out of 41 (66%) were in common between the chip and microbatch, and between microbatch and hanging drop, respectively.

Figures 56A, 56B:
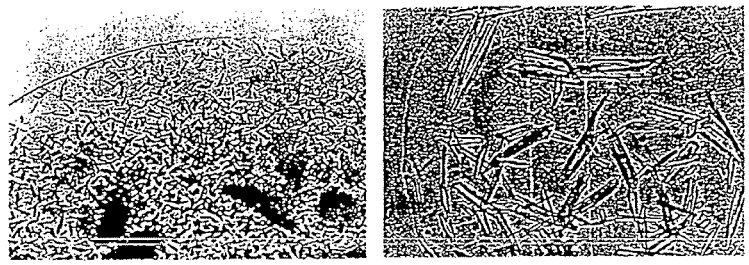
FIG. 56A shows a photograph of the beef liver catalase protein crystals formed by conventional microbatch techniques.
FIG. 56B shows a photograph of beef liver catalase protein crystals formed on a chip in accordance with an embodiment of the present invention.
Figure 57:
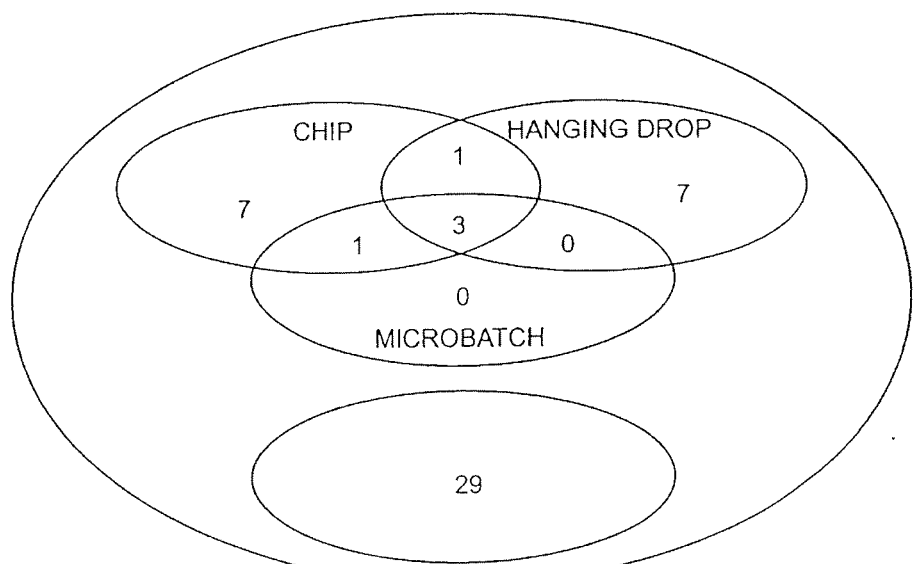
FIG. 57 is a Venn diagram summarizing experiments for crystallization of the bovine pancreas trypsin protein.

FIG. 56A shows that beef liver catalase crystals obtained by conventional microbatch techniques resulted in a morphology similar to crystals formed on chip (FIG. 56B). Eight out of 17 hits that were needles in the chip were also needles in microbatch.

k. Bovine Pancreas Trypsin Crystallization

Bovine Pancreas Trypsin was set up once each in hanging drop, microbatch, and chip. Conditions 1-24 were set up on one chip, and conditions 25-48 were set up on a second chip. The chip containing conditions 25-48 lost containment on day 4, but no change or few changes are expected in those conditions after day 4. Microbatch and hanging drop experiments were observed for 7 days and microbatch crystals were confirmed, similar to glucose isomerase, with a crystal probe. Table 4 summarizes the data from the experiment.

TABLE 4

Bovine Pancreas Trypsin Crystallization Results.

| Reagent number | precipitant classification | salt condition | acid/base | micro-batch day 7 | hanging drop day 7 | chip day 6 |
|---|---|---|---|---|---|---|
| 1 | organic | low | acid | | | |
| 2 | salt | high | no buffer | | | |
| 3 | salt | high | no buffer | | | |
| A4 | salt | high | base | C1 | | C1 |
| 5 | organic | high | weak base | | | |
| 6 | polymer | high | base | | | |
| 7 | salt | high | weak acid | | | |
| 8 | organic | high | weak acid | | | |
| 9 | polymer | high | acid | | | C1 |
| 10 | polymer | high | acid | | | |
| 11 | salt | high | acid | | | |
| 12 | organic | high | weak base | | | |
| 13 | polymer | high | base | | | |
| 14 | polymer | high | weak base | | | |
| A15 | polymer | high | weak acid | A1 | A1 | C1 |
| A16 | salt | high | weak base | | C1 | |
| 17 | polymer | high | base | A1 | | B1 |
| 18 | polymer | high | weak acid | | | C1 |
| 19 | organic | high | base | | C1 | |
| A20 | polymer | high | acid | | | C1 |
| 21 | organic | high | weak acid | | | |
| 22 | polymer | high | base | | | |
| 23 | polymer | high | weak base | | | |
| 24 | organic | high | acid | | | |
| 25 | salt | high | weak acid | | | |
| 26 | organic | high | acid | | | C1 |
| 27 | organic | high | weak base | | X | |
| A28 | polymer | high | weak acid | | | |
| 29 | salt | high | weak base | | | |
| A30 | polymer | high | no buffer | A1 | A1 | A1 |
| A31 | polymer | high | no buffer | A1 | C1 | A1 |
| 32 | salt | high | no buffer | | C1 | |
| 33 | salt | high | no buffer | | C1 | |
| 34 | salt | high | acid | | | |
| 35 | salt | high | weak base | | | |
| 36 | polymer | one | base | | | |
| 37 | polymer | one | acid | | | |
| 38 | salt | high | weak base | | C1 | |
| 39 | polymer | one | weak base | | C1 | |
| 40 | organic | one | acid | | | C1 |
| 41 | organic | one | weak base | | | |
| 42 | polymer | low | no buffer | | | C1 |
| 43 | polymer | one | no buffer | | | |
| 44 | salt | high | no buffer | | | |
| 45 | polymer | high | weak acid | | | C1 |
| 46 | polymer | high | weak acid | | | |
| 47 | salt | high | acid | | C1 | |
| 48 | salt | high | base | | | |
| X49 | polymer | high | no buffer | X | X | X |
| X50 | polymer | high | no buffer | X | X | X |
| | | | | 4 | 11 | 12 |

Key:
A1 = Crystal;
B1 = Needle; Plate, or Rod;
C1 = Precipitate;
X = N/A or Failed As seen in Table 4, 28 conditions did not give hits in any of the three methods and only 3 conditions gave hits in all three techniques. Seven conditions resulted in hits in the chip only, and 7 other conditions produced hits in hanging drop only. No conditions were unique to microbatch. Despite the unique hits in chip and hanging drop, there is good agreement between the three methods. Thirty-two out of 48 conditions produced hits both in chip and hanging drop (67%), 32 out of 41 conditions resulted in hits in chip and microbatch (78%), and 31 out of 41 conditions gave hits in microbatch and hanging drop (76%).

FIG. 58A shows Bovine pancreas trypsin crystals observed in microbatch. FIG. 58B shows Bovine pancreas trypsin crystals observed from the chip.

l. Lysozyme Crystallization

The crystallization of Lysozyme was evaluated, in chip, microbatch, and in hanging drop. Hits in these experiments were defined as crystals, microcrystals, needles, plates, rods, or spherulites, while precipitation was not counted as a hit. The microbatch experiment was run for 2 weeks, while the chip experiment was run for 7 days. The hanging drop experiment was terminated after 3 days due to temperature fluctuations that resulted from the plates being left in direct sunlight. It is likely that had the hanging drop experiment been continued, further crystallization conditions would have been revealed. The results of these experiments are summarized in the Venn Diagram shown in FIG. 59.

Inspection of FIG. 59 shows that the chip revealed the most crystallization conditions, and that approximately 40% of these crystallization conditions were also observed using conventional techniques. This agreement may have been improved had the hanging drop experiments not been terminated prematurely. Also of note is that although Lysosyme is typically considered a very easy protein to crystallize, and gave numerous hits both in chip, and in hanging drop, it showed only 4 hits in the micro batch experiment.

Contrary to the results for Glucose Isomerase, in which crystallization was accelerated in chip, crystallization of Lysosyme was slower in chip. While one day revealed 63% of hits in hanging drop, and 75% of hit in micro-batch, only 1 of 23 chip hits occurred within the first 24 hrs of incubation.

All three methods produced large single crystals of x-ray diffraction quality. FIGS. 60A-B show a comparison of crystals formed in chip and microbatch, respectively.

m. Xylanase Crystallization

The crystallization of Xylanase was evaluated, in chip, microbatch, and in hanging drop. Hits in these experiments were defined as crystals, microcrystals, needles, plates, rods, or spherulites, while precipitation was not counted as a hit. The microbatch experiment was run for 2 weeks, while the chip experiment was run for 10 days. The hanging drop experiment was terminated after 3 days due to temperature fluctuations that resulted from the plates being left in direct sunlight. It is likely that had the hanging drop experiment been continued, further crystallization conditions would have been revealed. The results of these experiments are summarized in the Venn Diagram shown in FIG. 61.

Inspection of FIG. 61 shows that 75% of the hits in chip were reproduced in hanging drop or micro batch. The highest quality crystals, both in chip, and in microbatch, were formed using condition 14. FIGS. 62A-B shows a comparison of these crystals, grown in microbatch, and on chip, respectively. While 6 of the 7 micro batch hits occurred within the first day of incubation, 7 of the 8 chip hits occurred at incubation times greater than 48 hrs. Condition 14 was reproduced with 6-fold redundancy in a subsequent experiment, and showed only two hits (occurring at 72 hrs) during a 7 day incubation. These crystals grew to full size (approx. 100 μm) over-night. The long time for crystal formation, inconsistent results, and quick subsequent growth of the crystals, suggests that nucleation is the rate limiting step for crystallization of Xylanase in chip.

The information provided by Hampton Research indicates that Xylanase can be crystallized using Na/K Phosphate solution in a pH range of 7 to 8.2, and at concentrations between 0.6 and 1.4 Mol. In two separate experiments, a systematic screen of Xylanase vs. Na/K Phosphate was conducted in chip.

One experiment tested 50% stock Xylanase against a grid of Na/K Phosphate conditions, covering pH values from 6.4 to 7.8 in steps of 0.2, and concentration from 1.0 Molar to 3.0 Molar in steps of 0.4. The other experiment tested 25% stock Xylanase against the same grid. After 1 day, microcrystals (less than 10 um largest dimension) were seen in both experiments for all pH values with concentrations higher than 1.4 Molar. The wells showed no further change for the next 6 days.

On the seventh day, large plate/star structures where observed in the same condition (pH 6.4, 1M) on both chips. The 50% Xylanase chip showed this hit in the mpms (medium protein:medium solvent) condition, while the 25% Xylanase chip showed the hit in the lpss (large protein:small solvent) condition; consistent with the concentration of protein being similar. These hits are shown in FIGS. 63A-B. This result indicates crystallization of Xylanase to be sensitive to changes in pH and changes in Na/K Phosphate concentration. The chip/chip correspondence also shows repeatability to be good, even at long incubation times. Although the hit did occur at the corner of the grid, the result further suggests that even after 7 days, conditions on the chip were not sufficiently blended (in pH and salt concentration), so as to make nearby wells show crystallization.

n. B Subunit of Topoisomerase VI

The B subunit of topoisomerase VI was tested in chip against the following 3 commercial sparse matrix screens, Hampton Crystal Screen I (HCS1), Hampton Crystal Screen II (HCS2), and Emerald Wizard Screen II (WIZ2). Since only a small volume of protein solution was available (50 uL), bulk controls were not done. All three experiments were incubated for 8 days. The results of these experiments are tabulated in Table 5.

TABLE 5

B Subunit of Topoisomerase VI Results

| Morphology | HCS1 | HCS2 | WIZ2 |
| --- | --- | --- | --- |
| Crystals | | | |
| Plates | 22, 9, 6, 17, 18, 36, 46, 37, 28, 41, | 48 | 3, 18, 28 |
| Needles | 15, 40 | | 8, 18 |
| Stars | 15, 40, 1, 10 | 16, 14, 25 | 7, 8, 24, 47 |
| Micro Crystals/ Specs | 4, 3, 30, 32, 35, 45, 31, 43 | 10, 24, 23, 31, 36 | 20, 30, 32, 44, 36 |
| Aggregate | 2, 5, 7, 8, 16, 21, 15, 26, 27, 29, 33, 25, 37, 38, 47 | | 16, 15, 35, 48, 45, 31, 37 |
| Lost Condition | | 26, 27 | |

Figure 64A:
FIGS. 64A-B show photographs of large, high quality crystals of the B subunit of topoisomerase VI protein formed utilizing a ship in accordance with one embodiment of the present invention.
Figure 64B:
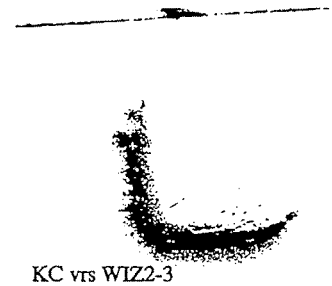

The chip shows many large plate crystals, with some of sufficient size for x-ray diffraction. Two examples of these plates are shown in FIG. 64A-B. Prior experiments have revealed that the B subunit of topoisomerase VI crystallizes well in PEG conditions, and typically displays the plate morphology. The chip results demonstrate an excellent reproduction of this behavior, with all 14 plate hits being on PEG conditions. Furthermore, the chip outperformed the hanging drop and micro batch experiments, showing more frequent hits. Comparing the chip results to those of micro-batch shows that the chip uncovered 23 conditions that gave rise to plate crystals, while only 10 were discovered in micro-batch. Furthermore, 6 of the 10 conditions that gave crystals in micro-batch also gave crystals in chip, while 3 gave granular precipitate, and only one did not produce a hit in chip. Lastly, crystals formed in micro-batch were not present for several days, while chip crystals began to form in less than 6 hours.

o. Negative Controls

No protein controls were set up on chips to help identify protein crystals versus salt crystals. Chips were set up as described for protein crystallization experiments. 1 mM calcium chloride, 25 mM HEPES, pH 7.0 was used as a negative control for proteinase K and 20 mM calcium chloride, 25 mM HEPES, pH 7.0 was used as a negative control for bovine pancreas trypsin (calcium chloride concentration should have been 10 mM and benzamidine hydrochloride was not added). Controls were also set up in microbatch and hanging drop with 1 mM calcium chloride, 25 mM HEPES, pH 7.0, and filtered distilled deionized water. Specific no-protein controls (respective buffer with no-protein) were done for Lysosyme, Glucose Isomerase, Xylanase, and the B subunit of topoisomerase VI. Where crystals have been reported, the no-protein controls were clear.

7. Analysis of Crystal Structure from Protein on Chip

The utility of the chip is ultimately dependent on its' ability to quickly generate high quality diffraction patterns at a reduced cost. A clear path from the chip-to-protein structure is therefore invaluable. Several paths from in-chip crystals to diffraction data are discussed below.

a. On-Chip Crystallization as Screening for Reproducing Crystals Using Conventional Techniques One possible application for a chip is determination of favorable crystallization conditions that can subsequently be reproduced using conventional techniques. Correspondence between the chip and two conventional techniques (micro batch and hanging drop) has been shown to be variable (between 45% and 80%). However, this variation is not a feature unique to the chip. These widely used crystallization techniques show only marginal correspondence (e.g. 14 of 16 hanging drop hits for lysosyme do not occur in microbatch), and often show variation within themselves, for example Table 2 (Proteinase K). As a tool for screening initial crystallization conditions, the chip may be able to identify as many promising conditions.

Figure 65:
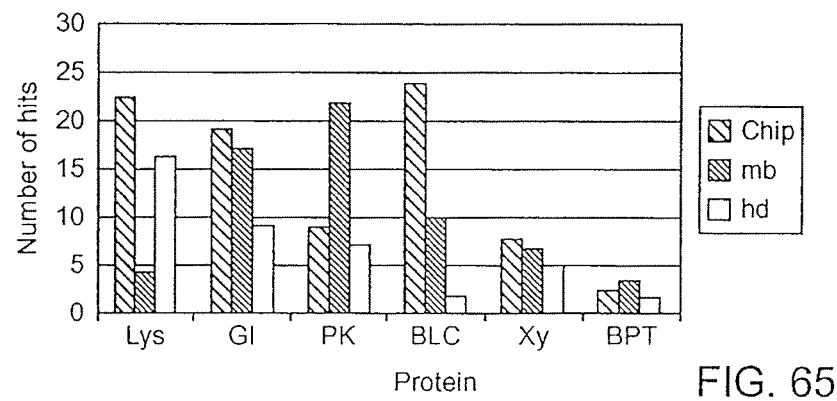
FIG. 65 plots a bar graph of crystallization hits generated on the various proteins for the conventional microbatch and hanging drop techniques, and for a chip in accordance with one embodiment of the present invention.

FIG. 65 shows a comparison of the number of hits generated on each protein using the three different technologies. In FIG. 65 only crystals, microcrystals, rods, and needles are counted as hits, while spherulites and precipitation is not counted. The data on Proteinase K is a sum of the experiments with and without PMSF, and data for the B subunit of topoisomerase VI has not been included for lack of hanging drop data (although the chip far outperformed micro-batch in this case). Inspection of FIG. 65 shows that in 4 of the 6 cases, the chip produced more hits than either conventional method. Only for Proteinase K did the conventional techniques provide significantly more favorable results.

In order to understand differences between crystallization methods to identify possible reasons for productivity of the chip, we must appreciate that the three methods produce different thermodynamic conditions on both short and long time scales. In order to induce protein crystallization, one must make the crystallization energetically favorable (supersaturation condition), and maintain these conditions long enough for crystal growth to occur.

There are also different degrees of supersaturation. In low supersaturation, crystal growth tends to be supported, while nucleation of new crystals is relatively unlikely. In high supersaturation, nucleation is rapid, and many small low quality crystals may often be formed. In the three methods considered here, the condition of supersaturation is achieved through the manipulation of the relative, and absolute, concentration of protein and counter-solvent.

Figure 66:
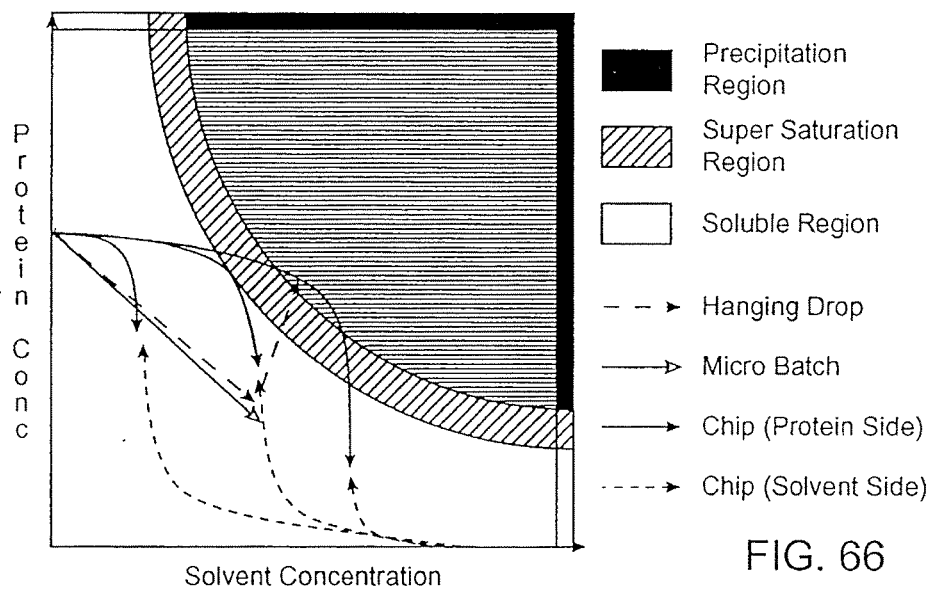
FIG. 66 compares the phase space evolution and equilibration of the conventional microbatch and hanging drop methods, and for the microfluidic device in accordance with the embodiment of the present invention.
Figure 67A:
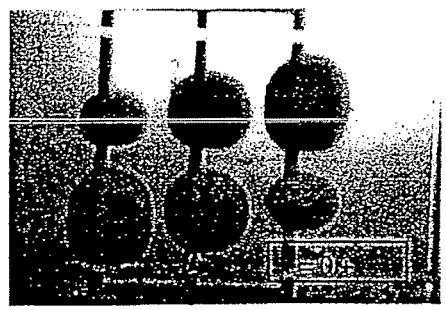
FIGS. 67A-C show photographs of equilibrium of dyes present in three compared wells of the chip shown in FIG. 45, at elapsed diffusion times of 0 s, 10 min, and 45 min.
Figure 67B:
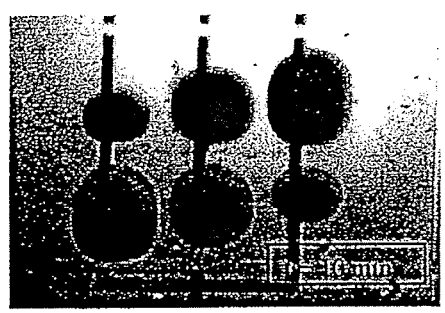
Figure 67C:
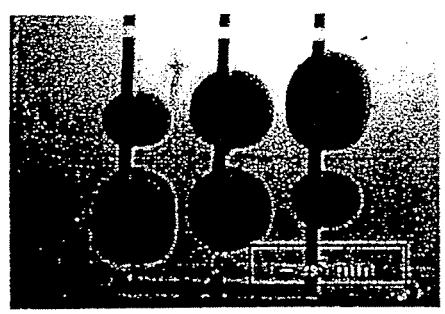

A comparison of the phase space evolution/equilibration of the three methods is shown in FIG. 66. For the micro batch technique, mixing of the two solutions is quick, and when kept under impermeable oil layers, little significant concentration occurs over time. Micro batch therefore tends to sample only a single point in phase space, maintaining approximately the same condition over time.

Hanging drop starts out like micro batch, with rapid mixing of the two solutions, but then undergoes a concentration on a longer timescale (hours to days) due to vapor equilibration with the more concentrated salt/precipitant reservoir. During the evaporative dehydration of the drop, the ratio of protein to precipitant remains constant.

As described in detail below in the description of Microfluidic Free Interfaces, on the short time scale the chip dynamics most closely resemble a free interface diffusion experiment. Mixing is slow, and the rate of species equilibration (protein/precipitant/proton/salt) depends on species' diffusion constants. Small molecules such as salts have large diffusion constants, and hence equilibrate quickly. Large molecules (e.g. proteins) have small diffusion constants, and equilibrate more slowly.

FIG. 67A-D show photographs of time-resolved equilibration of two dyes in three compound wells. The dye used has a molecular weight of approximately 700 Da. From these pictures the equilibration time of the dye is estimated to be approximately 1.5 hours. The dimensional Einstein equation may be used to get a rough estimate of diffusion times.

$$t = \frac{x^2}{4D}; \tag{2}$$

where:

$t$ = diffusion time, $x$ = longest diffusion length;

and $D$ = diffusion coefficent

Generally, the diffusion coefficient varies inversely with the radius of gyration, and therefore as one over the cube root of molecular weight.

$$D \propto \frac{1}{r} \propto \frac{1}{m^{1/3}}; \tag{3}$$

where:

$D$ = diffusion coefficent;

$r$ = radius of gyration;

and $m$ = molecular weight

As compared with the rough 1.5 hr equilibration time for the dye, an approximate equilibration time for a protein of 20 KDa over the same distance is estimated to be approximately 45 hours. The equilibration time for a small salt of a molecular weight of 100 Da over the same distance is about 45 minutes.

Soon after the chip interface valves are opened, the protein concentration on the protein-side has changed very little, while the salt concentration has increased to one of three final values determined by the relative size of the protein and solvent wells. Next, over a time of approximately 45 hours, the protein concentration equilibrates, increasing on the solvent side, and decreasing on the protein side. The final protein concentration is once again determined by the relative chamber sizes. A similar process occurs on the solvent side of the chip, with solvent concentration starting at its' highest value, and protein concentration starting at zero. The chip therefore samples more of phase-space, and consequently has a better chance of detecting conditions favorable to crystallization. On time scales larger than those shown in FIG. 66, there may be subsequent changes in the chip conditions due to the permeability of PDMS to some solutes and solvents.

If it is desirable to slow down or halt the equilibration process, the interface valves may be gated, adjusting the equilibration rate by changing the valve actuation duty cycle. This provides the opportunity to gain temporal control of the equilibration process, a key advantage of embodiments in accordance with the present invention. Additional discussion of temporal control over the equilibrium process is described below in conjunction with FIGS. 76A-C.

The crystallization technique of free interface diffusion in capillaries may more closely emulate the chip results. Traditionally this method is not often used due to the difficulty of reliably setting up a well-defined interface. However, in microfluidic environments it is relatively easy to establish reliable free-interface diffusion experiments. Additional discussion of the formation of microfluidic free-interfaces is presented below in conjunction with FIGS. 71-75.

Figure 68A:
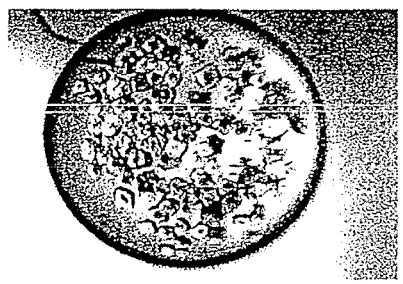
FIG. 68A shows a photograph of crystal formation in silicone oil.
Figure 68B:
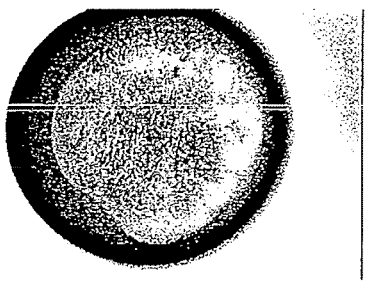
FIG. 68B shows a photograph evidencing the absence of crystal formation in paraffin oil.

It may also be possible to develop a macroscopic crystallization technique, based on free-interface diffusion, emulating chip conditions while providing easy harvesting of crystals.

b. On-Chip Crystallization to Obtain Seed Crystals for Crystallization Using Conventional Techniques In another application of the crystallization chip, crystals may be grown for harvesting using conventional methods. Inspection of FIG. 66 suggests that exporting a favorable condition from the chip to another method, will likely require screening around this condition. In a preliminary experiment, 10 conditions that produced Glucose Isomerase crystals in chip, but that did not produce crystals in micro batch, were used as a basis for additional screening in micro batch. Each condition was mixed with the stock protein solution at 1:4, 1:1, and 4:1 ratios, both under paraffin oil, and silicone oil. Silicone oil was used since it has permeability similar to that of the PDMS. At the end of 6 days, 6 of the ten proteins that did not previously crystallize in micro batch showed crystals. Of particular interest was that of HCSI-6, which formed high quality crystals at a 4:1 ratio of protein to solution, under silicone oil. This condition showed no crystals in any of the other conditions, including the identical condition under paraffin oil. FIG. 68A shows crystals formed under the silicone oil, and FIG. 68B shows the negative result under paraffin oil. This result shows that the permeability of the containment material can have significant impact on protein crystallization.

This also suggests that materials with permeability similar to that of PDMS may be useful in establishing a macro crystallization technique that more closely resembles the chip.

c. Direct Analysis of Crystals Grown On-Chip

Figure 69:
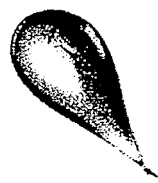
FIG. 69 shows a photograph of the Xylanase crystal of FIG. 62B grown on-chip, as mounted in a cryo-loop.
Figure 70A:
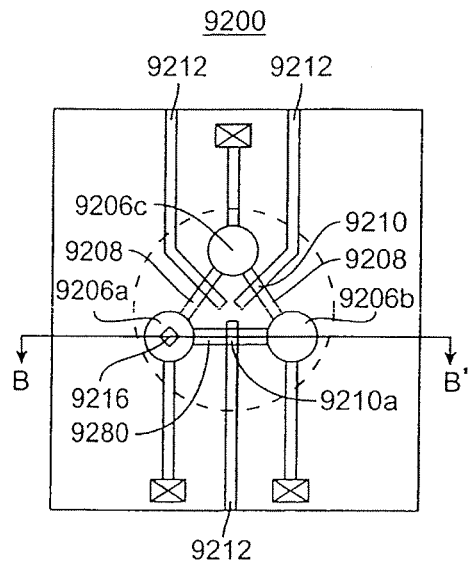
FIG. 70A shows a plan view of one embodiment of a crystallization growing chip in accordance with an embodiment of the present invention.
Figure 70B:
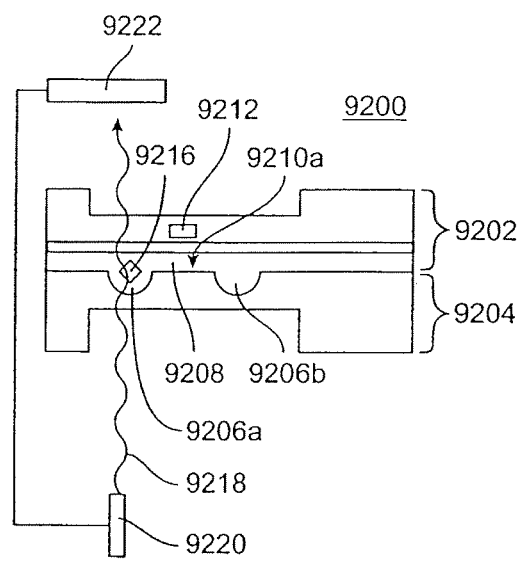
FIG. 70B shows a simplified cross-sectional view of the embodiment of the crystal growing chip shown in FIG. 70A along line B-B.

If high quality crystals can be grown in, and extracted from the chip, crystallization conditions need not be exported. As shown in FIGS. 50-51 (glucose isomerase), 60A (lysozyme), 62B (Xylanase), and 64A-B (B subunit of topoisomerase VI), high quality crystals of sufficient size for x-ray crystallography, can be grown on the chip. Since the chip can be removed from the glass substrate, it is also possible to extract protein crystals. Six crystals (1 of Xylanase, 5 of the B subunit of topoisomerase VI) have been removed from chip, mounted in a cryo-loop, and flash frozen in liquid nitrogen. In one case, with a Xylanase crystal grown in HCS1-14, the chip was peeled off, and 5 uL of 30% glycerol, 70% solvent, was pipetted onto the well. The crystal was then extracted using a 300 um cryo-loop, and flash-frozen in liquid nitrogen. FIG. 69 shows this Xylanase (the same as shown in FIG. 62A-B), mounted in the cryo-loop.

d. Growing/Harvesting Chip

As previously described, once a protein crystal has been formed, information about its three dimensional structure can be obtained from diffraction of x-rays by the crystal. However, application of highly energetic radiation to the protein tends to generate creates heat. X-rays are also ionizing, and can result in the production of free radicals and broken covalent bonds. Either heat or ionization may destroy or degrade the ability of a crystal to diffract incident x-rays.

Accordingly, upon formation of a crystal a cryogenic material is typically added to preserve the crystalline material in its altered state. However, the sudden addition of cryogen can also damage a crystal. Therefore, it would be advantageous for an embodiment of a crystallization chip in accordance with the present invention to enable the direct addition of cryogen to the crystallization chamber once a crystalline material is formed therein.

In addition, protein crystals are extremely delicate, and can quickly crumble or collapse in response to physical trauma. Accordingly, harvesting a crystal unharmed from the small chambers of a chip poses a potential obstacle to obtaining valuable information about the crystalline material.

Therefore, it would also be advantageous for an alternative embodiment of a crystallization chip in accordance with the present invention to allow direct interrogation by x-ray radiation of crystalline materials formed in a chip, thereby obviating entirely the need for separate crystal harvesting procedures.

Figure 71A:
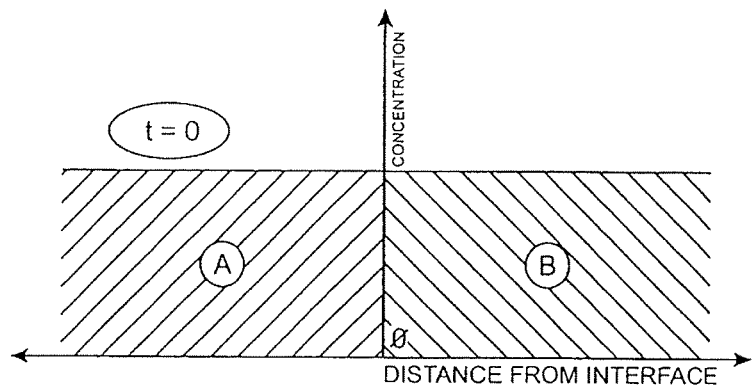
FIGS. 71A-D are simplified schematic drawings plotting concentration versus distance from a free interface.
Figure 71B:
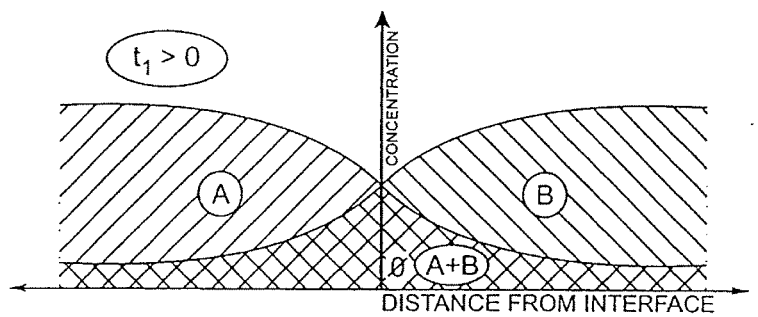
Figure 71C:
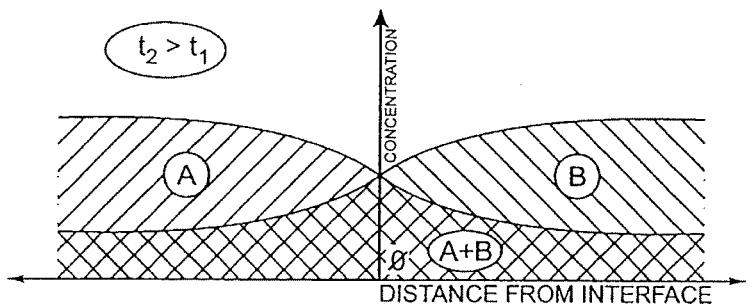
Figure 71D:
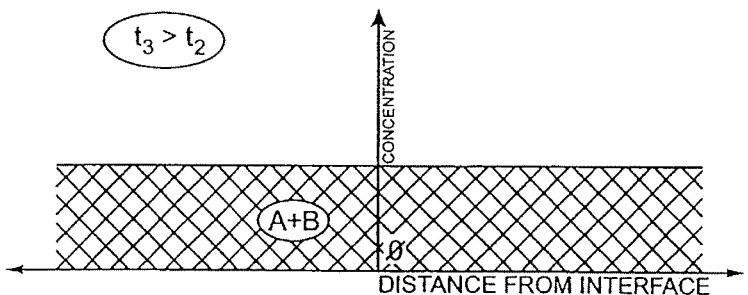

Accordingly, FIG. 71A shows a plan view of a simplified embodiment of a crystal growing chip in accordance with the present invention. FIG. 71B shows a simplified cross-sectional view of the embodiment of the crystal growing chip shown in FIG. 71A along line B-B'.

Harvesting/growing chip 9200 comprises elastomer portion 9202 overlying glass substrate 9204. Glass substrate 9204 computes three etched wells 9206a, 9206b and 9206c. Placement of elastomer portion 9202 over glass substrate 9204 thus defines three corresponding chambers in fluid communication with each other through flow channels 9208. The flow of materials through flow channels 9208 is controlled by valves 9210 defined by the overlap of control lines 9212 over control channels 9208.

During operation of growth/harvesting chip 9200, valves 9210 are initially activated to prevent contact between the contents of chambers 9206a, 9206b and 9206c. Chambers 9206a, 9206b and 9206c are then separately charged through wells 9214 with different materials for effecting crystallization. For example, chamber 9206a may be charged with a protein solution, chamber 9206b may be charged with a crystallizing agent, and chamber 9206c may be charged with a cryogen.

The first control line 9212 may then be deactivated to open valve 9210a, and thereby allowing diffusion of protein solution and crystallizing agent. Upon formation of a crystal 9216, the remaining control lines 9212 may be deactivated to allow the diffusion of cryogen from chamber 9206c to preserve the crystal 9216.

Next, the entire chip 9200 may be mounted in an x-ray diffraction apparatus, with x-ray beam 9218 applied from source 9220 against crystal 9216 with diffraction sensed by detector 9222. As shown in FIG. 71B, the general location of wells 9206 corresponds to regions of reduced thickness of both elastomer portion 9202 and underlying glass portion 9204. In this manner, radiation beam 9218 is required to traverse a minimum amount of elastomer and glass material prior to and subsequent to encountering crystal 9216, thereby reducing the deleterious effect of noise on the diffracted signal received.

While one example of a protein growth/harvesting chip has been described above in connection with FIGS. 71A-B, embodiments in accordance with the present invention are not limited to this particular structure. For example, while the embodiment of the current embodiment that is described utilizes a glass substrate in which microchambers have been etched, fabrication of microfluidic structures in accordance with the present invention is not limited to the use of glass substrates. Possible alternatives for fabricating features in a substrate include injection molding of plastics, hot embossing of plastics such as PMMA, or fabricating wells utilizing a photocurable polymer such as SU8 photoresist. In addition, features could be formed on a substrate such as glass utilizing laser ablation, or features could be formed by isotropic or aniosotropic etching of a substrate other than glass, such as silicon.

Potential advantages conferred by alternative fabrication methods include but are not limited to, more accurate definition of features allowing for more dense integration, and ease of production (e.g. hot embossing). Moreover, certain materials such as carbon based plastics impose less scattering of X-rays, thereby facilitating collection of diffraction data directly from a chip.

An embodiment of a microfluidic structure facilitating crystal growth and analysis comprises an elastomer portion bearing a recess on a lower surface. A substrate is in contact with the lower surface of the elastomer portion to define a first microfluidic chamber, a second microfluidic chamber, and a third microfluidic chamber, the first, second, and third microfluidic chambers in fluid communication through a flow channel defined between elastomer portion and the substrate. The first chamber may be primed with a target material solution, the second chamber may be primed with a crystallizing agent, and the third chamber may be primed with a cryogen, such that crystals formed in the structure by diffusion of the crystallizing agent and the target solution may be preserved through a reduction in temperature afforded by introduction of the cryogen.

e. Crystal Off-Loading Methods

An additional possibility for the harvesting of crystals is to have a method of off-loading from chip. Off-loading could be performed once crystals have formed, or alternatively, prior to incubation. These off-loaded crystals could then be used to seed macroscopic reactions, or be extracted and mounted in a cryo-loop. If a method for the addition of cryogen was also developed, the crystals could be flash frozen and mounted directly into the x-ray beam.

8. Micro-Free Interface Diffusion

Since it may be difficult to determine, a priori, which thermodynamic conditions will induce crystallization, a screening method should sample as much of phase-space (as many conditions) as possible. This can be accomplished by conducting a plurality of assays, and also through the phase space sampled during the evolution of each assay in time. One conventional method that is particularly effective at sampling a wide range of conditions is macroscopic free-interface diffusion. This technique requires the creation of a well-defined fluidic interface between two or more solutions, typically the protein stock, and the precipitating agent, and the subsequent equilibration of the two solutions via a diffusive process. As the solutions diffuse into one another, a gradient is established along the diffusion path, and a continuum of conditions is simultaneously sampled. Since there is a variation in the conditions, both in space, and in time, information regarding the location and time of crystal formation may be used in further optimization. FIGS. 71A-71D are simplified schematic diagrams plotting concentration versus distance for a solution A and a solution B in contact along a free interface. FIGS. 71A-D show that over time, a continuous and broad range of concentration profiles of the two solutions is ultimately created.

Despite the efficiency of macroscopic free-interface diffusion techniques, technical difficulties have rendered it unsuitable for high throughput screening applications, and it is not widely used in the crystallographic community for several reasons. First, the fluidic interfaces are typically established by dispensing the solutions into a narrow container; such as a capillary tube or a deep well in a culture plate. FIGS. 72A-B show simplified cross-sectional views of the attempted formation of a macroscopic free-interface in a capillary tube 9300. The act of dispensing a second solution 9302 into a first solution 9304 creates convective mixing and results in a poorly defined fluidic interface 9306.

Moreover, the solutions may not be sucked into a capillary serially to eliminate this problem. FIGS. 73A-B show the mixing, between a first solution 9400 and a second solution 9402 in a capillary tube 9404 that would result due to the parabolic velocity distribution of pressure driven Poiseuille flow, resulting in a poorly defined fluidic interface 9406. Furthermore, the container for a macro free-interface crystallization regime must have dimensions making them accessible to a pipette tip or dispensing tool, and necessitating the use of large (10-100 µl) volumes of protein and precipitant solutions.

Figure 74A:
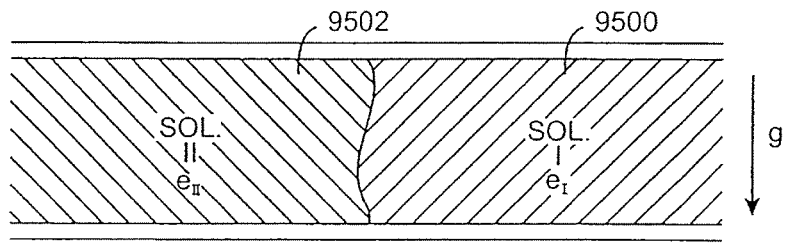
FIGS. 74A-C show the microscopic free interface formed by solutions having different densities.
Figure 74B:
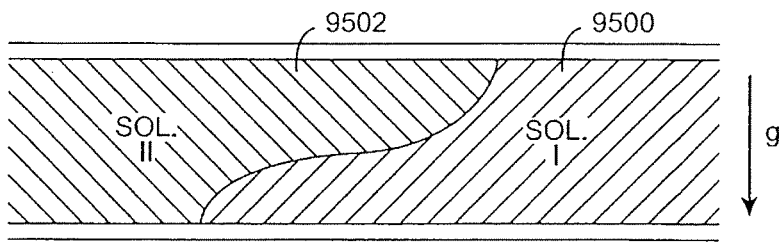
Figure 74C:
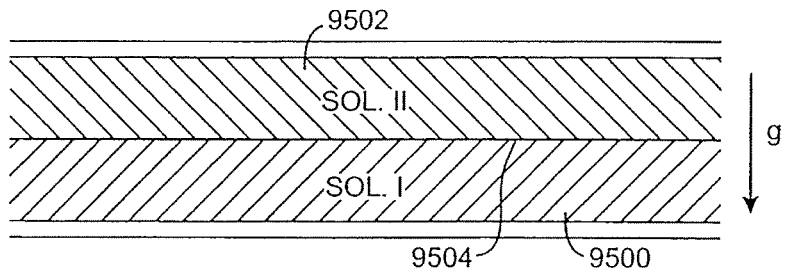

In order to avoid unwanted convective mixing, care must be taken both during dispensing and during crystal incubation. For this reason cumbersome protocols are often used to define a macro free-interface. For example, freezing one solution prior to the addition of the second. Moreover, two solutions of differing density will mix by gravity induced convection if they are not stored at the proper orientation, additionally complicating the storage of reactions. This is shown in FIGS. 74A-C, wherein over time first solution 9500 having a density greater than the density of second solution 9502 merely sinks to form a static bottom layer 9504 that is not conducive to formation of a diffusion gradient along the length of a capillary tube.

In accordance with embodiments of the present invention, a crystallization technique analogous to traditional macro-free interface diffusion, called gated micro free interface diffusion (Gated µ-FID), has been developed. Gated µ-FID retains the efficient sampling of phase space achieved by macroscopic free interface diffusion techniques, with the added advantages of parsimonious use of sample solutions, ease of set-up, creation of well defined fluidic interfaces, control over equilibration dynamics, and the ability to conduct high-throughput parallel experimentation. These advantages are made possible by a number of features of the instant invention.

Microfluidics enables the handling of fluids on the sub-nanoliter scale. Consequently, there is no need to use large containment chambers, and hence, assays may be performed on the nanoliter, or subnanoliter scale. The utilization of extremely small volumes allows for thousands of assays to be performed to consume the same sample volume required for one macroscopic free-interface diffusion experiment. This reduces costly and time-consuming amplification and purification steps, and makes possible the screening of proteins that are not easily expressed, and hence must be purified from a bulk sample.

Microfluidics further offers savings in preparation times, as hundreds, or even thousands of assays may be performed simultaneously. The use of scaleable metering techniques as previously described, allow for parallel experimentation to be conducted without increased complexity in control mechanisms.

The elastomeric material from which microfluidic structures in accordance with embodiments of the present invention may be formed, is relatively permeable to certain gases. This gas permeability property may be exploited utilizing the technique of pressurized out-gas priming (POP) to form well-defined, reproducible fluidic interfaces.

Figure 75A:
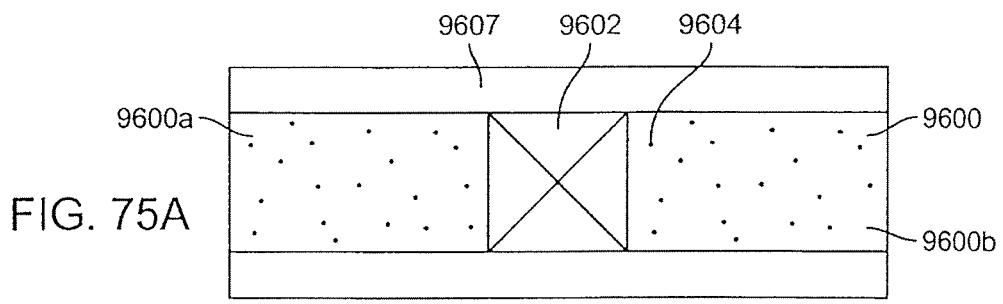
FIGS. 75A-D show a simplified schematic view of the formation of a high quality microfluidic free interface resulting from pressurized out-gas priming (POP) of a microfluidic structure in accordance with an embodiment of the present invention.

FIG. 75A shows a cross-sectional view of a flow channel 9600 of a macrofluidic device in accordance with an embodiment of the present invention. Flow channel 9600 is separated into two halves by actuated valve 9602. Prior to the introduction of material, flow channel 9600 contains a gas 9604.

Figure 75B:
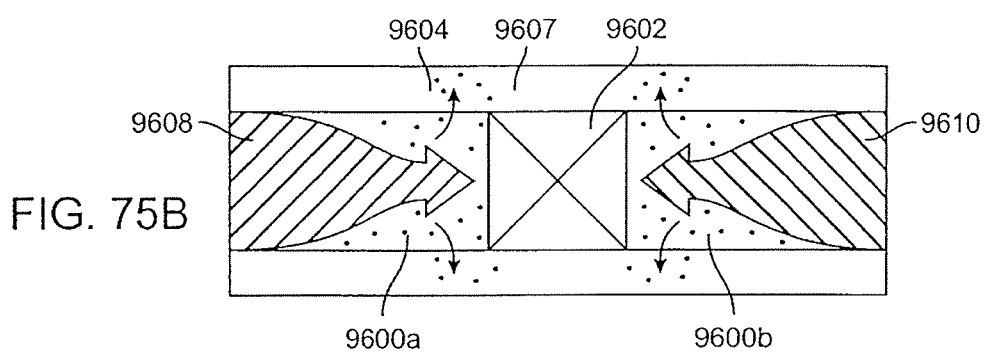

FIG. 75B shows the introduction of a first solution 9606 to first flow channel portion 9600a under pressure, and the introduction of a second solution 9608 to second flow channel portion 9600b under pressure. Because of the gas permeability of the surrounding elastomer material 9607, gas 9604 is displaced by the incoming solutions 9608 and 9610 and out-gasses through elastomer 9607.

Figure 75C:
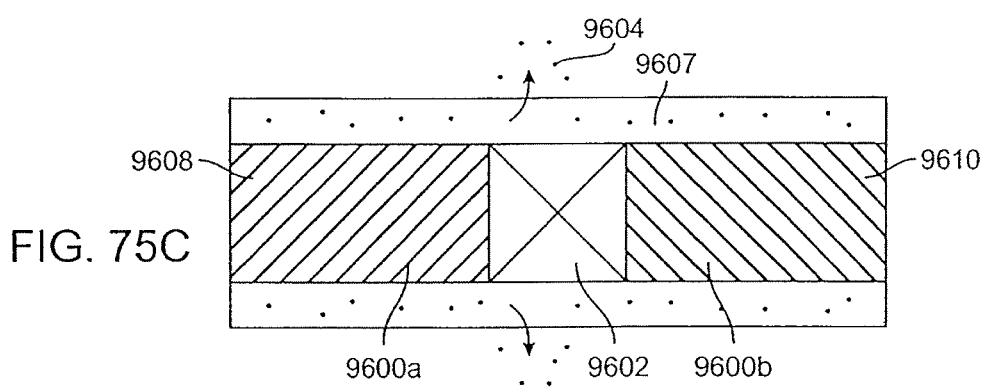
Figure 75D:
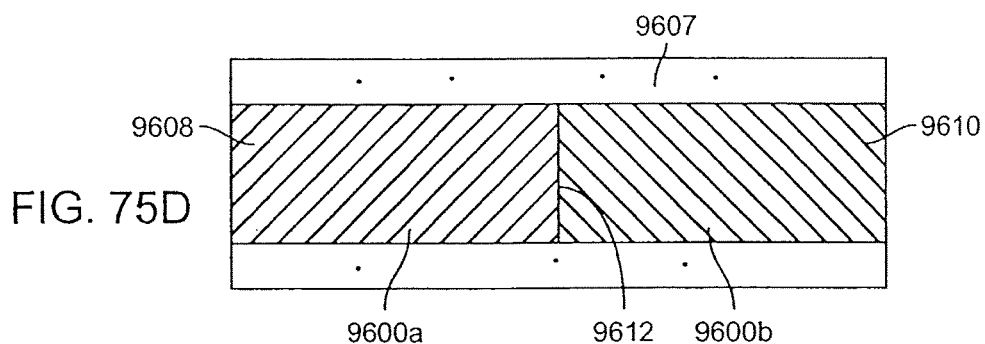

As shown in FIG. 75C, the pressurized out-gas priming of flow channel portions 9600a and 9600b allows uniform filling of these dead-ended flow channel portions without air bubbles. Upon deactuation of valve 9602 as shown in FIG. 75D, a well-defined fluidic interface 9612 is created, allowing for formation of a diffusion gradient.

To summarize, conventional macro free-interface techniques employ capillary tubes or other containers having dimensions on the order of mm. By contrast, the fluidic interface in accordance with embodiments of the present invention is created in a microchannel having dimensions on the order of µm. At such small dimensions, unwanted convection is suppressed due to viscosity effects, and mixing is dominated by diffusion. A well-defined fluidic interface may thus be established without significant undesirable convective mixing.

An embodiment of a method for crystallizing a target material comprises defining a first microfluidic chamber, priming the first microfluidic chamber with a solution including the target material, defining a second microfluidic chamber, and priming the second microfluidic chamber with a solution including a crystallizing agent. The first microfluidic chamber is placed into fluid communication with the second microfluidic chamber to define a microfluidic free interface between the target material and the crystallizing agent. Diffusion is permitted to occur between the target material and the crystallizing agent, such that a change in the solvent environment of the target material causes the target material to form a crystal.

9. Temporal Control Over Equilibration

The growth and quality of crystals is determined not only by thermodynamic conditions explored during the equilibration, but also by the rate at which equilibration takes place. It is therefore potentially valuable to control the dynamics of equilibration.

In conventional crystallization methods, course control only over the dynamics of equilibration may be available through manipulation of initial conditions. For macroscopic free interface diffusion, once diffusion begins, the experimenter has no control over the subsequent equilibration rate. For hanging drop experiments, the equilibration rate may be changed by modifying the size of the initial drop, the total size of the reservoir, or the temperature of incubation. In microbatch experiments, the rate at which the sample is concentrated may be varied by manipulating the size of the drop, and the identity and amount of the surrounding oil. Since the equilibration rates depend in a complicated manner on these parameters, the dynamics of equilibration may only be changed in a coarsely manner. Moreover, once the experiment has begun, no further control over the equilibration dynamics is available.

By contrast, the fluidic interface in a gated µ-FID experiment may be controlled by opening or closing the interface valve, allowing precise regulation of the equilibration dynamics. For example, FIG. 76A shows a simplified plan view of two microfluidic chambers 9700 and 9702, whose communication through flow channel 9704 is controlled by valve 9706. FIG. 76B plots the concentration of the first solution in the first chamber over time, where the valve is actuated at a duty cycle of 100%. FIG. 76C plots the concentration of the first solution in the first chamber over time, where the valve is actually at a duty cycle of 50% that in FIG. 76B. Inspection of FIG. 76C indicates that it takes twice as long for the concentration of the first solution in chamber A to fall to one-half its original value ($t^{50\%}_{1/2} = 2t^{100\%}_{1/2}$).

In accordance with an alternative embodiment of the present invention, rather than being opened and closed on a regular basis according to a duty cycle, the connecting valve may be closed at an intermediate time or over an irregular series of actuations, thereby halting equilibration once a favorable condition has been achieved.

An embodiment of a method of exercising temporal control over diffusion between two fluids comprises providing a microfluidic flow channel in an elastomer material, a membrane portion of the elastomer material positioned within the flow channel to define a valve. A first portion of the flow channel on one side of the membrane is primed with a first fluid. A second portion of the flow channel on the opposite side of the flow channel is primed with a second fluid. The elastomer membrane is repeatedly moved into and out of the flow channel over time to allow diffusion between the first fluid and the second fluid across the valve.

The equilibration rate may also be controlled by manipulation of the dimensions of the reaction chambers and of the connecting channels. To good approximation, the time required for equilibration varies as the square of the required diffusion length. The equilibration rate also depends on the cross-sectional area of the connecting channels. The required time for equilibration may therefore be controlled by changing both the length, and the cross-sectional area of the connecting channels.

Figure 77A:
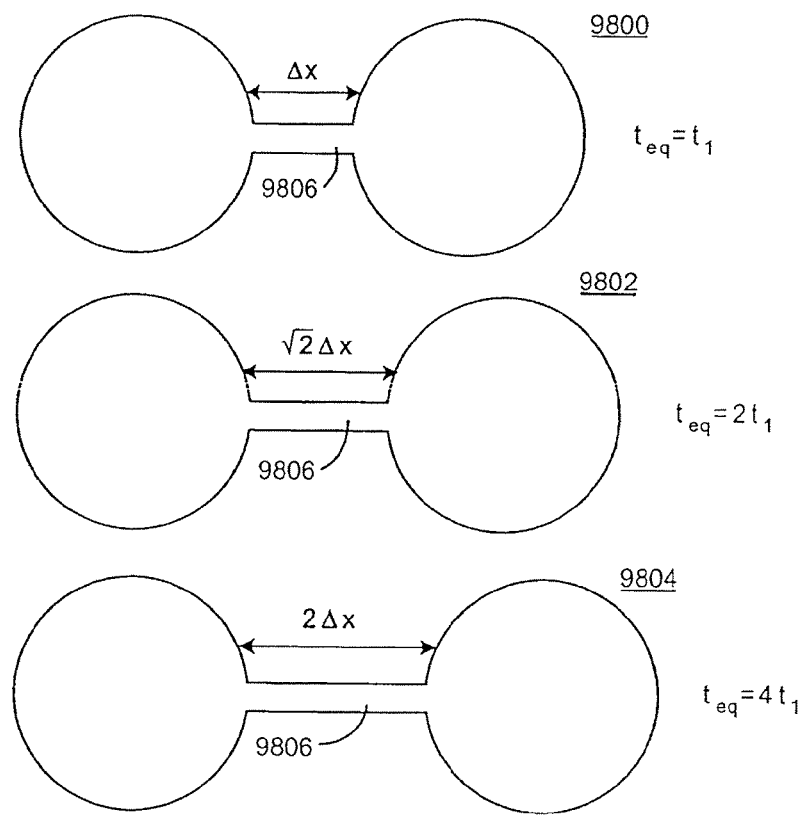
FIG. 77A shows three sets of pairs of compound chambers connected by microchannels of different length.
Figure 77B:
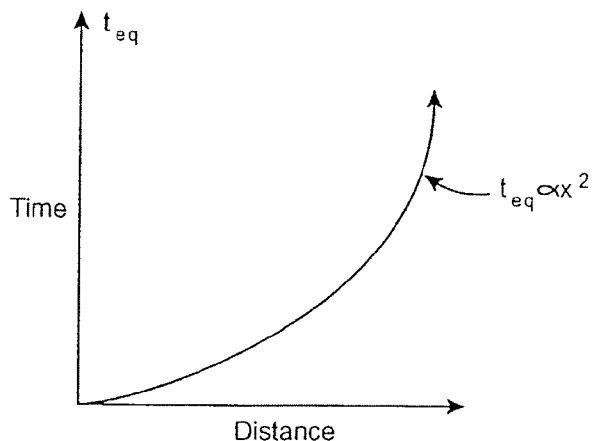
FIG. 77B plots equilibration time versus equilibration distance.

FIG. 77A shows three sets of pairs of compound chambers 9800, 9802, and 9804, each pair connected by microchannels 9806 of a different length Δx. FIG. 77B plots equilibration time versus equilibration distance. FIG. 77B shows that the required time for equilibration of the chambers of FIG. 77A varies as the square of the length of the connecting channels.

Figure 78:
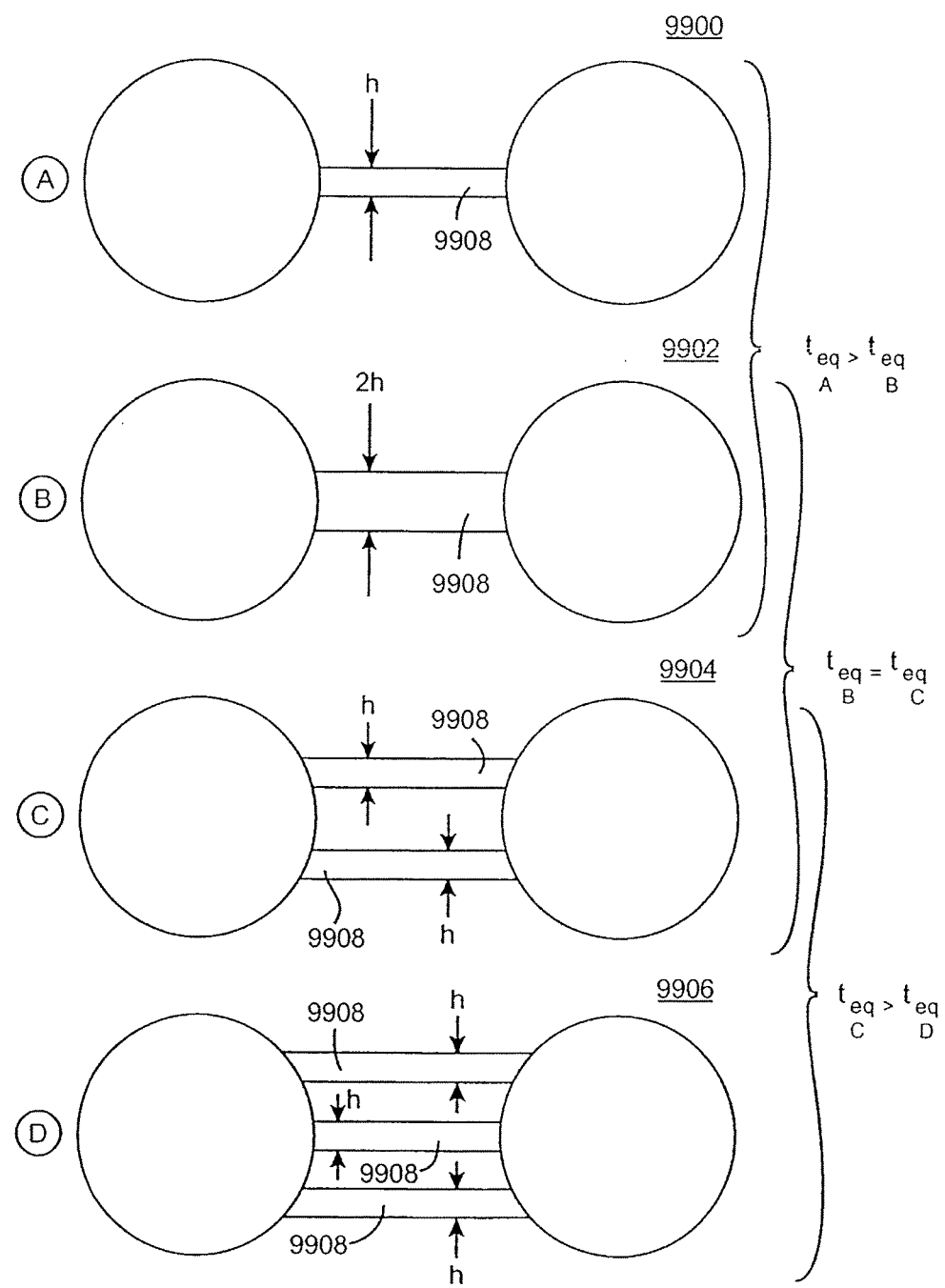
FIG. 78 shows four compound chambers with different connecting microchannels.

FIG. 78 shows four compound chambers 9900, 9902, 9904, and 9906, each having different arrangements of connecting microchannel(s) 9908. Microchannels 9908 have the same length, but differ in cross-sectional area and/or number of connecting channels. The rate of equilibration may thus be increased/decreased by decreasing/increasing the cross-sectional area, for example by decreasing/increasing the number of connecting channels or the dimensions of those channels.

Varying the equilibration rate by changing the geometry of connecting channels may be used on a single device to explore the effect of equilibration dynamics on crystal growth. FIGS. 79A-D show an embodiment in which a gradient of concentrations, initially established by the partial diffusive equilibration of two solutions from a micro-free interface, can be maintained by the actuation of containment valves.

Figure 79A:
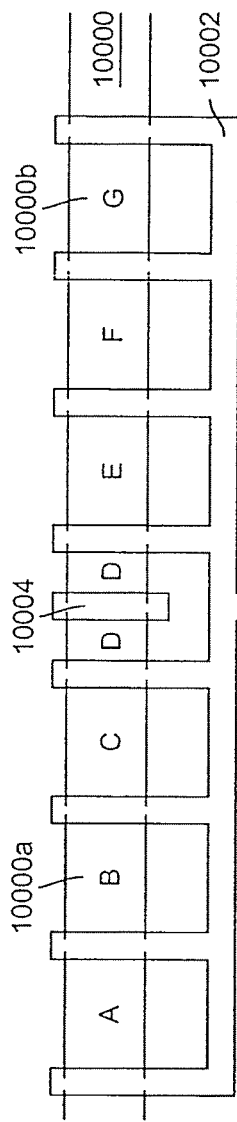
FIG. 79A shows a microfluidic architecture designed to capture a concentration gradient over a distance.
Figure 79B:
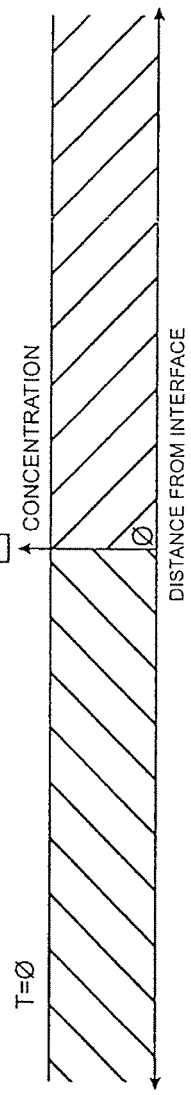
FIG. 79B plots concentration versus distance from a free interface at an initial time.
Figure 79C:
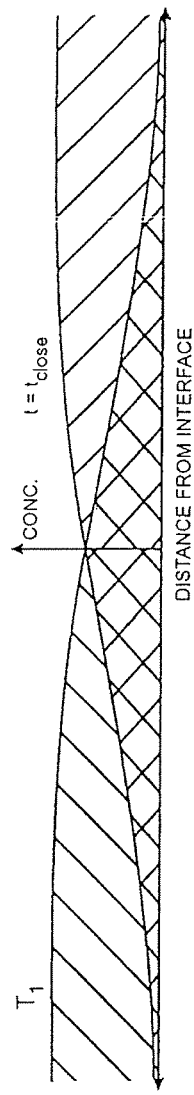
FIG. 79C plots concentration versus distance from a free interface at a subsequent time.
Figure 79D:
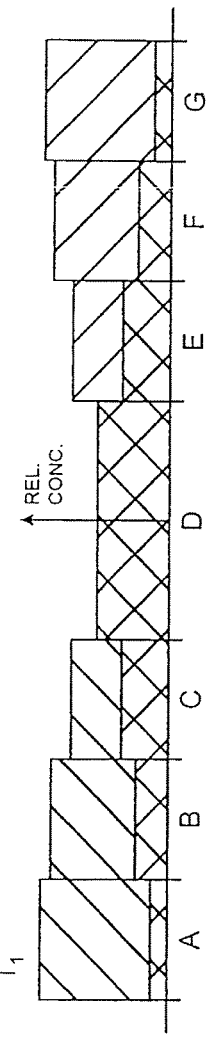
FIG. 79D plots relative chamber concentration versus distance at the subsequent time.

FIG. 79A shows flow channel 10000 that is overlapped at intervals by a forked control channel 10002 to define a plurality of chambers (A-G) positioned on either side of a separately-actuated interface valve 10004. FIG. 79B plots solvent concentration at an initial time, when interface valve 10004 is actuated and a first half 10000a of the flow channel has been mixed with a first solution, and a second half 10000b of the flow channel has been primed with a second solution. FIG. 79C plots solvent concentration at a subsequent time $T_1$, when control channel 10002 is actuated to define the seven chambers (A-G), which capture the concentration gradient at that particular point in time. FIG. 79D plots relative concentration of the chambers (A-G) at time $T_1$.

In the embodiment shown in FIG. 79A, actuation of the forked control channel simultaneously creates the plurality of chambers A-G. However, this is not required, and in alternative embodiments of the present invention multiple control channels could be utilized to allow independent creation of chambers A-G at different time intervals, thereby allow additional diffusion to occur after an initial set of chambers are created immediately adjacent to the free interface.

An embodiment of a method of capturing a concentration gradient between two fluids comprises providing a first fluid on a first side of an elastomer membrane present within a microfluidic flow channel, and providing a second fluid on a second side of the elastomer membrane. The elastomer membrane is displaced from the microfluidic flow channel to define a microfluidic free interface between the first fluid and the second fluid. The first fluid and the second fluid are allowed to diffuse across the microfluidic free interface. A group of elastomer valves positioned along the flow channel at increasing distances from the microfluidic free interface are actuated to define a succession of chambers whose relative concentration of the first fluid and the second fluid reflects a time of diffusion across the microfluidic free interface.

10. Chip Holder

As previously illustrated, embodiments of microfluidic devices in accordance with the present invention may utilize on-chip reservoirs or wells. However, in a microfluidic device requiring the loading of a large number of solutions, the use of a corresponding large number of input tubes with separate pins for interfacing each well may be impractical given the relatively small dimensions of the fluidic device. In addition, the automated use of pipettes for dispensing small volumes of liquid is known, and thus it therefore may prove easiest to utilize such techniques to pipette solutions directly on to wells present on the face of a chip.

Capillary action may not be sufficient to draw solutions from on-chip wells into active regions of the chip, particularly where dead-ended chambers are to be primed with material. In such embodiments, one way of loading materials into the chip is through the use of external pressurization. Again however, the small dimensions of the device coupled with a large number of possible material sources may render impractical the application of pressure to individual wells through pins or tubing.

Figure 80:
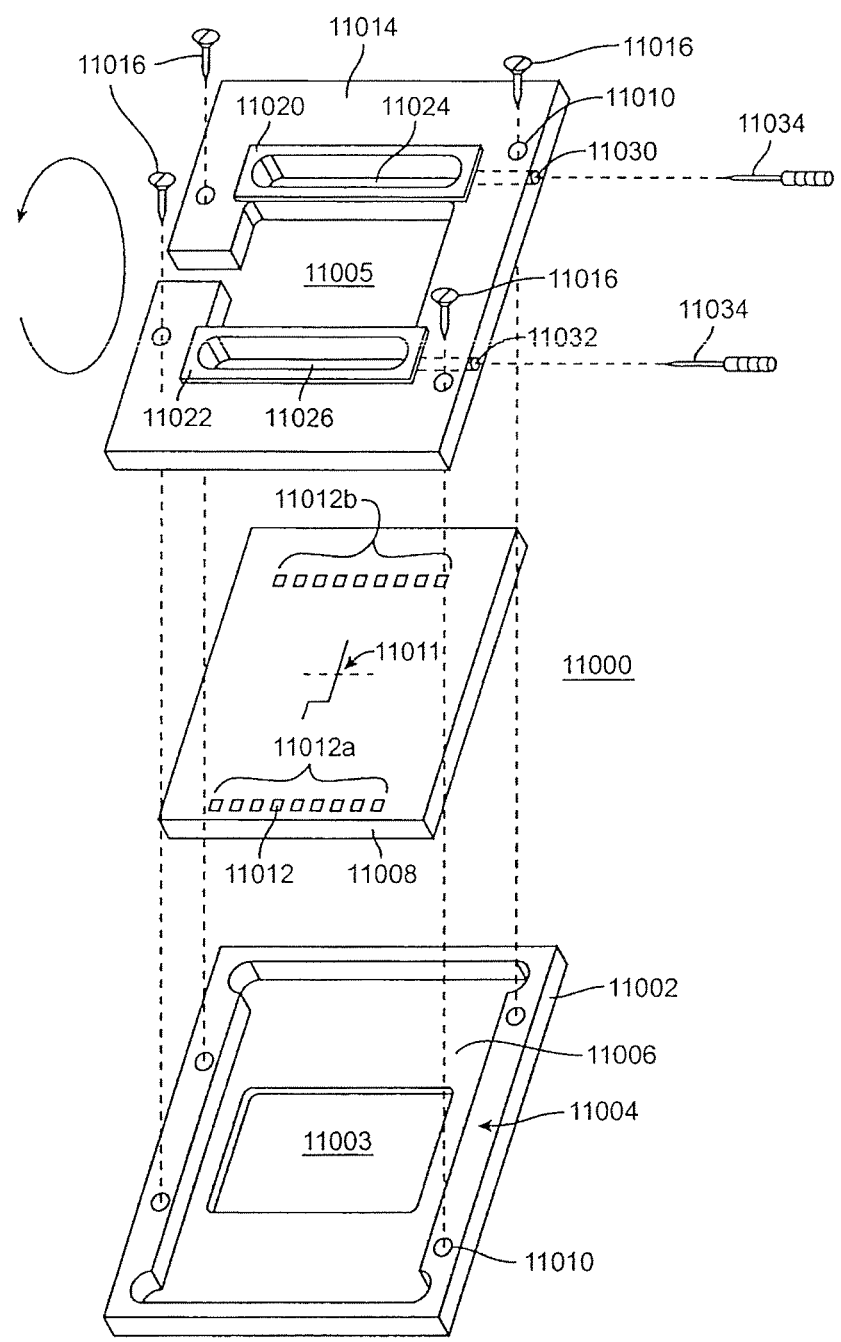
FIG. 80 shows an exploded view of one embodiment of a chip holder device in accordance with the present invention.

Accordingly, FIG. 80 shows an exploded view of a chip holder 11000 in accordance with one embodiment of the present invention. Bottom portion 11002 of chip holder 11000 includes raised peripheral portion 11004 surrounding recessed area 11006 corresponding in size to the dimensions of chip 11008, allowing microfluidic chip 11008 to be positioned therein. Peripheral region 11004 further defines screw holes 11010.

Microfluidic device 11008 is positioned within recessed area 11006 of bottom portion 11002 of chip holder 11000. Microfluidic device 11008 comprises an active region 11011 that is in fluidic communication with peripheral wells 11012 configured in first and second rows 11012a and 11012b, respectively. Wells 11012 hold sufficient volumes of material to allow device 11008 to function. Wells 11012 may contain, for example, solutions of crystallizing agents, solutions of target materials, or other chemical reagents such as stains. Bottom portion 11002 contains a window 11003 that enables active region 11011 of chip 11008 to be observed.

Top portion 11014 of chip holder 11000 fits over bottom chip holder portion 11002 and microfluidic chip 11008 positioned therein. For ease of illustration, in FIG. 80 top chip holder portion 11014 is shown inverted relative to its actual position in the assembly. Top chip holder portion 11014 includes screw holes 11010 aligned with screw holes 11010 of lower holder portion 11002, such that screws 11016 may be inserted through holes 11010 secure chip between portions 11002 and 11014 of holder 11000. Chip holder upper portion 11014 contains a window 11005 that enables active region 11011 of chip 11008 to be observed.

Lower surface 11014a of top holder portion 11014 includes raised annular rings 11020 and 11022 surrounding recesses 11024 and 11026, respectively. When top portion 11014 of chip holder 11000 is pressed into contact with chip 11008 utilizing screws 11016, rings 11020 and 11022 press into the soft elastomeric material on the upper surface of chip 11008, such that recess 11024 defines a first chamber over top row 11012a of wells 11012, and recess 11026 defines a second chamber over bottom row 11012b of wells 11012. Holes 11030 and 11032 in the side of top holder portion 11014 are in communication with recesses 11024 and 11026 respectively, to enable a positive pressure to be applied to the chambers through pins 11034 inserted into holes 11030 and 11032, respectively. A positive pressure can thus simultaneously be applied to all wells within a row, obviating the need to utilize separate connecting devices to each well.

In operation, solutions are pipetted into the wells 11012, and then chip 11008 is placed into bottom portion 11002 of holder 11000. The top holder portion 11014 is placed over chip 11008, and is pressed down by screws. Raised annular rings 11020 and 11022 on the lower surface of top holder portion 11014 make a seal with the upper surface of the chip where the wells are located. Solutions within the wells are exposed to positive pressures within the chamber, and are thereby pushed into the active area of microfluidic device.

The downward pressure exerted by the chip holder may also pose the advantage of preventing delamination of the chip from the substrate during loading. This prevention of delamination may enable the use of higher priming pressures.

The chip holder shown in FIG. 80 represents only one possible embodiment of a structure in accordance with the present invention. For example, a chip holder may also include a third portion which fits over control line outlet ports on the front or back side of the chip, thereby enabling the application of pressure to control lines to control valve actuation within the chip. In addition, while the described holder embodiment includes a window for viewing of the chip, this may not be necessary if the chip is to be removed from the holder once the chip filling process is complete.

In still other alternative embodiments, a chip holder in accordance with the present invention could be equipped with heating elements to provide spatial and temporal temperature profile to the chip positioned therein. Such alternative embodiments would eliminate the complexity and expense associated with incorporating heating elements directly onto a substrate that may be disposable.

In the particular embodiment of the chip holder illustrated in FIG. 80, the top piece is pressed to the chip by turning screws. However, in alternative embodiments in accordance with the present invention, the downward force could be applied through a press or robotic arm, thereby potentially eliminating the need for a bottom holder piece.

Furthermore, in the particular embodiment of the chip holder illustrated in FIG. 80, the seal over the wells allowing application of a positive pressure is created by pressing the raised ring into the compliant top surface of the elastomer chip. However, in accordance with alternative embodiments of the present invention, a seal could be created by the addition of flexible o-rings to the chip holder. Such o-rings would permit use of a chip holder with embodiments of microfluidic devices that feature a rigid top surface.

Finally, it is important to recognize that use of a chip holder structure in accordance with embodiments of the present invention is not limited to protein crystallization, but enables loading of a large number of solutions onto a microfluidic chip for performance of a variety of applications.

An embodiment of a structure for applying pressure to a elastomeric microfluidic device in accordance with the present invention comprises, a holder portion including a continuous raised rim on a lower surface thereof configured to contact a top surface of the microfluidic device and surround a plurality of material wells located therein. Contact between the raised rim and the top surface of the microfluidic device defines an airtight chamber over the material wells, an orifice in communication with the chamber enabling application of positive pressure to the airtight chamber to drive the contents of the material wells into an active area of the microfluidic device.

An embodiment of a method of priming a microfluidic device with a liquid material in accordance with the present invention comprises loading a plurality of wells on an upper surface of a microfluidic device with a liquid material. A holder piece is biased against the upper surface such that a continuous raised rim of the holder piece presses against the upper surface surrounding the wells, such that a chamber is created over the wells. A positive pressure is applied to the airtight chamber to drive the material from the wells into an active area of the elastomeric microfluidic structure.

An embodiment of a method of actuating a valve within a microfluidic elastomer device comprises applying a holder piece having a continuous raised rim against a surface of a microfluidic device having a plurality of control line outlets to create a chamber over the outlets. A positive or negative pressure is applied to the airtight chamber to control a pressure within the control line and thereby actuate a elastomeric valve membrane of the microfluidic device that is in communication with the control line.

11. Target Materials

Typical targets for crystallization are diverse. A target for crystallization may include but is not limited to: 1) biological macromolecules (cytosolic proteins, extracellular proteins, membrane proteins, DNA, RNA, and complex combinations thereof), 2) pre- and post-translationally modified biological molecules (including but not limited to, phosphorylated, sulfolated, glycosylated, ubiquitinated, etc. proteins, as well as halogentated, abasic, alkylated, etc. nucleic acids); 3) deliberately derivatized macromolecules, such as heavy-atom lableled DNAs, RNAs, and proteins (and complexes thereof), selenomethionine-labeled proteins and nucleic acids (and complexes thereof), halogenated DNAs, RNAs, and proteins (and complexes thereof), 4) whole viruses or large cellular particles (such as the ribosome, replisome, spliceosome, tubulin filaments, actin filaments, chromosomes, etc.), 5) small-molecule compounds such as drugs, lead compounds, ligands, salts, and organic or metallo-organic compounds, and 6) small-molecule/biological macromolecule complexes (e.g., drug/protein complexes, enzyme/substrate complexes, enzyme/product complexes, enzyme/regulator complexes, enzyme/inhibitor complexes, and combinations thereof). Such targets are the focus of study for a wide range of scientific disciplines encompassing biology, biochemistry, material sciences, pharmaceutics, chemistry, and physics.

A nonexclusive listing of possible protein modifications is as follows: 5' dephospho; Desmosine (from Lysine); decomposed carboxymethylated Methionine; Ornithine (from Arginine); Lysinoalanine (from Cysteine); Lanthionine (from Cysteine); Dehydroalanine (from Cysteine); Homoserine formed from Met by CNBr treatment; Dehydration (—H2O); S-gamma-Glutamyl (crosslinked to Cysteine); O-gamma-Glutamyl-(Crosslink to Serine); Serine to Dehydroalanine; Alaminohistidine (Serine crosslinked to theta or pi carbon of Histidine); Pyroglutamic Acid formed from Gln; N-pyrrolidone carboxyl (N terminus); N alpha-(gamma-Glutamyl)-lysine; N-(beta-Aspartyl)-Lysine (Crosslink); 3,3',5,5'-Ter-Tyr (Crosslink); Disulphide bond formation (Cystine); S-(2-Histidyl)-(Crosslinked to Cysteine); S-(3-Tyr) (Crosslinked to Cysteine); 3,3'-BiTyr (Crosslink); IsodiTyr (Crosslink); Allysine (from Lysine); Amide formation (C terminus); Deamidation of Asparagine and Glutamine to Aspartate and Glutamate; Citruline (from Arginine); Syndesine (from Lysine); Methylation (N terminus, N epsilon of Lysine, O of Serine, Threonine or C terminus, N of Asparagine); delta-Hydroxy-allysine (from Lysine); Hydroxylation (of delta C of Lysine, beta C of Tryptophan, C3 or C4 of Proline, beta C of Aspartate); Oxidation of Methionine (to Sulphoxide); Sulfenic Acid (from Cysteine); Pyruvoyl-(Serine); 3,4-Dihydroxy-Phenylalanine (from Tyrosine) (DOPA); Sodium; Ethyl; N,N dimethylation (of Arginine or Lysine); 2,4-Bis-Trp-6,7-dione (from Tryptophan); Formylation (CHO); 6,7 Dione (from Tryptophan); 3,4,6-Trihydroxy-Phenylalanine (from Tyrosine) (TOPA); 3,4-Dihydroxylation (of Proline); Oxidation of Methionine (to Sulphone); 3-Chlorination (of Tyrosine with 35C1); 3-Chlorination (of Tyrosine with 37C1); Potassium; Carbamylation; Acetylation (N terminus, N epsilon of Lysine, O of Serine) (Ac); N-Trimethylation (of Lysine); gamma Carboxylation of Glutamate or beta Carboxylation of Aspartate; disodium; Nitro (NO2); t-butyl ester (OtBu) and t-butyl (tBu); Glycyl (-G-,-Gly-); Carboxymethyl (on Cystine); sodium+potassium; Selenocysteine (from Serine); 3,5-Dichlorination (of Tyrosine with 35C1); Dehydroalanine (Dha); 3,5-Dichlorination (of Tyrosine with mixture of 35C1 and 37C1)); Pyruvate; Acrylamidyl or Acrylamide adduct; Sarcosyl; Alanyl (-A-, -Ala-); Acetamidomethyl (Acm); 3,5-Dichlorination (of Tyrosine with 37C1); S-(sn-1-Glyceryl) (on Cysteine); Glycerol Ester (on Glutamic acid side chain); Glycine (G, Gly); Beta mercaptoethanol adduct; Phenyl ester (OPh) (on acidic); 3-Bromination (of Tyrosine with 79Br); Phosphorylation (O of Serine, Threonine, Tyrosine and Aspartate, N epsilon of Lysine); 3-Bromination (of Tyrosine with 81Br); Sulphonation (SO3H) (of PMC group); Sulphation (of O of Tyrosine); Cyclohexyl ester (OcHex); Homoseryl lactone; Dehydroamino butyric acid (Dhb); Gamma Aminobutyryl; 2-Aminobutyric acid (Abu); 2-Aminoisobutyric acid (Aib); Diaminopropionyl; t-butyloxymethyl (Bum); N-(4-NH2-2-OH-butyl)-(of Lysine) (Hypusine); Seryl (-S-, -Ser-); t-butylsulfenyl (StBu); Alanine (A, Ala); Sarcosine (Sar); Anisyl; Benzyl (Bzl) and benzly ester (OBzl); 1,2-ethanedithiol (EDT); Dehydroprolyl; Trifluoroacetyl (TFA); N-hydroxysuccinimide (ONSu, OSu); Prolyl (-P-, -Pro-); Valyl (-V-, -Val-); Isovalyl (-I-, -Iva-); t-Butyloxycarbonyl (tBoc); Threoyl (-T-, -Thr-); Homoseryl (-Hse-); Cystyl (-C-, -Cys-); Benzoyl (Bz); 4-Methylbenzyl (Meb); Serine (S, Ser); HMP (hydroxymethylphenyl) linker; Thioanisyl; Thiocresyl; Diphthamide (from Histidine); Pyroglutamyl; 2-Piperidinecarboxylic acid (Pip); Hydroxyprolyl (-Hyp-); Norleucyl (-Nle-); Isoleucyl (-I-, -Ile-); Leucyl (-L-, -Leu-); Ornithyl (-Orn-); Asparagyl (-N-, -Asn-); t-amyloxycarbonyl (Aoc); Proline (P, Pro); Aspartyl (-D-, -Asp-); Succinyl; Valine (V, Val); Hydroxybenzotriazole ester (HOBt); Dimethylbenzyl (diMeBzl); Threonine (T, Thr); Cysteinylation; Benzyloxymethyl (Bom); p-methoxybenzyl (Mob, Mbzl); 4-Nitrophenyl, p-Nitrophenyl (ONp); Cysteine (C, Cys); Chlorobenzyl (ClBzl); Iodination (of Histidine[C4] or Tyrosine[C3]); Glutamyl (-Q-, -Gln-); N-methyl Lysyl; Lysyl (-K-, -Lys-); O-Methyl Aspartamyl; Glutamyl (-E-, -Glu-); N alpha-(gamma-Glutamyl)-Glu; Norleucine (Nle); Hydroxy Aspartamyl; Hydroxyproline (Hyp); bb-dimethyl Cystenyl; Isoleucine (I, Ile); Leucine (L, Leu); Methionyl (-M-, -Met-); Asparagine (N, Asn); Pentoses (Ara, Rib, Xyl); Aspartic Acid (D, Asp); Dmob (Dimethoxybenzyl); Benzyloxycarbonyl (Z); Adamantyl (Ada); p-Nitrobenzyl ester (ONb); Histidyl (-H-, -His-); N-methyl Glutamyl; O-methyl Glutamyl; Hydroxy Lysyl (-Hyl-); Methyl Methionyl; Glutamine (Q, Gln); Aminoethyl Cystenyl; Pentosyl; Deoxyhexoses (Fuc, Rha); Lysine (K, Lys); Aminoethyl cystenyl (-AECys-); 4-Glycosyloxy-(pentosyl, C5) (of Proline); Methionyl Sulfoxide; Glutamic Acid (E, Glu); Phenylalanyl- (-F-, -Phe-); Pyridyl Alanyl; Fluorophenylalanyl; 2-Nitrobenzoyl (NBz); Methionine (M, Met); 3-methyl Histidyl; 2-Nitrophenylsulphenyl (Nps); 4-Toluenesulphonyl (Tosyl, Tos); 3-nitro-2-pyridinesulfenyl (Npys); Histidine (H, His); 3,5-Dibromination (of Tyrosine with 79Br); Arginyl (-R-, -Arg-); Citrulline; 3,5-Dibromination (of Tyrosine with mixture of 79Br and 81Br); Dichlorobenzyl (Dcb); 3,5-Dibromination (of Tyrosine with 81Br); Carboxyamidomethyl Cystenyl; Carboxymethyl Cystenyl; Methylphenylalanyl; Hexosamines (GalN, GlcN); Carboxymethyl cysteine (Cmc); N-Glucosyl (N terminus or N epsilon of Lysine) (Aminoketose); O-Glycosyl-(to Serine or Threonine); Hexoses (Fru, Gal, Glc, Man); Inositol; MethionylSulphone; Tyrosinyl (-Y-, -Tyr-); Phenylalanine (F, Phe); 2,4-dinitrophenyl (Dnp); Pentafluorophenyl (Pfp); Diphenylmethyl (Dpm); Phospho Seryl; 2-Chlorobenzyloxycarbonyl (ClZ); Napthyl acetyl; Isopropyl Lysyl; N-methyl Arginyl; Ethaneditohiol/TFA cyclic adduct; Carboxy Glutamyl (Gla); Acetamidomethyl Cystenyl; Acrylamidyl Cystenyl; Arginine (R, Arg); N-Glucuronyl (N terminus); delta-Glycosyloxy-(of Lysine or beta-Glycosyloxy-(of Phenylalanine or Tyrosine); 4-Glycosyloxy-(hexosyl, C6) (of Proline); Benzyl Seryl; N-methyl Tyrosinyl; p-Nitrobenzyloxycarbonyl (4Nz); 2,4,5-Trichlorophenyl; 2,4,6-trimethyloxyphenyl (Tmob); Xanthyl (Xan); Phospho Threonyl; Tyrosine (Y, Tyr); Chlorophenylalanyl; Mesitylene-2-sulfonyl (Mts); Carboxymethyl Lysyl; Tryptophanyl (-W-, -Trp-); N-Lipoyl-(on Lysine); Matrix alpha cyano MH+; Benzyl Threonyl; Benzyl Cystenyl; Napthyl Alanyl; Succinyl Aspartamyl; Succinimidophenyl carb.; HMP (hydroxymethylphenyl)/TFA adduct; N-acetylhexosamines (GalNAc, GlcNAc); Tryptophan (W, Trp); Cystine ((Cys)2); Farnesylation; S-Farnesyl-; Myristoleylation (myristoyl with one double bond); Pyridylethyl Cystenyl; Myristoylation; 4-Methoxy-2,3,6-trimethylbenzenesulfonyl (Mtr); 2-Bromobenzyloxycarbonyl (BrZ); Formyl Tryptophanyl; Benzyl Glutamyl; Anisole Adducted Glutamyl; S-cystenyl Cystenyl; 9-Flourenylmethyloxycarbonyl (Fmoc); Lipoic acid (amide bond to lysine); Biotinylation (amide bond to lysine); Dimethoxybenzhydryl (Mbh); N-Pyridoxyl (on Lysine); Pyridoxal phosphate (Schiff Base formed to lysine); Nicotinyl Lysyl; Dansyl (Dns); 2-(p-biphenyl)isopropyl-oxycarbonyl (Bpoc); Palmitoylation; "Triphenylmethyl (Trityl, Trt)"; Tyrosinyl Sulphate; Phospho Tyrosinyl; Pbf (pentamethyldihydrobenzofuransulfonyl); 3,5-Diiodination (of Tyrosine); 3,5-di-I"; N alpha-(gamma-Glutamyl)-Glu2; O-GlcNAc-1-phosphorylation (of Serine); "2,2,5,7,8-Pentamethylchroman-6-sulphonyl (Pmc)"; Stearoylation; Geranylgeranylation; S-Geranylgeranyl; 5'phos dCytidinyl; iodo Tyrosinyl; Aldohexosyl Lysyl; Sialyl; N-acetylneuraminic acid (Sialic acid, NeuAc, NANA, SA); 5'phos dThymidinyl; 5'phos Cytidinyl; Glutathionation; O-Uridinylylation (of Tyrosine); 5'phos Uridinyl; 5-farnesyl Cystenyl; N-glycolneuraminic acid (NeuGc); 5'phos dAdenosyl; O-pantetheinephosphorylation (of Serine); SucPhencarb Lysyl; 5'phos dGuanosyl; 5'phos Adenosinyl; O-5'-Adenosylation (of Tyrosine); 4'-Phosphopantetheine; GL2; S-palmityl Cystenyl; 5'phos Guanosyl; Biotinyl Lysyl; Hex-HexNAc; N alpha-(gamma-Glutamyl)-Glu3; Dioctyl Phthalate; PMC Lysyl; Aedans Cystenyl; Dioctyl Phthalate Sodium Adduct; di-iodo Tyrosinyl; PMC Arginyl; S-Coenzyme A; AMP Lysyl; 3,5,3'-Triiodothyronine (from Tyrosine); S-(sn-1-Dipalmitoyl-glyceryl)-(on Cysteine); S-(ADP-ribosyl)-(on Cysteine); N-(ADP-ribosyl)-(on Arginine); O-ADP-ribosylation (on Glutamate or C terminus); ADP-rybosylation (from NAD); S-Phycocyanobilin (on Cysteine); S-Heme (on Cysteine); N theta-(ADP-ribosyl)diphthamide (of Histidine); NeuAc-Hex-HexNAc; MGDG; O-8 alpha-Flavin [FAD])-(of Tyrosine); S-(6-Flavin [FAD])-(on Cysteine); N theta and N pi-(8alpha-Flavin) (on Histidine); (Hex)3-HexNAc-HexNAc; (Hex)3-HexNAc-(dHex)HexNAc.

A nonexclusive listing of possible nucleic acid modifications, such as base-specific, sugar-specific, or phospho-specific is as follows: halogenation (F, Cl, Br, I); Abasic sites; Alkylation; Crosslinkable adducts such as thiols or azides; Thiolation; Deamidation; Fluorescent-group labeling, and glycosylation.

A nonexclusive listing of possible heavy atom derivatizing agents is as follows: potassium hexachloroiridate (III); Potassium hexachloroiridate (IV); Sodium hexachloroiridate (IV); Sodium hexachloroiridate (III); Potassium hexanitritoiridate (III); Ammnoium hexachloroiridate (III); Iridium (III) chloride; Potassium hexanitratoiridate (III); Iridium (III) bromide; Barium (II) chloride; Barium (II) acetate; Cadmium (II) nitrate; Cadmium (II) iodide; Lead (II) nitrate; Lead (II) acetate; Trimethyl lead (IV) chloride; Trimethyl lead (IV) acetate; Ammonium hexachloro plumbate (IV); Lead (II) chloride; Sodium hexachlororhodiate (III); Strontium (II) acetate; Disodium thiomalonato aurate (I); Potassium dicyano aurate (I); Sodium dicyano aurate (I); Sodium thiosulphato aurate (III); Potassium tetracyano aurate (III); Potassium tetrachloro aurate (III); Hydrogen tetrachloro aurate (III); Sodium tetrachloro aurate (III); Potassium tetraiodo aurate (III); Potassium tetrabromo aurate (III); (acetato-o) methylmercury; Methyl (nitrato-o) mercury; Chloromethylmercury; Iodomethylmercury; Chloroethylmercury; Methyl mercury cation; Triethyl (m3-phosphato(3-)-0,0',0") tri mercury eth; [3-[(aminocarbonyl)amino]-2-methoxypropyl]chlorome; 1,4 diacetoxymercury 2-3 dimethoxy butane; Meroxyl mercuhydrin; Tetrakis(acetoxy mercuri)-methane; 1,4-bis(chloromercuri)-2,3-butanediol; Ethyl diacetoxymercurichloro acetate (dame); Mercuric (II) oxide; Methyl mercuri-2-mercaptoethanol; 3,6 bis(mercurimethyl dioxane acetate); Ethyl mercury cation; Billman's dimercurial; Para chloromercury phenyl acetate (pcma); Mercury phenyl glyoxal (mpg); Thiomersal, ethyl mercury thiosalicylate [emts]; 4-chloromercuribenesulphonic acid; 2,6 dichloromercuri-4-nitrophenol (dcmnp); [3-[[2(carboxymethoxy)benzoyl] mino-2 methoxy prop; Parachloromercury benzoate (pcmb), 4-chloromercury; (acetato-o)phenyl mercury; Phenyl mercuri benzoate (pmb); Para hydroxy mercuri benzoate (phmb); Mercuric imidosuccinate/mercury succinimide; 3-hydroxymercurybenzaldehyde; 2-acetoxy mercuri sulhpanilamide; 3-acetoxymercuri-4-aminobenzenesulphonamide; Methyl mercuri thioclycolic acid (mmtga); 2-hydroxymercuri-tolulen-4-sulphonic acid (hmts); Acetamino phenyl mercury acetate (apma); [3-[(aminocarbonyl)amino]-3-methoxypropyl 2-chloro; Para-hydroxymercuri benzene sulphonate (phmbs); Ortho-chloromercuri phenol (ocmp); Diacetoxymercury dipopylene dioxide (dmdx); Para-acetoxymercuri aniline (pama); (4-aminophenyl)chloromercury; Aniline mercury cation; 3-hydroxy-mercuri-s sulphosalicylic acid (msss); 3 or 5 hydroxymercuri salicylic acid (hmsa); Diphenyl mercury; 2,6 diacetoxymercurimethyl 1-4 thioxane (dmmt); 2,5-b1s (chloromercury) furan; Ortho-chloromercuri nitrophenol (ocmnp); 5-mercurydeoxyuridine monosulphate; Mercury salicylate; [3-[[2-(carboxymethoxy)benzoyl] amino-2-methoxypro; 3,3 bis(hydroximercuri)-3-nitratomercuri pyruvic; 3-chloro mercuri pyridine; 3,5 bis acetoxymercuri methyl morpholine; Ortho-mercury phenol cation; Para-carboxymethyl mercaptomercuri benzensulphonyl; Para-mercuribenzoyl glucosamine; 3-acetetoxymercuri-5-nitrosalicyladehyde (msa); Ammonium tetrachloro mercurate (II); Potassium tetrathiocyanato mercurate (II); Sodium tetrathiocyanato mercurate (II); Potassium tetraisothiocyanto mercurate (II); Potassium tetraido mercurate (II); Ammonium tetrathiocyananato mercurate (II); Potassium tetrabromo mercurate (II); Potassium tetracyano mercurate (II); Mercury (II) bromide; Mercury (II) thiocyanate; Mercury (II) cyanide; Mercury (II) iodide; Mercuric (II) chloride; Mercury (II) acetate; Mercury (I) acetate; Dichlorodiamino mercurate (II); Beta mercury-mercaptoethylamine hydrochloride; Mercury (II) sulphate; Mercury (II) chloroanilate; Dimercuriacetate; Chloro(2-oxoethyl)mercury; Phenol mercury nitrate; Mercury mercaptoethanol; Mercury mercaptoethylamine chloride; Mercury thioglycollic acid (sodium salt); 0-hydroxymercuri-p-nitrophenol/2-hydroxymercuri-4-; Para chloromercuri phenol (pcmp); Acetylmercurithiosalicylate (amts); Iodine; Potassium iodide (iodine); 4-iodopyrazole; O-iodobenzoylglucasamine; P-iodobenzoylglucasamine; Potassium iodide/chloramine t; Ammonium iodide; 3-isothio-cyanato-4-iodobenzene sulphonate; Potassium iodide; 3'-iodo phenyltrazine; 4'-iodo phenyltrazine; Sodium iodide/iodine; Silver nitrate; Silver( )trinitridosulphoxylate; Tobenamed; Samarium (III) chloride; Thulium (III) chloride; Lutetium (III) chloride; Europium (III) chloride; Terbium (III) chloride; Gadolinium (III) chloride; Erbium (III) chloride; Lanthanum (III) chloride; Samarium (III) nitrate; Samarium (III) acetate; Samarium (III) cation; Praseodymium (III) chloride; Neodymium (III) chloride; Ytterbium (III) chloride; Thulium (III) sulphate; Ytterbium (III) sulphate; Gadolinium (III) sulphate; Gadolinium (III) acetate; Dysprosium (III) chloride; Erbium (III) nitrate; Holmium (III) chloride; Penta amino ruthenium (III) chloride; Cesium nitridotiroxo osmium (viii); Potassium tetraoxo osmiate; Hexa amino osmium (III) iodide; Ammonium hexachloroosmiate (IV); Osmium (III) chloride; Potassium hexachloro osmiate (IV); Cesium trichloro triscarbonyl osmiate (?); Dinitritodiamine platinum (II); C is dichlorodimethylammido platinum (II); Dichlorodiammine platinum (II); Dibromodiammine platinum (II); Dichloroethylene diamine platinum (II); Potassium dicholodinitrito platinate (II); Diethylenediamene platinum (II); Potassium dioxylato platinate (II); Dichlorobis (pyridine) platinum (II); Potassium (thimethyl dibenzyloamine) platinum (?); Potassium tetrabromoplatinate (II); Potassium tetrachloro platinate (II); Potassium tetranitrito platinum (II); Potassium tetracyano platinate (II); Sodium tetracyano platinate (II); Potassium tetrathiocyanato platinate (II); Ammonium tetranitrito platinate (II); Potassium tetraisocyanato platinate (II); Ammonium tetracyano platinum (II); Ammonium tetrachloro platinate (II); Potassium dinitritodioxalato platinate (IV); Dichlorotetraammino platinium (IV); Dibromodinitrito diammine platinium (IV); Potassium hexanitrito platinate (IV); Potassium hexachloro platinate (IV); Potassium hexabromo platinate (IV); Sodium hexachloroplatinate (IV); Potassium hexaiodo platinate (IV); Potassium hexathiocyanato platinate (IV); Tetrachloro bis(pyridine) platinum (IV); Ammonium hexachloro platinate (IV); Di-mu-iodo bis(ethylenediamine) di platinum (II) n; Potassium hexaisothiocyanato platinate (IV); Potassium tetraiodo platinate (II); 2,2',2" terpyridyl platinium (II); 2 hydroxyethanethiolate (2,2',2" terpyeidine) pla; Potassium tetranitro platinate (II); Trimethyl platinum (II) nitrate; Sodium tetraoxo rhenate (VII); Potassium tetraoxo rhenate (VI); Potassium tetraoxo rhenate (VII); Potassium hexachloro rhenium (IV); Rhenium (III) chloride; Ammonium hexachloro rhenate (IV); Dimethyltin (II) dichloride; Thorium (IV) nitrate; Uranium (VI) oxychloride; Uranium (VI) oxynitrate; Uranium (VI) oxyacetate; Uranium (VI) oxypyrophosphate; Potassium pentafluoro oxyuranate (VI); Sodium pentafluoro oxyuranate (VI); Potassium nanofluoro dioxyuranate (VI); Sodium triacetate oxyuranate (VI); Uranium (VI) oxyoxalate; Selenocyanate anion; Sodium tungstate; Sodium 12-tungstophosphate; Thallium (I) acetate; Thallium (I) fluoride; Thallium (I) nitrate; Potassium tetrachloro palladate (II); Potassium tetrabromo palladate (II); Potassium tetracyano palladate (II); Potassium tetraiodo palladate (II); Cobalt (II) chloride.

The PDMS material from which the chip can be formed is well suited for many of these targets, particularly biological samples. PDMS is a non-reactive and biologically inert compound that allows such molecules to maintain their appropriate shape, fold, and activity in a solublized state. The matrix and system can accommodate a range of target sizes and molecular weights, from a few hundred Daltons to the mega-Dalton regime. Biological targets, from small proteins and peptides to viruses and macromolecular complexes, fall within this range, and are generally anywhere from 3-10 kDa to >1-2 MDa in size.

12. Solute/Reagent Types

During crystallization screening, a large number of chemical compounds may be employed. These compounds include salts, small and large molecular weight organic compounds, buffers, ligands, small-molecule agents, detergents, peptides, crosslinking agents, and derivatizing agents. Together, these chemicals can be used to vary the ionic strength, pH, solute concentration, and target concentration in the drop, and can even be used to modify the target. The desired concentration of these chemicals to achieve crystallization is variable, and can range from nanomolar to molar concentrations. A typical crystallization mix contains set of fixed, but empirically-determined, types and concentrations of 'precipitants', buffers, salts, and other chemical additives (e.g., metal ions, salts, small molecular chemical additives, cryo protectants, etc.). Water is a key solvent in many crystallization trials of biological targets, as many of these molecules may require hydration to stay active and folded.

As described above in connection with the pressurized out-gas priming (POP) technique, the permeability of PDMS to gases, and the compatibility of solvents with PDMS may be a significant factor in deciding upon precipitating agents to be used.

'Precipitating' agents act to push targets from a soluble to insoluble state, and may work by volume exclusion, changing the dielectric constant of the solvent, charge shielding, and molecular crowding. Precipitating agents compatible with the PDMS material of certain embodiments of the chip include, but are not limited to, non-volatile salts, high molecular weight polymers, polar solvents, aqueous solutions, high molecular weight alcohols, divalent metals.

Precipitating compounds, which include large and small molecular weight organics, as well as certain salts are used from under 1% to upwards of 40% concentration, or from <0.5M to greater than 4M concentration. Water itself can act in a precipitating manner for samples that require a certain level of ionic strength to stay soluble. Many precipitants may also be mixed with one another to increase the chemical diversity of the crystallization screen. The microfluidics devices described in this document are readily compatible with a broad range of such compounds. Moreover, many precipitating agents (such as long- and short-chain organics) are quite viscous at high concentrations, presenting a problem for most fluid handling devices, such as pipettes or robotic systems. The pump and valve action of microfluidics devices in accordance with embodiments of the present invention enable handling of viscous agents.

An investigation of solvent/precipitating agent compatibility with particular elastomer materails may be conducted to identify optimum crystallizing agents, which may be employed develop crystallization screening reactions tailored for the chip that are more effective than standard screens.

A nonexclusive list of salts which may be used as precipitants is as follows: Tartrate (Li, Na, K, Na/K, NH4); Phosphate (Li, Na, K, Na/K, NH4); Acetate (Li, Na, K, Na/K, Mg, Ca, Zn, NH4); Formate (Li, Na, K, Na/K, Mg, NH4); Citrate (Li, Na, K, Na/K, NH4); Chloride (Li, Na, K, Na/K, Mg, Ca, Zn, Mn, Cs, Rb, NH4); Sulfate (Li, Na, K, Na/K, NH4); Malate (Li, Na, K, Na/K, NH4); Glutamate (Li, Na, K, Na/K, NH4.

A nonexclusive list of organic materials which may be used as precipitants is as follows: PEG 400; PEG 1000; PEG 1500; PEG 2k; PEG 3350; PEG 4k; PEG 6k; PEG 8k; PEG 10k; PEG 20k; PEG-MME 550; PEG-MME 750; PEG-MME 2k; PEG-MME 5k; PEG-DME 2k; Dioxane; Methanol; Ethanol; 2-Butanol; n-Butanol; t-Butanol; Jeffamine M-600; Isopropanol; 2-methyl-2,4-pentanediol; 1,6 hexanediol.

Solution pH can be varied by the inclusion of buffering agents; typical pH ranges for biological materials lie anywhere between values of 3.5-10.5 and the concentration of buffer, generally lies between 0.01 and 0.25 M. The microfluidics devices described in this document are readily compatible with a broad range of pH values, particularly those suited to biological targets.

A nonexclusive list of possible buffers is as follows: Na-Acetate; HEPES; Na-Cacodylate; Na-Citrate; Na-Succinate; Na—K-Phosphate; TRIS; TRIS-Maleate; Imidazole-Maleate; BisTrisPropane; CAPSO, CHAPS, MES, and imidizole.

Additives are small molecules that affect the solubility and/or activity behavior of the target. Such compounds can speed crystallization screening or produce alternate crystal forms of the target. Additives can take nearly any conceivable form of chemical, but are typically mono and polyvalent salts (inorganic or organic), enzyme ligands (substrates, products, allosteric effectors), chemical crosslinking agents, detergents and/or lipids, heavy metals, organo-metallic compounds, trace amounts of precipitating agents, and small molecular weight organics.

The following is a nonexclusive list of possible additives: 2-Butanol; DMSO; Hexanediol; Ethanol; Methanol; Isopropanol; sodium flouride; potassium flouride; ammonium flouride; lithium chloride anhydrous; magnesium chloride hexahydrate; sodium chloride; Calcium chloride dihydrate; potassium chloride; ammonium chloride; sodium iodide; potassium iodide; ammonium iodide; sodium thiocyanate; potassium thiocyanate; lithium nitrate; magnesium nitrate hexahydrate; sodium nitrate; potassium nitrate; ammonium nitrate; magnesium formate; sodium formate; potassium formate; ammonium formate; lithium acetate dihydrate; magnesium acetate tetrahydrate; zinc acetate dihydrate; sodium acetate trihydrate; calcium acetate hydrate; potassium acetate; ammonium acetate; lithium sulfate monohydrate; magnesium sulfate heptahydrate; sodium sulfate decahydrate; potassium sulfate; ammonium sulfate; di-sodium tartate dihydrate; potassium sodium tartrate tetrahydrate; di-ammonium tartrate; sodium dihydrogen phosphate monohydrate; di-sodium hydrogen phosphate dihydrate; potassium dihydrogen phosphate; di-potassium hydrogen phosphate; ammonium dihydrogen phosphate; di-ammonium hydrogen phosphate; tri-lithium citrate tetrahydrate; tri-sodium citrate dihydrate; tri-potassium citrate monohydrate; di-ammonium hydrogen citrate; barium chloride; cadmium chloride dihydrate; cobaltous chloride dihydrate; cupric chloride dihydrate; strontium chloride hexahydrate; yttrium chloride hexahydrate; ethylene glycol; Glycerol anhydrous; 1,6 hexanediol; MPD; polyethylene glycol 400; trimethylamine HCl; guanidine HCl; urea; 1,2,3-heptanetriol; benzamidine HCl; dioxane; ethanol; iso-propanol; methanol; sodium iodide; L-cysteine; EDTA sodium salt; NAD; ATP disodium salt; D(+)-glucose monohydrate; D(+)-sucrose; xylitol; spermidine; spermine tetra-HCl; 6-aminocaproic acid; 1,5-diaminopentane di-HCl; 1,6-diaminohexane; 1,8-diaminooctane; glycine; glycyl-glycyl-glycine; hexaminecobalt trichloride; taurine; betaine monohydrate; polyvinylpyrrolidone K15; non-detergent sulfo-betaine 195; non-detergent sulfo-betaine 201; phenol; DMSO; dextran sulfate sodium salt; jeffamine M-600; 2,5 Hexanediol; (+/−)-1,3 butanediol; polypropylene glycol P400; 1,4 butanediol; tert-butanol; 1,3 propanediol; acetonitrile; gamma butyrolactone; propanol; ethyl acetate; acetone; dichloromethane; n-butanol; 2,2,2 trifluoroethanol; DTT; TCEP; nonaethylene glycol monododecyl ether, nonaethylene glycol monolauryl ether; polyoxyethylene (9) ether; octaethylene glycol monododecyl ether, octaethylene glycol monolauryl ether; polyoxyethylene (8) lauryl ether; Dodecyl-β-D-maltopyranoside; Lauric acid sucrose ester; Cyclohexyl-pentyl-β-D-maltoside; Nonaethylene glycol octylphenol ether; Cetyltrimethylammonium bromide; N,N-bis(3-D-gluconamidopropyl)-deoxycholamine; Decyl-β-D-maltopyranoside; Lauryldimethylamine oxide; Cyclohexyl-pentyl-β-D-maltoside; n-Dodecylsulfobetaine, 3-(Dodecyldimethylammonio)propane-1-sulfonate; Nonyl-β-D-glucopyranoside; Octyl-β-D-thioglucopyranoside, OSG; N,N-Dimethyldecylamine-β-oxide; Methyl-6-O—(N-heptylcarbamoyl)-a-D-glucopyranoside; Sucrose monocaproylate; n-Octanoyl-β-D-fructofuranosyl-a-D-glucopyranoside; Heptyl-β-D-thioglucopyranoside; Octyl-β-D-glucopyranoside, OG; Cyclohexyl-propyl-β-D-maltoside; Cyclohexylbutanoyl-N-hydroxyethylglucamide; n-decylsulfobetaine, 3-(Decyldimethylammonio)propane-1-sulfonate; Octanoyl-N-methylglucamide, OMEGA; Hexyl-β-D-glucopyranoside; Brij 35; Brij 58; Triton X-114; Triton X-305; Triton X-405; Tween 20; Tween 80; polyoxyethylene(6)decyl ether; polyoxyethylene(9)decyl ether; polyoxyethylene(10)dodecyl ether; polyoxyethylene(8)tridecyl ether; Isopropyl-β-D-thiogalactoside; Decanoyl-N-hydroxyethylglucamide; Pentaethylene glycol monooctyl ether; 3-[(3-cholamidopropyl)-dimethylammonio]-1-propane sulfonate; 3-[(3-Cholamidopropyl)-dimethylammonio]-2-hydroxy-1-propane sulfonate; Cyclohexylpentanoyl-N-hydroxyethylglucamide; Nonanoyl-N-hydroxyethyglucamide; Cyclohexylpropanol-N-hydroxyethylglucamide; Octanoyl-N-hydroxyethylglucamide; Cyclohexylethanoyl-N-hydroxyethylglucamide; Benzyldimethyldodecyl ammonium bromide; n-Hexadecyl-β-D-maltopyranoside; n-Tetradecyl-β-D-maltopyranoside; n-Tridecyl-β-D-maltopyranoside; Dodecylpoly(ethyleneglycoether)n; n-Tetradecyl-N,N-dimethyl-3-ammonio-1-propanesulfonate; n-Undecyl-β-D-maltopyranoside; n-Decyl-β-D-thiomaltopyranoside; n-dodecylphosphocholine; a-D-glucopyranoside, β-D-fructofuranosyl monodecanoate, sucrose mono-caprate; 1-s-Nonyl-β-D-thioglucopyranoside; n-Nonyl-β-D-thiomaltoyranoside; N-Dodecyl-N,N-(dimethlammonio)butyrate; n-Nonyl-β-D-maltopyranoside; Cyclohexyl-butyl-β-D-maltoside; n-Octyl-β-D-thiomaltopyranoside; n-Decylphosphocholine; n-Nonylphosphocholine; Nonanoyl-N-methylglucamide; 1-s-Heptyl-β-D-thioglucopyranoside; n-Octylphosphocholine; Cyclohexyl-ethyl-β-D-maltoside; n-Octyl-N,N-dimethyl-3-ammonio-1-propanesulfonate; Cyclohexyl-methyl-β-D-maltoside.

Cryosolvents are agents that stabilize a target crystal to flash-cooling in a cryogen such as liquid nitrogen, liquid propane, liquid ethane, or gaseous nitrogen or helium (all at approximately 100-120° K) such that crystal becomes embedded in a vitreous glass rather than ice. Any number of salts or small molecular weight organic compounds can be used as a cryoprotectant, and typical ones include but are not limited to: MPD, PEG-400 (as well as both PEG derivatives and higher molecular-weight PEG compounds), glycerol, sugars (xylitol, erythritol, sucrose, glucose, etc.), ethylene glycol, alcohols (both short- and long chain, both volatile and nonvolatile), LiOAc, LiCl, $LiCHO_2$, $LiNO_3$, $Li_2SO_4$, $Mg(OAc)_2$, NaCl, $NaCHO_2$, $NaNO_3$, etc. Again, materials from which microfluidics devices in accordance with the present invention are fabricated may be compatible with a range of such compounds.

Many of these chemicals can be obtained in predefined screening kits from a variety of vendors, including but not limited to Hampton Research of Laguna Niguel, Calif., Emerald Biostructures of Bainbridge Island, Wash., and Jena BioScience of Jena, Germany, that allow the researcher to perform both 'sparse matrix' and 'grid' screening experiments. Sparse matrix screens attempt to randomly sample as much of precipitant, buffer, and additive chemical space as possible with as few conditions as possible. Grid screens typically consist of systematic variations of two or three parameters against one another (e.g., precipitant concentration vs. pH). Both types of screens have been employed with success in crystallization trials, and the majority of chemicals and chemical combinations used in these screens are compatible with the chip design and matrices in accordance with embodiments of the present invention.

Moreover, current and future designs of microfluidic devices may enable flexibly combinatorial screening of an array of different chemicals against a particular target or set of targets, a process that is difficult with either robotic or hand screening. This latter aspect is particularly important for optimizing initial successes generated by first-pass screens.

13. Additional Screening Variables for Crystallization

In addition to chemical variability, a host of other parameters can be varied during crystallization screening. Such parameters include but are not limited to: 1) volume of crystallization trial, 2) ratio of target solution to crystallization solution, 3) target concentration, 4) cocrystallization of the target with a secondary small or macromolecule, 5) hydration, 6) incubation time, 7) temperature, 8) pressure, 9) contact surfaces, 10) modifications to target molecules, and 11) gravity.

Volumes of crystallization trials can be of any conceivable value, from the picoliter to milliliter range. Typical values may include but are not limited to: 0.1, 0.2, 0.25, 0.4, 0.5, 0.75, 1, 2, 4, 5, 10, 15, 20, 25, 30, 35, 40, 45, 50, 60, 70, 75, 80, 90, 100, 125, 150, 175, 200, 225, 250, 275, 300, 350, 400, 450, 500, 550, 600, 700, 750, 800, 900, 1000, 1100, 1200, 1250, 1300, 1400, 1500, 1600, 1700, 1800, 1900, 2000, 2250, 2500, 3000, 4000, 5000, 6000, 7000, 7500, 8000, 9000, and 10000 mL. The microfluidics devices previously described can access these values.

In particular, access to the low volume range for crystallization trials (<100 nL) is a distinct advantage of embodiments of the microfluidics chips in accordance with embodiments of the present invention, as such small-volume crystallization chambers can be readily designed and fabricated, minimizing the need the need for large quantities of precious target molecules. The low consumption of target material of embodiments in accordance with the present invention is particularly useful in attempting to crystallize scarce biological samples such as membrane proteins, protein/protein and protein/nucleic acid complexes, and small-molecule drug screening of lead libraries for binding to targets of interest.

The ratios of a target solution to crystallization mix can also constitute an important variable in crystallization screening and optimization. These rations can be of any conceivable value, but are typically in the range of 1:100 to 100:1 target:crystallization-solution. Typical target:crystallization-solution or crystallization-solution:target ratios may include but are not limited to: 1:100, 1:90, 1:80, 1:70, 1:60, 1:50, 1:40, 1:30, 1:25, 1:20, 1:15, 1:10, 1:9, 1:8, 1:7.5, 1:7, 1:6, 1:5, 1:4, 1:3, 1:2.5, 1:2, 1:1, 2:3, 3:4, 3:5, 4:5, 5:6, 5:7, 5:9, 6:7, 7:8, 8:9, and 9:10. As previously described, microfluidics devices in accordance with embodiments of the present invention can be designed to access multiple ratios simultaneously on a single chip.

Target concentration, like crystallization chemical concentration, can lie in a range of values and is an important variable in crystallization screening. Typical ranges of concentrations can be anywhere from <0.5 mg/ml to >100 mg/ml, with most commonly used values between 5-30 mg/ml. The microfluidics devices in accordance with embodiments of the present invention are readily compatible with this range of values.

Cocrystallization generally describes the crystallization of a target with a secondary factor that is a natural or nonnatural binding partner. Such secondary factors can be small, on the order of about 10-1000 Da, or may be large macromolecules. Cocrystallization molecules can include but are not limited to small-molecule enzyme ligands (substrates, products, allosteric effectors, etc.), small-molecule drug leads, singlestranded or double-stranded DNAs or RNAs, complement proteins (such as a partner or target protein or subunit), monoclonal antibodies, and fusion-proteins (e.g, maltose binding proteins, glutathione S-transferase, protein-G, or other tags that can aid expression, solubility, and target behavior). As many of these compounds are either biological or of a reasonable molecular weight, cocrystallization molecules can be routinely included with screens in the microfluidics chips. Indeed, because many of these reagents are expensive and/or of limited quantity, the small-volumes afforded by the microfluidics chips in accordance with embodiment of the present invention make them ideally suited for cocrystallization screening.

Hydration of targets can be an important consideration. In particular, water is by far the dominant solvent for biological targets and samples. The microfluidics devices described in this document are relatively hydrophobic, and are compatible with water-based solutions.

The length of time for crystallization experiments can range from minutes or hours to weeks or months. Most experiments on biological systems typically show results within 24 hours to 2 weeks. This regime of incubation time can be accommodated by the microfluidics devices in accordance with embodiments of the present invention.

The temperature of a crystallization experiment can have a great impact on success or failure rates. This is particularly true for biological samples, where temperatures of crystallization experiments can range from 0-42° C. Some of the most common crystallization temperatures are: 0, 1, 2, 4, 5, 8, 10, 12, 15, 18, 20, 22, 25, 30, 35, 37, and 42. Microfluidics devices in accordance with embodiments of the present invention can be stored at the temperatures listed, or alternatively may be placed into thermal contact with small temperature control structures such as resistive heaters or Peltier cooling structures.

In addition, the small footprint and rapid setup time of embodiments in accordance with the present invention allow faster equilibration to desired target temperatures and storage in smaller incubators at a range of temperatures. Moreover, as the microfluidics systems in accordance with embodiments of the present invention do not place the crystallization experiment in contact with the vapor phase, condensation of water from the vapor phase into the drop as temperatures change, a problem associated with conventional macroscopic vapor-diffusion techniques, is avoided. This feature represents an advance over many conventional manual or robotic systems, where either the system must be maintained at the desired temperature, or the experiment must remain at room temperature for a period before being transferred to a new temperature.

Variation in pressure is an as yet understudied crystallization parameter, in part because conventional vapor-diffusion and microbatch protocols do not readily allow for screening at anything typically other than atmospheric pressure. The rigidity of the PDMS matrix enables experiments to probe the effects of pressure on target crystallization on-chip.

The surface on which the crystallization 'drop' sits can affect experimental success and crystal quality. Examples of solid support contact surfaces used in vapor diffusion and microbatch protocols include either polystyrene or silanized glass. Both types of supports can show different propensities to promote or inhibit crystal growth, depending on the target. In addition, the crystallization 'drop' is in contact with either air or some type of poly-carbon oil, depending on whether the experiment is a vapor-diffusion or microbatch setup, respectively. Air contact has the disadvantage in that free oxygen reacts readily with biological targets, which can lead to protein denaturation and inhibit or degrade crystallization success. Oil allows trace hydrocarbons to leach into the crystallization experiment, and can similarly inhibit or degrade crystallization success.

Microfluidics device designs in accordance with embodiments of the present invention may overcome these limitations by providing a nonreactive, biocompatible environment that completely surrounds the crystallization reaction. Moreover, the composition of the crystallization chambers in the microfluidics chips can conceivably be varied to provide new surfaces for contacting the crystallization reaction; this would allow for routine screening of different surfaces and surface properties to promote crystallization.

Crystallization targets, particularly those of biological origin, may often be modified to enable crystallization. Such modifications include but are not limited to truncations, limited proteolytic digests, site-directed mutants, inhibited or activated states, chemical modification or derivatization, etc. Target modifications can be time consuming and costly; modified targets require the same thorough screening as do unmodified targets. Microfluidics devices of the present invention work with such modified targets as readily as with the original target, and provide the same benefits.

The effect of gravity as a parameter for crystallization is yet another understudied crystallization parameter, because of the difficulty of varying such a physical property. Nonetheless, crystallization experiments of biological samples in zero gravity environments have resulted in the growth of crystals of superior quality than those obtained on Earth under the influence of gravity.

The absence of gravity presents problems for traditional vapor-diffusion and microbatch setups, because all fluids must be held in place by surface tension. The need to often set up such experiments by hand also poses difficulties because of the expense of maintaining personnel in space. Microfluidics devices in accordance with embodiments of the present invention, however, would enable further exploration of microgravity as a crystallization condition. A compact, automated metering and crystal growth system would allow for: 1) launching of satellite factory containing target molecules in a cooled, but liquid state, 2) distribution of targets and growth of crystals, 3) harvesting and cryofreezing of resultant crystals, and 4) return of cryo-stored crystals to land-based stations for analysis.

14. In Situ Crystallization Screening

The ability to observe the growth of crystals with a microscope is a step in deciding upon success or failure of crystallization trials. Conventional crystallization protocols may use transparent materials such as polystyrene or silanized glass to allow for visualization. The transparency of the PDMS matrix of embodiments in accordance with the present invention is particularly suited to the two primary methods by which crystallization trials are traditionally scored: 1) direct observation in the visible light regime by optical microscopes and 2) birefringence of polarized light.

Birefringence may be difficult to judge in conventional experiments as many plastics are themselves birefringent, interfering with sample assessment. However, the microfluidics devices described herein can be made without such optical interference properties, allowing for the design of an automated scanning system that routinely allows direct visualization with both polarizing and non-polarizing features.

In addition, robotic and, in particular, manually-set crystallization experiments can vary the placement of a crystallization drop on a surface by tens to hundreds of microns. This variability presents a problem for automated scanning systems, as it is difficult to program in the need for such flexible positioning without stable fiducials. However, the fixed placement of crystallization chambers in the microfluidics chips of embodiments of the present invention overcomes such problems, as every well can be positioned in a particular location with submicron accuracy. Moreover, such a system is readily scalable for the design of differently sized and positioned crystallization chambers, as masks and other templates used to design microfluidics devices in accordance with embodiments of the present invention can be simply digitized and ported into scanning software for visualization.

Once crystals are obtained by visual inspection, it may be possible to screen for diffraction directly through the chip itself. For example, a crystallization chamber within a chip could be outfitted with transparent 'windows' comprising glass, quartz, or thinned portions of the elastomer material itself, on opposite walls of the chamber. Crystals could then be exposed directly to x-rays through the chip to assay for diffraction capabilities, eliminating the need to remove, and thereby possibly damage, the crystalline sample. Such an approach could be used to screen successes from initial crystallization trials to determine the best starting candidate conditions for follow-up study. Similarly, crystals grown under a particular set of conditions could be 're-equilibrated' with new solutions (e.g., cryo-stabilizing agents, small-molecule drug leads or ligands, etc.), and the stability of the crystals to such environment changes monitored directly by x-ray diffraction.

15. Utilizing Microfluidic Devices for Purification/Crystallization

Crystallization of target biological samples such as proteins is actually the culmination of a large number of prior complex and difficult steps, including but not limited to protein expression, purification, derivitization, and labeling. Such steps prior to crystallization comprise shuttling liquids from a chamber with one set of solution properties to another area with a different set of properties. Mircofluidics technology is suited to perform such tasks, allowing for the combination of all necessary steps within the confines of a single chip.

Examples of microfluidic handling structures enabling performance of pre-crystallization steps have been described under section I above. For example, a microfluidics chip could act as a regulated bioreactor, allowing nutrients to flow into growing cells contained in cell pen structure while removing wastes and inducing recombinantly-modified organisms to produce target molecules (e.g., proteins) at a desired stage of cell growth. Following induction, these cells could be shunted from the cell pen to a different region of the chip for lysis by enzymatic or mechanical means. Solubilized target molecules could then be separated from cellular debris by molecular filtration units incorporated directly onto a chip.

The crude mixture of target molecules and contaminating cellular proteins and nucleic acids could then be funneled through porous matrices of differing chemical properties (e.g., cation-exchange, anion-exchange, affinity, size-exclusion) to achieve separation. If a target molecule were tagged with a fusion protein of a particular type to promote solubility, it could be affinity purified, briefly treated with a similarly-tagged, site-specific protease to separate the fusion product, and then repassaged though the affinity matrix as a clean-up step.

Once pure, the target could be mixed with different stabilizing agents, assayed for activity, and then transported to crystallization staging areas. Localized heating (such as an electrode) and refrigeration (such as a Peltier cooler) units stationed at various points on a chip or a chip holder would allow for differential temperature regulation at all stages throughout the processing and crystallization. Thus, the production, purification, and crystallization of proteins may be accomplished on an embodiment of a single microfluidics device in accordance with the present invention.

16. Applications Other than Crystallization Screening

Thus far, the instant application has focused upon the ability of microfluidics devices in accordance with embodiments of the present invention to meter small volumes of material in the context of performing crystallization of target material. However, embodiments of microfluidic structures in accordance with the present invention may be employed for other applications. Examples of such applications are summarized below. A more complete description of possible applications may be found in PCT application PCT/US01/44869, filed Nov. 16, 2001 and entitled "Cell Assays and High Throughput Screening", hereby incorporated by reference for all purposes. Examples of microfluidic structures suitable for performing such applications include those described herein, as well as others described in U.S. nonprovisional patent application Ser. No. 10/118,466, "Nucleic Acid Amplification Utilizing Microfluidic Devices", filed Apr. 5, 2002, hereby incorporated by reference for all purposes.

A wide variety of binding assays can be conducted utilizing the microfluidic devices disclosed herein. Interactions between essentially any ligand and antiligand can be detected. Examples of ligand/antiligand binding interactions that can be investigated include, but are not limited to, enzyme/ligand interactions (e.g., substrates, cofactors, inhibitors); receptor/ligand; antigen/antibody; protein/protein (homophilic/heterophilic interactions); protein/nucleic; DNA/DNA; and DNA/RNA. Thus, the assays can be used to identify agonists and antagonists to receptors of interest, to identify ligands able to bind receptors and trigger an intracellular signal cascade, and to identify complementary nucleic acids, for example. Assays can be conducted in direct binding formats in which a ligand and putative antiligand are contacted with one another or in competitive binding formats well known to those of ordinary skill in the art.

Heterogenous binding assays involve a step in which complexes are separated from unreacted agents so that labeled complexes can be distinguished from uncomplexed labeled reactants. Often this is achieved by attaching either the ligand or antiligand to a support. After ligands and antiligands have been brought into contact, uncomplexed reactants are washed away and the remaining complexes subsequently detected.

The binding assays conducted with the microfluidic devices provided herein can also be conducted in homogeneous formats. In the homogeneous formats, ligands and antiligands are contacted with one another in solution and binding complexes detected without having to remove uncomplexed ligands and antiligands. Two approaches frequently utilized to conduct homogenous assays are fluorescence polarization (FP) and FRET assays.

The microfluidic devices can also be utilized in a competitive formats to identify agents that inhibit the interaction between known binding partners. Such methods generally involve preparing a reaction mixture containing the binding partners under conditions and for a time sufficient to allow the binding partners to interact and form a complex. In order to test a compound for inhibitory activity, the reaction mixture is prepared in the presence (test reaction mixture) and absence (control reaction mixture) of the test compound. Formation of complexes between binding partners is then detected, typically by detecting a label borne by one or both of the binding partners. The formation of more complexes in the control reaction then in the test reaction mixture at a level that constitutes a statistically significant difference indicates that the test compound interferes with the interaction between the binding partners.

Immunological assays are one general category of assays that can be performed with the microfluidic devices in accordance with embodiments of the present invention. Certain assays are conducted to screen a population of antibodies for those that can specifically bind to a particular antigen of interest. In such assays, a test antibody or population of antibodies is contacted with the antigen. Typically, the antigen is attached to a solid support. Examples of immunological assays include enzyme linked immunosorbent assays (ELISA) and competitive assays as are known in the art.

Utilizing the microfluidic devices provided herein, a variety of enzymatic assays can be performed. Such enzymatic assays generally involve introducing an assay mixture containing the necessary components to conduct an assay into the various branch flow channels. The assay mixtures typically contain the substrate(s) for the enzyme, necessary cofactors (e.g., metal ions, NADH, NAPDH), and buffer, for example. If a coupled assay is to be performed, the assay solution will also generally contain the enzyme, substrate(s) and cofactors necessary for the enzymatic couple.

Microfluidic devices in accordance with embodiments of the present invention can be arranged to include a material that selectively binds to an enzymatic product that is produced. In some instances, the material has specific binding affinity for the reaction product itself. Somewhat more complicated systems can be developed for enzymes that catalyze transfer reactions. Certain assays of this type, for example, involve incubating an enzyme that catalyzes the transfer of a detectable moiety from a donor substrate to an acceptor substrate that bears an affinity label to produce a product bearing both the detectable moiety and the affinity label. This product can be captured by material that includes a complementary agent that specifically binds to the affinity label. This material typically is located in a detection region such that captured product can be readily detected. In certain assays, the material is coated to the interior channel walls of the detection section; alternatively, the material can be a support located in the detection region that is coated with the agent.

Certain assays utilizing the present devices are conducted with vesicles rather than cells. Once example of such an assay is a G-protein coupled receptor assay utilizing fluorescent correlation spectroscopy (FCS). Membrane vesicles constructed from cells that over-express the receptor of interest are introduced into a main flow channel. Vesicles can either be premixed with inhibitor and introduced via branch flow channels or via one of the main flow channels prior to being mixed with a fluorescent natural ligand which is also introduced by a main flow channel. Components are allowed to incubate for the desired time and fluorescent signals may be analyzed directly in the flow chamber using an FCS reader such as the Evotec/Zeiss Confocor (a single or dual photon counting device).

FRET assays can also be utilized to conduct a number of ligand-receptor interactions using the devices disclosed herein. For example, a FRET peptide reporter can be constructed by introducing a linker sequence (corresponding to an inducible domain of a protein such as a phosphorylation site) into a vector encoding for a fluorescent protein composed of blue- and red-shifted GFP variants. The vector can be a bacterial (for biochemical studies) or a mammalian expression vector (for in vivo studies).

Assays of nuclear receptors can also be performed with the present microfluidic devices. For example, FRET-based assays for co-activator/nuclear receptor interaction can be performed. As a specific example, such assays can be conducted to detect FRET interactions between: (a) a ligand binding domain of a receptor tagged with CFP (cyan fluorescent protein, a GFP derivative), and (b) a receptor binding protein (a coactivator) tagged with the Yellow fluorescent protein (YFP).

Fluorescence polarization (FP) can be utilized to develop high throughput screening (HTS) assays for nuclear receptor-ligand displacement and kinase inhibition. Because FP is a solution-based, homogeneous technique, there is no requirement for immobilization or separation of reaction components. In general, the methods involve using competition between a fluorescently labeled ligand for the receptor and related test compounds.

A number of different cell reporter assays can be conducted with the provided microfluidic devices. One common type of reporter assay that can be conducted include those designed to identify agents that can bind to a cellular receptor and trigger the activation of an intracellular signal or signal cascade that activates transcription of a reporter construct. Such assays are useful for identifying compounds that can activate expression of a gene of interest. Two-hybrid assays, discussed below, are another major group of cell reporter assays that can be performed with the devices. The two-hybrid assays are useful for investigating binding interactions between proteins.

Often cell reporter assays are utilized to screen libraries of compounds. In general such methods involve introducing the cells into the main flow channel so that cells are retained in the chambers located at the intersection between the main flow channel and branch channels. Different test agents (e.g., from a library) can then be introduced into the different branch channels where they become mixed with the cells in the chambers. Alternatively, cells can be introduced via the main flow channel and then transferred into the branch channel, where the cells are stored in the holding areas. Meanwhile, different test compounds are introduced into the different branch flow channels, usually to at least partially fill the chambers located at the intersection of the main and branch flow channels. The cells retained in the holding area can be released by opening the appropriate valves and the cells transferred to the chambers for interaction with the different test compounds. Once the cells and test compounds have been mixed, the resulting solution is returned to the holding space or transported to the detection section for detection of reporter expression. The cells and test agents can optionally be further mixed and incubated using mixers of the design set forth above.

Cells utilized in screening compounds to identify those able to trigger gene expression typically express a receptor of interest and harbor a heterologous reporter construct. The receptor is one which activates transcription of a gene upon binding of a ligand to the receptor. The reporter construct is usually a vector that includes a transcriptional control element and a reporter gene operably linked thereto. The transcriptional control element is a genetic element that is responsive to an intracellular signal (e.g., a transcription factor) generated upon binding of a ligand to the receptor under investigation. The reporter gene encodes a detectable transcriptional or translational product. Often the reporter (e.g., an enzyme) can generate an optical signal that can be detected by a detector associated with a microfluidic device.

A wide variety of receptor types can be screened. The receptors often are cell-surface receptors, but intracellular receptors can also be investigated provided the test compounds being screened are able to enter into the cell. Examples of receptors that can be investigated include, but are not limited to, ion channels (e.g., calcium, sodium, potassium channels), voltage-gated ion channels, ligand-gated ion channels (e.g., acetyl choline receptors, and GABA (gamma-aminobutyric acid) receptors), growth factor receptors, muscarinic receptors, glutamate receptors, adrenergic receptors, dopamine receptors.

Another general category of cell assays that can be performed is the two hybrid assays. In general, the two-hybrid assays exploit the fact that many eukaryotic transcription factors include a distinct DNA-binding domain and a distinct transcriptional activation domain to detect interactions between two different hybrid or fusion proteins. Thus, the cells utilized in two-hybrid assays include the construct(s) that encode for the two fusion proteins. These two domains are fused to separate binding proteins potentially capable of interacting with one another under certain conditions. The cells utilized in conducting two-hybrid assays contain a reporter gene whose expression depends upon either an interaction, or lack of interaction, between the two fusion proteins.

In addition to the assays just described, a variety of methods to assay for cell membrane potential can be conducted with the microfluidic devices disclosed herein. In general, methods for monitoring membrane potential and ion channel activity can be measured using two alternate methods. One general approach is to use fluorescent ion shelters to measure bulk changes in ion concentrations inside cells. The second general approach is to use of FRET dyes sensitive to membrane potential.

The microfluidic devices disclosed herein can be utilized to conduct a variety of different assays to monitor cell proliferation. Such assays can be utilized in a variety of different studies. For example, the cell proliferation assays can be utilized in toxicological analyses, for example. Cell proliferation assays also have value in screening compounds for the treatment of various cell proliferation disorders including tumors.

The microfluidic devices disclosed herein can be utilized to perform a variety of different assays designed to identify toxic conditions, screen agents for potential toxicity, investigate cellular responses to toxic insults and assay for cell death. A variety of different parameters can be monitored to assess toxicity. Examples of such parameters include, but are not limited to, cell proliferation, monitoring activation of cellular pathways for toxicological responses by gene or protein expression analysis, DNA fragmentation; changes in the composition of cellular membranes, membrane permeability, activation of components of death-receptors or downstream signaling pathways (e.g., caspases), generic stress responses, NF-kappaB activation and responses to mitogens. Related assays are used to assay for apoptosis (a programmed process of cell death) and necrosis.

By contacting various microbial cells with different test compounds, one can also utilize the devices provided herein to conduct antimicrobial assays, thereby identifying potential antibacterial compounds. The term "microbe" as used herein refers to any microscopic and/or unicellular fungus, any bacteria or any protozoan. Some antimicrobial assays involve retaining a cell in a cell cage and contacting it with at least one potential antimicrobial compound. The effect of the compound can be detected as any detectable change in the health and/or metabolism of the cell. Examples of such changes, include but are not limited to, alteration in growth, cell proliferation, cell differentiation, gene expression, cell division and the like.

Certain of the microfluidic devices provided herein can be utilized to conduct mini-sequencing reactions or primer extension reactions to identify the nucleotide present at a polymorphic site in a target nucleic acid. In general, in these methods a primer complementary to a segment of a target nucleic acid is extended if the reaction is conducted in the presence of a nucleotide that is complementary to the nucleotide at the polymorphic site. Often such methods are single base pair extension (SBPE) reactions. Such method typically involve hybridizing a primer to a complementary target nucleic acid such that the 3' end of the primer is immediately adjacent the polymorphic site, or is a few bases upstream of the polymorphic site. The extension reaction is conducted in the presence of one or more labeled non-extendible nucleotides (e.g., dideoxynucleotides) and a polymerase. Incorporation of a non-extendible nucleotide onto the 3' end of the primer prevents further extension of the primer by the polymerase once the non-extendible nucleotide is incorporated onto the 3' end of the primer.

Related to the methods just described, the present devices can also be utilized to amplify and subsequently identify target nucleic acids in multiple samples using amplification techniques that are well established in the art. In general such methods involve contacting a sample potentially containing a target nucleic acid with forward and reverse primers that specifically hybridize to the target nucleic acid. The reaction includes all four dNTPs and polymerase to extend the primer sequences.

An embodiment of a method of fabricating a microfluidic device in accordance with the present invention comprises etching a top surface of a glass substrate to produce a plurality of wells, molding an elastomer block such that a bottom surface bears a patterned recess, placing a bottom surface of the molded elastomer block into contact with the top surface of the glass substrate, such that the patterned recess is aligned with the wells to form a flow channel between the wells.

An embodiment of a method for forming crystals of a target material comprises priming a first chamber of an elastomeric microfluidic device with a first predetermined volume of a target material solution. A second chamber of an elastomer microfluidic device is primed with a second predetermined volume of a crystallizing agent. The first chamber is placed into fluidic contact with the second chamber to allow diffusion between the target material and the crystallizing agent, such that an environment of the target material is changed to cause formation of crystal.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the claims.

What is claimed is:

1. A method of priming a microfluidic device with a liquid material, the method comprising:
    loading a plurality of wells on an upper surface of a microfluidic device with a liquid material;
    biasing a holder piece against the upper surface such that a continuous raised rim of the holder piece presses against the upper surface surrounding the wells, such that a chamber is created over the wells; and applying a positive pressure to the chamber to drive the material from the wells into an active area of the microfluidic device.

2. The method of claim 1, wherein applying the positive pressure to the chamber comprises applying the positive pressure at between 5 and 7 pounds per square inch.

3. The method of claim 1, wherein the raised rim deforms to engage the upper surface.

4. The method of claim 1, wherein the upper surface deforms to engage the raised rim.

5. The method of claim 1, wherein the active area of the microfluidic device comprises a dead-ended chamber or channel.

6. The method of claim 1, wherein the liquid material is a crystallizing agent, wherein the active area contains a target material, and wherein applying the positive pressure to the chamber to drive the material into the active area of the microfluidic device includes driving a calibrated volume of the crystallizing agent into the active area to promote crystallization of the target material.

* * * * *